US011999787B2

United States Patent
Yan et al.

(10) Patent No.: US 11,999,787 B2
(45) Date of Patent: Jun. 4, 2024

(54) TIE2-BINDING AGENTS AND METHODS OF USE

(71) Applicant: Genentech, Inc., South San Francisco, CA (US)

(72) Inventors: Minhong Yan, Foster City, CA (US); Gu Zhang, Millbrae, CA (US); Nicholas John Agard, San Francisco, CA (US); Danielle Marie Dicara, San Francisco, CA (US); Philip E. Hass, Moss Beach, CA (US); Julie Q. Hang, San Jose, CA (US); Erin L. Christensen, Corte Madera, CA (US); Robert Paul Morse, San Diego, CA (US); Sarah Sanowar, San Francisco, CA (US); Vittal Shivva, Foster City, CA (US)

(73) Assignee: Genentech, Inc., South San Francisco, CA (US)

(*) Notice: Subject to any disclaimer, the term of this patent is extended or adjusted under 35 U.S.C. 154(b) by 5 days.

(21) Appl. No.: 17/208,292

(22) Filed: Mar. 22, 2021

(65) Prior Publication Data
US 2021/0332142 A1    Oct. 28, 2021

Related U.S. Application Data

(60) Provisional application No. 63/046,318, filed on Jun. 30, 2020, provisional application No. 62/993,930, filed on Mar. 24, 2020.

(51) Int. Cl.
| | |
|---|---|
| *C07K 16/28* | (2006.01) |
| *A61K 9/00* | (2006.01) |
| *A61K 39/00* | (2006.01) |
| *A61K 39/395* | (2006.01) |
| *A61K 45/06* | (2006.01) |
| *A61K 47/60* | (2017.01) |
| *A61K 47/68* | (2017.01) |
| *A61P 27/02* | (2006.01) |

(52) U.S. Cl.
CPC ........ *C07K 16/2863* (2013.01); *A61K 9/0048* (2013.01); *A61K 39/3955* (2013.01); *A61K 45/06* (2013.01); *A61K 47/60* (2017.08); *A61K 47/6849* (2017.08); *A61P 27/02* (2018.01); *A61K 2039/505* (2013.01); *A61K 2039/54* (2013.01); *C07K 2317/24* (2013.01); *C07K 2317/55* (2013.01); *C07K 2317/565* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,365,154 B1 | 4/2002 | Holmes et al. |
| 6,376,653 B1 | 4/2002 | Holmes et al. |
| 6,858,736 B2 | 2/2005 | Nho et al. |
| 8,268,314 B2 | 9/2012 | Baehner et al. |
| 8,957,022 B2 | 2/2015 | VanSlyke et al. |
| 9,017,670 B2 | 4/2015 | Thurston |
| 9,683,051 B2 | 6/2017 | Kamohara et al. |

FOREIGN PATENT DOCUMENTS

| | | |
|---|---|---|
| EP | 3170841 A1 | 5/2017 |
| EP | 3805265 A1 | 4/2021 |
| WO | 00/18437 A1 | 4/2000 |
| WO | 2019/235856 A1 | 12/2019 |
| WO | WO 2021/194913 | * 9/2021 |

OTHER PUBLICATIONS

Bogdanovic, E., et al., "Oligomerized Tie2 localizes to clathrin-coated pits in response to angiopoietin-1" Histochem Cell Biol 132(2):225-237 (Aug. 1, 2009).
Campochiaro, P., et al., "Targeting Tie2 for Treatment of Diabetic Retinopathy and Diabetic Macular Edema" Curr Diab Rep 16(12 Suppl 126):1-11 (Dec. 1, 2016).
David, S., et al., "Effects of a synthetic PEG-ylated Tie-2 agonist peptide on endotoxemic lung injury and mortality" Am J Physiol Lung Cell Mol Physiol 300(6):L851-L862 (Jun. 1, 2011).
Davis, S., et al., "Angiopoietins have distinct modular domains essential for receptor binding, dimerization and superclustering" Nat Struct Biol 10(1):38-44 (Jan. 1, 2003).
Frye, M., et al., "Interfering with VE-PTP stabilizes endothelial junctions in vivo via Tie-2 in the absence of VE-cadherin" J Exp Med 212(13):2267-2287 (Dec. 14, 2015).
Han, S., et al., "Amelioration of sepsis by TIE2 activation-induced vascular protection" Sci Transl Med 8(335 Suppl 335ra55):1-11 (Apr. 20, 2016).
Hanala, S., et al., "The new ParaDIgm: IgM from bench to clinic, Nov. 15-16, 2011, Frankfurt, Germany" MABS 4(5):555-561 (Sep. 1, 2012).
Hussain, R., et al., "Tie-2/Angiopoietin pathway modulation as a therapeutic strategy for retinal disease" Expert Opin Investig Drugs 28(10):861-869 (Oct. 1, 2019).
Hwang, B., et al., "Stimulation of angiogenesis and survival of endothelial cells by human monoclonal Tie2 receptor antibody" Biomaterials 51:119-128 (May 1, 2015).
"International Search Report—PCT/US2021/023381" :pp. 1-5 (dated Jun. 14, 2021).
Issa, E., et al., "Development of an Orthogonal Tie2 Ligand Resistant to Inhibition by Ang2" Mol Pharm 15(9):3962-3968 (Sep. 4, 2018).

(Continued)

*Primary Examiner* — Marianne P Allen
(74) *Attorney, Agent, or Firm* — Jennifer L. Hsu

(57) ABSTRACT

The invention provides Tie-2 antibodies and fragments thereof and conjugates and methods of using the same.

30 Claims, 43 Drawing Sheets
Specification includes a Sequence Listing.

(56) References Cited

OTHER PUBLICATIONS

Kim, J., et al., "An essential role for angiopoietin-Tie2 signaling in wet age-related macular degeneration (AMD)" Abstract (3264; IOVS—ARVO Journals 59:9; ARVO Annual Meeting Apr. 29-May 3, 2018) ARVO Annual Meeting, Honolulu, Hawaii, pp. 1-3 ( Jul. 1, 2018).

Kim, J., et al., "Tie2 activation promotes choriocapillary regeneration for alleviating neovascular age-related macular degeneration" Science Advances 5(2):eaau6732 (1-17) (Feb. 13, 2019).

Kim, K., et al., "Oligomerization and multimerization are critical for angiopoietin-1 to bind and phosphorylate Tie2" J Biol Chem 280(20):20126-20131 (May 20, 2005).

Saharinen, P., et al., "Therapeutic targeting of the angiopoietin-TIE pathway" Nat Rev Drug Discov 16(9):635-661 (Sep. 1, 2017).

Wang, L., et al., "Angiopoietin-1/Tie2 signaling pathway contributes to the therapeutic effect of thymosin β4 on diabetic peripheral neuropathy" Neurosci Res 147:1-8 (Oct. 1, 2019).

"International Preliminary Report on Patentability—PCT/US2021/023381" (dated Sep. 22, 2022; Chapter I),:pp. 1-12 (Oct. 6, 2022).

Peters et al., "A VE-PTP antibody activates Tie2 and suppresses VEGF-induced retinal vascular leakage" ARVO Annual Meeting Abstract 59(9) (Jul. 2018).

\* cited by examiner

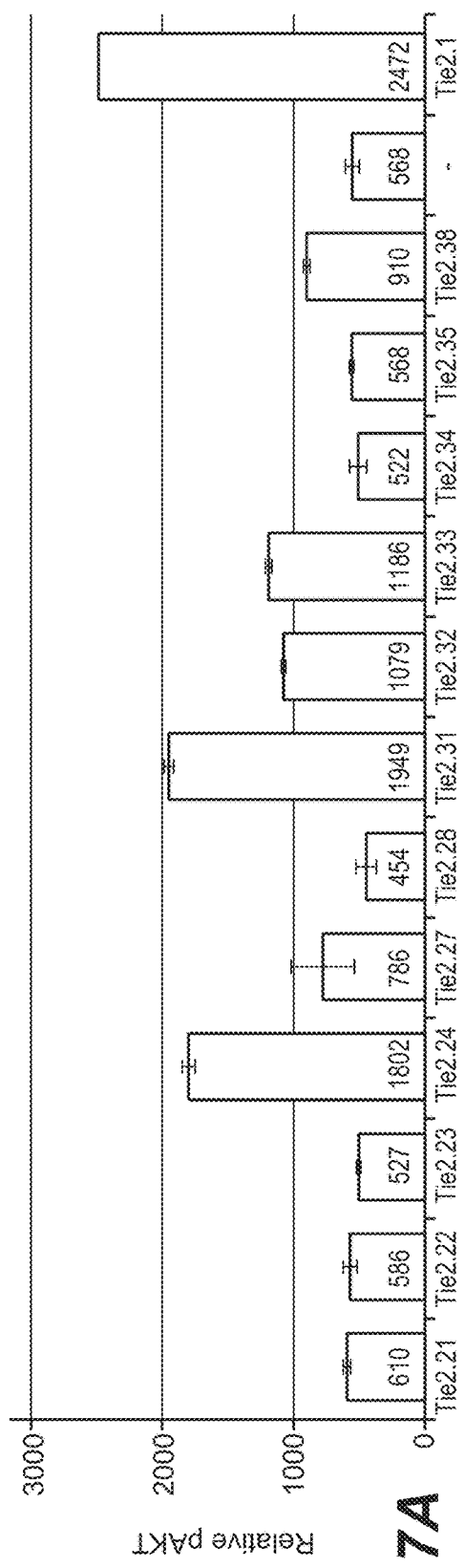
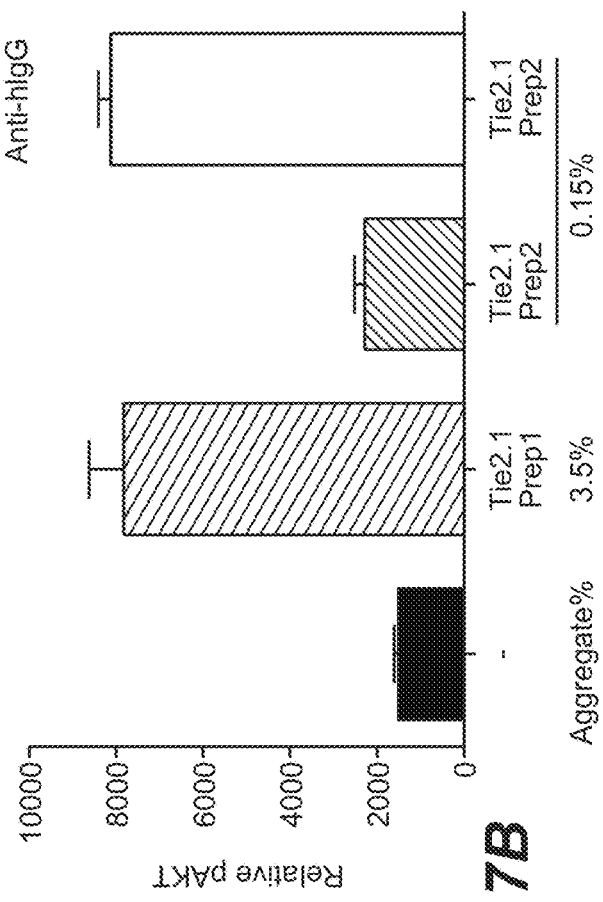
FIG. 7A
FIG. 7B

FIG. 10A

Light chain variable region:

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Tie 2.1 (no mutations) | D | I | Q | M | T | Q | S | P | S | S | L | S | A | S | V | G | D | R | V | T | I | T | C | R | A | S | Q | D | V | S | T | A | V | A | W | Y | Q | Q | K | P | G | K |
| Tie 2.1.M100cF | D | I | Q | M | T | Q | S | P | S | S | L | S | A | S | V | G | D | R | V | T | I | T | C | R | A | S | Q | D | V | S | T | A | V | A | W | Y | Q | Q | K | P | G | K |
| Tie 2.12 | D | I | Q | M | T | Q | S | P | S | S | L | S | A | S | V | G | D | R | V | T | I | T | C | R | A | S | Q | D | V | S | T | A | V | A | W | Y | Q | Q | K | P | G | K |
| Tie 2.24 | D | I | Q | M | T | Q | S | P | S | S | L | S | A | S | V | G | D | R | V | T | I | T | C | R | A | S | Q | D | V | S | T | A | V | A | W | Y | Q | Q | K | P | G | K |
| Tie 2.33 | D | I | Q | M | T | Q | S | P | S | S | L | S | A | S | V | G | D | R | V | T | I | T | C | R | A | S | Q | D | V | S | T | A | V | A | W | Y | Q | Q | K | P | G | K |
| Tie 2.38 | D | I | Q | M | T | Q | S | P | S | S | L | S | A | S | V | G | D | R | V | T | I | T | C | R | A | S | Q | D | V | S | T | A | V | A | W | Y | Q | Q | K | P | G | K |

CDR L1 - Contact: 30-36; CDR L1 - Kabat: 24-34

| Kabat number | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Tie 2.1 (no mutations) | A | P | K | L | L | I | Y | S | A | S | F | L | Y | S | G | V | P | S | R | F | S | G | S | G | S | G | T | D | F | T | L | T | I | S | S | L | Q | P | E | D | F | A |
| Tie 2.1.M100cF | A | P | K | L | L | I | Y | S | A | S | F | L | Y | S | G | V | P | S | R | F | S | G | S | G | S | G | T | D | F | T | L | T | I | S | S | L | Q | P | E | D | F | A |
| Tie 2.12 | A | P | K | L | L | I | Y | S | A | S | F | L | Y | S | G | V | P | S | R | F | S | G | S | G | S | G | T | D | F | T | L | T | I | S | S | L | Q | P | E | D | F | A |
| Tie 2.24 | A | P | K | L | L | I | Y | S | A | S | F | L | Y | S | G | V | P | S | R | F | S | G | S | G | S | G | T | D | F | T | L | T | I | S | S | L | Q | P | E | D | F | A |
| Tie 2.33 | A | P | K | L | L | I | Y | S | A | S | F | L | Y | S | G | V | P | S | R | F | S | G | S | G | S | G | T | D | F | T | L | T | I | S | S | L | Q | P | E | D | F | A |
| Tie 2.38 | A | P | K | L | L | I | Y | S | A | S | F | L | Y | S | G | V | P | S | R | F | S | G | S | G | S | G | T | D | F | T | L | T | I | S | S | L | Q | P | E | D | F | A |

CDR L2 - Contact: 46-55; CDR L2 - Kabat: 50-56

| Kabat number | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|
| Tie 2.1 (no mutations) | T | Y | Y | C | Q | Q | S | Y | T | T | P | P | T | F | G | Q | G | T | K | V | E | — | K |
| Tie 2.1.M100cF | T | Y | Y | C | Q | Q | S | Y | T | T | P | P | T | F | G | Q | G | T | K | V | E | — | K |
| Tie 2.12 | T | Y | Y | C | Q | Q | S | Y | T | T | P | P | T | F | G | Q | G | T | K | V | E | — | K |
| Tie 2.24 | T | Y | Y | C | Q | Q | S | Y | T | T | P | P | T | F | G | Q | G | T | K | V | E | — | K |
| Tie 2.33 | T | Y | Y | C | Q | Q | S | Y | T | T | P | P | T | F | G | Q | G | T | K | V | E | — | K |
| Tie 2.38 | T | Y | Y | C | Q | Q | S | Y | T | T | P | P | T | F | G | Q | G | T | K | V | E | — | K |

CDR L3 - Contact: 89-96; CDR L3 - Kabat: 89-97

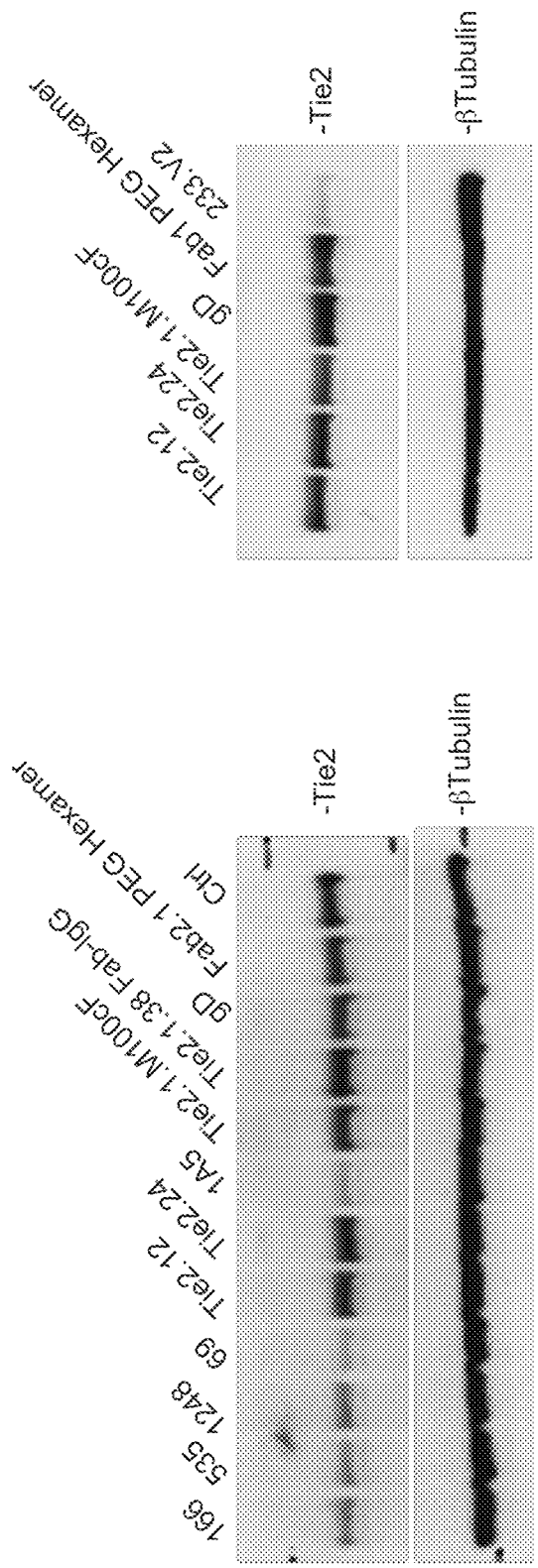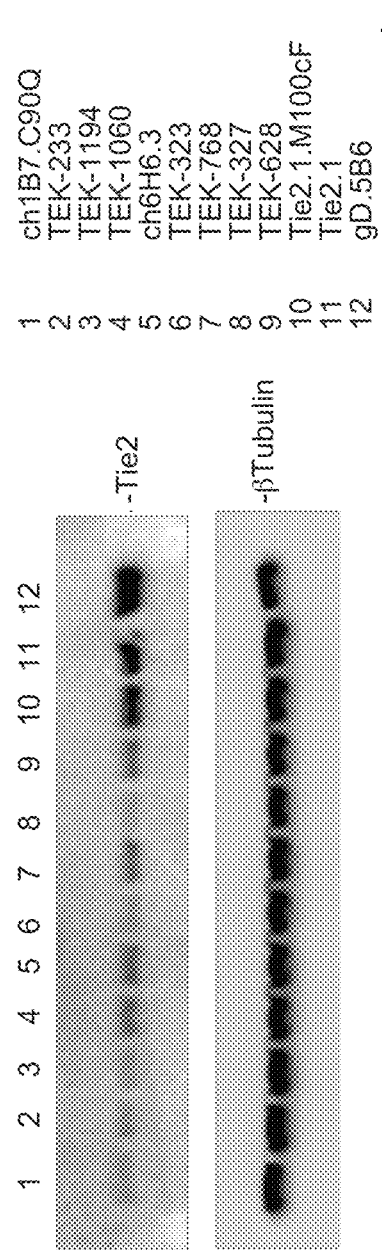
FIG. 16A
FIG. 16B
FIG. 16C

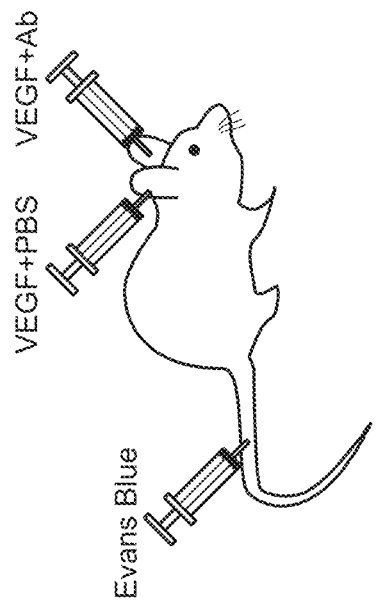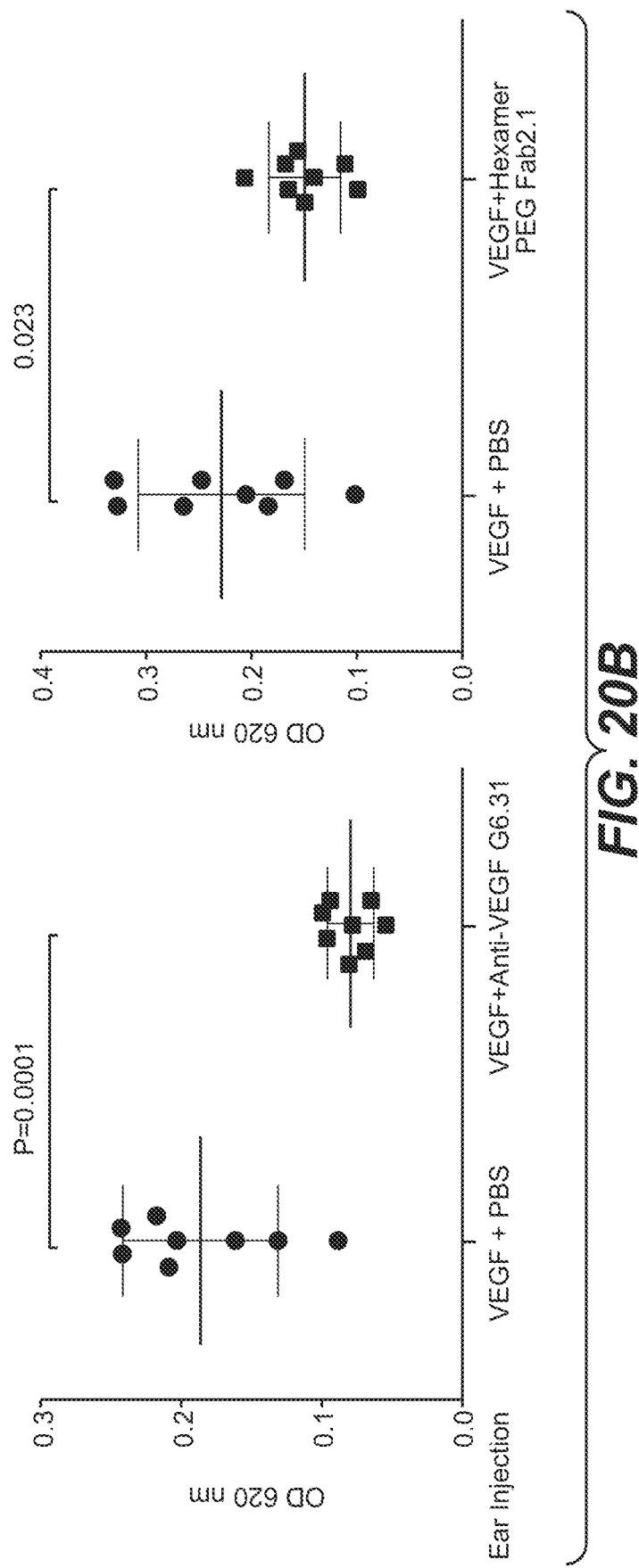
FIG. 20A
FIG. 20B

SEQUENCE LISTING

<160> NUMBER OF SEQ ID NOS: 92

<210> SEQ ID NO 1
<211> LENGTH: 689
<212> TYPE: PRT
<213> ORGANISM: Homo sapiens

<400> SEQUENCE: 1

Met Phe Thr Met Thr Arg Ala Met Glu Glu Ala Leu Phe Gln His Phe
1               5                   10                  15

Met His Gln Lys Leu Gly Ile Ala Tyr Ala Ile His Lys Pro Phe Pro
            20                  25                  30

Phe Phe Glu Gly Leu Leu Asp Asn Ser Ile Ile Thr Lys Arg Met Tyr
        35                  40                  45

Met Glu Ser Leu Glu Ala Cys Arg Asn Leu Ile Pro Val Ser Arg Val
    50                  55                  60

Val His Asn Ile Leu Thr Gln Leu Glu Arg Thr Phe Asn Leu Ser Leu

-continued

```
             65                  70                  75                  80
Leu Val Thr Leu Phe Ser Gln Ile Asn Leu Arg Glu Tyr Pro Asn Leu
                     85                  90                  95
Val Thr Ile Tyr Arg Ser Phe Lys Arg Val Gly Ala Ser Tyr Glu Trp
                    100                 105                 110
Gln Ser Arg Asp Thr Pro Ile Leu Leu Glu Ala Pro Thr Gly Leu Ala
                    115                 120                 125
Glu Gly Ser Ser Leu His Thr Pro Leu Ala Leu Pro Pro Gln Pro
            130                 135                 140
Pro Gln Pro Ser Cys Ser Pro Cys Ala Pro Arg Val Ser Glu Pro Gly
145                 150                 155                 160
Thr Ser Ser Gln Gln Ser Asp Glu Ile Leu Ser Glu Ser Pro Ser Pro
                    165                 170                 175
Ser Asp Pro Val Leu Pro Leu Pro Ala Leu Ile Gln Glu Gly Arg Ser
                    180                 185                 190
Thr Ser Val Thr Asn Asp Lys Leu Thr Ser Lys Met Asn Ala Glu Glu
                    195                 200                 205
Asp Ser Glu Glu Met Pro Ser Leu Leu Thr Ser Thr Val Gln Val Ala
            210                 215                 220
Ser Asp Asn Leu Ile Pro Gln Ile Arg Asp Lys Glu Asp Pro Gln Glu
225                 230                 235                 240
Met Pro His Ser Pro Leu Gly Ser Met Pro Glu Ile Arg Asp Asn Ser
                    245                 250                 255
Pro Glu Pro Asn Asp Pro Glu Glu Pro Gln Glu Val Ser Ser Thr Pro
                    260                 265                 270
Ser Asp Lys Lys Gly Lys Lys Arg Lys Cys Ile Trp Ser Thr Pro
                    275                 280                 285
Lys Arg Arg His Lys Lys Ser Leu Pro Gly Gly Thr Ala Ser Ser
            290                 295                 300
Arg His Gly Ile Gln Lys Lys Leu Lys Arg Val Asp Gln Val Pro Gln
305                 310                 315                 320
Lys Lys Asp Asp Ser Thr Cys Asn Ser Thr Val Glu Thr Arg Ala Gln
                    325                 330                 335
Lys Ala Arg Thr Glu Cys Ala Arg Lys Ser Arg Ser Glu Glu Ile Ile
                    340                 345                 350
Asp Gly Thr Ser Glu Met Asn Glu Gly Lys Arg Ser Gln Lys Thr Pro
            355                 360                 365
Ser Thr Pro Arg Arg Val Thr Gln Gly Ala Ala Ser Pro Gly His Gly
            370                 375                 380
Ile Gln Glu Lys Leu Gln Val Val Asp Lys Val Thr Gln Arg Lys Asp
385                 390                 395                 400
Asp Ser Thr Trp Asn Ser Glu Val Met Met Arg Val Gln Lys Ala Arg
                    405                 410                 415
Thr Lys Cys Ala Arg Lys Ser Arg Leu Lys Glu Lys Lys Glu Lys
                    420                 425                 430
Asp Ile Cys Ser Ser Ser Lys Arg Arg Phe Gln Lys Asn Ile His Arg
            435                 440                 445
Arg Gly Lys Pro Lys Ser Asp Thr Val Asp Phe His Cys Ser Lys Leu
            450                 455                 460
Pro Val Thr Cys Gly Glu Ala Lys Gly Ile Leu Tyr Lys Lys Met
465                 470                 475                 480
Lys His Gly Ser Ser Val Lys Cys Ile Arg Asn Glu Asp Gly Thr Trp
                    485                 490                 495
```

-continued

```
Leu Thr Pro Asn Glu Phe Glu Val Glu Gly Lys Gly Arg Asn Ala Lys
            500                 505                 510

Asn Trp Lys Arg Asn Ile Arg Cys Glu Gly Met Thr Leu Gly Glu Leu
        515                 520                 525

Leu Lys Arg Lys Asn Ser Asp Glu Cys Glu Val Cys Cys Gln Gly Gly
    530                 535                 540

Gln Leu Leu Cys Cys Gly Thr Cys Pro Arg Val Phe His Glu Asp Cys
545                 550                 555                 560

His Ile Pro Pro Val Glu Ala Lys Arg Met Leu Trp Ser Cys Thr Phe
                565                 570                 575

Cys Arg Met Lys Arg Ser Ser Gly Ser Gln Gln Cys His His Val Ser
            580                 585                 590

Lys Thr Leu Glu Arg Gln Met Gln Pro Gln Asp Gln Leu Ile Arg Asp
        595                 600                 605

Tyr Gly Glu Pro Phe Gln Glu Ala Met Trp Leu Asp Leu Val Lys Glu
    610                 615                 620

Arg Leu Ile Thr Glu Met Tyr Thr Val Ala Trp Phe Val Arg Asp Met
625                 630                 635                 640

Arg Leu Met Phe Arg Asn His Lys Thr Phe Tyr Lys Ala Ser Asp Phe
                645                 650                 655

Gly Gln Val Gly Leu Asp Leu Glu Ala Glu Phe Glu Lys Asp Leu Lys
            660                 665                 670

Asp Val Leu Gly Phe His Glu Ala Asn Asp Gly Gly Phe Trp Thr Leu
        675                 680                 685

Pro

<210> SEQ ID NO 2
<211> LENGTH: 1124
<212> TYPE: PRT
<213> ORGANISM: Macaca fascicularis

<400> SEQUENCE: 2

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp His Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175
```

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn Arg Leu Cys
    210                 215                 220

Thr Val Cys Val Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Arg His Thr Phe Gly Arg Thr Cys Lys Glu Arg Cys Ser Gly Gln Asp
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His His
    290                 295                 300

Gly Phe Tyr Gly Pro Asp Cys Lys Leu Arg Cys Ser Cys Ser Asn Gly
305                 310                 315                 320

Glu Thr Cys Asp Arg Phe Gln Gly Cys Leu Cys Ser Pro Gly Arg Gln
                325                 330                 335

Gly Leu Gln Cys Glu Arg Glu Gly Ile Pro Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
    370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Ala Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Arg His Ile Gln
                485                 490                 495

Val Thr Asn Glu Ile Val Thr Leu Asn His Leu Glu Pro Arg Thr Glu
            500                 505                 510

Tyr Glu Leu Cys Val Gln Leu Val Arg Arg Gly Glu Gly Gly Glu Gly
        515                 520                 525

His Pro Gly Pro Val Arg Arg Phe Thr Thr Ala Ser Ile Gly Leu Pro
    530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
            580                 585                 590

Val Pro Gly Asn Leu Thr Ser Val Leu Leu Asn Asn Leu His Pro Arg
            595                 600                 605

Glu Gln Tyr Val Val Arg Ala Arg Val Asn Thr Lys Ala Gln Gly Glu
610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
            645                 650                 655

Ile Ser Trp Thr Ile Leu Asp Gly Tyr Ser Ile Ser Ile Thr Ile
            660                 665                 670

Arg Tyr Lys Val Gln Gly Lys Asn Glu Asp Gln His Ile Asp Val Lys
            675                 680                 685

Ile Lys Asn Ala Thr Ile Thr Gln Tyr Gln Leu Lys Gly Leu Glu Pro
            690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Glu
            725                 730                 735

Ala Pro Ala Asp Leu Gly Gly Gly Lys Met Leu Leu Ile Ala Ile Leu
            740                 745                 750

Gly Ser Ala Gly Met Thr Cys Leu Thr Val Leu Leu Ala Phe Leu Ile
            755                 760                 765

Ile Leu Gln Leu Lys Arg Ala Asn Val Gln Arg Arg Met Ala Gln Ala
            770                 775                 780

Phe Gln Asn Val Arg Glu Glu Pro Ala Val Gln Phe Asn Ser Gly Thr
785                 790                 795                 800

Leu Ala Leu Asn Arg Lys Val Lys Asn Asn Pro Asp Pro Thr Ile Tyr
            805                 810                 815

Pro Val Leu Asp Trp Asn Asp Ile Lys Phe Gln Asp Val Ile Gly Glu
            820                 825                 830

Gly Asn Phe Gly Gln Val Leu Lys Ala Arg Ile Lys Lys Asp Gly Leu
            835                 840                 845

Arg Met Asp Ala Ala Ile Lys Arg Met Lys Glu Tyr Ala Ser Lys Asp
850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
            885                 890                 895

Tyr Leu Tyr Leu Ala Ile Glu Tyr Ala Pro His Gly Asn Leu Leu Asp
            900                 905                 910

Phe Leu Arg Lys Ser Arg Val Leu Glu Thr Asp Pro Ala Phe Ala Ile
            915                 920                 925

Ala Asn Ser Thr Ala Ser Thr Leu Ser Ser Gln Gln Leu Leu His Phe
            930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
            965                 970                 975

Val Ala Lys Ile Ala Asp Phe Gly Leu Ser Arg Gly Gln Glu Val Tyr
            980                 985                 990

Val Lys Lys Thr Met Gly Arg Leu Pro Val Arg Trp Met Ala Ile Glu
            995                 1000                1005

Ser Leu Asn Tyr Ser Val Tyr Thr Thr Asn Ser Asp Val Trp Ser

-continued

```
                1010                1015                1020

Tyr Gly  Val Leu Leu Trp  Glu Ile Val Ser Leu  Gly Gly Thr Pro
    1025                 1030                 1035

Tyr Cys  Gly Met Thr Cys  Ala Glu Leu Tyr Glu  Lys Leu Pro Gln
    1040                 1045                 1050

Gly Tyr  Arg Leu Glu Lys  Pro Leu Asn Cys Asp  Asp Glu Val Phe
    1055                 1060                 1065

Asp Leu  Met Arg Gln Cys  Trp Arg Glu Lys Pro  Tyr Glu Arg Pro
    1070                 1075                 1080

Ser Phe  Ala Gln Ile Leu  Val Ser Leu Asn Arg  Met Leu Glu Glu
    1085                 1090                 1095

Arg Lys  Thr Tyr Val Asn  Thr Thr Leu Tyr Glu  Lys Phe Thr Tyr
    1100                 1105                 1110

Ala Gly  Ile Asp Cys Ser  Ala Glu Glu Ala Ala
    1115                 1120

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3

Asn Thr Asp Ile Ser
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic Construct

<400> SEQUENCE: 4

Arg Ile Ser Pro Ser Asp Gly Asn Thr Tyr Tyr Ala Asp Ser Val Lys
1               5                   10                  15

Gly

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: Xaa is Met, Leu, Lys, Phe, Tyr, Arg, Asn, Gln,
      His, of Trp
<220> FEATURE:
<221> NAME/KEY: misc_feature
<222> LOCATION: (9)..(9)
<223> OTHER INFORMATION: Xaa is Phe, Tyr, Leu, Gln, Ile, Lys, or His

<400> SEQUENCE: 5

Arg Thr Arg Trp Ala Ser Xaa Ala Xaa Asp Tyr
1               5                   10

<210> SEQ ID NO 6
<211> LENGTH: 11
<212> TYPE: PRT
<213> ORGANISM: Artificial Sequence
<220> FEATURE:
```

<223> OTHER INFORMATION: Synthetic Construct

<400> SEQUENCE: 6

Arg Thr Arg Trp Ala Ser Trp Ala Met Asp Tyr
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

Arg Thr Arg Trp Ala Ser Trp Ala Phe Asp Tyr
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Arg Ala Ser Gln Asp Val Ser Thr Ala Val Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Ser Ala Ser Phe Leu Tyr Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Gln Gln Ser Tyr Thr Thr Pro Pro Thr
1               5

<210> SEQ ID NO 11
<211> LENGTH: 30
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 12
<211> LENGTH: 14
<212> TYPE: PRT

```
<213> ORGANISM: Artificial Sequence
<220> FEATURE:
<223> OTHER INFORMATION: Synthetic Construct

<400> SEQUENCE: 12

Trp Val Arg Gln Ala Pro Gly Lys Gly Leu Glu Trp Val Gly
1               5                   10

<210> SEQ ID NO 13
<211> LENGTH: 32
<212> TYPE: PRT
<213> ORGANISM: Artificial Sequence
<220> FEATURE:
<223> OTHER INFORMATION: Synthetic Construct

<400> SEQUENCE: 13

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct

<400> SEQUENCE: 14

Gln Gly Thr Leu Val Thr Val Ser Ser
1               5

<210> SEQ ID NO 15
<211> LENGTH: 23
<212> TYPE: PRT
<213> ORGANISM: Artificial Sequence
<220> FEATURE:
<223> OTHER INFORMATION: Synthetic Construct

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 15
<212> TYPE: PRT
<213> ORGANISM: Artificial Sequence
<220> FEATURE:
<223> OTHER INFORMATION: Synthetic Construct

<400> SEQUENCE: 16

Trp Tyr Gln Gln Lys Pro Gly Lys Ala Pro Lys Leu Leu Ile Tyr
1               5                   10                  15

<210> SEQ ID NO 17
<211> LENGTH: 32
<212> TYPE: PRT
<213> ORGANISM: Artificial Sequence
<220> FEATURE:
<223> OTHER INFORMATION: Synthetic Construct

<400> SEQUENCE: 17

Gly Val Pro Ser Arg Phe Ser Gly Ser Gly Ser Gly Thr Asp Phe Thr
1               5                   10                  15
```

Leu Thr Ile Ser Ser Leu Gln Pro Glu Asp Phe Ala Thr Tyr Tyr Cys
            20                  25                  30

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Phe Gly Gln Gly Thr Lys Val Glu Ile
1               5

<210> SEQ ID NO 19
<211> LENGTH: 120
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Arg Trp Ala Ser Xaa Ala Xaa Asp Tyr Trp Gly Gln
            100                 105                 110

Gly Thr Leu Val Thr Val Ser Ser
        115                 120

<210> SEQ ID NO 20
<211> LENGTH: 120
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val

```
            50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg Thr Arg Trp Ala Ser Trp Ala Phe Asp Tyr Trp Gly Gln
                100                 105                 110

Gly Thr Leu Val Thr Val Ser Ser
            115                 120

<210> SEQ ID NO 21
<211> LENGTH: 107
<212> TYPE: PRT
<213> ORGANISM: Artificial Sequence
<220> FEATURE:
<223> OTHER INFORMATION: Synthetic Construct

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Thr Pro Pro
                 85                  90                  95

Thr Phe Gly Gln Gly Thr Lys Val Glu Ile Lys
                100                 105

<210> SEQ ID NO 22
<211> LENGTH: 120
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Thr
             20                  25                  30

Asp Ile Ser Trp Val Arg Gln Ala Pro Gly Lys Gly Leu Glu Trp Val
         35                  40                  45

Gly Arg Ile Ser Pro Ser Asp Gly Asn Thr Tyr Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg Thr Arg Trp Ala Ser Trp Ala Met Asp Tyr Trp Gly Gln
                100                 105                 110

Gly Thr Leu Val Thr Val Ser Ser
            115                 120
```

<210> SEQ ID NO 23
<211> LENGTH: 224
<212> TYPE: PRT
<213> ORGANISM: Artificial Sequence
<220> FEATURE:
<223> OTHER INFORMATION: Synthetic Construct

<400> SEQUENCE: 23

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Thr Arg Trp Ala Ser Trp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

<210> SEQ ID NO 24
<211> LENGTH: 224
<212> TYPE: PRT
<213> ORGANISM: Artificial Sequence
<220> FEATURE:
<223> OTHER INFORMATION: Synthetic Construct

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ala Arg Arg Thr Arg Trp Ala Ser Trp Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Cys Lys Val Asp Lys Lys Val Glu Pro Lys Ser Cys Asp
            210                 215                 220
```

<210> SEQ ID NO 25
<211> LENGTH: 214
<212> TYPE: PRT
<213> ORGANISM: Artificial Sequence
<220> FEATURE:
<223> OTHER INFORMATION: Synthetic Construct

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 26

<211> LENGTH: 104
<212> TYPE: PRT
<213> ORGANISM: Artificial Sequence
<220> FEATURE:
<223> OTHER INFORMATION: Synthetic Construct

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Cys Lys Val Asp Lys
                85                  90                  95

Lys Val Glu Pro Lys Ser Cys Asp
            100

<210> SEQ ID NO 27
<211> LENGTH: 107
<212> TYPE: PRT
<213> ORGANISM: Artificial Sequence
<220> FEATURE:
<223> OTHER INFORMATION: Synthetic Construct

<400> SEQUENCE: 27

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 28
<211> LENGTH: 5
<212> TYPE: PRT
<213> ORGANISM: Artificial Sequence
<220> FEATURE:
<223> OTHER INFORMATION: Synthetic Construct

<400> SEQUENCE: 28

Ser Tyr Trp Ile His
1               5

<210> SEQ ID NO 29
<211> LENGTH: 17
<212> TYPE: PRT
<213> ORGANISM: Artificial Sequence
<220> FEATURE:

```
<223> OTHER INFORMATION: Synthetic Construct

<400> SEQUENCE: 29

Ala Ile Ser Pro Asn Asp Gly Ser Thr Tyr Tyr Ala Asp Ser Val Lys
1               5                   10                  15

Gly

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

Ser Arg Tyr Tyr Gly Gln Arg Leu Val Tyr Tyr Val Met Asp Tyr
1               5                   10                  15

<210> SEQ ID NO 31
<211> LENGTH: 124
<212> TYPE: PRT
<213> ORGANISM: Artificial Sequence
<220> FEATURE:
<223> OTHER INFORMATION: Synthetic Construct

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Ile His Trp Val Arg Gln Ala Pro Gly Lys Gly Leu Glu Trp Val
            35                  40                  45

Ala Ala Ile Ser Pro Asn Asp Gly Ser Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Arg Tyr Tyr Gly Gln Arg Leu Val Tyr Tyr Val Met Asp
                100                 105                 110

Tyr Trp Gly Gln Gly Thr Leu Val Thr Val Ser Ser
            115                 120

<210> SEQ ID NO 32
<211> LENGTH: 228
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Ile His Trp Val Arg Gln Ala Pro Gly Lys Gly Leu Glu Trp Val
            35                  40                  45

Ala Ala Ile Ser Pro Asn Asp Gly Ser Thr Tyr Tyr Ala Asp Ser Val
        50                  55                  60

Lys Gly Arg Phe Thr Ile Ser Ala Asp Thr Ser Lys Asn Thr Ala Tyr
```

```
            65                  70                  75                  80
Leu Gln Met Asn Ser Leu Arg Ala Glu Asp Thr Ala Val Tyr Tyr Cys
                85                  90                  95

Ala Arg Ser Arg Tyr Tyr Gly Gln Arg Leu Val Tyr Val Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Lys Val Glu Pro
    210                 215                 220

Lys Ser Cys Asp
225

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct

<400> SEQUENCE: 33

Ser Ser Gly Ile Ser
1               5

<210> SEQ ID NO 34
<211> LENGTH: 17
<212> TYPE: PRT
<213> ORGANISM: Artificial Sequence
<220> FEATURE:
<223> OTHER INFORMATION: Synthetic Construct

<400> SEQUENCE: 34

Thr Ile Asn Pro Tyr Gly Gly Asp Thr Tyr Tyr Ala Asp Ser Val Lys
1               5                   10                  15

Gly

<210> SEQ ID NO 35
<211> LENGTH: 11
<212> TYPE: PRT
<213> ORGANISM: Artificial Sequence
<220> FEATURE:
<223> OTHER INFORMATION: Synthetic Construct

<400> SEQUENCE: 35

Phe Tyr Arg Phe Leu Ser Ser Gly Met Asp Tyr
1               5                   10

<210> SEQ ID NO 36
<211> LENGTH: 120
<212> TYPE: PRT
<213> ORGANISM: Artificial Sequence
<220> FEATURE:
```

<223> OTHER INFORMATION: Synthetic Construct

<400> SEQUENCE: 36

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Ser
            20                  25                  30

Gly Ile Ser Trp Val Arg Gln Ala Pro Gly Lys Gly Leu Glu Trp Val
        35                  40                  45

Ala Thr Ile Asn Pro Tyr Gly Gly Asp Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Tyr Arg Phe Leu Ser Ser Gly Met Asp Tyr Trp Gly Gln
            100                 105                 110

Gly Thr Leu Val Thr Val Ser Ser
        115                 120
```

<210> SEQ ID NO 37
<211> LENGTH: 224
<212> TYPE: PRT
<213> ORGANISM: Artificial Sequence
<220> FEATURE:
<223> OTHER INFORMATION: Synthetic Construct

<400> SEQUENCE: 37

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Ser
            20                  25                  30

Gly Ile Ser Trp Val Arg Gln Ala Pro Gly Lys Gly Leu Glu Trp Val
        35                  40                  45

Ala Thr Ile Asn Pro Tyr Gly Gly Asp Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Tyr Arg Phe Leu Ser Ser Gly Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220
```

<210> SEQ ID NO 38
<211> LENGTH: 5
<212> TYPE: PRT
<213> ORGANISM: Artificial Sequence
<220> FEATURE:
<223> OTHER INFORMATION: Synthetic Construct

<400> SEQUENCE: 38

Gly Ser Trp Ile Ser
1               5

<210> SEQ ID NO 39
<211> LENGTH: 17
<212> TYPE: PRT
<213> ORGANISM: Artificial Sequence
<220> FEATURE:
<223> OTHER INFORMATION: Synthetic Construct

<400> SEQUENCE: 39

Arg Ile Asn Pro Tyr Asp Gly Asn Thr Tyr Tyr Ala Asp Ser Val Lys
1               5                   10                  15

Gly

<210> SEQ ID NO 40
<211> LENGTH: 10
<212> TYPE: PRT
<213> ORGANISM: Artificial Sequence
<220> FEATURE:
<223> OTHER INFORMATION: Synthetic Construct

<400> SEQUENCE: 40

Asn Asn Arg Phe Pro Thr Trp Phe Asp Tyr
1               5                   10

<210> SEQ ID NO 41
<211> LENGTH: 119
<212> TYPE: PRT
<213> ORGANISM: Artificial Sequence
<220> FEATURE:
<223> OTHER INFORMATION: Synthetic Construct

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Trp Ile Ser Trp Val Arg Gln Ala Pro Gly Lys Gly Leu Glu Trp Val
        35                  40                  45

Ala Arg Ile Asn Pro Tyr Asp Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Asn Arg Phe Pro Thr Trp Phe Asp Tyr Trp Gly Gln Gly
            100                 105                 110

Thr Leu Val Thr Val Ser Ser
        115

<210> SEQ ID NO 42
<211> LENGTH: 223

<212> TYPE: PRT
<213> ORGANISM: Artificial Sequence
<220> FEATURE:
<223> OTHER INFORMATION: Synthetic Construct

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Trp Ile Ser Trp Val Arg Gln Ala Pro Gly Lys Gly Leu Glu Trp Val
        35                  40                  45

Ala Arg Ile Asn Pro Tyr Asp Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Asn Arg Phe Pro Thr Trp Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp
    210                 215                 220
```

<210> SEQ ID NO 43
<211> LENGTH: 5
<212> TYPE: PRT
<213> ORGANISM: Artificial Sequence
<220> FEATURE:
<223> OTHER INFORMATION: Synthetic Construct

<400> SEQUENCE: 43

```
Asp Thr Tyr Ile His
1               5
```

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct

<400> SEQUENCE: 44

```
Val Ile Tyr Pro Asp Asn Gly Ala Thr Tyr Tyr Ala Asp Ser Val Lys
1               5                   10                  15

Gly
```

<210> SEQ ID NO 45

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Glu Phe Ala Cys Ala Arg Cys Val Tyr Gly
1               5                   10

<210> SEQ ID NO 46
<211> LENGTH: 235
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Thr
            20                  25                  30

Tyr Ile His Trp Val Arg Gln Ala Pro Gly Lys Gly Leu Glu Trp Val
        35                  40                  45

Ala Val Ile Tyr Pro Asp Asn Gly Ala Thr Tyr Tyr Ala Asp Ser Val
    50                  55                  60

Lys Gly Thr Tyr Tyr Ala Asp Ser Val Lys Gly Arg Phe Thr Ile Ser
65                  70                  75                  80

Ala Asp Thr Ser Lys Asn Thr Ala Tyr Leu Gln Met Asn Ser Leu Arg
                85                  90                  95

Ala Glu Asp Thr Ala Val Tyr Tyr Cys Ala Arg Glu Phe Ala Cys Ala
            100                 105                 110

Arg Cys Val Tyr Gly Met Asp Tyr Trp Gly Gln Gly Thr Leu Val Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Asp
225                 230                 235

<210> SEQ ID NO 47
<211> LENGTH: 131
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Thr
            20                  25                  30

Tyr Ile His Trp Val Arg Gln Ala Pro Gly Lys Gly Leu Glu Trp Val
        35                  40                  45

Ala Val Ile Tyr Pro Asp Asn Gly Ala Thr Tyr Tyr Ala Asp Ser Val
    50                  55                  60

Lys Gly Thr Tyr Tyr Ala Asp Ser Val Lys Gly Arg Phe Thr Ile Ser
65                  70                  75                  80

Ala Asp Thr Ser Lys Asn Thr Ala Tyr Leu Gln Met Asn Ser Leu Arg
                85                  90                  95

Ala Glu Asp Thr Ala Val Tyr Tyr Cys Ala Arg Glu Phe Ala Cys Ala
            100                 105                 110

Arg Cys Val Tyr Gly Met Asp Tyr Trp Gly Gln Gly Thr Leu Val Thr
        115                 120                 125

Val Ser Ser
    130

<210> SEQ ID NO 48
<211> LENGTH: 5
<212> TYPE: PRT
<213> ORGANISM: Artificial Sequence
<220> FEATURE:
<223> OTHER INFORMATION: Synthetic Construct

<400> SEQUENCE: 48

Asn Ser Ala Ile His
1               5

<210> SEQ ID NO 49
<211> LENGTH: 17
<212> TYPE: PRT
<213> ORGANISM: Artificial Sequence
<220> FEATURE:
<223> OTHER INFORMATION: Synthetic Construct

<400> SEQUENCE: 49

Ser Ile Thr Pro Tyr Asn Gly Tyr Thr Tyr Tyr Ala Asp Ser Val Lys
1               5                   10                  15

Gly

<210> SEQ ID NO 50
<211> LENGTH: 10
<212> TYPE: PRT
<213> ORGANISM: Artificial Sequence
<220> FEATURE:
<223> OTHER INFORMATION: Synthetic Construct

<400> SEQUENCE: 50

Arg Gln Ser Tyr Ser Tyr Val Met Asp Tyr
1               5                   10

<210> SEQ ID NO 51
<211> LENGTH: 119
<212> TYPE: PRT
<213> ORGANISM: Artificial Sequence
<220> FEATURE:
<223> OTHER INFORMATION: Synthetic Construct

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
```

```
                    20                  25                  30
Ala Ile His Trp Val Arg Gln Ala Pro Gly Lys Gly Leu Glu Trp Val
            35                  40                  45

Ala Ser Ile Thr Pro Tyr Asn Gly Tyr Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Gln Ser Tyr Ser Tyr Val Met Asp Tyr Trp Gly Gln Gly
            100                 105                 110

Thr Leu Val Thr Val Ser Ser
            115

<210> SEQ ID NO 52
<211> LENGTH: 223
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Ala Ile His Trp Val Arg Gln Ala Pro Gly Lys Gly Leu Glu Trp Val
            35                  40                  45

Ala Ser Ile Thr Pro Tyr Asn Gly Tyr Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Gln Ser Tyr Ser Tyr Val Met Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp
    210                 215                 220

<210> SEQ ID NO 53
<211> LENGTH: 214
<212> TYPE: PRT
<213> ORGANISM: Artificial Sequence
<220> FEATURE:
<223> OTHER INFORMATION: Synthetic Construct
```

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 54
<211> LENGTH: 684
<212> TYPE: PRT
<213> ORGANISM: Artificial Sequence
<220> FEATURE:
<223> OTHER INFORMATION: Synthetic Construct

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Thr Arg Trp Ala Ser Trp Ala Met Asp Tyr Trp Gly Gln
            100                 105                 110

Gly Thr Leu Val Thr Val Ser Ser Ala Ser Thr Lys Gly Pro Ser Val
        115                 120                 125

```
Phe Pro Leu Ala Pro Ser Ser Lys Ser Thr Ser Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Gly Gly Gly Ser Gly Gly Glu Val Gln Leu Val
225                 230                 235                 240

Glu Ser Gly Gly Gly Leu Val Gln Pro Gly Gly Ser Leu Arg Leu Ser
                245                 250                 255

Cys Ala Ala Ser Gly Phe Thr Phe Ser Asn Ser Ala Ile His Trp Val
            260                 265                 270

Arg Gln Ala Pro Gly Lys Gly Leu Glu Trp Val Ala Ser Ile Thr Pro
        275                 280                 285

Tyr Asn Gly Tyr Thr Tyr Tyr Ala Asp Ser Val Lys Gly Arg Phe Thr
    290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ala Arg Arg Gln Ser
                325                 330                 335

Tyr Ser Tyr Val Met Asp Tyr Trp Gly Gln Gly Thr Leu Val Thr Val
            340                 345                 350

Ser Ser Ala Ser Thr Lys Gly Pro Ser Val Phe Pro Leu Ala Pro Ser
        355                 360                 365

Ser Lys Ser Thr Ser Gly Gly Thr Ala Ala Leu Gly Cys Leu Val Lys
    370                 375                 380

Asp Tyr Phe Pro Glu Pro Val Thr Val Ser Trp Asn Ser Gly Ala Leu
385                 390                 395                 400

Thr Ser Gly Val His Thr Phe Pro Ala Val Leu Gln Ser Ser Gly Leu
                405                 410                 415

Tyr Ser Leu Ser Ser Val Val Thr Val Pro Ser Ser Ser Leu Gly Thr
            420                 425                 430

Gln Thr Tyr Ile Cys Asn Val Asn His Lys Pro Ser Asn Thr Lys Val
        435                 440                 445

Asp Lys Lys Val Glu Pro Lys Ser Cys Asp Lys Thr His Thr Cys Pro
450                 455                 460

Pro Cys Pro Ala Pro Glu Ala Ala Gly Gly Pro Ser Val Phe Leu Phe
465                 470                 475                 480

Pro Pro Lys Pro Lys Asp Thr Leu Met Ala Ser Arg Thr Pro Glu Val
                485                 490                 495

Thr Cys Val Val Val Asp Val Ser His Glu Asp Pro Glu Val Lys Phe
            500                 505                 510

Asn Trp Tyr Val Asp Gly Val Glu Val His Asn Ala Lys Thr Lys Pro
        515                 520                 525

Arg Glu Glu Gln Tyr Asn Ser Thr Tyr Arg Val Val Ser Val Leu Thr
530                 535                 540

Val Leu Ala Gln Asp Trp Leu Asn Gly Lys Glu Tyr Lys Cys Lys Val
```

```
            545                 550                 555                 560
        Ser Asn Lys Ala Leu Gly Ala Pro Ile Glu Lys Thr Ile Ser Lys Ala
                        565                 570                 575

Lys Gly Gln Pro Arg Glu Pro Gln Val Tyr Thr Leu Pro Pro Ser Arg
                        580                 585                 590

Glu Glu Met Thr Lys Asn Gln Val Ser Leu Thr Cys Leu Val Lys Gly
                        595                 600                 605

Phe Tyr Pro Ser Asp Ile Ala Val Glu Trp Glu Ser Asn Gly Gln Pro
                        610                 615                 620

Glu Asn Asn Tyr Lys Thr Thr Pro Pro Val Leu Asp Ser Asp Gly Ser
        625                 630                 635                 640

Phe Phe Leu Tyr Ser Lys Leu Thr Val Asp Lys Ser Arg Trp Gln Gln
                        645                 650                 655

Gly Asn Val Phe Ser Cys Ser Val Met His Glu Ala Leu His Asn Ala
                        660                 665                 670

Tyr Thr Gln Lys Ser Leu Ser Leu Ser Pro Gly Lys
                        675                 680

<210> SEQ ID NO 55
<211> LENGTH: 224
<212> TYPE: PRT
<213> ORGANISM: Artificial Sequence
<220> FEATURE:
<223> OTHER INFORMATION: Synthetic Construct

<400> SEQUENCE: 55

Glu Val Gln Leu Val Glu Ser Gly Gly Gly Leu Val Gln Pro Gly Gly
        1               5                   10                  15

Ser Leu Arg Leu Ser Cys Ala Ala Ser Gly Phe Thr Phe Ser Asn Thr
                        20                  25                  30

Asp Ile Ser Trp Val Arg Gln Ala Pro Gly Lys Gly Leu Glu Trp Val
                        35                  40                  45

Gly Arg Ile Ser Pro Ser Asp Gly Asn Thr Tyr Tyr Ala Asp Ser Val
                50                  55                  60

Lys Gly Arg Phe Thr Ile Ser Ala Asp Thr Ser Lys Asn Thr Ala Tyr
        65                  70                  75                  80

Leu Gln Met Asn Ser Leu Arg Ala Glu Asp Thr Ala Val Tyr Tyr Cys
                        85                  90                  95

Ala Arg Arg Thr Arg Trp Ala Ser Trp Ala Phe Asp Tyr Trp Gly Gln
                        100                 105                 110

Gly Thr Leu Val Thr Val Ser Ser Ala Ser Thr Lys Gly Pro Ser Val
                        115                 120                 125

Phe Pro Leu Ala Pro Ser Ser Lys Ser Thr Ser Gly Gly Thr Ala Ala
                        130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                        180                 185                 190

Ser Ser Ser Leu Gly Thr Gln Thr Tyr Ile Cys Asn Val Asn His Lys
                        195                 200                 205

Pro Ser Asn Cys Lys Val Asp Lys Lys Val Glu Pro Lys Ser Cys Asp
                        210                 215                 220
```

-continued

```
<210> SEQ ID NO 56
<211> LENGTH: 214
<212> TYPE: PRT
<213> ORGANISM: Artificial Sequence
<220> FEATURE:
<223> OTHER INFORMATION: Synthetic Construct

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Cys Lys Ser
        195                 200                 205

Phe Asn Arg Gly Glu Cys
    210

<210> SEQ ID NO 57
<211> LENGTH: 232
<212> TYPE: PRT
<213> ORGANISM: Artificial Sequence
<220> FEATURE:
<223> OTHER INFORMATION: Synthetic Construct

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ala Arg Arg Thr Arg Trp Ala Ser Trp Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Ser Pro Pro Cys
225                 230

<210> SEQ ID NO 58
<211> LENGTH: 224
<212> TYPE: PRT
<213> ORGANISM: Artificial Sequence
<220> FEATURE:
<223> OTHER INFORMATION: Synthetic Construct

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Thr Arg Trp Ala Ser Trp Ala Phe Asp Tyr Trp Gly Gln
            100                 105                 110

Gly Thr Leu Val Thr Val Ser Ser Ala Ser Cys Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

```
<210> SEQ ID NO 59
<211> LENGTH: 224
<212> TYPE: PRT
<213> ORGANISM: Artificial Sequence
<220> FEATURE:
<223> OTHER INFORMATION: Synthetic Construct

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Arg Trp Ala Ser Trp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Cys Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

<210> SEQ ID NO 60
<211> LENGTH: 224
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ala Arg Arg Thr Arg Trp Ala Ser Trp Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Cys Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

<210> SEQ ID NO 61
<211> LENGTH: 224
<212> TYPE: PRT
<213> ORGANISM: Artificial Sequence
<220> FEATURE:
<223> OTHER INFORMATION: Synthetic Construct

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
            35                  40                  45

Gly Arg Ile Ser Pro Ser Asp Gly Asn Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Arg Thr Arg Trp Ala Ser Trp Ala Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Cys Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

<210> SEQ ID NO 62

<211> LENGTH: 214
<212> TYPE: PRT
<213> ORGANISM: Artificial Sequence
<220> FEATURE:
<223> OTHER INFORMATION: Synthetic Construct

<400> SEQUENCE: 62

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Cys Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 63
<211> LENGTH: 214
<212> TYPE: PRT
<213> ORGANISM: Artificial Sequence
<220> FEATURE:
<223> OTHER INFORMATION: Synthetic Construct

<400> SEQUENCE: 63

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
```

```
                 100                 105                 110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Cys Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 64
<211> LENGTH: 214
<212> TYPE: PRT
<213> ORGANISM: Artificial Sequence
<220> FEATURE:
<223> OTHER INFORMATION: Synthetic Construct

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Cys Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 214
<212> TYPE: PRT
```

<213> ORGANISM: Artificial Sequence
<220> FEATURE:
<223> OTHER INFORMATION: Synthetic Construct

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Cys Ser Ser Pro Val Thr Lys Ser
        195                 200                 205

Phe Asn Arg Gly Glu Cys
    210

<210> SEQ ID NO 66
<211> LENGTH: 214
<212> TYPE: PRT
<213> ORGANISM: Artificial Sequence
<220> FEATURE:
<223> OTHER INFORMATION: Synthetic Construct

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Cys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 67
<211> LENGTH: 214
<212> TYPE: PRT
<213> ORGANISM: Artificial Sequence
<220> FEATURE:
<223> OTHER INFORMATION: Synthetic Construct

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Cys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 68
<211> LENGTH: 214
<212> TYPE: PRT
<213> ORGANISM: Artificial Sequence
<220> FEATURE:

<223> OTHER INFORMATION: Synthetic Construct

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Cys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 69
<211> LENGTH: 138
<212> TYPE: PRT
<213> ORGANISM: Artificial Sequence
<220> FEATURE:
<223> OTHER INFORMATION: Synthetic Construct

<400> SEQUENCE: 69

Glu Arg Thr Phe Val Met Ile Lys Pro Asp Gly Val Gln Arg Gly Leu
1               5                   10                  15

Ile Gly Glu Ile Ile Ser Arg Phe Glu Arg Lys Gly Leu Lys Ile Val
            20                  25                  30

Ala Met Lys Met Met Arg Ile Ser Arg Glu Met Ala Lys His Lys Tyr
        35                  40                  45

Ala Glu His Arg Glu Lys Pro Phe Phe Ser Ala Leu Val Asp Tyr Ile
    50                  55                  60

Thr Ser Gly Pro Val Val Ala Met Val Leu Glu Gly Lys Asn Ala Val
65                  70                  75                  80

Glu Val Val Arg Lys Met Val Gly Ala Thr Asn Pro Lys Glu Ala Ala
                85                  90                  95

Pro Gly Thr Ile Arg Gly Asp Phe Gly Leu Asp Val Gly Lys Asn Val
            100                 105                 110

Ile Phe Ala Ser Asp Ser Pro Glu Ser Ala Glu Arg Glu Ile Ser Leu
        115                 120                 125

Phe Phe Lys Asp Glu Glu Leu Val Glu Trp
    130                 135

<210> SEQ ID NO 70
<211> LENGTH: 138
<212> TYPE: PRT
<213> ORGANISM: Artificial Sequence
<220> FEATURE:
<223> OTHER INFORMATION: Synthetic Construct

<400> SEQUENCE: 70

Glu Arg Thr Phe Val Met Ile Lys Pro Asp Gly Val Gln Arg Gly Leu
1               5                   10                  15

Ile Gly Glu Ile Ile Ser Arg Phe Glu Arg Lys Gly Phe Lys Ile Val
            20                  25                  30

Ala Met Lys Leu Met Arg Ile Ser Gln Glu Leu Ala Glu Lys His Tyr
        35                  40                  45

Ala Glu His Arg Glu Lys Pro Phe Phe Ser Gly Leu Val Asp Phe Ile
    50                  55                  60

Thr Ser Gly Pro Val Val Ala Met Val Leu Glu Gly Lys Asn Val Val
65                  70                  75                  80

Glu Val Val Arg Lys Met Ile Gly Ala Thr Asn Pro Lys Glu Ala Ala
                85                  90                  95

Pro Gly Thr Ile Arg Gly Asp Phe Gly Met Ser Val Gly Lys Asn Val
            100                 105                 110

Ile Phe Gly Ser Asp Ser Leu Glu Ser Ala Glu Arg Glu Ile Ser Leu
        115                 120                 125

Phe Phe Lys Asp Glu Glu Leu Val Glu Trp
    130                 135

<210> SEQ ID NO 71
<211> LENGTH: 154
<212> TYPE: PRT
<213> ORGANISM: Artificial Sequence
<220> FEATURE:
<223> OTHER INFORMATION: Synthetic Construct

<400> SEQUENCE: 71

Ser Thr Asn Lys Val Asn Lys Glu Arg Thr Phe Leu Ala Val Lys Pro
1               5                   10                  15

Asp Gly Val Ala Arg Gly Leu Val Gly Glu Ile Ile Ala Arg Tyr Glu
            20                  25                  30

Lys Lys Gly Phe Val Leu Val Gly Leu Lys Gln Leu Val Pro Thr Lys
        35                  40                  45

Asp Leu Ala Glu Ser His Tyr Ala Glu His Lys Glu Arg Pro Phe Phe
    50                  55                  60

Gly Gly Leu Val Ser Phe Ile Thr Ser Gly Pro Val Val Ala Met Val
65                  70                  75                  80

Phe Glu Gly Lys Gly Val Val Ala Ser Ala Arg Leu Met Ile Gly Val
                85                  90                  95

Thr Asn Pro Leu Ala Ser Ala Pro Gly Ser Ile Arg Gly Asp Phe Gly
            100                 105                 110

Val Asp Val Gly Arg Asn Ile Ile Phe Gly Ser Asp Ser Val Glu Ser
        115                 120                 125

Ala Asn Arg Glu Ile Ala Leu Trp Phe Lys Pro Glu Glu Leu Leu Thr
    130                 135                 140

Glu Val Lys Pro Asn Pro Asn Leu Tyr Glu 145             150

<210> SEQ ID NO 72
<211> LENGTH: 151
<212> TYPE: PRT
<213> ORGANISM: Artificial Sequence
<220> FEATURE:
<223> OTHER INFORMATION: Synthetic Construct

<400> SEQUENCE: 72

Ala Asn Ser Glu Arg Thr Phe Ile Ala Ile Lys Pro Asp Gly Val Gln
1               5                   10                  15

Arg Gly Leu Val Gly Glu Ile Ile Lys Arg Phe Glu Gln Lys Gly Phe
            20                  25                  30

Arg Leu Val Gly Leu Lys Phe Leu Gln Ala Ser Glu Asp Leu Leu Lys
        35                  40                  45

Glu His Tyr Thr Asp Leu Lys Asp Arg Pro Phe Phe Thr Gly Leu Val
    50                  55                  60

Lys Tyr Met His Ser Gly Pro Val Val Ala Met Val Trp Glu Gly Leu
65                  70                  75                  80

Asn Val Val Lys Thr Gly Arg Val Met Leu Gly Glu Thr Asn Pro Ala
                85                  90                  95

Asp Ser Lys Pro Gly Thr Ile Arg Gly Asp Phe Cys Ile Gln Val Gly
            100                 105                 110

Arg Asn Ile Ile Phe Gly Ser Asp Ser Val Lys Ser Ala Glu Lys Glu
        115                 120                 125

Ile Ser Leu Trp Phe Gln Pro Glu Glu Leu Val Glu Tyr Lys Ser Cys
    130                 135                 140

Ala Gln Asn Trp Ile Tyr Glu
145             150

<210> SEQ ID NO 73
<211> LENGTH: 151
<212> TYPE: PRT
<213> ORGANISM: Artificial Sequence
<220> FEATURE:
<223> OTHER INFORMATION: Synthetic Construct

<400> SEQUENCE: 73

Ala Asn Leu Glu Arg Thr Phe Ile Ala Ile Lys Pro Asp Gly Val Gln
1               5                   10                  15

Arg Gly Leu Val Gly Glu Ile Ile Lys Arg Phe Glu Gln Lys Gly Phe
            20                  25                  30

Arg Leu Val Ala Met Lys Phe Leu Arg Ala Ser Glu Glu His Leu Lys
        35                  40                  45

Gln His Tyr Ile Asp Leu Lys Asp Arg Pro Phe Phe Pro Gly Leu Val
    50                  55                  60

Lys Tyr Met Asn Ser Gly Pro Val Val Ala Met Val Trp Glu Gly Leu
65                  70                  75                  80

Asn Val Val Lys Thr Gly Arg Val Met Leu Gly Glu Thr Asn Pro Ala
                85                  90                  95

Asp Ser Lys Pro Gly Thr Ile Arg Gly Asp Phe Cys Ile Gln Val Gly
            100                 105                 110

Arg Asn Ile Ile Phe Gly Ser Asp Ser Val Glu Ser Ala Glu Lys Glu
        115                 120                 125

Ile His Leu Trp Phe Lys Pro Glu Glu Leu Ile Asp Tyr Lys Ser Cys
    130                 135                 140

Ala His Asp Trp Val Tyr Glu
145                 150

<210> SEQ ID NO 74
<211> LENGTH: 386
<212> TYPE: PRT
<213> ORGANISM: Artificial Sequence
<220> FEATURE:
<223> OTHER INFORMATION: Synthetic Construct

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Thr Arg Trp Ala Ser Trp Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Ser Thr Asn Lys Val Asn Lys Glu
225                 230                 235                 240

Arg Thr Phe Leu Ala Val Lys Pro Asp Gly Val Ala Arg Gly Leu Val
                245                 250                 255

Gly Glu Ile Ile Ala Arg Tyr Glu Lys Lys Gly Phe Val Leu Val Gly
            260                 265                 270

Leu Lys Gln Leu Val Pro Thr Lys Asp Leu Ala Glu Ser His Tyr Ala
        275                 280                 285

Glu His Lys Glu Arg Pro Phe Phe Gly Gly Leu Val Ser Phe Ile Thr
    290                 295                 300

Ser Gly Pro Val Val Ala Met Val Phe Glu Gly Lys Gly Val Val Ala
305                 310                 315                 320

Ser Ala Arg Leu Met Ile Gly Val Thr Asn Pro Leu Ala Ser Ala Pro
                325                 330                 335

Gly Ser Ile Arg Gly Asp Phe Gly Val Asp Val Gly Arg Asn Ile Ile
            340                 345                 350

```
                                         -continued

Phe Gly Ser Asp Ser Val Glu Ser Ala Asn Arg Glu Ile Ala Leu Trp
        355                 360                 365

Phe Lys Pro Glu Glu Leu Leu Thr Glu Val Lys Pro Asn Pro Asn Leu
    370                 375                 380

Tyr Glu
385

<210> SEQ ID NO 75
<211> LENGTH: 6
<212> TYPE: PRT
<213> ORGANISM: Artificial Sequence
<220> FEATURE:
<223> OTHER INFORMATION: Synthetic Construct

<400> SEQUENCE: 75

Cys Asp Lys Thr His Thr
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic Construct

<400> SEQUENCE: 76

Cys Asp Lys Thr His Leu
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic Construct

<400> SEQUENCE: 77

Cys Asp Lys Thr His
1               5

<210> SEQ ID NO 78
<211> LENGTH: 4
<212> TYPE: PRT
<213> ORGANISM: Artificial Sequence
<220> FEATURE:
<223> OTHER INFORMATION: Synthetic Construct

<400> SEQUENCE: 78

Cys Asp Lys Thr
1

<210> SEQ ID NO 79
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: Xaa can be any amino acid other than Thr

<400> SEQUENCE: 79

Cys Asp Lys Thr His Xaa
1               5
```

```
<210> SEQ ID NO 80
<211> LENGTH: 7
<212> TYPE: PRT
<213> ORGANISM: Artificial Sequence
<220> FEATURE:
<223> OTHER INFORMATION: Synthetic Construct

<400> SEQUENCE: 80

Cys Asp Lys Thr His Thr Cys
1               5

<210> SEQ ID NO 81
<211> LENGTH: 10
<212> TYPE: PRT
<213> ORGANISM: Artificial Sequence
<220> FEATURE:
<223> OTHER INFORMATION: Synthetic Construct

<400> SEQUENCE: 81

Cys Asp Lys Thr His Thr Cys Pro Pro Cys
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic Construct

<400> SEQUENCE: 82

Cys Asp Lys Thr His Thr Cys Pro Pro Ser
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic Construct

<400> SEQUENCE: 83

Cys Asp Lys Thr His Thr Ser Pro Pro Cys
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic Construct

<400> SEQUENCE: 84

Cys Asp Lys Thr His Thr Ala Pro Pro Cys
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic Construct

<400> SEQUENCE: 85

Cys Asp Lys Thr His Thr Ser Gly Gly Cys
1               5                   10

<210> SEQ ID NO 86
```

```
<211> LENGTH: 6
<212> TYPE: PRT
<213> ORGANISM: Artificial Sequence
<220> FEATURE:
<223> OTHER INFORMATION: Synthetic Construct

<400> SEQUENCE: 86

Cys Tyr Gly Pro Pro Cys
1               5

<210> SEQ ID NO 87
<211> LENGTH: 4
<212> TYPE: PRT
<213> ORGANISM: Artificial Sequence
<220> FEATURE:
<223> OTHER INFORMATION: Synthetic Construct

<400> SEQUENCE: 87

Cys Pro Pro Cys
1

<210> SEQ ID NO 88
<211> LENGTH: 4
<212> TYPE: PRT
<213> ORGANISM: Artificial Sequence
<220> FEATURE:
<223> OTHER INFORMATION: Synthetic Construct

<400> SEQUENCE: 88

Ser Pro Pro Ser
1

<210> SEQ ID NO 89
<211> LENGTH: 232
<212> TYPE: PRT
<213> ORGANISM: Artificial Sequence
<220> FEATURE:
<223> OTHER INFORMATION: Synthetic Construct

<400> SEQUENCE: 89
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Thr Arg Trp Ala Ser Trp Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Ser Pro Pro Cys
225                 230

<210> SEQ ID NO 90
<211> LENGTH: 224
<212> TYPE: PRT
<213> ORGANISM: Artificial Sequence
<220> FEATURE:
<223> OTHER INFORMATION: Synthetic Construct

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Thr Arg Trp Ala Ser Trp Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

<210> SEQ ID NO 91
<211> LENGTH: 224
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (105)..(105)
<223> OTHER INFORMATION: Xaa is Met, Leu, Lys, Phe, Tyr, Arg, Asn, Gln,
      His, of Trp
<220> FEATURE:
<221> NAME/KEY: misc_feature
<222> LOCATION: (107)..(107)
<223> OTHER INFORMATION: Xaa is Phe, Tyr, Leu, Gln, Ile, Lys, or His

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Thr Arg Trp Ala Ser Xaa Ala Xaa Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

<210> SEQ ID NO 92
<211> LENGTH: 224
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (105)..(105)
<223> OTHER INFORMATION: Xaa is Met, Leu, Lys, Phe, Tyr, Arg, Asn, Gln,
      His, of Trp
<220> FEATURE:
<221> NAME/KEY: misc_feature
<222> LOCATION: (107)..(107)
<223> OTHER INFORMATION: Xaa is Phe, Tyr, Leu, Gln, Ile, Lys, or His

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Asp Ile Ser Trp Val Arg Gln Ala Pro Gly Lys Gly Leu Glu Trp Val
        35                  40                  45

Gly Arg Ile Ser Pro Ser Asp Gly Asn Thr Tyr Tyr Ala Asp Ser Val
50                  55                  60

Lys Gly Arg Phe Thr Ile Ser Ala Asp Thr Ser Lys Asn Thr Ala Tyr

```
        65                  70                  75                  80
Leu Gln Met Asn Ser Leu Arg Ala Glu Asp Thr Ala Val Tyr Tyr Cys
                85                      90                  95

Ala Arg Arg Thr Arg Trp Ala Ser Xaa Ala Xaa Asp Tyr Trp Gly Gln
               100                 105                 110

Gly Thr Leu Val Thr Val Ser Ser Ala Ser Thr Lys Gly Pro Ser Val
           115                 120                 125

Phe Pro Leu Ala Pro Ser Ser Lys Ser Thr Ser Gly Gly Thr Ala Ala
       130                 135                 140

Leu Gly Cys Leu Val Lys Asp Tyr Phe Pro Glu Pro Val Thr Val Ser
145             150                 155                 160

Trp Asn Ser Gly Ala Leu Thr Ser Gly Val His Thr Phe Pro Ala Val
               165                 170                 175

Leu Gln Ser Ser Gly Leu Tyr Ser Leu Ser Ser Val Val Thr Val Pro
           180                 185                 190

Ser Ser Ser Leu Gly Thr Gln Thr Tyr Ile Cys Asn Val Asn His Lys
           195                 200                 205

Pro Ser Asn Cys Lys Val Asp Lys Lys Val Glu Pro Lys Ser Cys Asp
       210                 215                 220
```

TIE2-BINDING AGENTS AND METHODS OF USE

CROSS-REFERENCE TO RELATED APPLICATIONS

This application claims priority to U.S. provisional patent application Nos. 62/993,930, filed 24 Mar. 2020, and 66/046,318, filed +Jun. 2016, which applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jul. 13, 2021, is named P35891-US-2_SeqList.txt and is 107,433 bytes in size.

FIELD OF THE INVENTION

The presently disclosed subject matter relates to Tie2-binding agents including anti-Tie2 antibodies and conjugates and methods of using the same.

BACKGROUND

Tie2 is a promising therapeutic target for the treatment of various ocular disorders (see, e.g., Campochiaro and Peters, 2016, Curr Diab Rep, 16:126, Whitehead et al., 2019, J Diabetes Res, 2019:5140521, Hussain et al., 2019, Expert Opin Investig Drug, 28:861-869). Tie2 is a receptor tyrosine kinase specifically expressed by endothelial cells and has been shown to promote endothelial stabilization and reduce vascular permeability. Vascular leakage is known to contribute to visual impairment in several common ocular disorders, including but not limited to diabetic macular edema (DME), diabetic retinopathy (DR) and age-related macular degeneration (AMD).

The most extensively studied ligands of Tie2 are angiopoietin 1 (Ang1) and angiopoietin 2 (Ang2). Ang1 is a strong Tie2 agonist and has been shown to inhibit ocular neovascularization and breakdown of the blood-retinal barrier (see, e.g., Nambu et al., 2004, Gene Therapy, 11:865-873). Ang2 is a context-dependent antagonist of Tie2 and its expression is increased in association with several ocular disorders including DME, wet AMD, DR, metastasis, sepsis, and inflammation. Among other things, Ang2 competitively binds to Tie2 and inhibits Ang1 signaling, leading to endothelial and vascular destabilization, breakdown of the blood-retinal barrier, and inflammation (Klaassen et al., 2013, Prog Retin Eye Res, 34:19-48, Saharinen et al., 2017, Nat Rev Drug Discov, 16:635-661).

Tie receptors, including Tie1 and Tie2, are type 1 transmembrane protein receptor tyrosine kinases (RTKs) (Ramsauer, M. & D'Amore, P. A. J. Clin. Invest. (2002); 110: 1615-1617). Tie stands for Tyosine kinase receptors with immunoglobulin and EGF homology domains. Tie2 is located in endothelial cells of all forming blood vessels and in the endocardium of mouse embryos (Korhonen et al., Blood (1992); 80:2548-2555). The ectodomains or extracellular domain ("ECD") of Tie2 includes three Immunoglobulin (Ig) domains (Ig1, Ig2 and Ig3), three epidermal growth factor (EGF) domains and a fibronectin type III domain (FNIII). The Ig-EGF region of Tie2 mediates angiopoietin recognition and binding (Fiedler, U. et al., J. Biol. Chem. (2003); 278:1721-1727; Barton, W. A., et al., Structure (2005); 13:825-832).

Two ligands for the Tie2 receptor have been identified: Angiopoietin-1 (Ang1) and Angiopoietin-2 (Ang2). Ang-1, a Tie2 agonist, binds and induces the tyrosine phosphorylation of Tie2 and its expression in vivo is in close proximity with developing blood vessels (Davis et al., Cell (1996); 87: 1161-1169). Mice lacking Ang-1 exhibit angiogenic deficits reminiscent of those seen in mice lacking Tie2, which supports that Ang-1 is a primary physiologic ligand for Tie2 and that Tie2 has critical in vivo angiogenic actions (Suri et al., Cell (1996); 87:1171-1180). Ang-1 is anti-inflammatory, and promotes vascular integrity, reduces vascular permeability. Ang2 was identified to be a naturally occurring antagonist for Tie2. Transgenic overexpression of Ang2 disrupts blood vessel formation in the mouse embryo (Maisonpierre et al., Science 277: 55-60, 1997). Ang2 can be pro-inflammatory, disrupt EC quiescence, and increase vascular permeability. Together, studies support that the Ang1/Ang2/Tie2 system plays a critical role in angiogenesis. Given the significant role for Tie2 in angiogenesis, agents that recognize Tie2, and methods of using such agents, are desired. Moreover, compositions which function as Tie2 agonists and which can reduce vascular permeability or enhance vascular integrity have great potential as therapeutics, especially for treatment of ocular disorders.

SUMMARY

The invention provides anti-Tie2 antibodies, compositions (e.g., conjugates) comprising the anti-Tie2 antibodies or fragments thereof, and methods of using the same.

The presently disclosed subject matter provides an isolated antibody that specifically binds Tie2, or an antigen-binding fragment thereof, a composition comprising at least one or more anti-Tie2 antibodies or antigen-binding fragments thereof, and methods of using the same. In an exemplary embodiment, the anti-Tie2 antibody is a Fab.

In one aspect, an antibody that specifically binds Tie2 or an antigen-binding fragment thereof is provided, wherein the anti-Tie2 antibody comprises a heavy chain (HC) variable domain (VH domain) comprising a CDR-H1 comprising the amino acid sequence of NTDIS (SEQ ID NO:3), CDR-H2 comprising the amino acid sequence of RISPSDGNTYYADSVKG (SEQ ID NO:4), and CDR-H3 comprising the amino acid sequence of (a) RTRWASX1AX2DY (SEQ ID NO:5 wherein X1 is M, L, K, F, Y, R, N, Q, H or W and/or X2 is F, Y L, Q, I, K, or H), (b) RTRWASWAMDY (SEQ ID NO:6), or (c) RTRWAS-WAFDY (SEQ ID NO:7); and a light chain (LC) variable domain (VL domain) comprising CDR-L1 comprising the amino acid sequence of RASQDVSTAVA (SEQ ID NO:8), CDR-L2 comprising the amino acid sequence of SASFLYS (SEQ ID NO:9), and CDR-L3 comprising the amino acid sequence of QQSYTTPPT (SEQ ID NO:10). In some embodiments, CDR-H3 comprises SEQ ID NO:6 or SEQ ID NO:7. In particular embodiments, CDR-H3 comprises SEQ ID NO:7.

In some embodiments, the anti-Tie2 antibody comprises a VH framework FR1 sequence of SEQ ID NO:11, a VH framework FR2 sequence of SEQ ID NO:12, a VH framework FR3 sequence of SEQ ID NO:13, and/or a VH framework FR4 sequence of SEQ ID NO:14. In other embodiments, the anti-Tie2 antibody comprises a VL framework FR1 sequence of SEQ ID NO:15, a VL framework FR2 sequence of SEQ ID NO:16, a VL framework FR3 sequence of SEQ ID NO:17, and/or a VL framework FR3 sequence of SEQ ID NO:18.

In some embodiments, the anti-Tie2 antibody comprises a VH domain comprising CDR-H1 comprising the amino acid sequence of SEQ ID NO:3, CDR-H2 comprising the amino acid sequence of SEQ ID NO:4, and CDR-H3 comprising the amino acid sequence of (a) SEQ ID NO:5 wherein X1 is M, L, K, F, Y, R, N, Q, H or W and/or X2 is F, Y L, Q, I, K, or H, (b) SEQ ID NO:6, or (c) SEQ ID NO:7; and a VL domain comprising CDR-L1 comprising the amino acid sequence of SEQ ID NO:8, CDR-L2 comprising the amino acid sequence of SEQ ID NO:9, and CDR-L3 comprising the amino acid sequence of SEQ ID NO:10. In other embodiments, CDR-H3 comprises SEQ ID NO:6 or SEQ ID NO:7. In particular embodiments, CDR-H3 comprises SEQ ID NO:7. In still other embodiments, the VH domain is at least 90%, 95%, 96%, 97%, 98%, or 99% identical to SEQ ID NO:20 and the VL domain is at least 90%, 95%, 96%, 97%, 98%, or 99% identical to SEQ ID NO:21.

In some embodiments, the anti-Tie2 antibody or antigen-binding fragment thereof comprises the VH domain sequence of SEQ ID NO:19 or SEQ ID NO:22 and the VL domain sequence of SEQ ID NO:21.

In some embodiments, the anti-Tie2 antibody comprises a VH domain sequence of SEQ ID NO:20. In other embodiments, the anti-Tie2 antibody comprises a VL domain sequence of SEQ ID NO:21. In still other embodiments, the anti-Tie2 antibody comprises a VH domain sequence of SEQ ID NO:20 and a VL domain sequence of SEQ ID NO:21

In some embodiments, the anti-Tie2 antibody or fragment thereof comprises a heavy chain (HC) domain sequence of SEQ ID NO:55 and a light chain (LC) domain sequence of SEQ ID NO:25. In other embodiments, the anti-Tie2 antibody or fragment thereof comprises a heavy chain (HC) domain sequence of SEQ ID NO:23 and a light chain (LC) domain sequence of SEQ ID NO:56.

In some aspects, an antibody that specifically binds Tie2, or antigen-binding fragment thereof, is provided, which comprises a VH domain comprising a CDR-H1 comprising the amino acid sequence of SEQ ID NO:28, CDR-H2 comprising the amino acid sequence of SEQ ID NO:29, and CDR-H3 comprising the amino acid sequence of SEQ ID NO:30, and a VL domain comprising CDR-L1 comprising the amino acid sequence of SEQ ID NO:8, CDR-L2 comprising the amino acid sequence of SEQ ID NO:9, and CDR-L3 comprising the amino acid sequence of SEQ ID NO:10. In some embodiments, the VH domain comprises an amino acid sequence having at least 90%, 95%, 96%, 97%, 98%, or 99% identity to SEQ ID NO:31 and the VL domain comprises an amino acid sequence having at least 90%, 95%, 96%, 97%, 98%, or 99% identity to SEQ ID NO:21. In still other embodiments, the VH domain comprises SEQ ID NO:31 and the VL domain comprises SEQ ID NO:21. In other embodiments, the HC comprises SEQ ID NO:32 and the LC comprises SEQ ID NO:25.

In some aspects, an antibody that specifically binds Tie2, or antigen-binding fragment thereof, is provided, which comprises a VH domain comprising a CDR-H1 comprising the amino acid sequence of SEQ ID NO:33, CDR-H2 comprising the amino acid sequence of SEQ ID NO:34, and CDR-H3 comprising the amino acid sequence of SEQ ID NO:35, and a VL domain comprising CDR-L1 comprising the amino acid sequence of SEQ ID NO:8, CDR-L2 comprising the amino acid sequence of SEQ ID NO:9, and CDR-L3 comprising the amino acid sequence of SEQ ID NO:10. In some embodiments, the VH domain comprises an amino acid sequence having at least 90%, 95%, 96%, 97%, 98%, or 99% identity to SEQ ID NO:36 and the VL domain comprises an amino acid sequence having at least 90%, 95%, 96%, 97%, 98%, or 99% identity to SEQ ID NO:21. In still other embodiments, the VH domain comprises SEQ ID NO:36 and the VL domain comprises SEQ ID NO:21. In other embodiments, the HC comprises SEQ ID NO:37 and the LC comprises SEQ ID NO:25.

In some aspects, an antibody that specifically binds Tie2, or antigen-binding fragment thereof, is provided, which comprises a VL domain comprising CDR-L1 comprising SEQ ID NO:8, CDR-L2 comprising SEQ ID NO:9, and CDR-L3 comprising SEQ ID NO:10; and a VH domain comprising: (a) CDR-H1 comprising SEQ ID NO:38, CDR-H2 comprising SEQ ID NO:39, and CDR-H3 comprising SEQ ID NO:40; (b) CDR-H1 comprising SEQ ID NO:43, CDR-H2 comprising SEQ ID NO:44, and CDR-H3 comprising SEQ ID NO:45; or (c) CDR-H1 comprising SEQ ID NO:48, CDR-H2 comprising SEQ ID NO:49, and CDR-H3 comprising SEQ ID NO:50. In other embodiments, the VL domain comprises an amino acid sequence having at least 90%, 95%, 96%, 97%, 98%, or 99% identity to SEQ ID NO:21; and the VH domain comprises of (a), (b), or (c) comprises an amino acid sequence having at least 90%, 95%, 96%, 97%, 98%, or 99% identity to (d) SEQ ID NO:41; (e) SEQ ID NO:46; or (f) SEQ ID NO:51, respectively.

In some embodiments, the antibody or antigen-binding fragment thereof comprises a LC of SEQ ID NO:21 and a HC comprising SEQ ID NO:42, SEQ ID NO:46, or SEQ ID NO:52.

In some aspects, an antibody that specifically binds Tie2, or antigen-binding fragment thereof, is provided, which comprises a 2 VH domains comprising, in an N-terminal to C-terminal direction, a CDR-H1 comprising SEQ ID NO:6, CDR-H2 comprising SEQ ID NO:8, a CDR-H3 comprising SEQ ID NO:9, a CDR-H1 comprising SEQ ID NO:48, CDR-H2 comprising SEQ ID NO:49, a CDR-H3 comprising SEQ ID NO:50, and 2 VL domains comprising, in an N-terminal to C-terminal direction, CDR-L1 comprising the amino acid sequence of SEQ ID NO:8, CDR-L2 comprising the amino acid sequence of SEQ ID NO:9, CDR-L3 comprising the amino acid sequence of SEQ ID NO:10, CDR-L1 comprising the amino acid sequence of SEQ ID NO:8, CDR-L2 comprising the amino acid sequence of SEQ ID NO:9, and CDR-L3 comprising the amino acid sequence of SEQ ID NO:10. In some embodiments, the HC comprises SEQ ID NO:54 and the LC comprises SEQ ID NO:53.

In some embodiments, the anti-Tie2 antibody or antigen-binding fragment thereof comprises an engineered cysteine, wherein the engineered cysteine is in a HC constant domain and/or in a LC constant domain. In other embodiments, the engineered cysteine is selected from T120C, G166C, G178C, T187C, and T209C in the heavy chain, and Q124C, R142C, Q155C, L201C, T206C, K107C, K126C and K149C in the light chain, wherein the residue number is according to EU numbering. In other embodiments, the anti-Tie2 antibody or antigen-binding fragment thereof is a Fab wherein the HC of the Fab ends in the amino acids CDKTHTSPPC (SEQ ID NO:83). In some embodiments, the Fab ends in the amino acid sequence of SEQ ID NO:81, SEQ ID NO:82, SEQ ID NO:84, SEQ ID NO:85, or SEQ ID NO:86.

In some embodiments, the anti-Tie2 antibody is a monoclonal antibody.

In some embodiments, the anti-Tie2 antibody is a humanized, chimeric or human antibody.

In some embodiments, the anti-Tie2 antibody is a full length IgG1 or full length IgM antibody.

In some embodiments, the anti-Tie2 antibody or fragment thereof binds Tie2, wherein Tie2 is a protein having at least 95%, 96%, 97%, 98%, 99%, or 100% identity to SEQ ID NO:1.

In preferred embodiments, the anti-Tie2 antibody or fragment thereof is a Fab.

In some embodiments, the anti-Tie2 antibody is an antibody or Fab that competes with the anti-Tie2 antibody comprising a VH sequence of SEQ ID NO:22 and a VL sequence of SEQ ID NO:21.

In some embodiments, the anti-Tie2 antibody or fragment thereof does not bind to the Ig1 domain of Tie2. In other embodiments, the anti-Tie2 antibody or fragment thereof does not bind to an EGF domain of Tie2. In still other embodiments, the anti-Tie2 antibody or fragment thereof does not bind to the Ig3 domain of Tie2. In yet other embodiments, the anti-Tie2 antibody or fragment thereof does not bind to a FNIII domain of the Tie2 protein.

In some embodiments, the antibody or antigen-binding fragment thereof binds to cynomolgus monkey Tie2. In other embodiments, the cynomolgus monkey Tie2 comprises the amino acid sequence of SEQ ID NO:2 or variant thereof.

In some embodiments, the antibody or antigen-binding fragment thereof that binds Tie2 is a multi-specific antibody. In other embodiments, the multi-specific antibody binds Tie2 and VEGF. In other embodiments, the multi-specific antibody binds Tie2 and Factor D. In still other embodiments, the multi-specific antibody binds Tie2 and Ang2.

In some embodiments, the anti-Tie2 antibody is a multi-specific antibody which activates Tie2. In other embodiments, the multi-specific antibody binds Tie2 and VEGF, wherein the multi-specific antibody can activate Tie2. In other embodiments, the multi-specific antibody binds Tie2 and Factor D, wherein the multi-specific antibody can activate Tie2. In still other embodiments, the multi-specific antibody binds Tie2 and Ang2, wherein the multi-specific antibody can activate Tie2.

In one aspect, an isolated nucleic acid encoding the anti-Tie2 antibody or antigen-binding fragment thereof is provided.

In one aspect, a host cell comprising the isolated nucleic acid encoding the anti-Tie2 antibody or antigen-binding fragment thereof is provided.

In one aspect, a method of producing an antibody or antigen-binding fragment thereof that binds Tie2 is provided. In some embodiments, the method comprises culturing the host cell comprising the nucleic acid encoding the anti-Tie2 antibody under conditions suitable for expression of the anti-Tie2 antibody. In other embodiments, the method further comprises recovering the anti-Tie2 antibody from the host cell.

In one aspect, an anti-Tie2 antibody produced by the above method is provided.

In one aspect, a conjugate is provided, comprising at least two antibodies that specifically bind Tie2, or antigen-binding fragment thereof, according to the embodiments disclosed herein, and a multi-armed moiety. In preferred embodiments, each of the at least two anti-Tie2 antibodies is a Fab.

In some embodiments, the conjugate comprises an anti-Tie2 Fab which binds Tie2, and a multi-armed moiety wherein the multi-armed moiety is linked to at least 2 anti-Tie2 Fabs. In some embodiments, the multi-armed moiety is linked to at least 2, 3, 4, 5, 6, 7, 8, 9 or 10 anti-Tie2 Fabs. In other embodiments, the multi-armed moiety is linked to 2, 3, 4, 5, 6, 7, 8, 9 or 10 anti-Tie2 Fabs. In still other embodiments, the multi-armed moiety is linked to 6 or 8 anti-Tie2 Fabs. In yet other embodiments, the multi-armed moiety is linked to 8 anti-Tie2 Fabs. In preferred embodiments, the multi-armed moiety is linked to 6 anti-Tie2 Fabs.

In one aspect, the conjugate binds to and activates Tie2 activity.

In some embodiments, the conjugate which binds to Tie2 activates AKT phosphorylation. In other embodiments, activation of AKT phosphorylation is demonstrated by an increase in phosphorylated AKT protein in an in vitro assay. In other embodiments, the Tie2 binding agent activates phosphorylation of Tie2. In still other embodiments, the activation of Tie2 phosphorylation is measured in vitro.

In some embodiments, exposing Tie2-expressing cells to the conjugate does not reduce Tie2 protein levels in the cells. In other embodiments, the exposing does not reduce Tie2 protein levels in the cells by more than 5%, 10%, 15%, 20%, 25%, 30%, 40%, 50%, 60%, or 75%. In yet other embodiments, the exposing reduces Tie2 protein levels in the cells by less than 5%, 10%, 15%, 20%, 25%, 30%, 40%, 50%, 60%, or 75%. In still other embodiments, the exposing reduces Tie2 protein levels in the cell by more than about 25% and less than about 75%, by more than about 50% and less than about 75%, or by more than about 60% and less than about 80%. In some embodiments, the Tie2 protein levels are measured by western blot before and after in vitro incubation of the Tie2 binding agent with Tie2-expressing cells. In other embodiments, the incubation is at 37° C. for 10 to 36 hours or from 12 to 24 hours.

In some embodiments, the anti-Tie2 antibody or antigen-binding fragment thereof has an equilibrium dissociation constant (Kd) ranging from 0.1 uM to 10 uM, from 0.01 uM to 10 uM, or from 0.1 to 100 uM.

In some embodiments, the conjugate comprising the multi-armed moiety and the anti-Tie2 antibody or antigen-binding fragment thereof increases translocation of Tie2 to cell-cell junctions.

In some embodiments, the conjugate reduces vascular permeability.

In some embodiments, the conjugate facilitates vascular stability, and/or increases vascular integrity.

In some embodiments, the conjugate does not inhibit or reduce binding of Ang1 to Tie2.

In some embodiments, the conjugate inhibits or reduces binding of Ang2 to Tie2.

In some embodiments, the conjugate activities are measured using an in vitro assay.

In some embodiments, the multi-armed polyol is selected from the group consisting of a dimer, a tetramer, a hexamer, and an octamer. In preferred embodiments, the multi-armed polyol is a hexamer or an octamer. In more preferred embodiments, the multi-armed polyol is a hexamer.

In some embodiments, the polyol is a poly(alkylene oxide) polymer. In other embodiments, the polyol is a poly(alkylene glycol). In yet other embodiments, the polyol is a polyethylene glycol (PEG). In some embodiments, the PEG is a functionalized multi-armed PEG.

In some embodiments, the PEG has the structure of general formula (Ia):

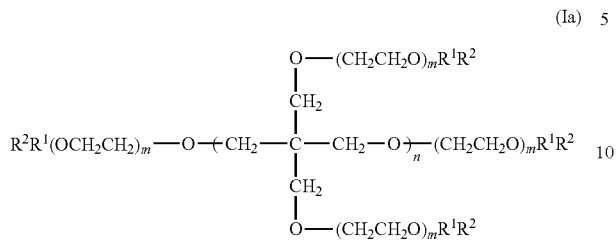

(Ia)

wherein each m denotes the length or size of the particular arm of the polyol (PEG) and is independently an integer of from about 45 to about 1000, about 20 to about 1000, about 10 to about 1000, about 3 to about 250, about 3 to about 200, about 3 to about 100, about 10 to about 50, about 10 to about 30, about 20 to about 30, about 50 to about 200, or from about 100 to about 150; and n is an integer from about 1 to about 10; each $R^1$ is independently either absent, or is a linking group; and each $R^2$ is independently either hydrogen or a terminal reactive group; wherein at least one $R^2$ is a terminal reactive group. In some embodiments, $R^2$ is independently selected from a thiol reactive group, an amino reactive group, and combinations thereof.

In some embodiments, the PEG has the structure of general formula (Ia), wherein n is an integer from 1 to 3.

In some embodiments, the PEG has the structure of general formula (Ia), wherein n is 1, and the multi-armed PEG is a tetramer.

In some embodiments, the PEG has the structure of general formula (Ia), wherein n is 2, and the multi-armed PEG is a hexamer. In such embodiments, the hexamer has the structure of general formula (Ib):

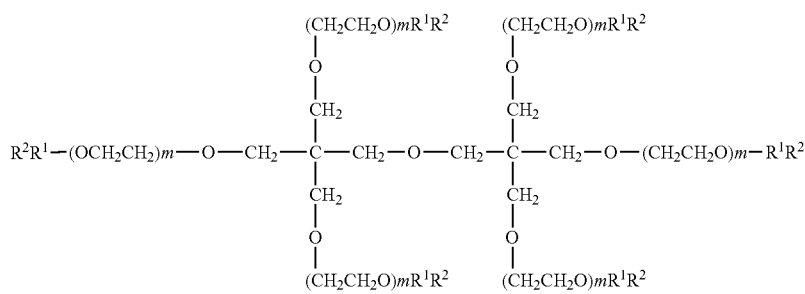

wherein each m is independently an integer of from about 45 to about 1000, about 20 to about 1000, about 10 to about 1000, about 3 to about 250, about 3 to about 200, about 3 to about 100, about 10 to about 50, about 10 to about 30, about 20 to about 30, about 50 to about 200, or from about 100 to about 150; each $R^1$ is independently either absent or is a linking group; and each $R^2$ is independently either hydrogen or a terminal reactive group; wherein at least one $R^2$ is a terminal reactive group and is covalently linked to an anti-Tie2 antibody fragment or Fab as described above. In some embodiments, each m is independently an integer from about 15 to 35 or from about 20 to 30. In other embodiments, each m is independently an integer of about 22.

In some embodiments, $R^1$ and $R^2$ taken together has the structure

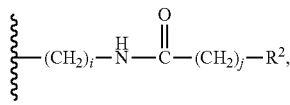

where $R^2$ is a maleamide;

In some embodiments, the PEG has the structure of general formula (Ia), wherein n is 3, and the multi-armed PEG is an octamer. In such embodiments, the octamer has the structure of general formula (Ic):

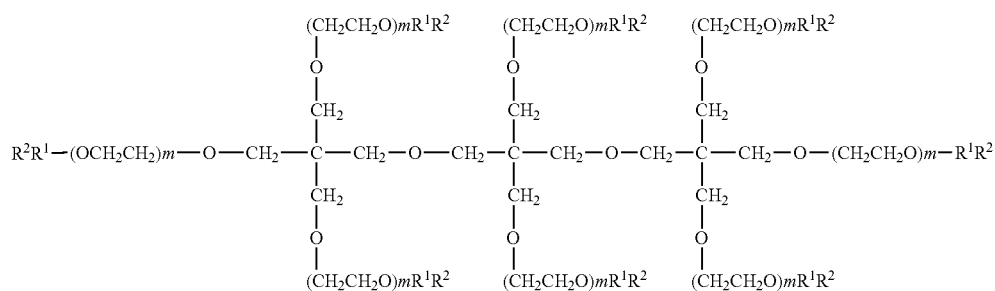

wherein each m is independently an integer from 3-250; each $R^1$ is independently either absent or is a linking group; and each $R^2$ is independently either hydrogen or a terminal reactive group; wherein at least one $R^2$ is a terminal reactive group and is covalently linked to an anti-Tie2 Fab as described above. In some embodiments, each m is independently an integer from 15 to 35. In other embodiments, each m is independently an integer of about 22.

In some embodiments, the at least two anti-Tie2 antibody fragments or Fabs described herein are covalently linked to the multi-armed polyol. In other embodiments, the multi-armed polyol of the conjugate is covalently linked to the at least two anti-Tie2 antibody fragments or Fabs through a free sulfhydryl group of a cysteine amino acid. In other embodiments, the cysteine amino acid is an engineered cysteine. In yet other embodiments, the cysteine amino acid is in the anti-Tie2 constant domain. In other embodiments, the cysteine amino acid is at the C-terminus of the heavy chain (HC) or the light chain (LC) of the anti-Tie2 Fab. In a preferred embodiment, the cysteine amino acid is not at the N-terminus or the C-terminus of the HC or the LC.

In some embodiments, the conjugate comprising an anti-Tie2 antibody or antigen-binding fragment thereof which comprises an engineered cysteine in its HC and/or LC. In other embodiments, the engineered cysteine is selected from a T120C, G166C, G178C, T187C, and T209C in the HC; or the engineered cysteine is selected from Q124C, R142C, Q155C, L201C, T206C, K107C, K126C, and K149C in the LC; wherein the residue number of the engineered cysteine is according to EU numbering.

In some embodiments, the conjugate comprises a multi-armed polyol that is covalently linked to the at least two anti-Tie2 antibody fragments or Fabs through a free amino group of a lysine amino acid. In other embodiments, the lysine amino acid is in the constant region of the anti-Tie2 antibody fragment or Fab. In still other embodiments, the lysine amino acid is at the C-terminus of the heavy chain or the light chain of the anti-Tie2 antibody fragment or Fab. In an alternative embodiment, the Tie2 binding agent is not covalently linked to the at least two anti-Tie2 Fabs through a free amino group of a lysine.

In some embodiments, the conjugate deconjugates less than 20%, less than 15%, or less than 10% per month at physiological conditions in vitro. In other embodiments, the conjugate deconjugates less than 20%, less than 15%, or less than 10% per month at physiological conditions in vivo.

In some embodiments, the conjugate is stable over an extended period of time, with loss of Tie2 binding capacity of less than 20%, less than 15%, or less than 10% per month at physiological conditions.

In one aspect, a conjugate comprising an anti-Tie2 antibody or antigen-binding fragment thereof and a multi-armed moiety is provided, wherein the multi-armed moiety comprises an IgM molecule. In other embodiments, the IgM molecule comprises a J chain and the multi-armed moiety comprises 5 anti-Tie2 Fabs, wherein approximately each of the 5 anti-Tie2 Fabs is linked to the IgM molecule. In still other embodiments, the IgM molecule does not comprise a J chain and the multi-armed moiety comprises 6 anti-Tie2 Fabs, wherein each of the 6 anti-Tie2 Fabs is linked to the IgM molecule.

In some embodiments, the conjugate comprises an IgM molecule which is an IgM variant that has an amino acid substitution whereby the IgM variant reduces or eliminates complement-dependent cytotoxicity (CDC) activity. In preferred embodiments, the IgM variant comprises the substitution P436G based on EU numbering.

In one aspect, a conjugate comprising an anti-Tie2 antibody or antigen-binding fragment thereof and a multi-armed moiety is provided, wherein the multi-armed moiety comprises at least 2, 4, 6, 8 or 10 peptides, wherein approximately each of the peptides is covalently linked to an anti-Tie2 Fab. In some embodiments, the anti-Tie2 Fab sequence ends at residue 221, 222, 223, 224, or 225 (EU numbering). In other embodiments, each of the peptides is a nucleoside diphosphate kinase (NDK) peptide. In still other embodiments, each of the NDK peptides comprises an amino acid sequence which is at least 95%, 96%, 97%, 98%, 99% or 100% identical to SEQ ID NO:71.

In some embodiments, each of the NDK peptides is linked at its N-terminal end to the C-terminal end of the anti-Tie2 Fab heavy chain or light chain. In other embodiments, a linker is present between the Fab heavy chain or light chain and the peptide. In still other embodiments, the linker is an amino acid linker. In yet other embodiments, the amino acid linker comprises 2, 3, 4, 5, 6, 7, 8, 2 to 20, 5 to 10 or 4 to 10 amino acids. In other embodiments, the linker comprises glycines.

In some embodiments, the multi-armed moiety comprises 6 or 8 peptides. In other embodiments, the multi-armed moiety comprises 6 peptides. In a preferred embodiment, the multi-armed moiety comprises 6 NDK peptides.

In one aspect, a conjugate comprising an antibody or antigen-binding fragment thereof and a multi-armed moiety is provided, wherein the multi-armed moiety comprises an IgM molecule. In other embodiments, the IgM molecule comprises a J chain and the multi-armed moiety comprises 5 antibody fragments, Fabs, or antigen-binding fragments thereof, wherein approximately each of the 5 antibody fragments, Fabs, or antigen-binding fragments thereof is linked to the IgM molecule. In still other embodiments, the IgM molecule does not comprise a J chain and the multi-armed moiety comprises 6 antibody fragments, Fabs, or antigen-binding fragments thereof, wherein each of the 6 antibody fragments, Fabs, or antigen-binding fragments thereof is linked to the IgM molecule.

In some embodiments, the conjugate comprises an IgM molecule which is an IgM variant that has an amino acid substitution whereby the IgM variant reduces or eliminates complement-dependent cytotoxicity (CDC) activity. In preferred embodiments, the IgM variant comprises the substitution P436G based on EU numbering.

In one aspect, a conjugate comprising an antibody, antibody fragments, Fabs, or antigen-binding fragments thereof and a multi-armed moiety is provided, wherein the multi-armed moiety comprises at least 2, 4, 6, 8 or 10 peptides, wherein approximately each of the peptides is covalently linked to the antibody, antibody fragments, Fabs, or antigen-binding fragments thereof. In some embodiments, the antibody, antibody fragments, Fabs, or antigen-binding fragments thereof sequence ends at residue 221, 222, 223, 224, or 225 (EU numbering). In other embodiments, each of the peptides is a nucleoside diphosphate kinase (NDK) peptide. In still other embodiments, each of the NDK peptides comprises an amino acid sequence which is at least 95%, 96%, 97%, 98%, 99% or 100% identical to SEQ ID NO:71.

In some embodiments, each of the NDK peptides is linked at its N-terminal end to the C-terminal end of the heavy chain or light chain of the antibody, antibody fragments, Fabs, or antigen-binding fragments thereof. In other embodiments, a linker is present between the Fab heavy chain or light chain and the peptide. In still other embodiments, the linker is an amino acid linker. In yet other embodiments, the amino acid linker comprises 2, 3, 4, 5, 6, 7, 8, 2 to 20, 5 to 10 or 4 to 10 amino acids. In other embodiments, the linker comprises glycines.

In some embodiments, the multi-armed moiety comprises 6 or 8 peptides. In other embodiments, the multi-armed moiety comprises 6 peptides. In a preferred embodiment, the multi-armed moiety comprises 6 NDK peptides.

In one aspect, a pharmaceutical composition is provided comprising an anti-Tie2 antibody or fragment thereof according to the present disclosure and a pharmaceutically acceptable carrier, excipient, or diluent. In some embodiments, the pharmaceutical composition comprises an anti-Tie2 binding agent which comprises a plurality of anti-Tie2 Fabs linked to a multi-armed moiety as described herein, and a pharmaceutically acceptable carrier.

In some embodiments, the pharmaceutical composition comprising the anti-Tie2 antibody or the Tie2 binding agent further comprises an additional therapeutic agent. In other embodiments, the additional therapeutic agent is selected from the group consisting of an anti-VEGF antibody, an anti-Tie2 antibody, and an anti-Ang2 antibody. In some embodiments, the additional therapeutic agent is selected from an Ang2 antagonist, a VEGF antagonist, a VEGF trap, an anti-VEGF antibody, an anti-Ang2 antibody, and a complement component antagonist.

In some embodiments, any of the preceding pharmaceutical compositions can be used as a medicament.

In some embodiments, any of the preceding pharmaceutical compositions can be used in the manufacture of a medicament for treating an ocular disorder in a subject.

In some embodiments, any of the preceding pharmaceutical compositions can be used in reducing or inhibiting pathologic vascular permeability in a subject having an ocular disorder.

In another aspect, any of the preceding pharmaceutical compositions can be used in treating an ocular disorder in a subject.

In one aspect, a method for treating an individual in need thereof is provided comprising administering to the patient an anti-Tie2 antibody and/or a Tie2 binding agent as described herein. In some embodiments, the method comprises administering to the individual a pharmaceutical composition as described herein comprising an anti-Tie2 conjugate as described herein.

In some embodiments, the individual has been diagnosed with a vascular disorder. In other embodiments, the individual has been diagnosed with a vascular disorder of the eye.

In another aspect, the invention features a method of inhibiting vascular permeability in a subject suffering from a disorder associated with undesirable vascular permeability, the method comprising administering to the subject an effective amount of any one of the preceding antibodies or conjugates, thereby inhibiting vascular permeability in the subject.

In another aspect, the invention features a method of treating a disorder associated with undesirable vascular permeability, the method comprising administering an effective amount of any one of the preceding antibodies or conjugates to a subject in need of such treatment.

In some embodiments, the individual has been diagnosed with a disorder associated with the Tie2 pathway.

In some embodiments, the individual has been diagnosed with a an eye disorder selected from the group consisting of diabetic macular edema (DME), age-related macular degeneration (AMD), including dry and wet (non-exudative and exudative) forms, choroidal neovascularization (CNV), uveitis, diabetic retinopathy, ischemia-related retinopathy, pathological myopia, von Hippel-Lindau disease, histoplasmosis of the eye, Central Retinal Vein Occlusion (CRVO), corneal neovascularization, glaucoma, retinopathy in the absence of edema, and retinal neovascularization.

In some embodiments, the individual has received treatment with an anti-VEGF antibody. In other embodiments, the individual was did not experience therapeutic efficacy of the anti-VEGF antibody, experiences reduced therapeutic efficacy of the anti-VEGF antibody, and/or stopped experiencing therapeutic efficacy of the anti-VEGF antibody.

In some embodiments, the method further comprises administering to the individual a second therapeutic agent. In other embodiments, the second therapeutic agent is selected from the group consisting of an anti-VEGF antibody, an anti-Ang2 antibody, an anti-VEGF/anti-Ang2 bispecific antibody, a VEGF antagonist and an Ang2 antagonist.

BRIEF DESCRIPTION OF THE FIGURES

FIGS. 7A-7B show results of assays to assess activation of AKT phosphorylation by anti-Tie2 antibodies Tie2.1, Tie2.22, Tie2.23, Tie2.24, Tie2.27, Tie2.28, Tie2.31, Tie2.33, Tie2.34, Tie2.34, Tie2.38 and Tie2.1 (FIG. 7A). FIG. 7B shows the effects of anti-Tie2 antibody aggregation or anti-IgG cross-linking on the activity of anti-Tie2 antibody Tie2.1 to induce phosphorylation of AKT. Levels of phosphorylated AKT were determined by FRET analysis.

Figure 10A:
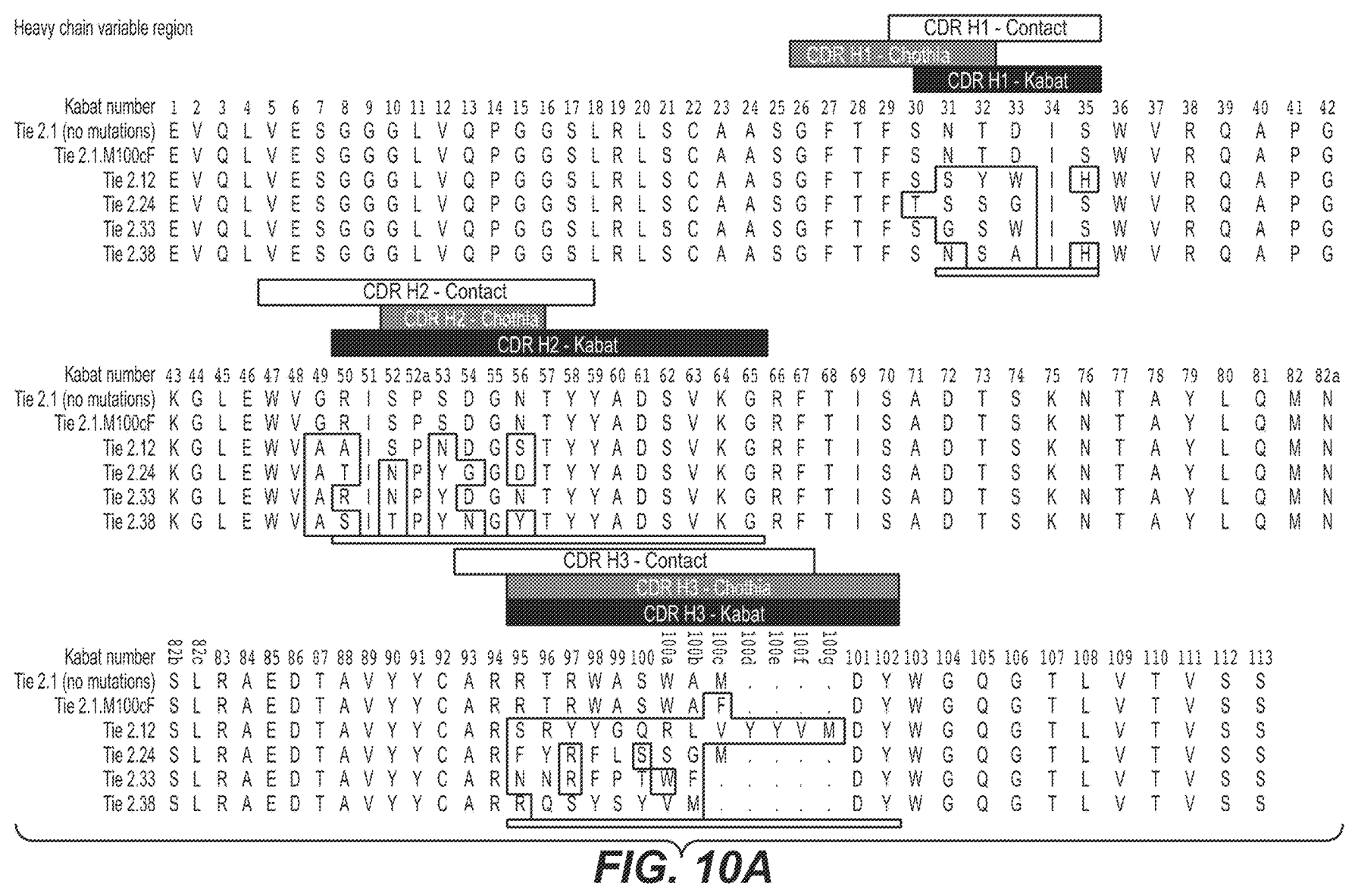

FIGS. 10A and 10B show sequence alignments of amino acid sequences of the heavy chain variable region (VH) of anti-Tie2 antibodies Tie2.1 (SEQ ID NO:22), Tie2.1.M100cF (SEQ ID NO:20), Tie2.12 (SEQ ID NO:31), Tie2.24 (SEQ ID NO:36), Tie2.33 (SEQ ID NO:41) and Tie2.38 (SEQ ID NO:51) (FIG. 10A) and of light chain variable region (VL) of anti-Tie2 antibodies Tie2.1 (SEQ ID NO:21), Tie2.1.M100cF (SEQ ID NO:21), Tie2.12 (SEQ ID NO:21), Tie2.24 (SEQ ID NO:21), Tie2.33 (SEQ ID NO:21) and Tie2.38 (SEQ ID NO:21) (FIG. 10B).

FIGS. 11A-11B illustrate results of a binning assay with various anti-Tie2.1 antibodies generated via phage display or animal immunization. FIG. 11A provides the list of covalently immobilized antibody and several of the antibodies in solution, while FIG. 11B provides the remaining list of antibodies in solution.

FIG. 12A compares AKT phosphorylation activation by Tie2.1 as a PEG hexamer and as a bi-epitopic FabIgG (1.38). FIG. 12B compares multimeric formats of anti-Tie2 antibodies.

FIG. 13E shows serum IgM levels.

FIG. 13G shows results of a complement assay to assess mutations in the IgM constant domain. FIG. 13H illustrates agonist activity of the anti-Tie antibody in an IgM hexamer format.

FIG. 14A is a schematic of the multimeric design. FIG. 14B shows results of an AKT phosphorylation assay comparing an anti-Tie2 antibody in a hexameric format via an NDK peptide, IgM, and a multi-armed PEG.

FIGS. 16A-16C show results of assays to assess the effect of anti-Tie2 antibodies on cellular levels of the Tie2 protein in an in vitro assay. Each of FIG. 16A, FIG. 16B, and FIG. 16C compares Tie2 levels upon exposure of HUVECs to anti-Tie2 antibodies generated via phage display and animal immunization. All assays, in FIG. 16A, FIG. 16B and FIG. 16C, were analyzed by western blot.

FIGS. 20A-20B illustrate an assay method (FIG. 20A) and results (FIG. 20B) of an in vivo vascular permeability assay to study the effects of an anti-Tie2.1 antibody or an anti-VEGF antibody on VEGF-induced vascular leak.

FIG. 38A shows pAKT activity with FIG. 38B shows total conjugate levels via ELISA.

DETAILED DESCRIPTION OF EMBODIMENTS OF THE INVENTION

I. Definitions

Figure 1:
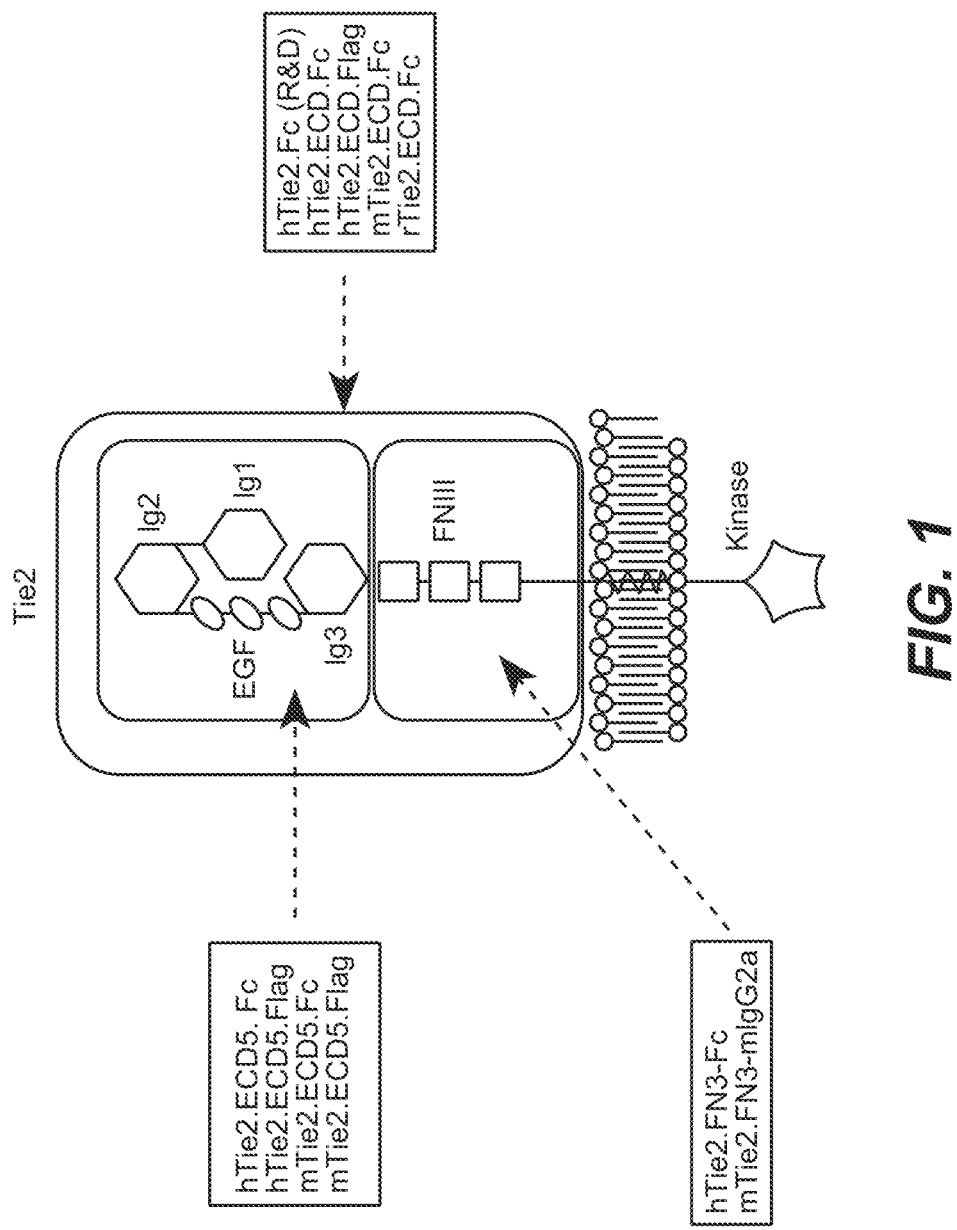
FIG. 1. Provides a schematic illustration of Tie2 domains used in panning VH libraries.

Unless otherwise defined herein, the term "comprising of" shall include the term "consisting of."

The term "about" as used herein in connection with a specific value (e.g., temperature, concentration, time and others) shall refer to a variation of +/−1% of the specific value that the term "about" refers to.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-Tie2 antibody," an "antibody that binds to Tie2," and "antibody that specifically binds Tie2" refer to an antibody that is capable of binding Tie2 with sufficient affinity such that the antibody is useful as a therapeutic and/or diagnostic agent in targeting Tie2. In one embodiment, the extent of binding of an anti-Tie2 antibody to an unrelated, non-Tie2 protein is less than about 10% of the binding of the antibody to Tie2 as measured, e.g., by a radioimmunoassay (RIA). In certain embodiments, an antibody that binds to Tie2 has a dissociation constant ($K_D$) of ≤1 μM, ≤100 nM, ≤10 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-Tie2 antibody binds to an epitope of Tie2 that is conserved among Tie2 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The terms "full length antibody," "intact antibody," and "whole antibody" are used herein interchangeably to refer to an antibody having a structure substantially similar to a native antibody structure or having heavy chains that contain an Fc region as defined herein.

As used herein, a "Fab" refers to an antibody that comprises a heavy chain constant region that comprises the CH1 domain, or a sufficient portion of the CH1 domain to form a disulfide bond with the light chain constant region, but does not contain a CH2 domain or a CH3 domain. As used herein, a Fab may comprise one or more amino acids of the hinge region. Thus, as used herein, the term "Fab" encompasses Fab' antibodies. A Fab may comprise additional non-native amino acids, such as a C-terminal cysteine, in which case it may be referred to as a Fab-C. As discussed below, the term Fab-C also encompasses Fabs comprising native amino acids of the hinge region, including a native cysteine at the C-terminus. In some embodiments, a Fab comprises an engineered cysteine (i.e., a Fab may be a THIOMAB). In some embodiments, an engineered cysteine is a cysteine amino acid residue in the Fab HC and/or LC polypeptide sequence that was substituted for a non-cysteine amino acid residue.

A "Fab-C" refers to a Fab with a C-terminal cysteine, which may be a native cysteine that occurs at that residue position (such as a cysteine from the hinge region), or may be a cysteine added to the C-terminus that does not correspond to a native cysteine.

A "Fab-SH" refers to a Fab with a free thiol group. In some embodiments, the free thiol group is located in the last 10 amino acids of the C-terminus of the Fab. Fab-C antibodies are typically also Fab-SH antibodies.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "conjugate" is used herein according to its broadest definition to mean joined or linked together. Molecules are "conjugated" when they act or operate as if joined. A "conjugate" is an antibody (e.g., Fab) conjugated to one or more heterologous molecule(s), including but not limited to a polyol. In particular embodiments, "conjugate" refers to an antibody (e.g., an antibody fragment, as detailed herein) covalently bound to a multi-armed moiety. In particular embodiments, the multi-armed moiety is a polyol, an IgM molecule, or a peptide in a multimeric (e.g., hexamer) format.

The term "Tie2," as used herein, refers to any native Tie2 from any vertebrate source, including mammals such as primates (e.g. humans) and rodents (e.g., mice and rats), unless otherwise indicated. The term encompasses "full-length," unprocessed Tie2 as well as any form of Tie2 that results from processing in the cell. The term also encompasses naturally occurring variants of Tie2, e.g., splice variants or allelic variants. The amino acid sequence of an exemplary human Tie2 protein has NCBI Reference No: NP_000450 (SEQ ID NO:1).

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, MD, 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology,* 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "hypervariable region," "HVR," or "HV," when used herein refers to the regions of an antibody variable domain which are hypervariable in sequence (also referred to herein as "complementarity determining regions" or "CDRs") and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "variable domain residue numbering as in Kabat" or "amino acid position numbering as in Kabat," and variations thereof, refers to the numbering system used for heavy chain variable domains or light chain variable domains of the compilation of antibodies in Kabat et al. supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al. supra). The "EU numbering system" or "EU index" is generally used when referring to a residue in an immunoglobulin heavy chain constant region (e.g., the EU index reported in Kabat et al. supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Pat. Appn. Pub. No. 2008/0181888, Figures for EU numbering).

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody," e.g., an anti-Tie2 antibody, refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "polyol" refers broadly to polyhydric alcohol compounds. Polyols can be any water-soluble poly(alkylene oxide) polymer for example, and can have a linear or branched chain. Preferred polyols include those substituted at one or more hydroxyl positions with a chemical group, such as an alkyl group having between one and four carbons. Typically, the polyol is a poly(alkylene glycol), preferably polyethylene glycol (PEG). However, those skilled in the art recognize that other polyols, such as, for example, poly (propylene glycol) and polyethylene-polypropylene glycol copolymers, can be employed using the techniques for conjugation described herein for PEG. The polyols of the disclosure include those well known in the art and those publicly available, such as from commercially available sources.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

A "port delivery system" or "PDS" is an implantable device for the eye with a refillable reservoir that allows delivery of a therapeutic agent over an extended period of time. The implant is constructed having a refill port in communication with a reservoir and a release control element that determines the rate of drug release into the eye. See, for example, US20100174272, 8,277,830; 8,399,006; 8,795,712; and 8,808,727.

A "small-bore needle" refers to a needle for injection of fluid composition of about 30, 29, 28, 27, 26, 25, 24, 23, or 22 gauge or higher, such as a 30 gauge needle. In some embodiments, the small-bore needle has standard sized walls. In another embodiment, the small-bore needle has thin walls, which may be preferred for viscous solutions.

II. Compositions and Methods

Provided herein are novel Tie2 agonists which activate Tie2 function as demonstrated by, e.g., phosphorylation of Tie2. Direct agonism may be therapeutically advantageous in its more potent activation of Tie2 signaling, driving vision improvement in cases where the endogenous agonist Ang1 is scarce or absent. An activator of Tie2 may be advantageous over an inhibitor of Ang2 because it may both block binding of Ang2 (block Ang2 antagonist function) and bind Tie2 directly to activate Tie2 activity, e.g., increase phosphorylation of Tie2 and/or Akt. Activation of Tie2 has been shown to require clustering of Tie2 upon binding of a ligand, accordingly, Tie2 agonists provided herein are multimeric, preferably hexameric or octameric. Multimeric Tie2 agonists described herein can have the added unexpected advantage of not significantly reducing cellular Tie2 levels, in vitro or in vivo. Moreover, the multimeric Tie2 agonists described herein can be formulated for intravitreal injection and possess a molecular size that imparts advantageous pharmacokinetics and thereby pharmacodynamics. Data are provided to show that the multimeric Tie2 agonists reduce endothelial cell membrane permeability and strengthen cell-cell junctions (see, e.g., Example 10).

In one aspect, the invention is based, in part, on antibodies that bind Tie2. In particular, provided herein are binding agents (also referred to herein as conjugates) comprising more than one anti-Tie2 antibody or antigen-binding fragment thereof, such as (but not limited to) an anti-Tie2 Fab. It may be preferred that the binding agent comprises more than 4 (e.g., comprises 5, 6, 7, 8, 9 or 10) anti-Tie2 antibodies, e.g., more than 4 anti-Tie2 Fabs, such that binding of the Tie2 binding agent to Tie2 located on a cellular surface is associated with Tie2 activation. Tie2 clustering can also occur upon binding of the binding agent to Tie2.

In some embodiments, it is advantageous to have a Tie2 binding agent that, upon binding to Tie2 on the protein surface, does not cause a significant reduction in Tie2 protein levels on the cell surface. In some embodiments, Tie2 binding agents which activate Tie2 comprise anti-Tie2 antibodies (Fabs) which have affinities for Tie2 ranging from about 0.1 uM to 10 uM.

Activation of the Tie2 protein can be measured in vitro by measuring an increase in phosphorylation of the Tie2 protein (e.g., by western blot) or measuring an increase in phosphorylation of the associated Akt protein (AKT serine/threonine kinase 1, e.g., GenBank Accession No. NP_001014431) using materials and methods readily known to the ordinarily skilled artisan. In certain embodiments, antibodies that bind to Tie2 are provided as well as compositions comprising more than one antibody that binds Tie2. Antibodies and compositions comprising multiple antibodies of the invention are useful, e.g., for the diagnosis or treatment of vascular permeability disorders, especially in the eye, that are associated with Tie2 function.

A. Exemplary Anti-Tie2 Binding Agents

In one aspect, the invention provides Tie2 binding agents comprising isolated antibodies that bind to Tie2. In some embodiments, the Tie2 binding agents comprise a multi-armed moiety wherein each of the arms is conjugated or linked to an anti-Tie2 antibody or fragment thereof. In preferred embodiments, the anti-Tie2 antibody or fragment thereof is an anti-Tie2 Fab. Examples of multi-armed moieties include but are not limited to multi-armed polyols (e.g., polyethylene glycols (PEGs)), IgMs, and multimeric, e.g., hexameric, peptides. In certain embodiments, Tie2 binding agents are provided which comprises more than one anti-Tie2 antibody or fragment thereof, wherein the anti-Tie2 antibody (when not part of the Tie2 binding agent, but optionally formatted as a full-length antibody) binds to Tie2 with an affinity such as with a $K_D$ of less than 100 uM, or less than 50 uM or less than 10 uM and/or a $K_D$ of greater than 1 uM. It is understood that the affinity is measured using the antibody, not the Tie2 binding agent comprising more than one anti-Tie2 antibody. In some embodiments, the affinity is monovalent affinity. Further, provided are Tie2 binding agents and Tie2 antibodies which activate Tie2 activity (e.g., function as Tie2 agonists). Activation of Tie2 is measured, for example, by measuring increases in phosphorylation of Tie2 and/or increases in phosphorylation of AKT in an in vitro assay. In some embodiments, the Tie2 binding agent does not downregulate (decrease) Tie2 proteins levels in a cell by more than about 5%, 10%, 15%, 20%, 25%, 30%, 40%, 50%, 60%, 75%, or 85%. In alternative embodiments, the Tie2 binding agent reduces Tie2 protein levels in a cell by less than about 5%, 10%, 15%, 20%, 25%, 30%, 40%, 50%, 60%, or 75%. In some embodiments, the Tie2 binding agent reduces vascular permeability. Reduction of vascular endothelial cell permeability can be measured in vitro or in vivo. In some embodiments, Tie2 binding agents may increase translocation of Tie2 to cell-cell junctions and/or facilitate structural organization of actin and/or cadherin. In preferred embodiments, the Tie2 binding agent comprises a hexameric PEG molecule wherein each of the 6 arms is conjugated to an anti-Tie2 Fab. Alternatively, the PEG molecule comprises 8 arms. In some embodiments, the Tie2 binding agent comprises more than 1 of the anti-Tie2 antibodies or fragment thereof as described herein. The invention also provides anti-Tie2 antibodies or fragments thereof which bind Tie2. In some embodiments, the anti- Tie2 antibodies or fragments thereof bind to the Ig2 domain of Tie2 (e.g., to an epitope at least partially present within amino acid residues 23 to 120 of SEQ ID NO:1).

In one aspect, the invention provides an antibody that specifically binds Tie2 or an antigen-binding fragment thereof comprising at least one, two, three, four, five, or six CDRs selected from (a) CDR-H1 comprising the amino acid sequence of SEQ ID NO:3; (b) CDR-H2 comprising the amino acid sequence of SEQ ID NO:4; (c) CDR-H3 comprising the amino acid sequence of SEQ ID NO:5 wherein X1 is M, L, K, F, Y, R, N, Q, H or W and/or X2 is F, Y L, Q, I, K, or H; SEQ ID NO:6; or SEQ ID NO:7; (d) CDR-L1 comprising the amino acid sequence of SEQ ID NO:8; (e) HVR-L2 comprising the amino acid sequence of SEQ ID NO:9; and (f) HVR-L3 comprising the amino acid sequence of SEQ ID NO:10. In particular embodiments, the CDR-H3 comprises SEQ ID NO:7.

In one aspect, the invention provides an antibody comprising at least one, at least two, or all three VH domain CDR sequences selected from (a) CDR-H1 comprising the amino acid sequence of SEQ ID NO:3; (b) CDR-H2 comprising the amino acid sequence of SEQ ID NO:4; and (c) CDR-H3 comprising the amino acid sequence of SEQ ID NO:5, wherein X1 is M, L, K, F, Y, R, N, Q, H or W and/or X2 is F, Y L, Q, I, K, or H. All possible combinations of the above substitutions are encompassed by the consensus sequences of SEQ ID NO:5. In one embodiment, the CDR-H3 comprises the amino acid sequence of SEQ ID NO:6. In another embodiment, the CDR-H3 comprises the amino acid sequence of SEQ ID NO:7

In another aspect, the invention provides an antibody comprising at least one, at least two, or all three VL domain CDR sequences selected from (a) HVR-L1 comprising the amino acid sequence of SEQ ID NO:8; (b) CDR-L2 comprising the amino acid sequence of SEQ ID NO:9; and (c) CDR-L3 comprising the amino acid sequence of SEQ ID NO:10. In one embodiment, the VL domain comprises (a) CDR-L1 comprising the amino acid sequence of SEQ ID NO:8; (b) CDR-L2 comprising the amino acid sequence of SEQ ID NO:9; and (c) CDR-L3 comprising the amino acid sequence of SEQ ID NO:10.

In another aspect, an antibody of the invention comprises (a) a VH domain comprising at least one, at least two, or all three VH CDR sequences selected from (i) CDR-H1 comprising the amino acid sequence of SEQ ID NO:3, (ii) CDR-H2 comprising the amino acid sequence of SEQ ID NO:4, and (iii) CDR-H3 comprising an amino acid sequence selected from SEQ ID NO:5, wherein X1 is M, L, K, F, Y, R, N, Q, H or W and/or X2 is F, Y L, Q, I, K, or H; SEQ ID NO:6; and SEQ ID NO:7; and (b) a VL domain comprising at least one, at least two, or all three VL CDR sequences selected from (i) CDR-L1 comprising the amino acid sequence of SEQ ID NO:8, (ii) CDR-L2 comprising the amino acid sequence of SEQ ID NO:9, and (c) CDR-L3 comprising the amino acid sequence of SEQ ID NO:10.

In another aspect, the invention provides an antibody comprising a VH domain comprising (a) CDR-H1 comprising the amino acid sequence of SEQ ID NO:3; (b) CDR-H2 comprising the amino acid sequence of SEQ ID NO:4; (c) HVR-H3 comprising the amino acid sequence of SEQ ID NO:5, wherein X1 is M, L, K, F, Y, R, N, Q, H or W and/or X2 is F, Y L, Q, I, K, or H, SEQ ID NO:6 or SEQ ID NO:7; and a VL domain comprising (d) CDR-L1 comprising the amino acid sequence of SEQ ID NO:8; (e) CDR-L2 comprising the amino acid sequence of SEQ ID NO:9; and (f) CDR-L3 comprising an amino acid sequence selected from SEQ ID NO:10. In some embodiments, the VH domain comprises a sequence having at least 90%, 91%, 92%, 93%, 94%, 95%, 96%, 97%, 98%, 99%, or 100% sequence identity to the amino acid sequence of SEQ ID NO:20 and the VL domain comprises a sequence having 90%, 91%, 92%, 93%, 94%, 95%, 96%, 97%, 98%, 99%, or 100% sequence identity to the amino acid sequence of SEQ ID NO:21.

In any of the above embodiments, an anti-Tie2 antibody may be humanized. In one embodiment, an anti-Tie2 antibody comprises CDRs as in any of the above embodiments, and further comprises an acceptor human framework, e.g. a human immunoglobulin framework or a human consensus framework. In another embodiment, an anti-Tie2 antibody comprises CDRs as in any of the above embodiments, and further comprises a VH framework FR1 sequence of SEQ ID NO:11, a VH framework FR2 sequence of SEQ ID NO:12, a VH framework FR3 sequence of SEQ ID NO:13, and/or a VH framework FR4 sequence of SEQ ID NO:14. In other embodiments, the anti-Tie2 antibody comprises a VL framework FR1 sequence of SEQ ID NO:15, a VL framework FR2 sequence of SEQ ID NO:16, a VL framework FR3 sequence of SEQ ID NO:17, and/or a VL framework FR3 sequence of SEQ ID NO:18.

In another aspect, an anti-Tie2 antibody or antigen-binding fragment thereof comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:20. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Tie2 antibody comprising that sequence retains the ability to bind to Tie2. In certain embodiments, a total of 1 to 10 amino acids have been substituted, inserted and/or deleted in SEQ ID NO:20. In certain embodiments, substitutions, insertions, or deletions occur in regions outside the CDRs (i.e., in the FRs). Optionally, the anti-Tie2 antibody comprises the VH sequence in SEQ ID NO:20, including post-translational modifications of that sequence. In a particular embodiment, the VH comprises one, two or three CDRs selected from: (a) CDR-H1 comprising the amino acid sequence of SEQ ID NO:3, (b) CDR-H2 comprising the amino acid sequence of SEQ ID NO:4, and (c) CDR-H3 comprising the amino acid sequence of SEQ ID NO:7.

In another aspect, an anti-Tie2 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:21. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Tie2 antibody comprising that sequence retains the ability to bind to Tie2. In certain embodiments, a total of 1 to 10 amino acids have been substituted, inserted and/or deleted in SEQ ID NO:21. In certain embodiments, the substitutions, insertions, or deletions occur in regions outside the HVRs (i.e., in the FRs). Optionally, the anti-Tie2 antibody comprises the VL sequence in SEQ ID NO:21, including post-translational modifications of that sequence. In a particular embodiment, the VL comprises one, two or three HVRs selected from (a) HVR-L1 comprising the amino acid sequence of SEQ ID NO:8; (b) HVR-L2 comprising the amino acid sequence of SEQ ID NO:9; and (c) HVR-L3 comprising the amino acid sequence of SEQ ID NO:10.

In another aspect, an anti-Tie2 antibody is provided, wherein the antibody comprises a VH as in any of the embodiments provided above, and a VL as in any of the embodiments provided above. In one embodiment, the antibody comprises the VH and VL sequences in SEQ ID NO:20 and SEQ ID NO:21, respectively, including post-translational modifications of those sequences. In a further aspect, the invention provides an antibody that binds to the same epitope as an anti-Tie2 antibody provided herein. For example, in certain embodiments, an antibody is provided that binds to the same epitope as an anti-Tie2 antibody comprising a VH sequence of SEQ ID NO:20 and a VL sequence of SEQ ID NO:21. In certain embodiments, an antibody is provided that binds to an epitope within a fragment of Tie2, such as the Ig1 domain of Tie2 wherein the Ig1 domain comprises amino acids 23-120 of SEQ ID NO:1.

In a further aspect of the invention, an anti-Tie2 antibody according to any of the above embodiments is a monoclonal antibody, including a chimeric, humanized or human antibody. In one embodiment, an anti-Tie2 antibody is an antibody fragment, e.g., a Fv, Fab, Fab', scFv, diabody, or F(ab')2 fragment. In another embodiment, the antibody is a full length antibody, e.g., an intact, e.g. IgG1, antibody or other antibody class or isotype as defined herein.

In a further aspect, an anti-Tie2 antibody according to any of the above embodiments may incorporate any of the features, singly or in combination, as described in Sections 1-7 below:

1. Antibody Affinity

In certain embodiments, an antibody provided herein has a dissociation constant (Kd) of ≤10 µM, ≤100 µM, ≤10 µM, ≤1 µM, ≤100 nM, ≤10 nM, ≤1 nM, ≤0.1 nM, ≤0.01 nM, or ≤0.001 nM, and/or ≥0.01 µM, 0.1 µM, or 1 µM (e.g., $10^{-5}$ M or less, $10^{-6}$ M or less, $10^{-8}$ M or less, e.g., from 1 µM to 10 µM, e.g., from 0.1 µM to 10 µM, e.g. from $10^{-6}$ M to $10^{-9}$ M, e.g. from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, NJ) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

In some embodiments, the C-terminus of the heavy chain of a Fab fragment ends in the amino acids "CDKTHT" (SEQ ID NO:75), "CDKTHL" (SEQ ID NO:76), "CDKTH" (SEQ ID NO:77), "CDKT" (SEQ ID NO:78), "CDK," or "CD." In some embodiments, the C-terminus of the heavy chain of the Fab fragment ends in the sequence CDKTHX (SEQ ID NO:79), wherein X is any amino acid except T. Truncations and/or mutations at the C terminus may be able to reduce or eliminate AHA-reactivity against the Fab, without compromising thermostability or expression. In some embodiments, the C-terminus of the heavy chain of a Fab fragment ends in the amino acids "CDKTHTC" (SEQ ID NO:80), "CDKTH- TCPPC" (SEQ ID NO:81), "CDKTHTCPPS" (SEQ ID NO:82), "CDKTHTSPPC" (SEQ ID NO:83), "CDKTHTAPPC" (SEQ ID NO:84), "CDKTHTSGGC" (SEQ ID NO:85), or "CYGPPC" (SEQ ID NO:86). In some such embodiments, a free cysteine in the C-terminal amino acids may be amenable to conjugation, for example, to a polymer such as PEG.

Diabodies are antibody fragments with two antigen-binding sites that may be bivalent or bispecific. See, for example, EP404097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods is known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, New Jersey, 2001) and further described, e.g., in the McCafferty et al., *Nature* 348:552-554; Clackson et al., *Nature* 352: 624-628 (1991); Marks et al., *J Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for Tie2 and the other is for any other antigen. In certain embodiments, bispecific antibodies may bind to two different epitopes of Tie2. Bispecific antibodies may also be used to localize cytotoxic agents to cells which express Tie2. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g., Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to Tie2 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |

TABLE 1-continued

| Original Residue | Exemplary Substitutions | Preferred Substitutions |
|---|---|---|
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/

0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (EU numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-Tie2 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-Tie2 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-Tie2 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)), baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TM cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR" CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

C. Assays

Anti-Tie2 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, BIACore®, FACS, or western blot.

In another aspect, competition assays may be used to identify an antibody that competes with an anti-Tie2 antibody which comprises the VH comprising the sequence of SEQ ID NO:20 and a VL comprising the sequence of SEQ ID NO:21 for binding to Tie2 (referred to herein as Tie2.1M100cF). In certain embodiments, such a competing antibody binds to the same epitope (e.g., a linear or a conformational epitope) that is bound by the anti-Tie2 antibody which comprises the VH comprising the sequence of SEQ ID NO:20 and a VL comprising the sequence of SEQ ID NO:21. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized Tie2 is incubated in a solution comprising a first labeled antibody that binds to Tie2 (e.g., Tie2.1M100cF) and a second unlabeled antibody that is being tested for its ability to compete with the first antibody for binding to Tie2. The second antibody may be present in a hybridoma supernatant. As a control, immobilized Tie2 is incubated in a solution comprising the first labeled antibody but not the second unlabeled antibody. After incubation under conditions permissive for binding of the first antibody to Tie2, excess unbound antibody is removed, and the amount of label associated with immobilized Tie2 is measured. If the amount of label associated with immobilized Tie2 is substantially reduced in the test sample relative to the control sample, then that indicates that the second antibody is competing with the first antibody for binding to Tie2. See Harlow and Lane (1988) *Antibodies: A Laboratory Manual* ch. 14 (Cold Spring Harbor Laboratory, Cold Spring Harbor, NY).

2. Activity Assays

In one aspect, assays are provided for identifying anti-Tie2 antibodies thereof having a desired biological activity. Biological activity may include, e.g., binding to Tie2 or a fragment thereof, competing with Ang1 and/or Ang2 for binding to Tie2, activating phosphorylation of the Tie2 protein, activating phosphorylation of Akt, and/or reduction of vascular endothelial cell permeability, either in vivo, in vitro, or ex vivo. Antibodies having such biological activity in vivo and/or in vitro are also provided. In certain embodiments, an antibody of the invention is tested for such biological activity.

In some embodiments, assays are provided for determining Tie2-activating (anti-Tie2 conjugate) activity, such as by a phospho-AKT (pAKT) assay wherein activation of AKT phosphorylation by the anti-Tie2 conjugate indicates that the conjugate as activating (agonist) activity. As readily known by the ordinarily skilled artisan, and as described in Example 3 below, activation of AKT can be demonstrated by a variety of methods, including, e.g., western blot detection of phosphorylated AKT using an antibody specific for phosphorylated AKT or by a FRET assay.

In some embodiments, assays are provided for determining the stability (e.g., thermostability) of an anti-Tie2 antibody, or an antibody conjugate, fusion protein, or polymeric formulation thereof. For example, the stability of an antibody, or an antibody conjugate, fusion protein, or polymeric formulation thereof, may be determined using any method known in the art, for example, differential scanning fluorimetry (DSF), circular dichroism (CD), intrinsic protein fluorescence, differential scanning calorimetry, spectroscopy, light scattering (e.g., dynamic light scattering (DLS) and static light scattering (SLS), self-interaction chromatography (SIC).

In some embodiments, assays are provided for determining the stability of anti-Tie2 conjugates. The stability of an assay may be determined as described herein, for example, using capillary electrophoresis laser induced fluorescence (CE-LIF), as described, for example, in Example 13.

D. Immunoconjugates

The invention also provides immunoconjugates comprising an anti-Tie2 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

E. Conjugates

The invention also provides conjugates comprising any anti-Tie2 antibody or Tie2-binding fragment thereof provided herein conjugated to one or more heterologous molecules, such as polyols.

1. Multi-Armed Polymers

In some embodiments, the conjugates of the present disclosure can be made by derivatizing the anti-Tie2 antibodies described herein by conjugating anti-Tie2 Fabs or variants thereof with a multi-armed polymer. It will be appreciated that any multi-armed polymer that provides the conjugate with the desired size or that has the selected average molecular weight as described herein is suitable for use in constructing the antibody-polymer conjugates of the inventions.

Many polymers are suitable for use in pharmaceuticals. See, e.g., Davis et al., Biomedical Polymers: Polymeric Materials and Pharmaceuticals for Biomedical Use, pp. 441-451 (1980). In some embodiments of the present disclosure, a non-proteinaceous polymer is used to form the conjugates of the disclosure. The non-proteinaceous polymer ordinarily is a hydrophilic synthetic polymer, i.e., a polymer not otherwise found in nature. However, polymers which exist in nature and are produced by recombinant or in vitro methods may also be useful, as are polymers which are isolated from native sources.

In some embodiments, the anti-Tie2 Fabs are derivitized by conjugating (e.g., covalently linking) the Fabs or variants thereof to a multi-armed polyol. Thus, in some embodiments, the disclosure is directed to a conjugate comprising one or more anti-Tie2 Fabs or variants thereof disclosed herein covalently linked to one or more multi-armed polyols, preferably a six-armed polyol. The polyol employed can be any water-soluble poly (alkylene oxide) polymer and can have a linear or branched chain. Suitable polyols include those substituted at one or more hydroxyl positions with a chemical group, such as an alkyl group having between one and four carbons. Typically, the polyol is a poly(alkylene glycol), such as polyethylene glycol (PEG), and thus, for ease of description, the remainder of the discussion relates to an exemplary embodiment wherein the polyol employed is PEG, and the process of conjugating the polyol to a polypeptide is termed "PEGylation." However, those skilled in the art will recognize that other polyols, for example, poly(propylene glycol) and polyethylene-polypropylene glycol copolymers, can be employed using the techniques for conjugation similar to those described herein for PEG.

The polyols used to form the conjugates of the present disclosure are multi-armed polyols. As used herein, "multi-armed polyol" refers to a polyol comprising a core structure to which at least two arms are attached. The multi-armed polyol may be, for example, a dimer (two arms), a tetramer (four arms), a hexamer (six arms), an octamer (eight arms), etc. In some aspects, the multi-armed polyol is a multi-armed PEG.

The weight average molecular weight of the multi-armed PEG used in the PEGylation of the anti-Tie2 antibodies and antibody variants can vary, and typically may range from about 500 to about 300,000 daltons (D). In some embodiments, the weight average molecular weight of the multi-armed PEG is from about 1,000 to about 100,000 D, from about 1,000 to about 40,000 D, from about 1,000 to about 20,000 D, from about 1,000 to about 10,000 D, from about 10,000 to about 20,000 D, from about 5,000 to about 10,000 D or from about 1,000 to about 5,000 D. In preferred embodiments, PEGylation is carried out with a multi-armed PEG having a weight average molecular weight of about 6,000 D.

A variety of methods for PEGylating proteins are known in the art. Specific methods of producing proteins conjugated to PEG include the methods described in U.S. Pat. Nos. 4,179,337, 4,935,465, and 5,849,535, all of which are herein incorporated by reference in their entirety. Typically, the protein is covalently bonded via one or more of the amino acid residues of the protein to a terminal reactive group on the polymer. The polymer with the reactive group(s) is designated herein as an activated or functionalized polymer (e.g., a functionalized PEG). The reactive group selectively reacts with free sulfhydryl or amino or other reactive groups on the antibody or antibody variant. The multi-armed PEG polymer can be coupled to the sulfhydryl or amino or other reactive group on the antibody or antibody variant in either a random or a site specific manner. It will be understood, however, that the type and amount of the reactive group chosen, as well as the type of polymer employed, to obtain optimum results, will depend on the particular antibody or antibody variant employed to limit, and preferably substantially prevent, the reactive group react with too many active groups on the antibody. As it may not be possible to sufficiently limit or prevent this in some instances, typically from about 0.05 to about 1000 moles, or, in some embodiments, from about 0.05 to about 200 moles of functionalized polymer per mole of antibody, depending on antibody concentration, may be employed. The final amount of functionalized polymer per mole of antibody is a balance to maintain optimum activity, while at the same time optimizing, if possible, the vitreous humor, retina, and/or aqueous humor half-life of the antibody.

While the residues may be any reactive amino acid on the antibody or antibody variant, such as the N-terminal amino acid group, in some embodiments, the reactive amino acid is cysteine, which is linked to the reactive group of the functionalized polymer through its free thiol group as shown, for example, in WO 99/03887, WO 94/12219, WO 94/22466, U.S. Pat. Nos. 5,206,344, 5,166,322, and 5,206,344, all of which are herein incorporated by reference in their entirety. In such embodiments, the polymer may comprise at least one terminal reactive group that is capable of reacting specifically with the free sulfhydryl or thiol group(s) on the parental antibody. Such groups include, but are not limited to, maleimide, a sulfhydryl, a thiol, trifluoromethanesulfonate, tosylate, aziridine, epoxide, a pyridyl disulfide, succinimidyl ester, —NH$_2$, an aldehyde, a haloacetate, a haloacetamide, and a para-nitrophenyl carbonate, among others. The polymer can be coupled to the parental antibody using any protocol suitable for the chemistry of the coupling system selected, such as the protocols and systems described in U.S. Pat. Nos. 4,179,337, 7,122,636, and Jevsevar, et al., Biotech J., Vol. 5, pp. 113-128 (2010). Alternatively, the reactive amino acid may be lysine, which is linked to the reactive group of the functionalized polymer through its free epsilon-amino group (see, e.g., WO 93/00109, incorporated by reference herein), or glutamic or aspartic acid, which is linked to the polymer through an amide bond. The reactive group of the polymer can then react with, for example, the α (alpha) and ε (epsilon) amines or sulfhydryl groups of proteins to form a covalent bond. It will be appreciated that the present disclosure is not limited to conjugates utilizing any particular type of linkage between an antibody or antibody fragment and a polymer.

Suitable functionalized multi-armed PEGs for use in preparing the conjugates of the disclosure can be produced by a number of conventional reactions. For example, a N-hydroxysuccinimide ester of a PEG (M-NHS-PEG) can be prepared from a PEG-monomethyl ether by reaction with N,N'-dicyclohexylcarbodiimide (DCC) and N-hydroxysuccinimide (NHS), according to the method of Buckmann and Merr, Makromol. Chem., Vol. 182, pp. 1379-1384 (1981). In addition, a PEG terminal hydroxy group can be converted to an amino group, for example, by reaction with thionyl bromide to form PEG-Br, followed by aminolysis with excess ammonia to form PEG-NH$_2$. The PEG-NH$_2$ can then be conjugated to the antibody or antibody variant of interest using standard coupling reagents, such as Woodward's Reagent K. Furthermore, a PEG terminal-CH$_2$OH group can be converted to an aldehyde group, for example, by oxidation with MnO$_2$. The aldehyde group can be conjugated to the antibody or antibody variant by reductive alkylation with a reagent such as cyanoborohydride.

In some embodiments, the multi-armed PEG used to prepare the conjugates of the present disclosure has the structure of general formula (I):

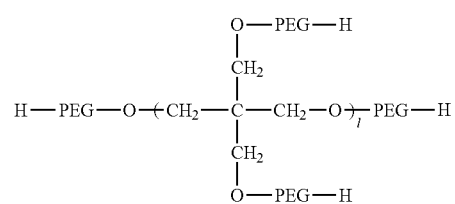

wherein the PEGs are the same or different —(CH$_2$CH$_2$O)m-, wherein each m denotes the length or size of the particular arm of the polyol (PEG) and is independently an integer of from about 45 to about 1000, about 3 to about 250, or from about 50 to about 200, or from about 100 to about 150; and l is an integer ≥2, preferably 2 or 3.

In some embodiments, the multi-armed PEG has the structure of general formula (I), wherein l is 2, and the multi-armed PEG is a hexamer. In another embodiment, the multi-armed PEG has the structure of general formula (I), wherein l is 3, and the multi-armed PEG is an octamer.

The multi-armed PEG having the structure of general formula (I) may be functionalized to, for example, attach a terminal reactive group suitable for reacting with or conjugating to the antibody (e.g., antibody fragment) using any of the techniques described above to produce a functionalized multi-armed PEG. In other embodiments, however, the multi-armed PEG can be covalently linked to the anti-Tie2 antibodies through a multifunctional crosslinking agent which reacts with the PEG and one or more amino acid residues of the antibody or antibody variant to be linked, as described in, for example, U.S. Pat. No. 7,122,636, which is herein incorporated by reference in its entirety.

In other aspects, the multi-armed PEG used to prepare the conjugates of the present disclosure is a functionalized multi-armed PEG comprising at least one terminal reactive group. The terminal reactive group can conjugate directly to the anti-Tie2 antibodies to form the conjugates of the present disclosure. In some embodiments, the functionalized multi-armed PEG has the structure of general formula (Ia):

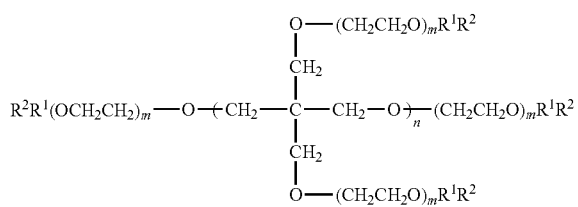

(Ia)

wherein each m denotes the length or size of the particular arm of the polyol (PEG) and is independently an integer of from about 45 to about 1000, about 3 to about 250, or from about 50 to about 200, or from about 20 to 30, or from about 100 to about 150; and n is an integer from about 1 to about 10; each $R^1$ is independently either absent, or is a linking group; and each $R^2$ is independently either hydrogen or a terminal reactive group; wherein at least one $R^2$ is a terminal reactive group. In some embodiments, $R^2$ is independently selected form a thiol reactive group, an amino reactive group, and combinations thereof.

Figure 39:
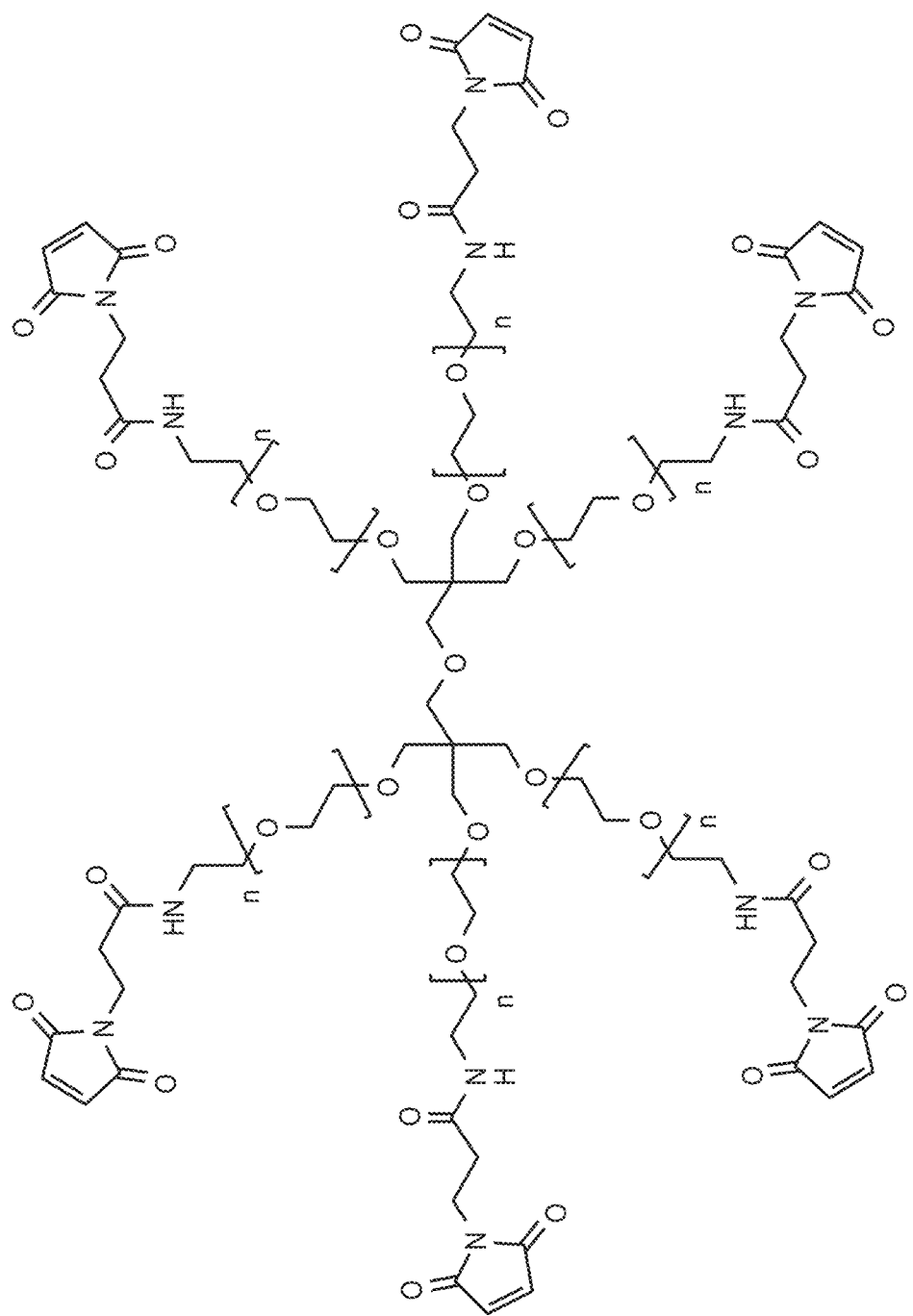
FIG. 39 shows the structure of the PEG conjugate hexamer core molecule which is conjugated to anti-Tie2 antibodies according to the present disclosure.

In some embodiments, the functionalized multi-armed PEG has the structure of general formula (Ia), wherein n is an integer from 2 to 3. In preferred embodiments, the functionalized multi-armed PEG has the structure of general formula (Ia), wherein n is 2, and the multi-armed PEG is a hexamer. In another embodiment, the functionalized multi-armed PEG has the structure of general formula (Ia), wherein n is 3, and the multi-armed PEG is an octamer. In a preferred embodiment, the functionalized multi-armed PEG has the structure of general formula (Ia) wherein n is 2 as shown in FIG. 39.

In another aspect, the multi-armed PEG used to prepare the conjugates of the present disclosure has the structure of general formula (II):

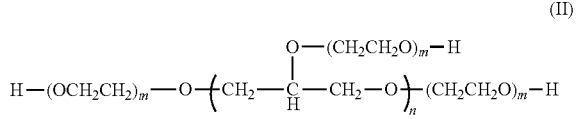

(II)

wherein each m denotes the length or size of the particular arm of the polyol (PEG) and is independently an integer of from about 45 to about 1000, about 3 to about 250, or from about 50 to about 200, or from about 100 to about 150; and n is an integer from about 1 to about 10.

In some embodiments, the multi-armed PEG has the structure of general formula (II), wherein n is 2, and the multi-armed PEG is a tetramer. In another embodiment, the multi-armed PEG has the structure of general formula (II), wherein n is 4, and the multi-armed PEG is a hexamer. In another embodiment, the multi-armed PEG has the structure of general formula (II), wherein n is 6, and the multi-armed PEG is an octamer.

In another aspect, the multi-armed PEG used to prepare the conjugates of the present disclosure has the structure of general formula (III):

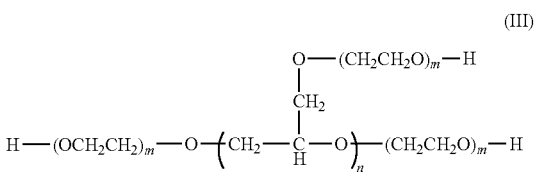

(III)

wherein each m denotes the length or size of the particular arm of the polyol (PEG) and is independently an integer of from about 45 to about 1000, about 3 to about 250, or from about 50 to about 200, or from about 100 to about 150; and n is an integer from about 1 to about 10.

In some embodiments, the multi-armed PEG has the structure of general formula (III), wherein n is 2, and the multi-armed PEG is a tetramer. In another embodiment, the multi-armed PEG has the structure of general formula (III), wherein n is 4, and the multi-armed PEG is a hexamer. In another embodiment, the multi-armed PEG has the structure of general formula (III), wherein n is 6, and the multi-armed PEG is an octamer.

In another aspect, the multi-armed PEG used to prepare the conjugates of the present disclosure has the structure of general formula (IV):

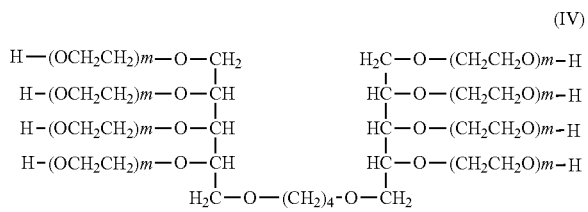

(IV)

wherein each m denotes the length or size of the particular arm of the polyol (PEG) and is independently an integer of from about 45 to about 1000, about 3 to about 250, or from about 50 to about 200, or from about 100 to about 150.

The multi-armed PEG having the structure of any of general formulas (I) to (IV) may be functionalized to, for example, attach a terminal reactive group suitable for reacting with or conjugating to the antibody (e.g., antibody fragment) using any of the techniques described above to produce a functionalized multi-armed PEG. In other embodiments, however, the multi-armed PEG can be covalently linked to the anti-Tie2 antibodies through a multifunctional crosslinking agent which reacts with the PEG and one or more amino acid residues of the antibody or antibody variant to be linked, as described in, for example, U.S. Pat. No. 7,122,636, which is herein incorporated by reference in its entirety.

In other aspects, the multi-armed PEG used to prepare the conjugates of the present disclosure is a functionalized multi-armed PEG comprising at least one terminal reactive group. The terminal reactive group can conjugate directly to the anti-Tie2 antibodies to form the conjugates of the present disclosure. In some embodiments, the functionalized multi-armed PEG has the structure of general formula (Ia):

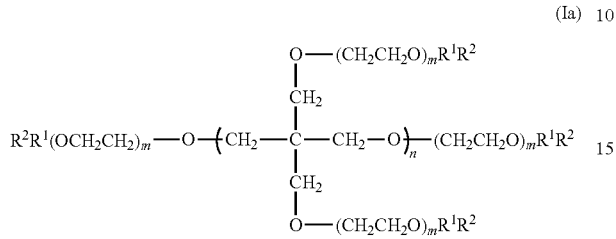

(Ia)

wherein each m denotes the length or size of the particular arm of the polyol (PEG) and is independently an integer of from about 45 to about 1000, about 3 to about 250, or from about 50 to about 200, or from about 100 to about 150; and n is an integer from about 1 to about 10; each $R^1$ is independently either absent, or is a linking group; and each $R^2$ is independently either hydrogen or a terminal reactive group; wherein at least one $R^2$ is a terminal reactive group. In some embodiments, $R^2$ is independently selected from a thiol reactive group, an amino reactive group, and combinations thereof.

In some embodiments, the functionalized multi-armed PEG has the structure of general formula (Ia), wherein n is an integer from 1 to 3. In some embodiments, the functionalized multi-armed PEG has the structure of general formula (Ia), wherein n is 1, and the multi-armed PEG is a tetramer. In another embodiment, the functionalized multi-armed PEG has the structure of general formula (Ia), wherein n is 2, and the multi-armed PEG is a hexamer. In another embodiment, the functionalized multi-armed PEG has the structure of general formula (Ia), wherein n is 3, and the multi-armed PEG is an octamer. In such embodiments, the hexamer has the structure of general formula (Ib):

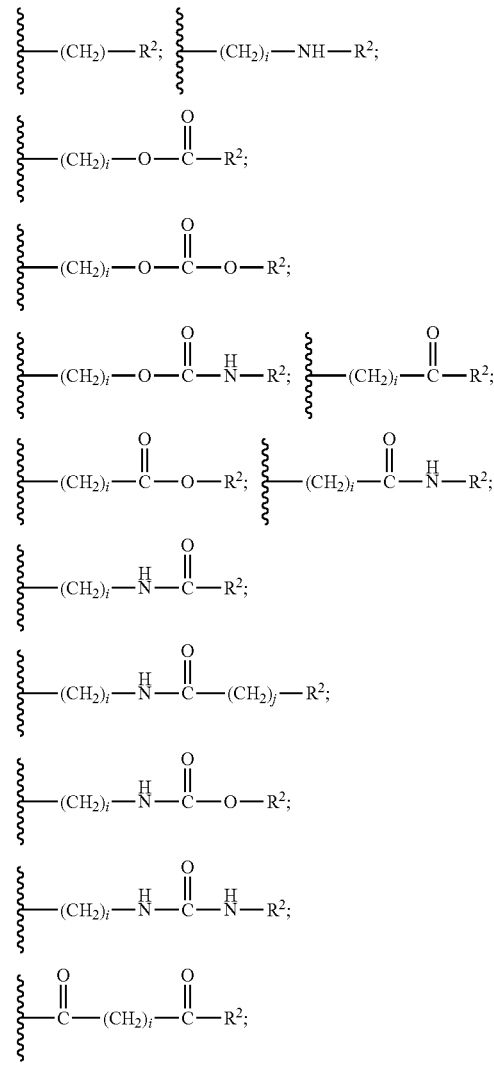

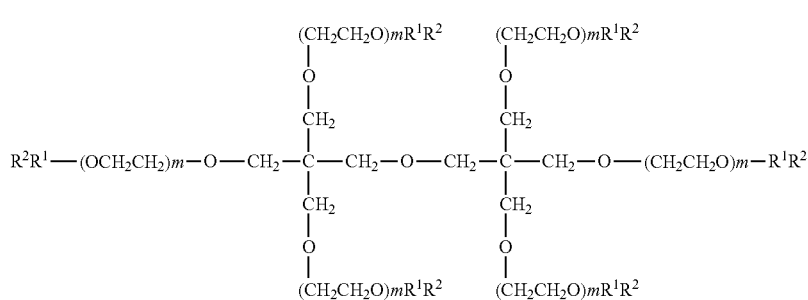
(Ib)

wherein m, le, and $R^2$ are as defined above.

Multi-armed PEGs having the structure of general formula (Ib) have a dipentaerythritol (DP) core structure, and are also referred to herein as DP hexamers.

In some embodiments, the functionalized multi-armed PEG has the structure of general formula (Ib) or (Ic), wherein each $R^1$, when present, is the same or different, and $R^1$ and $R^2$ when taken together are selected from -continued

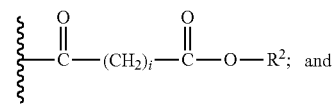

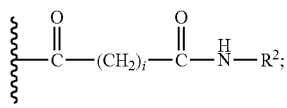

and combinations thereof; wherein each i is independently an integer of 0-10; j is an integer of 0-10; and $R^2$ is as defined herein. In some embodiments, each $R^1$ is a linking group.

In some embodiments, the functionalized multi-armed PEG has the structure of general formula (Ib) or (Ic), wherein $R^1$ and $R^2$, when taken together, are

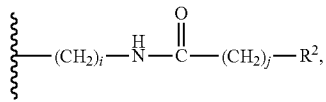

wherein i, j, and $R^2$ are as defined herein. In some embodiments, $R^1$ and $R^2$, when taken together, are

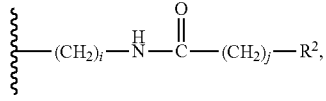

wherein i is 2; j is 2 or 3, and $R^2$ is as defined herein.

In some embodiments, the functionalized multi-armed PEG has the structure of general formula (Ib), wherein each $R^2$ is independently selected from a maleimide, a sulfhydryl, a thiol, trifluoromethanesulfonate, tosylate, aziridine, epoxide, a pyridyl disulfide, succinimidyl ester, $-NH_2$, an aldehyde, a haloacetate, a haloacetamide, and a para-nitrophenyl carbonate. In some embodiments, each $R^2$ is independently a haloacetate selected from bromoacetate, iodoacetate, chloroacetate, and combinations thereof. In some embodiments, each $R^2$ is independently a haloacetamide selected from bromoacetamide, iodoacetamide, chloroacetamide, and combinations thereof. In some embodiments, $R^2$ is a maleimide.

In some embodiments, the functionalized multi-armed PEG has the structure of general formula (Ia) or (Ib), wherein each $R^2$ is a maleimide. In some embodiments, the functionalized multi-armed PEG has the structure of general formula (Ia) or (Ib), wherein $R^1$ and $R^2$, when taken together, are

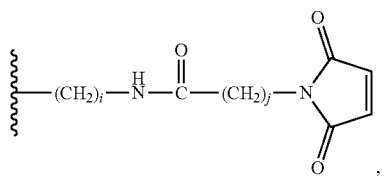

wherein i and j are as defined above. In some embodiments, the functionalized multi-armed PEG has the structure of general formula (Ia) or (Ib), wherein $R^1$ and $R^2$, when taken together, are

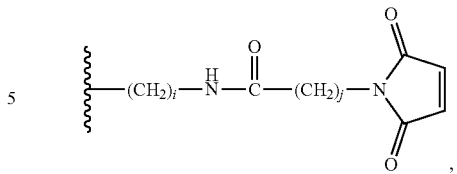

wherein i is 2 and j is 2.

In another aspect, the functionalized multi-armed PEG used to prepare the conjugates of the present disclosure has the structure of general formula (IIa):

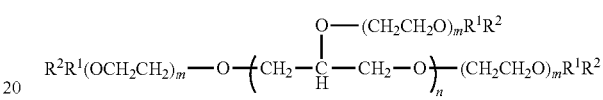

wherein each m denotes the length or size of the particular arm of the polyol (PEG) and is independently an integer of from about 45 to about 1000, about 3 to about 250, or from about 50 to about 200, or from about 100 to about 150; and n is an integer from about 1 to about 10; each $R^1$ is independently either absent, or is a linking group; and each $R^2$ is independently either hydrogen or a terminal reactive group; wherein at least one $R^2$ is a terminal reactive group. In some embodiments, $R^2$ is independently selected form a thiol reactive group, an amino reactive group, and combinations thereof.

In some embodiments, the functionalized multi-armed PEG has the structure of general formula (IIa), wherein n is an integer from 2 to 6. In some embodiments, the functionalized multi-armed PEG has the structure of general formula (IIa), wherein n is 2, and the multi-armed PEG is a tetramer. In some embodiments, the functionalized multi-armed PEG has the structure of general formula (IIa), wherein n is 3. In another embodiment, the functionalized multi-armed PEG has the structure of general formula (IIa), wherein n is 4, and the multi-armed PEG is a hexamer. In another embodiment, the functionalized multi-armed PEG has the structure of general formula (IIa), wherein n is 6, and the multi-armed PEG is an octamer. Octamers having the structure of general formula (IIa) have a hexaglycerin (HG) core structure, and are also referred to herein as HG octamers.

In some embodiments, the functionalized multi-armed PEG has the structure of general formula (IIa), wherein each $R^1$, when present, is the same or different, and $R^1$ and $R^2$ when taken together are selected from

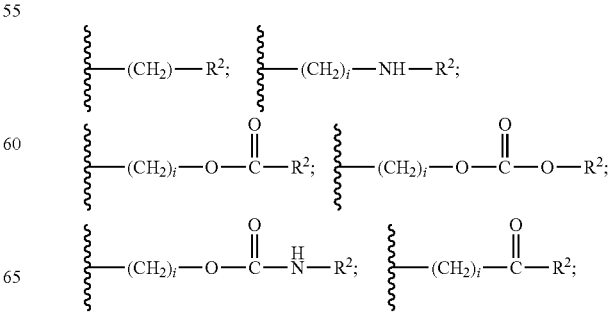

-continued

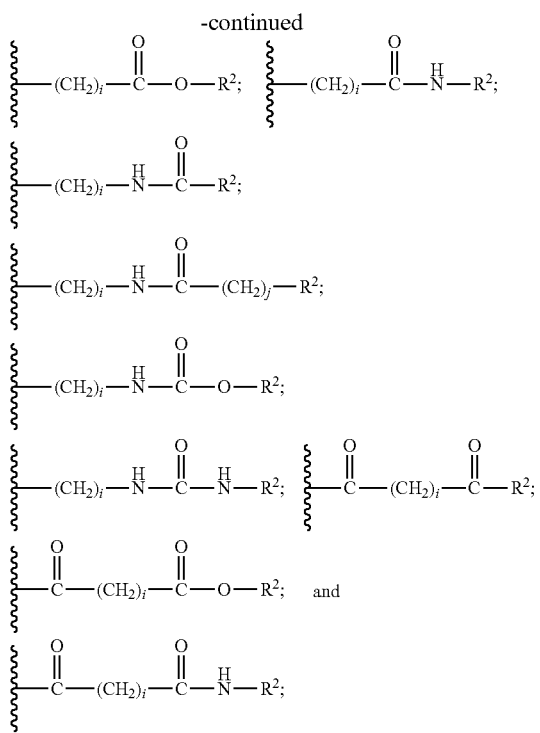

and combinations thereof; wherein each i is independently an integer of 0-10; j is an integer of 0-10; and $R^2$ is as defined herein. In some embodiments, each $R^1$ is a linking group.

In some embodiments, the functionalized multi-armed PEG has the structure of general formula (IIa), wherein $R^1$ and $R^2$, when taken together, are

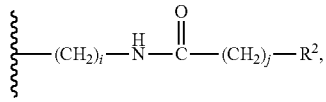

wherein i, j, and $R^2$ are as defined herein. In some embodiments, $R^1$ and $R^2$, when taken together, are

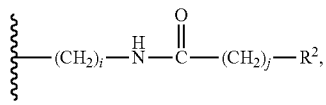

wherein i is 2; j is 2 or 3, and $R^2$ is as defined herein.

In some embodiments, the functionalized multi-armed PEG has the structure of general formula (IIa), wherein each $R^2$ is independently selected from a maleimide, a sulfhydryl, a thiol, trifluoromethanesulfonate, tosylate, aziridine, epoxide, a pyridyl disulfide, succinimidyl ester, —$NH_2$, an aldehyde, a haloacetate, a haloacetamide, and a para-nitrophenyl carbonate. In some embodiments, each $R^2$ is independently a haloacetate selected from bromoacetate, iodoacetate, chloroacetate, and combinations thereof. In some embodiments, each $R^2$ is independently a haloacetamide selected from bromoacetamide, iodoacetamide, chloroacetamide, and combinations thereof. In some embodiments, $R^2$ is a maleimide.

In some embodiments, the functionalized multi-armed PEG has the structure of general formula (IIa), wherein each $R^2$ is a maleimide. In some embodiments, the functionalized multi-armed PEG has the structure of general formula (IIa), wherein $R^1$ and $R^2$, when taken together, are

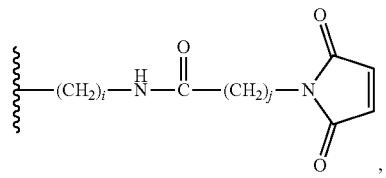

wherein i and j are as defined above. In some embodiments, the functionalized multi-armed PEG has the structure of general formula (IIa), wherein $R^1$ and $R^2$, when taken together, are

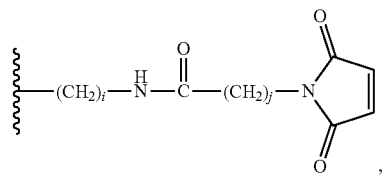

wherein i is 2 and j is 2.

In another aspect, the functionalized multi-armed PEG has the structure of general formula (IIIa):

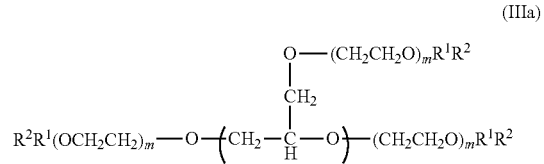

(IIIa)

wherein each m denotes the length or size of the particular arm of the polyol (PEG) and is independently an integer of from about 45 to about 1000, or from about 3 to about 250, or from about 50 to about 200, or from about 100 to about 150; and n is an integer from about 1 to about 10; each $R^1$ is independently either absent, or is a linking group; and each $R^2$ is independently either hydrogen or a terminal reactive group; wherein at least one $R^2$ is a terminal reactive group. In some embodiments, $R^2$ is independently selected form a thiol reactive group, an amino reactive group, and combinations thereof.

In some embodiments, the functionalized multi-armed PEG has the structure of general formula (IIIa), wherein n is an integer from 2 to 6. In some embodiments, the functionalized multi-armed PEG has the structure of general formula (IIIa), wherein n is 2, and the multi-armed PEG is a tetramer. In another embodiment, the functionalized multi-armed PEG has the structure of general formula (IIIa), wherein n is 4, and the multi-armed PEG is a hexamer. In another embodiment, the functionalized multi-armed PEG has the structure of general formula (IIIa), wherein n is 6, and the multi-armed PEG is an octamer. Octamers having the structure of general formula (IIIa) have a hexaglycerol (HGEO) core structure, and are also referred to herein as HGEO octamers.

In some embodiments, the functionalized multi-armed PEG has the structure of general formula (IIIa), wherein each $R^1$, when present, is the same or different, and $R^1$ and $R^2$ when taken together are selected from

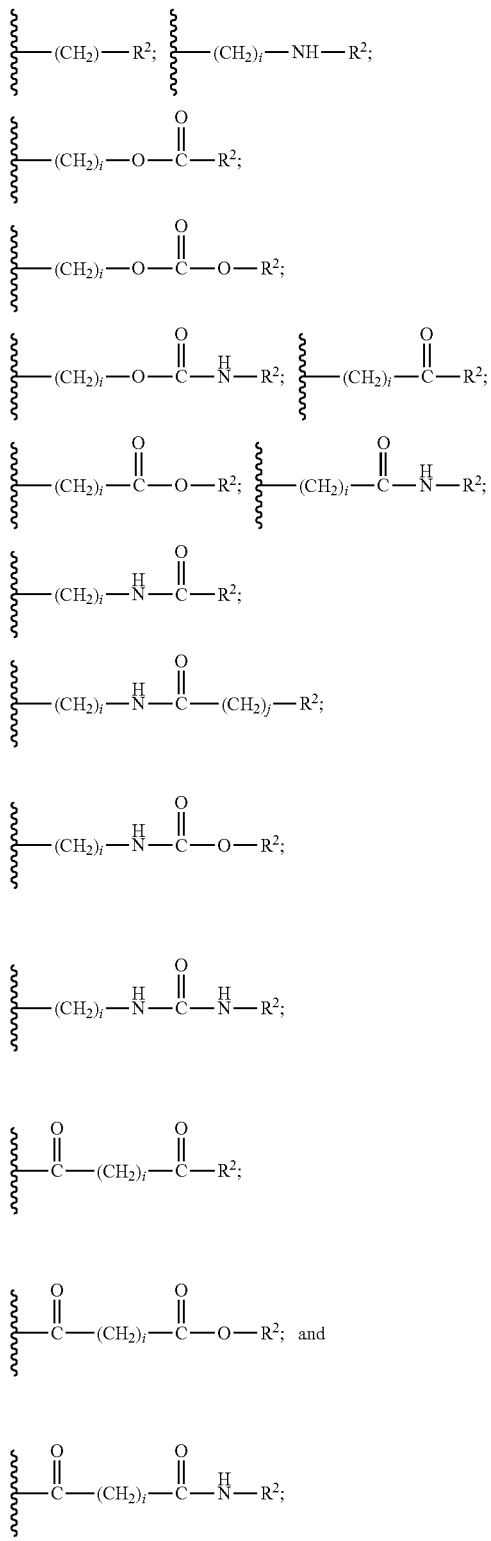

and combinations thereof; wherein each i is independently an integer of 0-10; j is an integer of 0-10; and $R^2$ is as defined herein. In some embodiments, each $R^1$ is a linking group.

In some embodiments, the functionalized multi-armed PEG has the structure of general formula (IIIa), wherein $R^1$ and $R^2$, when taken together, are

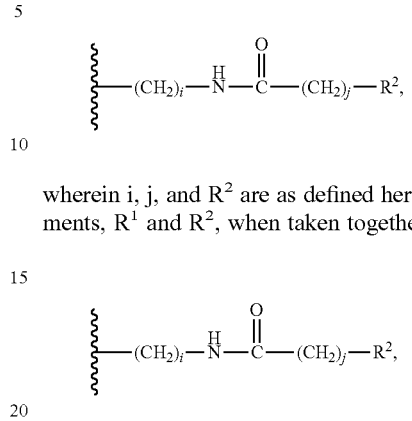

wherein i, j, and $R^2$ are as defined herein. In some embodiments, $R^1$ and $R^2$, when taken together, are

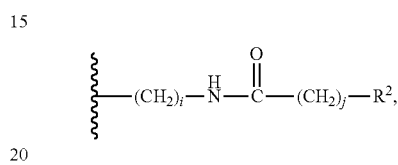

wherein i is 2; j is 2 or 3, and $R^2$ is as defined herein.

In some embodiments, the functionalized multi-armed PEG has the structure of general formula (IIIa), wherein each $R^2$ is independently selected from a maleimide, a sulfhydryl, a thiol, trifluoromethanesulfonate, tosylate, aziridine, epoxide, a pyridyl disulfide, succinimidyl ester, —$NH_2$, an aldehyde, a haloacetate, a haloacetamide, and a para-nitrophenyl carbonate. In some embodiments, each $R^2$ is independently a haloacetate selected from bromoacetate, iodoacetate, chloroacetate, and combinations thereof. In some embodiments, each $R^2$ is independently a haloacetamide selected from bromoacetamide, iodoacetamide, chloroacetamide, and combinations thereof. In some embodiments, $R^2$ is a maleimide.

In some embodiments, the functionalized multi-armed PEG has the structure of general formula (IIIa), wherein each $R^2$ is a maleimide. In some embodiments, the functionalized multi-armed PEG has the structure of general formula (IIIa), wherein $R^1$ and $R^2$, when taken together, are

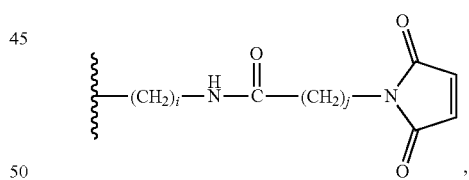

wherein i and j are as defined above. In some embodiments, the functionalized multi-armed PEG has the structure of general formula (IIIa), wherein $R^1$ and $R^2$, when taken together, are

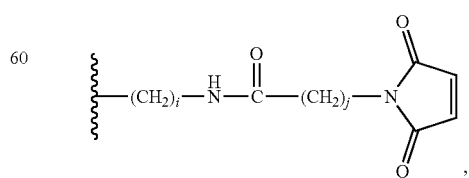

wherein i is 3 and j is 2.

In another aspect, the functionalized multi-armed PEG has the structure of general formula (IVa):

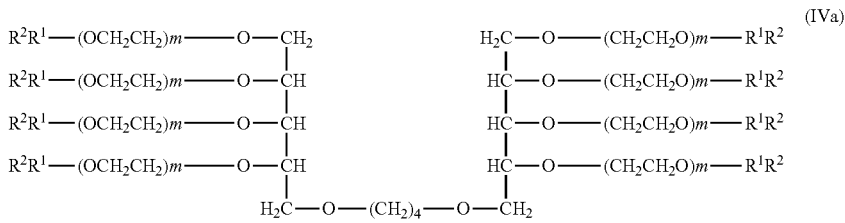

wherein each m denotes the length or size of the particular arm of the polyol (PEG) and is independently an integer of from about 45 to about 1000, or from about 3 to about 250, or from about 50 to about 200, or from about 100 to about 150; each $R^1$ is independently either absent, or is a linking group; and each $R^2$ is independently either hydrogen or a terminal reactive group; wherein at least one $R^2$ is a terminal reactive group. In some embodiments, $R^2$ is independently selected form a thiol reactive group, an amino reactive group, and combinations thereof.

Multi-armed PEGs having the structure of general formula (IVa) have a butanediol core structure, and are also referred to herein as DX octamers.

In some embodiments, the functionalized multi-armed PEG has the structure of general formula (IVa), wherein each $R^1$, when present, is the same or different, and $R^1$ and $R^2$ when taken together are selected from

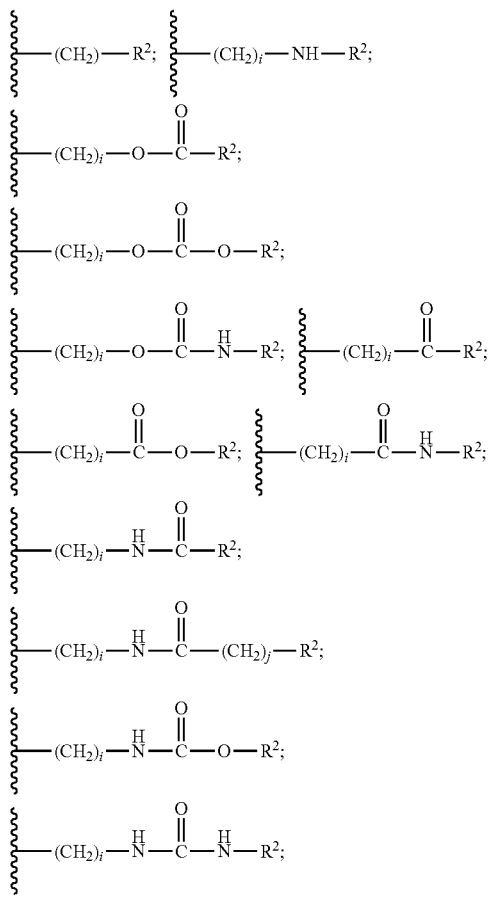

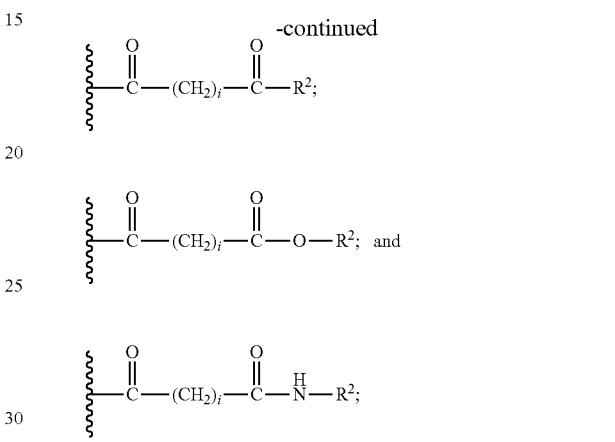

and combinations thereof; wherein each i is independently an integer of 0-10; j is an integer of 0-10; and $R^2$ is as defined herein. In some embodiments, each $R^1$ is a linking group.

In some embodiments, the functionalized multi-armed PEG has the structure of general formula (IVa), wherein $R^1$ and $R^2$, when taken together, are

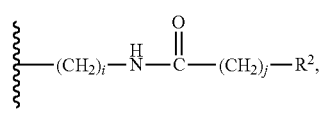

wherein i, j, and $R^2$ are as defined herein. In some embodiments, $R^1$ and $R^2$, when taken together, are

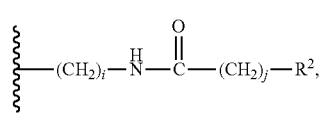

wherein i is 2; j is 2 or 3, and $R^2$ is as defined herein.

In some embodiments, each $R^2$ is independently selected from a maleimide, a sulfhydryl, a thiol, trifluoromethanesulfonate, tosylate, aziridine, epoxide, a pyridyl disulfide, succinimidyl ester, —$NH_2$, an aldehyde, a haloacetate, a haloacetamide, and a para-nitrophenyl carbonate. In some embodiments, each $R^2$ is independently a haloacetate selected from bromoacetate, iodoacetate, chloroacetate, and combinations thereof. In some embodiments, each $R^2$ is independently a haloacetamide selected from bromoacetamide, iodoacetamide, chloroacetamide, and combinations thereof. In some embodiments, $R^2$ is a maleimide.

In some embodiments, the functionalized multi-armed PEG has the structure of general formula (IVa), wherein each $R^2$ is a maleimide. In some embodiments, the functionalized multi-armed PEG has the structure of general formula (IVa), wherein $R^1$ and $R^2$, when taken together, are

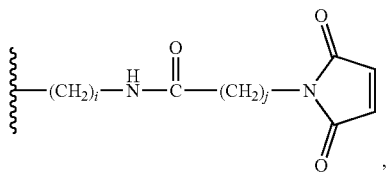

wherein i and j are as defined above. In some embodiments, the functionalized multi-armed PEG has the structure of general formula (IVa), wherein $R^1$ and $R^2$, when taken together, are

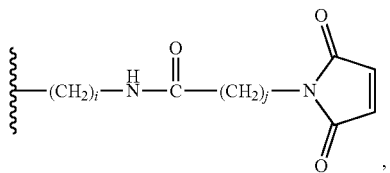

wherein i is 3 and j is 2.

Other functionalized multi-armed PEGs suitable for use in the present disclosure are described in U.S. Pat. App. Publ. No. 2011/0286956, and U.S. Pat. App. Publ. No. 2015/0073155, both of which are herein incorporated by reference in their entirety.

Functionalized multi-armed PEGs suitable for use in the present disclosure can also be purchased from a number of vendors. For example, JenKem Technology, USA sells maleimide-functionalized PEG hexamers and octamer (e.g., 6ARM (DP)-PEG-MAL and 8ARM (TP)-PEG-MAL). NOF America Corp. also sells maleimide functionalized PEG octamers (e.g., Sunbright® HGEO-400MA; Sunbright® DX-400MA) and tetramers (e.g., Sunbright® PTE-400MA).

In particular embodiments, the active derivative of multi-arm PEG as described is an active NHS ester derivative of the multi-arm PEG with the structure of the following general formula (IV):

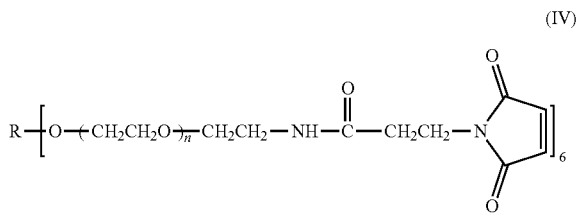

wherein R is dipentaerythritol.

1. Polyol Conjugates

In some embodiments, the disclosure is directed to a conjugate (e.g., Tie2 binding agent) comprising one or more anti-Tie2 antibodies or antibody variants disclosed herein and one or more multi-armed polyols, wherein the conjugate is prepared by covalently linking at least one anti-Tie2 Fab or Fab variant to the polyol. In some embodiments, the multi-armed polyol is a PEG. In preferred embodiments, the PEG is a hexamer. In other embodiments, the PEG is an octamer. In some embodiments, the PEG has the structure of general formula (Ia).

The conjugates of the present disclosure may be characterized by the number of anti-Tie2 antibodies (Fabs) conjugated to each multi-armed PEG. This is referred to herein as "fabylation" or "degree of fabylation." The number of anti-Tie2 Fabs conjugated to each PEG may vary depending on a variety of factors, including: 1) the number of arms in the PEG; 2) the number and/or reactivity of the terminal reactive groups on the PEG; 3) the core structure of the PEG; and/or, 4) PEGylation reaction conditions. A high polydispersity of the multi-armed PEG used to prepare the conjugate may in some instances complicate the analysis of the final conjugate, in particular making an accurate determination of the number of Fabs per PEG more difficult and uncertain. Accordingly, the PEG used to form the conjugate will typically have a polydispersity (determined using methods known in the art) within a range of about 1 to about 1.35, and in various embodiments will have a polydispersity of about 1 to about 1.25, about 1 to about 1.2, about 1 to about 1.15, about 1 to about 1.1, about 1.05, or even about 1.

In some embodiments, the conjugate of the disclosure comprises a six-armed PEG, wherein at least one anti-Tie2 Fab or variant is covalently linked to the PEG. In another embodiment, the conjugate of the disclosure comprises a six-armed PEG, wherein at least 2, at least 3, at least 4, at least 5, or at least 6 anti-Tie2 Fabs are covalently linked to the PEG. In another embodiment, the conjugate of the disclosure comprises an eight-armed PEG, wherein at least 2, at least 3, at least 4, at least 5, at least 6, at least 7 or at least 8 anti-Tie2 Fabs are covalently linked to the PEG. In another embodiment, the conjugate of the disclosure comprises a six-armed PEG, wherein at least 4, at least 5 or at least 6 anti-Tie2 Fabs are covalently linked to the PEG. In some embodiments, the conjugate of the disclosure comprises a six-armed PEG, wherein from 4-6 or 5-6 anti-Tie2 Fabs are covalently linked to the PEG. In another embodiment, the conjugate of the disclosure comprises a six-armed PEG, wherein from 4-6 anti-Tie2 Fabs are covalently linked to the PEG. In another embodiment, the conjugate of the disclosure comprises a six-armed PEG, wherein 4 to 6 or 5 to anti-Tie2 Fabs are covalently linked to the PEG.

In some embodiments, the conjugate of the disclosure comprises a multi-armed PEG having the structure of any one of general formulas (Ia), (IIa), (IIIa), or (IVa). In such embodiments, at least one $R^2$ is covalently linked to an anti-Tie2 Fab or variant described herein. In some embodiments, the multi-armed PEG having the structure of any one of general formulas (Ia), (IIa), (IIIa), or (IVa) is a hexamer, and at least 2, at least 3, at least 4, at least 5, or all 6 $R^2$ groups are covalently linked to an anti-Tie2 Fab or variant described herein.

In some embodiments, the conjugates of the present disclosure include species wherein the multi-armed polyol is covalently attached to a specific site or specific sites on the parental antibody; i.e., polymer attachment is targeted to a particular region or a particular amino acid residue or residues in the parental antibody or antibody fragments. Standard mutagenesis techniques can be used to alter the number and/or location of potential PEGylation sites in the parental antibody or antibody fragments. Thus, to the extent that amino acid substitutions introduce or replace amino acids such as cysteine and lysine, the anti-Tie2 antibodies and variants thereof of the present disclosure can contain a greater or lesser number of potential PEGylation sites than a native sequence anti-Tie2.

As discussed above, site specific conjugation of polymers is most commonly achieved by attachment to cysteine residues in the parental antibody or antibody fragment. In such embodiments, the coupling chemistry can, for example, utilize the free sulfhydryl group of a cysteine residue not in a disulfide bridge in the parental antibody.

In some embodiments, one or more cysteine residue(s) naturally present in the parental Fab is (are) used as attachment site(s) for polymer conjugation. In other embodiments, free amino groups on the Fab or variant can be thiolated with 2-imino-thiolane (Traut's reagent) and then coupled to, e.g., a maleimide-functionalized PEG, as described in Pedley, et al., *Br. J. Cancer*, Vol. 70, pp. 1126-1130 (1994). In another embodiment, one or more cysteine residue(s) is (are) engineered into a selected site or sites in the parental Fab for the purpose of providing a specific attachment site or sites for polymer.

Cysteine engineered antibodies have been described previously (U.S. Pat. Pub. No. 2007/0092940 and Junutula, J. R., et al, *J. Immunol Methods*, Vol. 332(1-2), pp. 41-52 (2008), all herein incorporated by reference in their entirety). In some embodiments, cysteine engineered antibodies can be parental antibodies. These are useful for generating antibody fragments having a free cysteine in a particular location, typically in a constant region, e.g., $C_L$ or $C_H1$. A parent antibody engineered to contain a cysteine is referred to herein as a "ThioMab" and Fab fragments produced from such cysteine engineered antibodies, regardless of the method of production, are referred to herein as "ThioFabs." As described previously (see, e.g., U.S. Pat. Pub. No. 2007/0092940 and Junutula, J. R., et al, *J. Immunol Methods*, Vol. 332(1-2), pp. 41-52 (2008)), mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. In addition to having a reactive thiol group, ThioMabs should be selected such that they retain antigen binding capability. The design, selection, and preparation of cysteine engineered antibodies were described in detail previously (see, e.g., WO 2011/069104, which is herein incorporated by reference). In some embodiments, engineered cysteines are introduced into the constant domains of heavy or light chains. As such, the cysteine engineered antibodies retain the antigen binding capability of their wild type, parent antibody counterparts and, as such, are capable of binding specifically, to antigens.

In some embodiments, the present disclosure relates to antibody fragment-polymer conjugates, wherein the antibody fragment is a Fab, and the polymer is attached to one or more cysteine residues in the light or heavy chain of the Fab fragment that would ordinarily form the inter-chain disulfide bond linking the light and heavy chains.

In another aspect, the present disclosure relates to antibody fragment-polymer conjugates, wherein the antibody fragment is a Fab-C, and the polymer attachment is targeted to the hinge region of the Fab-C fragment. In some embodiments, one or more cysteine residue(s) naturally present in the hinge region of the antibody fragment is (are) used to attach the polymer. In another embodiment, one or more cysteine residues is (are) engineered into the hinge region of the Fab-C fragment for the purpose of providing a specific attachment site or sites for polymer. In some embodiments, an anti-Tie2 Fab disclosed herein is modified by adding one cysteine at the C-terminal end for the purpose of providing one attachment site for polymer conjugation. In another embodiment, an anti-Tie2 Fab described herein is modified by adding four additional residues, CPPC (SEQ ID NO:87), at the C-terminal end for the purpose of providing two attachment sites for polymer conjugation. In still another embodiment, an anti-Tie2 Fab described herein is modified by adding four additional residues, SPPC (SEQ ID NO: 88), at the C-terminal end for the purpose of providing one attachment sites for polymer conjugation.

The degree and sites of PEGylation can also be manipulated by adjusting reaction conditions, such as the relative concentrations of the functionalized PEG and the protein as well as the pH. Suitable conditions for a desired degree of PEGylation can be determined empirically by varying the parameters of standard PEGylation reactions.

PEGylation of anti-Tie2 Fabs and variants is carried out by any convenient method. Suitable PEGylation conditions are set forth in WO 2011/069104 and WO 03/029420, both of which are herein incorporated by reference in their entirety.

3. Characterization of Polyol Conjugates

The PEGylated proteins can be characterized by SDS-PAGE, gel filtration, NMR, peptide mapping, liquid chromatography-mass spectrophotometry, and in vitro biological assays. The extent of fabylation is typically first shown by SDS-PAGE. Polyacrylamide gel electrophoresis in 10% SDS is typically run in 10 mM Tris-HCl pH 8.0, 100 mM NaCl as elution buffer. To demonstrate which residue is PEGylated, peptide mapping using proteases such as trypsin and Lys-C protease can be performed. Thus, samples of PEGylated and non-PEGylated antibodies can be digested with a protease such as Lys-C protease and the resulting peptides separated by a technique such as reverse phase HPLC. The chromatographic pattern of peptides produced can be compared to a peptide map previously determined for the anti-Tie2 polypeptide.

Each peak can then be analyzed by mass spectrometry to verify the size of the conjugate in the peak. Depending on the PEG used in the conjugation, and the size of the conjugate in the peak, the number of antibodies or variants thereof conjugated to the PEG can be estimated. The fragment(s) that conjugated to PEG groups are usually not retained on the HPLC column after injection and disappear from the chromatograph. Such disappearance from the chromatograph is an indication of PEGylation on that particular fragment that should contain at least one PEGylatable amino acid residue. PEGylated anti-Tie Fabs may further be assayed for ability to interact with Tie2 and other biological activities using known methods in the art.

PEGylation changes the physical and chemical properties of the antibody drug, and may results in improved pharmacokinetic behaviors such as improved stability, decreased immunogenicity, extended circulating life as well as increased ocular residence time.

In some embodiments, the conjugates of the present disclosure have an increased half-life after administration into a mammalian eye (e.g. human) via a single intravitreal injection, as compared to the corresponding unconjugated anti-Tie2 Fab. In some embodiments, the increase in half-life is at least 1.4 times, or at least 1.8 times, or at least 2 times the half-life of the corresponding unconjugated anti-Tie2 Fab.

3. IgM Multimers as Conjugates

In some embodiments, the Tie2 binding agents of the present disclosure can be made by linking more than one anti-Tie2 antibody described herein to the $C_{H1}$ domain of an IgM molecule, e.g., using recombinant expression methods to fuse (via peptide bond) the C-terminus of an IgM $C_{H1}$ domain to the N terminus of an anti-Tie2 antibody as described herein. IgMs are proving to be a viable format for antibody therapeutics (see, e.g., Hanala, 2012, MAbs, 4:555-561). The 'monomeric' component of an IgM consists of two light chains (LCs), each containing two Ig-domains, and two heavy chains (HCs), containing five Ig-domains and a short unstructured C-terminal tail piece. These four chains assemble to form a homodimer of HC-LC heterodimers. Subsequently the homodimers covalently associate into cyclic structures containing five homodimers and a J-chain (JC) (pentamers) or six homodimers (hexamers) containing ten and twelve binding sites, respectively. Without being bound by theory, it is possible that avid binding of multiple variable fragments (Fvs) enables IgMs to bind targets without substantial affinity maturation, and thus to serve as sentinel adaptive immune receptors.

In particular embodiments, the anti-Tie2 antibody is a Fab. The IgM protein (multimer) can include or not include the J chain such that in the presence of the J-chain, a pentamer is formed (and can comprise up to 5 anti-Tie2 antibodies), and in the absence of the J-chain, a hexamer is formed (and can comprise up to 5 anti-Tie2 antibodies). In some embodiments, a hexamer is generated by varying ratios of IgM heavy chain to light chain (to form a hexamer) or ratios of heavy chain to light chain to J-chain (to form a pentamer). Accordingly, in some embodiments, the Tie2 binding agent is a multimer comprising an IgM protein and at least 2, at least 3, at least 4, at least 5, or at least 6 anti-Tie2 antibodies described herein to form a multimer capable of activating Tie2. Anti-Tie2 IgM molecules were designed and shown to activate Tie2 activity (see Example 7).

An anti-Tie2, multimeric conjugate constructed using a recombinant IgM format as described herein can be useful for ocular therapeutics due to its relatively large molecular radius relative to a single Fab, potentially resulting in a slower diffusion of the molecule out of the vitreous humor into the aqueous humor and into the blood. As described in Example 7 below, assessment by light scattering found hydrodynamic radii ($R_h$) of approximately 12 nM with predicted molecular weights for the hexamers (~1050 kD) slightly exceeding those for the pentamers (~950 kD)

Also investigated was systemic half-life of the recombinant IgM molecules, as it can be desirable to have relatively rapid systemic clearance to restrict activity of ocular therapeutics to the eye. As shown in Example 7, recombinantly expressed IgM pentamers and hexamers were more rapidly cleared following intravenous injection than IgM isolated from human serum. It was further determined that these recombinant IgM molecules had a lower percentage of sialic acid with respect to N-linked glycans than the IgMs isolated from serum, suggesting that the rate of clearance of recombinant anti-Tie2 IgM molecules may be controlled by designing expression systems which modify the level of sialic acid in the N-linked glycosylation.

IgMs have previously been reported to potently recruit C1q and induce target cell-killing via complement-dependent cytotoxicity (CDC). Such activity can be undesirable for an ocular therapeutic. Accordingly, as described in Example 7, an IgM variant, P434G (EU numbering) was designed and shown to have removed all detectable complement activity.

3. Hexameric Peptide Multimers as Conjugates

Also encompassed by the present disclosure is a conjugate comprising multiple antigen-binding agents (e.g., antibodies or antigen-binding fragments thereof) by linking each antigen-binding agent to a peptide which naturally forms a multimer, e.g., a NDK peptide. In some embodiments, the Tie2 binding agents of the present disclosure can be made by linking more than one anti-Tie2 Fab described herein to a peptide multimer. A peptide multimer is comprised of at least 2, at least 3, at least 4, at least 5, at least 6, at least 7, or at least 8 peptides which, when expressed in a recombinant expression system, the multiple peptides naturally fold to form a single multi-armed structure. Routine molecular engineering techniques and materials are used to express the peptide, which will form a multimer, as a fusion protein in which an antigen-binding protein (e.g., antibody or fragment thereof) is expressed either at the N-terminus or the C-terminus of the peptide which forms a multimer. In particular embodiments, the multiple peptides in a multimer are identical and an expression vector is constructed to link (via peptide bond) the C-terminus or the N-terminus of the peptide to the N-terminus or the C-terminus, respectively, of an anti-Tie2 antibody or fragment thereof as taught in the present disclosure.

In particular embodiments, the peptides of the multimeric peptide are portions of eukaryotic nucleoside diphosphate kinase (NDK) enzymes that have a homo-hexameric quaternary structure. There are several NDK enzymes that can be used to design a multimer, including NDK1 (e.g., SEQ ID NO:69), NDK2 (e.g., SEQ ID NO:70), NDK3 (e.g., SEQ ID NO:71), NDK4 (e.g., SEQ ID NO:72), NDK5 (e.g., SEQ ID NO:73), In a preferred embodiment, the NDK peptide is an NDK3 peptide derived from, e.g., UniProt accession P22887. SEQ ID NO:74 provides the sequence of Tie2.1.M100cF linked at its C-terminus to the NDK3 N-terminus. In this preferred embodiment, the Fab light chain comprises SEQ ID NO:21. (See, e.g., Example 8 below.)

E. Methods and Compositions for Diagnostics and Detection

In certain embodiments, any of the anti-Tie2 antibodies provided herein is useful for detecting the presence of Tie2 in a biological sample. The term "detecting" as used herein encompasses quantitative or qualitative detection. In certain embodiments, a biological sample comprises a cell or tissue, such as retinal tissue (photoreceptors and the underlying retinal pigment epithelium (RPE) and choriocapilaris).

In one embodiment, an anti-Tie2 antibody for use in a method of diagnosis or detection is provided. In a further aspect, a method of detecting the presence of Tie2 in a biological sample is provided. In certain embodiments, the method comprises contacting the biological sample with an anti-Tie2 antibody as described herein under conditions permissive for binding of the anti-Tie2 antibody to Tie2, and detecting whether a complex is formed between the anti-Tie2 antibody and Tie2. Such method may be an in vitro or in vivo method. In one embodiment, an anti-Tie2 antibody is used to select subjects eligible for therapy with an anti-Tie2 antibody, e.g. where Tie2 is a biomarker for selection of patients.

In certain embodiments, labeled anti-Tie2 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-Tie2 antibody or Tie2 conjugates as described herein are prepared by mixing such anti-Tie2 antibody or Tie2 conjugates having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a second biological molecule selected from the group consisting of IL-6; IL-6R; IL-13; IL-13R; PDGF; angiopoietin; Ang2; Tie2; SIP; integrins αvβ3, αvβ5, and α5β1; betacellulin; apelin/APJ; erythropoietin; complement factor D; TNFα; HtrA1; a VEGF receptor; ST-2 receptor; and proteins genetically linked to AMD risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A. Additionally or alternatively, the second biological molecule is an antibody or fragment thereof which specifically binds a molecule selected from the group consisting of IL-6; IL-6R; IL-13; IL-13R; PDGF; angiopoietin; Ang2; Tie2; SIP; integrins αvβ3, αvβ5, and α5β1; betacellulin; apelin/APJ; erythropoietin; complement factor D; TNFα; HtrA1; a VEGF receptor; ST-2 receptor; and proteins genetically linked to AMD risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A. In certain embodiments, the additional compound is an antibody which binds VEGF and/or Ang2 and/or IL-1beta, or antigen-binding fragment thereof. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

The conjugates described herein for prevention or treatment of an ocular disease or condition are typically administered by ocular, intraocular, and/or intravitreal injection, and/or juxtascleral injection, and/or subtenon injection, and/or superchoroidal injection and/or topical administration in the form of eye drops and/or ointment. Such compositions of the disclosure may be delivered by a variety of methods, e.g. intravitreally as a device and/or a depot that allows for slow release of the compound into the vitreous, including those described in references such as Intraocular Drug Delivery, Jaffe, Jaffe, Ashton, and Pearson, editors, Taylor & Francis (March 2006). In one example, a device may be in the form of a min pump and/or a matrix and/or a passive diffusion system and/or encapsulated cells that release the compound for a prolonged period of time (Intraocular Drug Delivery, Jaffe, Jaffe, Ashton, and Pearson, editors, Taylor & Francis (March 2006). Other methods of administration may also be used, which includes but is not limited to, topical, parenteral, subcutaneous, intraperitoneal, intrapulmonary, intranasal, and intralesional administration. Parenteral infusions include intramuscular, intravenous, intraarterial, intraperitoneal, or subcutaneous administration.

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as DME and AMD, is direct intravitreal injection. Intravitrial injections are usually repeated at intervals which depend on the patient's condition, and the properties and half-life of the drug delivered. For intraocular (e.g. intravitreal) penetration, usually molecules of smaller size are preferred.

In some embodiments, the antibodies and conjugates described herein may be formulated for delivery using an implantable port delivery system (PDS). As noted previously, the PDS is a refillable device where release into the vitreous is controlled by a porous metal membrane comprising a titanium frit. Since the reservoir has a low volume, in some embodiments, a high protein concentration is required for effective delivery with the PDS. Accordingly, in some embodiments, the antibodies and conjugates described herein are formulated at high concentration. In some embodiments, the antibodies and conjugates described herein may be formulated at a concentration of at least 150 mg/ml, at least 160 mg/ml, at least 170 mg/ml, at least 180 mg/ml, at least 190 mg/ml, at least 200 mg/ml, or at least 210 mg/ml, or at least 220 mg/ml, or at least 230 mg/ml, or at least 240 mg/ml, or at least 250 mg/ml, or at least 260 mg/ml, or at least 270 mg/ml, or at least 280 mg/ml, or at least 290 mg/ml, or at least 300 mg/ml. In some embodiments, the antibodies and conjugates described herein may be formulated at a concentration of between 150 mg/ml and 350 mg/ml, between 150 mg/ml and 300 mg/ml, between 170 mg/ml and 300 mg/ml, between 200 mg/ml and 300 mg/ml, or between 170 mg/ml and 220 mg/ml.

G. Therapeutic Methods and Compositions

Any of the anti-Tie2 antibodies or conjugates provided herein may be used in therapeutic methods. An "individual," "patient," or "subject" according to any of the embodiments herein may be a human.

The anti-Tie2 conjugates of the present disclosure may be used to treat a mammal. In some embodiments, an anti-Tie2 conjugate is administered to a nonhuman mammal for the purposes of obtaining preclinical data, for example. Exemplary nonhuman mammals to be treated include nonhuman primates, dogs, cats, pigs, rodents and other mammals in which preclinical studies are performed. Such mammals may be established animal models for a disease to be treated with the antibody, or may be used to study toxicity of the antibody of interest. In each of these embodiments, dose escalation studies may be performed on the mammal.

An anti-Tie2 conjugate may be administered by any suitable means, including parenteral, subcutaneous, intraperitoneal, intravitreal, intrapulmonary, and intranasal, and, if desired for local immunosuppressive treatment, intralesional administration. Parenteral infusions include intramuscular, intravenous, intraarterial, intraperitoneal, intravitreal, and subcutaneous administration. In addition, the conjugate is suitably administered by pulse infusion, particularly with declining doses of the antibody, or antibody variant thereof or fragment thereof (e.g. antigen-binding fragment). In some embodiments, the dosing is given by injections, such as intravenous or subcutaneous injections, depending in part on whether the administration is brief or chronic.

For the prevention or treatment of disease, the appropriate dosage of the anti-Tie2 antibody or conjugate will depend on the type of disease to be treated, the severity and course of the disease, whether the antibody is administered for preventive or therapeutic purposes, previous therapy, the patient's clinical history and response to the antibody and the discretion of the attending physician.

Depending on the type and severity of the disease, about 1-25 mg/eye (0.015 mg/kg-0.36 mg/kg per eye) of the antibody is an initial candidate dosage for administration to the patient, whether, for example, by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188.

In one aspect, an anti-Tie2 antibody or conjugate for use as a medicament is provided. In further aspects, an anti-Tie2 antibody or conjugate for use in treating an ocular disease or disorder is provided. In certain embodiments, an anti-Tie2 antibody or conjugate for use in a method of treatment is provided. In certain embodiments, the invention provides an anti-Tie2 antibody or conjugate for use in a method of treating an individual having an ocular disease or disorder comprising administering to the individual an effective amount of the anti-Tie2 antibody or conjugate. In one such embodiment, the method further comprises administering to the individual an effective amount of at least one additional therapeutic agent, e.g., as described below. In further embodiments, the invention provides an anti-Tie2 antibody or conjugate for use in increasing vascular endothelial cellular membrane integrity and/or reducing vascular leakage. In certain embodiments, the invention provides an anti-Tie2 antibody or conjugate for use in a method of increasing vascular endothelial cellular membrane integrity and/or reducing vascular leakage in an individual comprising administering to the individual an effective of the anti-Tie2 antibody or conjugate to increase vascular endothelial cellular membrane integrity and/or reduce vascular leakage]. An "individual" according to any of the above embodiments is preferably a human.

The term "ocular disorder," as used herein, includes any ocular disorder (also referred to interchangeably herein as "ocular condition") associated with pathological angiogenesis and/or atrophy. An ocular disorder may be characterized by altered or unregulated proliferation and/or invasion of new blood vessels into the structures of ocular tissues such as the retina or cornea. An ocular disorder may be characterized by atrophy of retinal tissue (photoreceptors and the underlying retinal pigment epithelium (RPE) and choriocapillaris).

Diabetic macular edema (DME) is caused by a complication of diabetes referred to as diabetic retinopathy (DR). This eye condition can occur in people diagnosed with type 1 or type 2 diabetes. DME is defined as retinal thickening within 2 disc diameters of the center of the fovea and can be either focal or diffuse. DME is associated with retinal microvascular changes with compromise the blood-retinal barrier, causing leakage of plasma constituents into the surrounding retina, leading to retinal edema.

Non-limiting ocular disorders include, for example, diabetic macular edema (DME) (e.g., focal, non-center DME and diffuse, center-involved DME), diabetic retinopathy (DR) (e.g., proliferative DR (PDR), non-proliferative DR (NPDR), and high-altitude DR), retinopathy in the absence of edema, other ischemia-related retinopathies, AMD (e.g., wet AMD, dry AMD, intermediate AMD, advanced AMD, and geographic atrophy (GA)), macular degeneration, macular edema, retinopathy, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, central serous retinopathy (CSR), pathologic myopia, von Hippel-Lindau disease, histoplasmosis of the eye, FEVR, Coats' disease, Norrie Disease, retinal abnormalities associated with osteoporosis-pseudoglioma syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, including but not limited to CMV retinitis, ocular melanoma, retinal blastoma, conjunctivitis (e.g., infectious conjunctivitis and non-infectious (e.g., allergic) conjunctivitis), Leber congenital amaurosis (also known as Leber's congenital amaurosis or LCA), uveitis (including infectious and non-infectious uveitis), choroiditis (e.g., multifocal choroiditis), ocular histoplasmosis, blepharitis, dry eye, traumatic eye injury, Sjögren's disease, and other ophthalmic diseases wherein the disease or disorder is associated with ocular neovascularization, vascular leakage, and/or retinal edema or retinal atrophy. Additional exemplary ocular disorders include retinoschisis (abnormal splitting of the retina neurosensory layers), diseases associated with rubeosis (neovascularization of the angle) and diseases caused by the abnormal proliferation of fibrovascular or fibrous tissue, including all forms of proliferative vitreoretinopathy.

Exemplary diseases associated with corneal neovascularization include, but are not limited to, epidemic keratoconjunctivitis, vitamin A deficiency, contact lens overwear, atopic keratitis, superior limbic keratitis, terygium keratitis sicca, Sjögren's syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegener's sarcoidosis, scleritis, Stevens-Johnson syndrome, periphigoid radial keratotomy, and corneal graph rejection.

Exemplary diseases associated with choroidal neovascularization and defects in the retina vasculature, including increased vascular leak, aneurisms and capillary drop-out include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, retina edema (including macular edema), Eales disease, Behcet's disease, infections causing retinitis or choroiditis (e.g., multifocal choroidits), presumed ocular histoplasmosis, Best's disease (vitelliform macular degeneration), myopia, optic pits, pars planitis, retinal detachment (e.g., chronic retinal detachment), hyperviscosity syndromes, toxoplasmosis, trauma, and post-laser complications.

Exemplary diseases associated with atrophy of retinal tissues (photoreceptors and the underlying RPE) include, but are not limited to, atrophic or nonexudative AMD (e.g., geographic atrophy or advanced dry AMD), macular atrophy (e.g., atrophy associated with neovascularization and/or geographic atrophy), diabetic retinopathy, Stargardt's disease, Sorsby Fundus Dystrophy, retinoschisis and retinitis pigmentosa.

For example, in certain embodiments, any of the preceding methods further comprises administering one or more additional compounds. In certain embodiments, the Tie2-binding agent or conjugate or polymeric formulation thereof is administered simultaneously with the additional compound(s). In certain embodiments, the Tie2-binding agent or conjugate or polymeric formulation is administered before or after the additional compound(s). In certain embodiments, the additional compound binds to a second biological molecule selected from the group consisting of IL-1β; IL-6; IL-6R; IL-13; IL-13R; PDGF; angiopoietin; Ang2; Tie2; S1P; integrins $\alpha v\beta 3$, $\alpha v\beta 5$, and $\alpha 5\beta 1$; betacellulin; apelin/APJ; erythropoietin; complement factor D; TNFα; HtrA1; a VEGF receptor; ST-2 receptor; and proteins genetically linked to AMD risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A. In certain embodiments, the additional compound is an antibody or antigen-binding fragment thereof. In certain embodiments according to (or as applied to) any of the embodiments above, the ocular disorder is an intraocular neovascular disease selected from the group consisting of proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, retinal vein occlusion (RVO), including CRVO and BRVO, corneal neovascularization, retinal neovascularization, and retinopathy of prematurity (ROP). For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, OPR-003, MEDI5117, PF-04236921, or a variant thereof. In a still further example, in some instances, the additional compound is an anti-IL-6R antibody, for example, tocilizumab (ACTEMRA®) (see, e.g., WO 1992/019579), sarilumab, ALX-0061, SA237, or a variant thereof.

In some instances, a Tie2-binding agent or conjugate of the present disclosure, and/or polymeric formulation thereof, may be administered in combination with at least one additional therapeutic agent for treatment of an ocular disorder, for example, an ocular disorder described herein (e.g., DME, DR, AMD (e.g., wet AMD), RVO, or GA). Exemplary additional therapeutic agents for combination therapy for treatment of ocular disorders include, without limitation, anti-angiogenic agents, such as VEGF antagonists, including, for example, anti-VEGF antibodies (e.g., the anti-VEGF Fab LUCENTIS® (ranibizumab)), soluble receptor fusion proteins (e.g., the recombinant soluble receptor fusion protein EYLEA® (aflibercept, also known as VEGF Trap Eye; Regeneron/Aventis)), aptamers (e.g., the anti-VEGF pegylated aptamer MACUGEN® (pegaptanib sodium; NeXstar Pharmaceuticals/OSI Pharmaceuticals)), and VEGFR tyrosine kinase inhibitors (e.g., 4-(4-bromo-2-fluoroanilino)-6-methoxy-7-(1-methylpiperidin-4-yl-methoxy)quinazoline (ZD6474), 4-(4-fluoro-2-methylindol-5-yloxy)-6-methoxy-7-(3-pyrrolidin-1-ylpropoxy) quinazoline (AZD2171), vatalanib (PTK787), semaxaminib (SU5416; SUGEN), and SUTENT® (sunitinib)); Tryptophanyl-tRNA synthetase (TrpRS); squalamine; RETAANE® (anecortave acetate for depot suspension; Alcon, Inc.); Combretastatin A4 Prodrug (CA4P);

MIFEPREX® (mifepristone-ru486); subtenon triamcinolone acetonide; intravitreal crystalline triamcinolone acetonide; matrix metalloproteinase inhibitors (e.g., Prinomastat (AG3340; Pfizer)); fluocinolone acetonide (including fluocinolone intraocular implant; Bausch & Lomb/Control Delivery Systems); linomide; inhibitors of integrin (β3 function; angiostatin, and combinations thereof. These and other therapeutic agents that can be administered in combination with a Tie2-binding agent or conjugate of the invention are described, for example, in U.S. Patent Application No. US 2014/0017244, which is incorporated herein by reference in its entirety.

Further examples of additional therapeutic agents that can be used in combination with a Tie2-binding agent or conjugate, and/or polymeric formulation thereof, for treatment of an ocular disorder (e.g., DME, DR, AMD, RVO, or GA), include, but are not limited to, VISUDYNE® (verteporfin; a light-activated drug that is typically used in conjunction with photodynamic therapy with a non-thermal laser), PKC412, Endovion (NS 3728; NeuroSearch A/S), neurotrophic factors (e.g., glial derived neurotrophic factor (GDNF) and ciliary neurotrophic factor (CNTF)), diltiazem, dorzolamide, PHOTOTROP®, 9-cis-retinal, eye medication (e.g., phospholine iodide, echothiophate, or carbonic anhydrase inhibitors), veovastat (AE-941; AEterna Laboratories, Inc.), Sirna-027 (AGF-745; Sima Therapeutics, Inc.), neurotrophins (including, by way of example only, NT-4/5, Genentech), Candy (Acuity Pharmaceuticals), INS-37217 (Inspire Pharmaceuticals), integrin antagonists (including those from Jerini AG and Abbott Laboratories), EG-3306 (Ark Therapeutics Ltd.), BDM-E (BioDiem Ltd.), thalidomide (as used, for example, by EntreMed, Inc.), cardiotrophin-1 (Genentech), 2-methoxyestradiol (Allergan/Oculex), DL-8234 (Toray Industries), NTC-200 (Neurotech), tetrathiomolybdate (University of Michigan), LYN-002 (Lynkeus Biotech), microalgal compound (Aquasearch/Albany, Mera Pharmaceuticals), D-9120 (Celltech Group plc), ATX-S10 (Hamamatsu Photonics), TGF-beta 2 (Genzyme/Celtrix), tyrosine kinase inhibitors (e.g., those from Allergan, SUGEN, or Pfizer), NX-278-L (NeXstar Pharmaceuticals/Gilead Sciences), Opt-24 (OPTIS France SA), retinal cell ganglion neuroprotectants (Cogent Neurosciences), N-nitropyrazole derivatives (Texas A&M University System), KP-102 (Krenitsky Pharmaceuticals), cyclosporin A, therapeutic agents used in photodynamic therapy (e.g., VISUDYNE®; receptor-targeted PDT, Bristol-Myers Squibb, Co.; porfimer sodium for injection with PDT; verteporfin, QLT Inc.; rostaporfin with PDT, Miravent Medical Technologies; talaporfin sodium with PDT, Nippon Petroleum; and motexafin lutetium, Pharmacyclics, Inc.), antisense oligonucleotides (including, by way of example, products tested by Novagali Pharma SA and ISIS-13650, Ionis Pharmaceuticals), and combinations thereof.

A Tie2-binding agent or conjugate, and/or polymeric formulation thereof, may be administered in combination with a therapy or surgical procedure for treatment of an ocular disorder (e.g., DME, DR, AMD, RVO, or GA), including, for example, laser photocoagulation (e.g., panretinal photocoagulation (PRP)), drusen lasering, macular hole surgery, macular translocation surgery, implantable miniature telescopes, PHI-motion angiography (also known as micro-laser therapy and feeder vessel treatment), proton beam therapy, microstimulation therapy, retinal detachment and vitreous surgery, scleral buckle, submacular surgery, transpupillary thermotherapy, photosystem I therapy, use of RNA interference (RNAi), extracorporeal rheopheresis (also known as membrane differential filtration and rheotherapy), microchip implantation, stem cell therapy, gene replacement therapy, ribozyme gene therapy (including gene therapy for hypoxia response element, Oxford Biomedica; Lentipak, Genetix; and PDEF gene therapy, GenVec), photoreceptor/retinal cells transplantation (including transplantable retinal epithelial cells, Diacrin, Inc.; retinal cell transplant, e.g., Astellas Pharma US, Inc., ReNeuron, CHA Biotech), acupuncture, and combinations thereof.

In some instances, a Tie2-binding agent or conjugate of the invention, and/or polymeric formulation thereof, can be administered in combination with an anti-angiogenic agent for treatment of an ocular disorder (e.g., DME, DR, AMD, RVO, or GA). Any suitable anti-angiogenic agent can be used in combination with a Tie2-binding agent or conjugate of the invention, including, but not limited to, those listed by Carmeliet et al. Nature 407:249-257, 2000. In some embodiments, the anti-angiogenic agent is a VEGF antagonist, including, but not limited to, an anti-VEGF antibody (e.g., the anti-VEGF Fab LUCENTIS® (ranibizumab), RTH-258 (formerly ESBA-1008, an anti-VEGF single-chain antibody fragment; Novartis), or a bispecific anti-VEGF antibody (e.g., an anti-VEGF/anti-angiopoietin 2 bispecific antibody such as RG-7716; Roche)), a soluble recombinant receptor fusion protein (e.g., EYLEA® (aflibercept)), a VEGF variant, a soluble VEGFR fragment, an aptamer capable of blocking VEGF (e.g., pegaptanib) or VEGFR, a neutralizing anti-VEGFR antibody, a small molecule inhibitor of VEGFR tyrosine kinases, an anti-VEGF DARPin® (e.g., abicipar pegol, Molecular Partners AG/Allergan), a small interfering RNAs which inhibits expression of VEGF or VEGFR, a VEGFR tyrosine kinase inhibitor (e.g., 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy) quinazoline (AZD2171), vatalanib (PTK787), semaxaminib (SU5416; SUGEN), and SUTENT® (sunitinib)), and combinations thereof. In some instances, the anti-Tie2 antibody for fragment thereof can be combined with an antibody or fragment thereof or other therapeutic agent targeting a second biological molecule, including but not limited to IL-1β; IL-6; IL-6R; PDGF (e.g., PDGF-BB); angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor (e.g., VEGFR1, VEGFR2, VEGFR3, mbVEGFR, or sVEGFR); ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC; COL10A1; and TNFRSF10A. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof).

Other suitable anti-angiogenic agents that may be administered in combination with an anti-Tie2 conjugate, and/or polymeric formulation thereof, for treatment of an ocular disorder (e.g., DME, DR, AMD, RVO, or GA) include corticosteroids, angiostatic steroids, anecortave acetate, angiostatin, endostatin, tyrosine kinase inhibitors, matrix metalloproteinase (MMP) inhibitors, insulin-like growth factor-binding protein 3 (IGFBP3), stromal derived factor (SDF-1) antagonists (e.g., anti-SDF-1 antibodies), pigment epithelium-derived factor (PEDF), gamma-secretase, Delta-like ligand 4, integrin antagonists, hypoxia-inducible factor (HIF)-1α antagonists, protein kinase CK2 antagonists, agents that inhibit stem cell (e.g., endothelial progenitor cell) homing to the site of neovascularization (e.g., an anti-vascular endothelial cadherin (CD-144) antibody and/or an anti-SDF-1 antibody), and combinations thereof.

In a further example, in some instances, a Tie2-binding conjugate, and/or polymeric formulation thereof, can be administered in combination with an agent that has activity against neovascularization for treatment of an ocular disorder (e.g., DME, DR, AMD, RVO, or GA), such as an anti-inflammatory drug, a mammalian target of rapamycin (mTOR) inhibitor (e.g., rapamycin, AFINITOR® (everolimus), and TORISEL® (temsirolimus)), cyclosporine, a tumor necrosis factor (TNF) antagonist (e.g., an anti-TNFα antibody or antigen-binding fragment thereof (e.g., infliximab, adalimumab, certolizumab pegol, and golimumab) or a soluble receptor fusion protein (e.g., etanercept)), an anti-complement agent, a nonsteroidal antiinflammatory agent (NSAID), or combinations thereof.

In a still further example, in some instances, a Tie2-binding conjugate, and/or polymeric formulation thereof, can be administered in combination with an agent that is neuroprotective and can potentially reduce the progression of dry AMD to wet AMD, such as the class of drugs called the "neurosteroids," which include drugs such as dehydroepiandrosterone (DHEA) (brand names: PRASTERA™ and FIDELIN®), dehydroepiandrosterone sulfate, and pregnenolone sulfate.

Any suitable AMD therapeutic agent can be administered as an additional therapeutic agent in combination with a Tie2-binding conjugate of the invention, and/or polymeric formulation thereof, for treatment of an ocular disorder (e.g., DME, DR, AMD, RVO, or GA), including, but not limited to, a VEGF antagonist, for example, an anti-VEGF antibody (e.g., LUCENTIS® (ranibizumab), RTH-258 (formerly ESBA-1008, an anti-VEGF single-chain antibody fragment; Novartis), or a bispecific anti-VEGF antibody (e.g., an anti-VEGF/anti-angiopoietin 2 bispecific antibody such as RG-7716; Roche)), a soluble VEGF receptor fusion protein (e.g., EYLEA® (aflibercept)), an anti-VEGF DARPin® (e.g., abicipar pegol; Molecular Partners AG/Allergan), or an anti-VEGF aptamer (e.g., MACUGEN® (pegaptanib sodium)); a platelet-derived growth factor (PDGF) antagonist, for example, an anti-PDGF antibody, an anti-PDGFR antibody (e.g., REGN2176-3), an anti-PDGF-BB pegylated aptamer (e.g., FOVISTA®; Ophthotech/Novartis), a soluble PDGFR receptor fusion protein, or a dual PDGF/VEGF antagonist (e.g., a small molecule inhibitor (e.g., DE-120 (Santen) or X-82 (TyrogeneX)) or a bispecific anti-PDGF/anti-VEGF antibody)); VISUDYNE® (verteporfin) in combination with photodynamic therapy; an antioxidant; a complement system antagonist, for example, a complement factor C5 antagonist (e.g., a small molecule inhibitor (e.g., ARC-1905; Opthotech) or an anti-05 antibody (e.g., LFG-316; Novartis), a properdin antagonist (e.g., an anti-properdin antibody, e.g., CLG-561; Alcon), or a complement factor D antagonist (e.g., an anti-complement factor D antibody, e.g., lampalizumab; Roche)); a C3 blocking peptide (e.g., APL-2, Appellis); a visual cycle modifier (e.g., emixustat hydrochloride); squalamine (e.g., OHR-102; Ohr Pharmaceutical); vitamin and mineral supplements (e.g., those described in the Age-Related Eye Disease Study 1 (AREDS1; zinc and/or antioxidants) and Study 2 (AREDS2; zinc, antioxidants, lutein, zeaxanthin, and/or omega-3 fatty acids)); a cell-based therapy, for example, NT-501 (Renexus); PH-05206388 (Pfizer), huCNS-SC cell transplantation (StemCells), CNTO-2476 (umbilical cord stem cell line; Janssen), OpRegen (suspension of RPE cells; Cell Cure Neurosciences), or MA09-hRPE cell transplantation (Ocata Therapeutics); a tissue factor antagonist (e.g., hI-con1; Iconic Therapeutics); an alpha-adrenergic receptor agonist (e.g., brimonidine tartrate; Allergan); a peptide vaccine (e.g., S-646240; Shionogi); an amyloid beta antagonist (e.g., an anti-beta amyloid monoclonal antibody, e.g., GSK-933776); an S1P antagonist (e.g., an anti-S1P antibody, e.g., iSONEP™; Lpath Inc); a ROBO4 antagonist (e.g., an anti-ROBO4 antibody, e.g., DS-7080a; Daiichi Sankyo); a lentiviral vector expressing endostatin and angiostatin (e.g., RetinoStat); and any combination thereof. In some instances, AMD therapeutic agents (including any of the preceding AMD therapeutic agents) can be co-formulated. For example, the anti-PDGFR antibody REGN2176-3 can be co-formulated with aflibercept (EYLEA®). In some instances, such a co-formulation can be administered in combination with a Tie2-binding agent or conjugate of the invention. In some instances, the ocular disorder is DME and/or DR. In some instances, the ocular disorder is AMD (e.g., wet AMD).

A Tie2-binding conjugate, and/or polymeric formulation thereof, can be administered in combination with LUCENTIS® (ranibizumab) for treatment of an ocular disorder (e.g., DME, DR, AMD, RVO, or GA). In some instances, the ocular disorder is DME and/or DR. In some instances, the ocular disorder is AMD (e.g., wet AMD). In some instances, the ocular disorder is GA.

A Tie2-binding conjugate, and/or polymeric formulation thereof, can be administered in combination with EYLEA® (aflibercept) for treatment of an ocular disorder (e.g., DME, DR, AMD, RVO, or GA). In some instances, the ocular disorder is DME and/or DR. In some instances, the ocular disorder is AMD (e.g., wet AMD). In some instances, the ocular disorder is GA.

A Tie2-binding conjugate, and/or polymeric formulation thereof, can be administered in combination with MACUGEN® (pegaptanib sodium) for treatment of an ocular disorder (e.g., DME, DR, AMD, RVO, or GA). In some instances, the ocular disorder is DME and/or DR. In some instances, the ocular disorder is AMD (e.g., wet AMD). In some instances, the ocular disorder is GA.

A Tie2-binding conjugate, and/or polymeric formulation thereof, can be administered in combination with VISUDYNE® (verteporfin) in combination with photodynamic therapy for treatment of an ocular disorder (e.g., DME, DR, AMD, RVO, or GA). In some instances, the ocular disorder is DME and/or DR. In some instances, the ocular disorder is AMD (e.g., wet AMD). In some instances, the ocular disorder is GA.

A Tie2-binding conjugate, and/or polymeric formulation thereof, can be administered in combination with a PDGF antagonist for treatment of an ocular disorder (e.g., DME, DR, AMD, RVO, or GA). Exemplary PDGF antagonists which may be used in combination with a Tie2-binding conjugate of the invention include an anti-PDGF antibody, an anti-PDGFR antibody, a small molecule inhibitor (e.g., squalamine), an anti-PDGF-B pegylated aptamer such as FOVISTA® (E10030; Ophthotech/Novartis), or a dual PDGF/VEGF antagonist (e.g., a small molecule inhibitor (e.g., DE-120 (Santen) or X-82 (TyrogeneX)) or a bispecific anti-PDGF/anti-VEGF antibody). For example, FOVISTA® can be administered as an adjunct therapy to a Tie2-binding agent or conjugate of the invention. OHR-102 can be administered in combination with VEGF antagonists such as LUCENTIS® or EYLEA®. In some embodiments, a Tie2-binding agent or conjugate of the invention can be administered in combination with OHR-102, LUCENTIS®, and/ or EYLEA®. In some instances, the ocular disorder is DME and/or DR. In some instances, the ocular disorder is AMD (e.g., wet AMD). In some instances, the ocular disorder is GA.

A Tie2-binding conjugate, and/or polymeric formulation thereof, can be administered in combination with RTH-258 for treatment of an ocular disorder (e.g., DME, DR, AMD, RVO, or GA). RTH-258 can be administered, for example, by intravitreal injection or eye infusion. In some instances, the ocular disorder is DME and/or DR. In some instances, the ocular disorder is AMD (e.g., wet AMD). In some instances, the ocular disorder is GA.

A Tie2-binding conjugate, and/or polymeric formulation thereof, can be administered in combination with abicipar pegol for treatment of an ocular disorder (e.g., DME, DR, AMD, RVO, or GA). In some instances, the ocular disorder is DME and/or DR. In some instances, the ocular disorder is AMD (e.g., wet AMD). In some instances, the ocular disorder is GA.

A Tie2-binding conjugate, and/or polymeric formulation thereof, can be administered in combination with abicipar pegol for treatment of an ocular disorder (e.g., DME, DR, AMD, RVO, or GA). In some instances, the ocular disorder is DME and/or DR. In some instances, the ocular disorder is AMD (e.g., wet AMD). In some instances, the ocular disorder is GA.

Any suitable DME and/or DR therapeutic agent can be administered in combination with a Tie2-binding conjugate, and/or polymeric formulation thereof, for treatment of an ocular disorder (e.g., DME, DR, DME, RVO, or GA), including, but not limited, to a VEGF antagonist (e.g., LUCENTIS® or EYLEA®), a corticosteroid (e.g., a corticosteroid implant (e.g., OZURDEX® (dexamethasone intravitreal implant) or ILUVIEN® (fluocinolone acetonide intravitreal implant)) or a corticosteroid formulated for administration by intravitreal injection (e.g., triamcinolone acetonide)), or combinations thereof. In some instances, the ocular disorder is DME and/or DR.

A Tie2-binding conjugate, and/or polymeric formulation thereof, can be administered in combination with LUCENTIS® (ranibizumab) for treatment of DME and/or DR (e.g., NPDR or PDR).

A Tie2-binding conjugate, and/or polymeric formulation thereof, can be administered in combination with EYLEA® (aflibercept) for treatment of DME and/or DR (e.g., NPDR or PDR).

A Tie2-binding conjugate, and/or polymeric formulation thereof, can be administered in combination with OZURDEX® (dexamethasone intravitreal implant) for treatment of DME and/or DR.

A Tie2-binding conjugate, and/or polymeric formulation thereof, can be administered in combination with ILUVIEN® (dexamethasone intravitreal implant) for treatment of DME and/or DR.

In some cases, the TAO/PRN treatment regimen or TAE treatment regimen may be used to administer an AMD therapeutic agent (e.g., ranibizumab or aflibercept) in combination with a Tie2-binding conjugate, and/or polymeric formulation thereof. In some instances, the ocular disorder is DME and/or DR. In some instances, the ocular disorder is AMD (e.g., wet AMD). In some instances, the ocular disorder is GA.

Such combination therapies noted above encompass combined administration (where two or more therapeutic agents are included in the same or separate formulations), and separate administration, in which case, administration of the Tie2-binding conjugate of the invention can occur prior to, simultaneously, and/or following, administration of the additional therapeutic agent or agents. In one embodiment, administration of Tie2-binding conjugate, or polymeric formulation and administration of an additional therapeutic agent occur within about 1, 2, 3, 4, or 5 months, or within about 1, 3 or 4 weeks, or within about 1, 2, 3, 4, 5, or 6 days, of each other.

A Tie2-binding conjugate, and/or polymeric formulation thereof, is further contemplated for the treatment of glaucoma. Glaucoma is a group of ocular diseases characterized by progressive damage to the eye at least partly due to elevated intraocular pressure (TOP) (Merck Manual of Diagnosis and Therapy (1999)). Additionally, glaucoma is characterized by retinal ganglion cell (RGC) death, axon loss and an excavated appearance of the optic nerve head (Alward, "Medical Management of Glaucoma," N Eng J Med, 1998; 339:1298-1307). Glaucoma can be diagnosed before vision loss occurs by visual field testing and by ophthalmoscopic examination of the optic nerve to detect "cupping." The mean IOP in normal adults is 15 to 16 mm Hg; the normal range is 10 to 21 mm Hg. One form of management of glaucoma is based on lowering the IOP using topically applied medications ("Glaucoma," Lancet, 1999; 354:1803-1810).

Currently there are five major classes of medications that are used to lower the IOP: β-adrenergic antagonists, adrenergic agonists, parasympathomimetics, prostaglandin-like analogues and carbonic anhydrase inhibitors. Although most medications are applied topically to the eye, they can cause severe systemic side effects and adversely affect the quality of the patient's life. If additional lowering of IOP is indicated or if medication fails to sufficiently lower the IOP, laser trabeculoplasty is usually the next step. If IOP is still not adequately controlled, incisional glaucoma surgery is indicated (Id). The lowering of IOP, despite significantly reducing the extent of neuronal loss, does not ensure cessation of the disease process, because the loss of RGCs may continue. Recent studies of the association between IOP regulation and visual field loss after medical or surgical intervention showed that ongoing neuronal loss reflected in visual field tests can be diminished if the IOP is low. Glaucomatous optic neuropathy appears to result from specific pathophysiological changes and subsequent death of RGCs and their axons. The process of RGC death is thought to be biphasic: a primary injury responsible for initiation of damage followed by a slower, secondary degeneration attributable to the hostile environment surrounding the degenerating cells.

In a further aspect, the invention provides for the use of an anti-Tie2 conjugate in the manufacture or preparation of a medicament. In one embodiment, the medicament is for treatment of an ocular disorder (e.g., DME, DR, AMD, RVO, or GA). In a preferred embodiment, the medicament is for treatment of DME and/or DR. In a further embodiment, the medicament is for use in a method of treating an ocular disorder (e.g., DME, DR, AMD, RVO, or GA) comprising administering to an individual having the ocular disorder an effective amount of the medicament. In one such embodiment, the method further comprises administering to the individual an effective amount of at least one additional therapeutic agent, e.g., as described below. In a further embodiment, the medicament is for reducing vascular permeability, especially in the eye. In a further embodiment, the medicament is for use in a method of reducing vascular permeability, especially in the eye, in an individual comprising administering to the individual an amount effective of the medicament to reduce vascular permeability, especially in the eye. An "individual" according to any of the above embodiments may be a human.

In a further aspect, the invention provides a method for treating an ocular disorder (e.g., DME, DR, AMD, RVO, or GA). In one embodiment, the method comprises administering to an individual having such ocular disorder (e.g., DME, DR, AMD, RVO, or GA) an effective amount of a Tie2-binding conjugate of the invention. In one such embodiment, the method further comprises administering to the individual an effective amount of at least one additional therapeutic agent, as described below. An "individual" according to any of the above embodiments may be a human.

In a further aspect, the invention provides a method for reducing vascular permeability, especially in the eye of an individual. In one embodiment, the method comprises administering to the individual an effective amount of a Tie2-binding conjugate of the invention to reduce vascular permeability, especially in the eye. In one embodiment, an "individual" is a human.

In a further aspect, the invention provides pharmaceutical formulations comprising any of the Tie2-binding conjugates of the invention provided herein, e.g., for use in any of the above therapeutic methods. In one embodiment, a pharmaceutical formulation comprises any of the Tie2-binding conjugates of the invention provided herein and a pharmaceutically acceptable carrier. In another embodiment, a pharmaceutical formulation comprises any of the Tie2-binding conjugates of the invention provided herein and at least one additional therapeutic agent, e.g., as described above.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-Tie2 conjugate and administration of an additional therapeutic agent occur within about 1 month, or within about 1, 2 or 3 weeks, or within about 1, 2, 3, 4, 5, or 6 days, of each other.

A Tie2-binding conjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Tie2 binding conjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a conjugate of the invention (when used alone or in combination with one or more other additional therapeutic agents) will depend on the type of disease to be treated, the type of antibody, the severity and course of the disease, whether the conjugate is administered for preventive or therapeutic purposes, previous therapy, the patient's clinical history and response to the conjugate, and the discretion of the attending physician. The conjugate is suitably administered to the patient at one time or over a series of treatments. Depending on the type and severity of the disease, about 1 μg/kg to 15 mg/kg (e.g., 0.1 mg/kg-10 mg/kg) of conjugate can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the conjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or, e.g., about six doses of the conjugate). An initial higher loading dose, followed by one or more lower doses may be administered. The progress of this therapy is easily monitored by conventional techniques and assays It is understood that any of the above formulations or therapeutic methods may be carried out using an immunoconjugate of the invention in place of or in addition to a Tie2-binding conjugate of the invention.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example, the container may be an intravenous solution bag or a vial having a stopper pierceable by a hypodermic injection needle). At least one active agent in the composition is a Tie2 binding agent or conjugate of the invention. The label or package insert indicates that the composition is used for treating the condition of choice. Moreover, the article of manufacture may comprise (a) a first container with a composition contained therein, wherein the composition comprises a Tie2 binding agent or conjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to a Tie2-binding conjugate.

I. Specific Embodiments of the Invention

In the following, specific embodiments of the invention are listed.

1. An isolated antibody or fragment thereof that binds to Tie2, wherein the antibody comprises:
a heavy chain variable domain (VH) comprising (a) CDR-H1 comprising the amino acid sequence NTDIS (SEQ ID NO:3), (b) CDR-H2 comprising the amino acid sequence RISPSDGNTYYADSVKG (SEQ ID NO:4), and (c) CDR-H3 comprising the amino acid sequence RTRWASX1AX2DY (SEQ ID NO:5), where X1 is M, L, K, F, Y, R, N, Q, H or W and/or or X2 is F, Y L, Q, I, K, or H, and a light chain variable domain (VL) comprising (d) CDR-L1 comprising the amino acid sequence RASQDVSTAVA (SEQ ID NO:8), (e) CDR-L2 comprising the amino acid sequence SASFLYS (SEQ ID NO:9), and (f) CDR-L3 comprising the amino acid sequence QQSYTTPPT (SEQ ID NO:10).

2. The antibody of the preceding embodiment, wherein the CDR-H3 comprises the amino acid sequence RTRWASWAMDY (SEQ ID NO:6).

3. The antibody of embodiment 1, wherein the CDR-H3 comprises the amino acid sequence RTRWASWAFDY (SEQ ID NO:7).

4. The antibody of any one of the preceding embodiments, which is a monoclonal antibody.
5. The antibody of any one of the preceding embodiments, which is a humanized or chimeric antibody.

6. The antibody of any one of the preceding embodiments, which is an antibody fragment that binds Tie2.

7. The antibody of any one of the preceding embodiments, which is a Fab fragment.

10. The antibody of any one of embodiments 1 to 7, comprising a VL domain comprising an amino acid sequence having at least 95% sequence identity to the amino acid sequence of SEQ ID NO:21 and a VH domain comprising an amino acid sequence having at least 95% sequence identity to the amino acid sequence of SEQ ID NO:20.

11. The antibody of any one of embodiments 1 to 7, comprising a VL domain comprising an amino acid sequence having at least 96% sequence identity to the amino acid sequence of SEQ ID NO:21 and a VH domain comprising an amino acid sequence having at least 96% sequence identity to the amino acid sequence of SEQ ID NO:20.

12. The antibody of any one of embodiments 1 to 7, comprising a VL domain comprising an amino acid sequence having at least 97% sequence identity to the amino acid sequence of SEQ ID NO:21 and a VH domain comprising an amino acid sequence having at least 97% sequence identity to the amino acid sequence of SEQ ID NO:20.

13. The antibody of any one of embodiments 1 to 7, comprising a VL domain comprising an amino acid sequence having at least 98% sequence identity to the amino acid sequence of SEQ ID NO:21 and a VH domain comprising an amino acid sequence having at least 98% sequence identity to the amino acid sequence of SEQ ID NO:20.

14. The antibody of any one of embodiments 1 to 7, comprising a VL domain comprising an amino acid sequence having at least 99% sequence identity to the amino acid sequence of SEQ ID NO:21 and a VH domain comprising an amino acid sequence having at least 99% sequence identity to the amino acid sequence of SEQ ID NO:20.

15. The antibody of any one of the preceding embodiments, wherein the antibody comprises: the VL sequence of SEQ ID NO:21 and a VH sequence of SEQ ID NO:19; the VL sequence of SEQ ID NO:21 and a VH sequence of SEQ ID NO:22; or the VL sequence of SEQ ID NO:21 and a VH sequence of SEQ ID NO:20.

16. The antibody of any one of the preceding embodiments, wherein the antibody comprises an engineered cysteine.

17. The antibody of embodiment 16, wherein the engineered cysteine is selected from a T120C, G166C, G178C, T187C, and T209C in the HC; or the engineered cysteine is selected from Q124C, R142C, Q155C, L201C, T206C, K107C, K126C, and K149C in the LC; wherein the residue number of the engineered cysteine is according to EU numbering.

18. The antibody of embodiment 16 or 17, wherein the engineered cysteine is selected from T209C in the HC and T206C in the LC.

19. The antibody of any one of embodiments 16 to 18, wherein the engineered cysteine is T206C in the LC.

20. The antibody of any one of embodiments 16 to 18, wherein the engineered cysteine is T209C in the HC.

21. The antibody of any one of the preceding embodiments, comprising a LC comprising an amino acid sequence having at least 95% sequence identity to the amino acid sequence of SEQ ID NO:25 and a HC comprising an amino acid sequence having at least 95% sequence identity to the amino acid sequence of SEQ ID NO:55.

22. The antibody of any one of the preceding embodiments, comprising a LC comprising an amino acid sequence having at least 96% sequence identity to the amino acid sequence of SEQ ID NO:25 and a HC comprising an amino acid sequence having at least 96% sequence identity to the amino acid sequence of SEQ ID NO:55.

23. The antibody of any one of the preceding embodiments, comprising a LC comprising an amino acid sequence having at least 97% sequence identity to the amino acid sequence of SEQ ID NO:25 and a HC comprising an amino acid sequence having at least 97% sequence identity to the amino acid sequence of SEQ ID NO:55.

24. The antibody of any one of the preceding embodiments, comprising a LC comprising an amino acid sequence having at least 98% sequence identity to the amino acid sequence of SEQ ID NO:25 and a HC comprising an amino acid sequence having at least 98% sequence identity to the amino acid sequence of SEQ ID NO:55.

25. The antibody of any one of the preceding embodiments, comprising a LC comprising an amino acid sequence having at least 99% sequence identity to the amino acid sequence of SEQ ID NO:25 and a HC comprising an amino acid sequence having at least 99% sequence identity to the amino acid sequence of SEQ ID NO:55.

26. The antibody of any one of the preceding embodiments, wherein the antibody comprises a LC comprising the sequence of SEQ ID NO:25 and a HC comprising the sequence of SEQ ID NO:55.

27. The antibody of any one of embodiments 1 to 25, wherein the antibody comprises a LC comprising the sequence of SEQ ID NO:25 and a HC comprising the sequence selected from SEQ ID NO:89, SEQ ID NO:90, SEQ ID NO:91, and SEQ ID NO:92.

28. The antibody of any one of embodiments 1 to 20, comprising a LC comprising an amino acid sequence having at least 95% sequence identity to the amino acid sequence of SEQ ID NO:56 and a HC comprising an amino acid sequence having at least 95% sequence identity to the amino acid sequence of SEQ ID NO:23.

29. The antibody of any one of embodiments 1 to 20, comprising a LC comprising an amino acid sequence having at least 96% sequence identity to the amino acid sequence of SEQ ID NO:56 and a HC comprising an amino acid sequence having at least 96% sequence identity to the amino acid sequence of SEQ ID NO:23.

30. The antibody of any one of embodiments 1 to 20, comprising a LC comprising an amino acid sequence having at least 97% sequence identity to the amino acid sequence of SEQ ID NO:56 and a HC comprising an amino acid sequence having at least 97% sequence identity to the amino acid sequence of SEQ ID NO:23.

31. The antibody of any one of embodiments 1 to 20, comprising a LC comprising an amino acid sequence having at least 98% sequence identity to the amino acid sequence of SEQ ID NO:56 and a HC comprising an amino acid sequence having at least 98% sequence identity to the amino acid sequence of SEQ ID NO:23.

32. The antibody of any one of embodiments 1 to 20, comprising a LC comprising an amino acid sequence having at least 99% sequence identity to the amino acid sequence of SEQ ID NO:56 and a HC comprising an amino acid sequence having at least 99% sequence identity to the amino acid sequence of SEQ ID NO:23.

33. The antibody of any one of embodiments 1 to 20, wherein the antibody comprises a LC comprising the sequence of SEQ ID NO:56 and a HC comprising the sequence of SEQ ID NO:90, SEQ ID NO:91, or SEQ ID NO:23.

34. An antibody that specifically binds to Tie-2 wherein the antibody comprises a HC comprising the sequence of SEQ ID NO:55 and a LC comprising the sequence of SEQ ID NO:25.

35. An isolated nucleic acid encoding the antibody of any of the preceding embodiments.

36. A host cell comprising the nucleic acid of embodiment 38.

37. A method of producing an antibody that binds to Tie-2 comprising culturing the host cell of embodiment 39 under conditions suitable for the expression of the antibody.

38. A conjugate that binds to Tie2, wherein the conjugate comprises at least two, at least three, at least four, at least five, at least six, at least seven, or at least eight antibodies according to any one of embodiments 1 to 34, wherein each of the antibodies is linked to a multimerizing moiety.

39. The conjugate of embodiment 38, wherein the conjugate activates phosphorylation of Tie2 in an in vitro or in vivo cellular assay.

40. The conjugate of embodiment 38 or 39, wherein the conjugate causes a reduction in Tie2 protein levels in an in vitro assay by less than 25%, less than 50% or less than 75%; or wherein the conjugate does not cause a reduction in Tie-2 protein levels in an in vitro assay by more than 25%, more than 50%, or more than 75%.

41. The conjugate of any one of embodiments 38 to 40, wherein the conjugate reduces vascular permeability as determined by an in vitro barrier function assay.

42. The conjugate of any one of embodiments 38 to 42, wherein the multimerizing moiety comprises a polyol, a polypeptide, and/or a peptide.

43. The conjugate of embodiment 42, wherein the polyol is a multi-armed polyol, selected from a dimer, a tetramer, a hexamer, and an octamer.

44. The conjugate of embodiment 43, wherein the multi-armed polyol is a hexamer.

45. The conjugate of embodiment 43 or 44, wherein the multi-armed polyol is an octamer.

46. The conjugate of any one of embodiments 42 to 45, wherein the polyol is a polyethylene glycol (PEG).

47. The conjugate of any one of embodiments 42 to 45, wherein the polyol is covalently linked to the at least two antibodies through a free sulfhydryl group of a cysteine amino acid.

48. The conjugate of embodiment 47, wherein the cysteine amino acid is an engineered cysteine.

49. The conjugate of embodiment 48, wherein the engineered cysteine is in a HC and/or LC constant region of the antibody.

50. The conjugate of embodiment 48 or 49, wherein the engineered cysteine is selected from the group consisting of T120C, G166C, G178C, T187C, and T209C in the HC; or the engineered cysteine is selected from the group consisting of Q124C, R142C, Q155C, L201C, T206C, K107C, K126C, and K149C in the LC; wherein the residue number is according to EU numbering.

51. The conjugate of any one of embodiments 48 to 50, wherein the engineered cysteine is T206C in the LC, wherein the residue number is according to EU numbering.

52. The conjugate of any one of embodiments 48 to 50, wherein the engineered cysteine is T209C in the HC, wherein the residue number is according to EU numbering.

53. The conjugate of any one of embodiments 42 to 45, wherein the polyol is covalently linked to the at least one antibody through a free amino group of a lysine amino acid.

54. The conjugate of embodiment 53, wherein the lysine amino acid is in a HC or LC constant region of the antibody and/or the lysine amino acid is at the C-terminus of the heavy chain or light chain of the antibody.

55. The conjugate of any one of embodiments 46 to 54, wherein the PEG has a weight average molecular weight of from about 500 Daltons (Da) to about 300,000 Da or from about 500 Da to about 20,000 Da.

56. The conjugate of to any one of embodiments 46 to 55, wherein the PEG has a weight average molecular weight of about 6000 Da.

57. The conjugate of any one of embodiments 46 to 56, wherein the PEG comprises a dipentaerythritol hexamer or octamer core.

58. The conjugate of any one of embodiments 46 to 57, wherein the PEG has the structure of general formula (Ia):

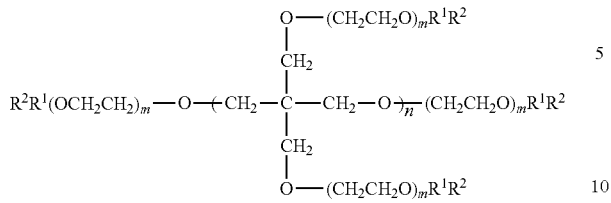

(Ia)

wherein n is an integer from 1-10; each m is independently an integer from 3-250; each $R^1$ is independently either absent or is a linking group; and each $R^2$ is independently either hydrogen or a terminal reactive group;

wherein at least one $R^2$ is a terminal reactive group and is covalently linked to the antibody of any one of claims 1 to 14.

59. The conjugate according to any one of embodiments 46 to 57, wherein the PEG has the structure of general formula (Ib):

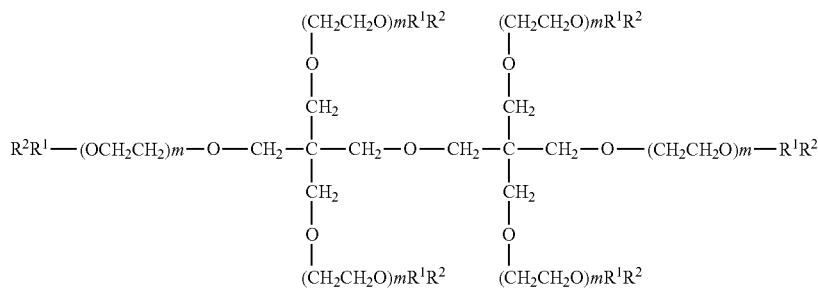

wherein each m is independently an integer from 3-250; each $R^1$ is independently either absent or is a linking group; and each $R^2$ is independently either hydrogen or a terminal reactive group;

wherein at least one $R^2$ is a terminal reactive group and is covalently linked to the antibody of any one of claims 1 to 14.

60. The conjugate of embodiment 59, wherein each m is independently an integer from 15 to 35, preferably about 20 to 30.

61. The conjugate of any one of embodiments 43 to 60, wherein the conjugate is prepared by covalently linking at least one antibody of any one of embodiments 1 to 34 to the multi-armed polyol.

62. A conjugate comprising an antibody that specifically binds to Tie-2 wherein the antibody comprises a VH sequence of SEQ ID NO:20 and a VL sequence of SEQ ID NO:21, wherein the antibody is covalently linked to a polyethylene glycol having the structure of general formula (Ib):

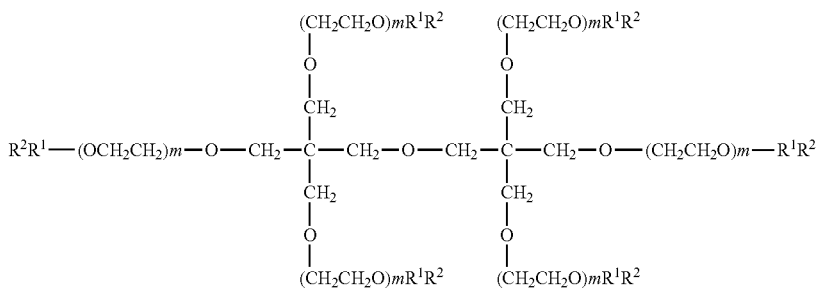

wherein each m is independently an integer from 3-250; each $R^1$ is independently either absent or is a linking group; and each $R^2$ is independently either hydrogen or a terminal reactive group;
wherein at least one $R^2$ is a terminal reactive group and is covalently linked to the antibody.

63. The conjugate of embodiment 62, wherein m is an integer of 10 to 200.

64. The conjugate of embodiment 62 or 63, wherein m is an integer of 20 to 30.

65. The conjugate of any one of embodiments 58 to 64, wherein $R^1$ is absent or where $R^1$ is selected from the group consisting of:

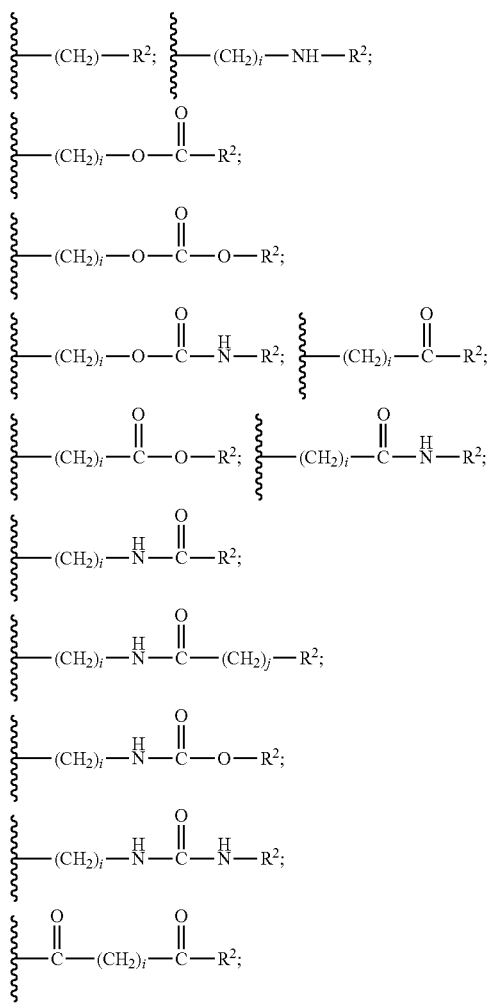

and combinations thereof; wherein each i is independently an integer of 0-10; j is an integer of 0-10; and $R^2$ is a terminal reactive group selected from the group consisting of a thiol reactive group, an amino reactive group, and combinations thereof.

66. The conjugate of any one of embodiments 58 to 65, wherein $R^2$ is a terminal reactive group selected from the group consisting of a maleimide, a sulfhydryl, a thiol, trifluoromethanesulfonate, tosylate, aziridine, epoxide, a pyridyl disulfide, succinimidyl ester, —$NH_2$, an aldehyde, a haloacetate, a haloacetamide, and a para-nitrophenyl carbonate.

67. The conjugate of any one of embodiments 58 to 66, wherein $R^2$ is a maleimide.

68. A conjugate of any one of embodiments 43 to 67, wherein the conjugate is prepared by covalently linking at least one antibody of any one of claims 1 to 34 to the multi-armed polyol.

69. A pharmaceutical composition comprising the conjugate according to any one of embodiments 38 to 68 and a pharmaceutically acceptable carrier.

70. The pharmaceutical composition according to embodiment 69, wherein the concentration of the conjugate is from about 50 mg/ml to about 300 mg/ml.

71. The pharmaceutical composition according embodiment 69 or 70, further comprising an additional therapeutic agent.

72. The pharmaceutical composition according to embodiment 71, wherein the additional therapeutic agent is selected from the group consisting of a VEGF antagonist, an Ang2 antagonist, an HtrA1 antagonist, and IL33 antagonist, a complement component antagonist, and a second Tie2 agonist.

73. The pharmaceutical composition according to embodiment 72, wherein the VEGF antagonist is selected from the group consisting of a VEGF trap and an anti-VEGF antibody.

74. A long acting delivery device for ocular delivery comprising the pharmaceutical composition according to any one of embodiments 79 to 73 and a means for delivering the composition intravitreally to a patient, wherein the composition remains effective on site for a prolonged period of time.

75. A method of treating a Tie2 pathway-mediated disorder in a subject comprising administering to the subject an effective amount of the antibody of any one of embodiments 1 to 34, the conjugate of any one of embodiments 38 to 68, or the pharmaceutical composition of any one of embodiments 69 to 73.

76. The method of embodiment 75, wherein the Tie2 pathway-mediated disorder is a vascular permeability disorder.

77. The method of embodiment 75 or 76, wherein the Tie2 pathway-mediated disorder is an eye condition.

78. The method of embodiment 77, wherein the eye condition is selected from diabetic macular edema (DME), diabetic retinopathy, age-related macular degeneration (AMD), including dry and wet (non-exudative and exudative) forms, choroidal neovascularization (CNV), uveitis, ischemia-related retinopathy, pathological myopia, von Hippel-Lindau disease, histoplasmosis of the eye, Central Retinal Vein Occlusion (CRVO), corneal neovascularization, glaucoma, and retinal neovascularization.

79. The method of any one of embodiments 75 to 78, wherein the eye condition is DME.

80. The method of any one of embodiments 75 to 79, wherein the method comprises administering the antibody, conjugate, or pharmaceutical formulation using an implantable port delivery system.

81. The method of any one of embodiments 75 to 79, wherein the method comprises administering the antibody, conjugate, or pharmaceutical formulation by intravitreal administration.

82. The method of embodiment 81, wherein the intravitreal administration is through a narrow bore needle.

83. The method of embodiment 82, wherein the narrow bore needle is about 30, 29, 28, 27, 26, 25, 24, 23, or 22 gauge.

84. The method of any one of embodiments 75 to 83, further comprising administering an additional therapeutic agent to the individual.

III. Examples

The following are examples of methods and compositions of the invention. It is understood that various other embodiments may be practiced, given the general description provided above.

Example 1—Generation of Anti-Tie 2 Antibodies Derived from Naive Phage Libraries Antibodies binding the extracellular domain (ECD) of Tie2 were initially selected from phage-displayed synthetic antibody libraries that were built on a single human framework by introducing synthetic diversity at solvent-exposed positions within the heavy chain CDRs as described below. The phage were screened against the ECD as well as various subdomains of the ECD.

Phagemid Vectors for Library Construction

Phagemids pV0350-2b and pV0350-4, were designed to display a Fab template monovalently or bivalently, respectively, on the surfaces of M13 phage particles. The Fab template was based on the h4D5 antibody, which antibody is a humanized antibody recognizing a cancer-associated antigen known as Her-2 (erbB2). The h4D5 sequence was obtained by polymerase chain reaction using the humAb4D5 version 8 ("humAb4D5-8") sequence (Carter et al., (1992) PNAS 89:4285-4289). The h4D5 nucleic sequence encodes modified CDR regions from a mouse monoclonal antibody specific for Her-2 in a human consensus sequence Fab framework. Specifically, the sequence contains a kappa light chain (LC region) upstream of VH and CH1 domains (HC region). The method of making the anti-Her-2 antibody and the identity of the variable domain sequences are provided in U.S. Pat. Nos. 5,821,337 and 6,054,297.

The vector pV0350-2b was constructed by modifying a previously described phagemid (pHGHam-gIII) that has been used for the phage display of human growth hormone (hGH) under the control of a phoA promoter. An open reading frame in phGHam-gIII that encodes for the stII secretion signal sequence and hGH fused to the C-terminal domain of the M13 minor coat protein P3 (cP3) was replaced with a DNA fragment containing two open reading frames. The first open reading frame encoded for the h4D5 light chain (version 8) and the second encoded for the variable (VH) and first constant (CH1) domains of the h4D5 heavy chain fused to cP3; each protein was directed for secretion by an N-terminal stII signal sequence. The amber stop codon between the heavy chain fragment and cP3 was deleted, as this modification has been shown to increase the levels of Fab displayed on phage. An epitope tag was added to the C terminus of the h4D5 light chain (gD tag). The vector for bivalent display (pV0350-4) was identical with pV0350-2b, except for the insertion of a DNA fragment encoding for a GCN4 leucine zipper between the heavy chain CH1 domain and cP3 as described. The light chain gene was further modified in both phagemids at three positions to encode for amino acids most commonly found in the Kabat database of natural antibody sequences; specifically, Arg66 was changed to Gly and Asn30 and His91 were changed to Ser. These changes were found to increase Fab expression and display on phage. Site-directed mutagenesis was performed using the method of Kunkel et al. (Kunkel, J. D., et al., (1987) Methods Enzymol 154:367-82).

Phage-displayed libraries were generated using oligonucleotide-directed mutagenesis and "stop template" versions of pV0350-2b or pV0350-4 as described (Lee, C. V., et al., (2004) J. Immunol. Methods 284:119-132; Lee, C. V., et al., (2004) JMB 340:1073-1093). Stop codons (TAA) were embedded in all three heavy-chain CDRs. These were repaired during the mutagenesis reaction by a mixture of degenerate oligonucleotides that annealed over the sequences encoding for CDR-H1, -H2 and -H3 and replaced codons at the positions chosen for randomization with tailored degenerate codons. Mutagenesis reactions were electroporated into E. coli SS320 cells, and the cultures were grown overnight at 30° C. in 2YT broth supplemented with KO7 helper phage, 50 g/ml of carbenicillin and 50 g/ml of kanamycin. Phage was harvested from the culture medium by precipitation with PEG/NaCl as described (Sidhu, S. S. et al., (2000), Methods Enzymol. 328:333-363). Each electroporation reaction used ~1011 E. coli cells and ~10 ug of DNA and resulted in 1×109-5×109 transformants.

A distinct library was made with degenerate oligonucleotides tailored to mimic the natural diversity of CDR-H1 and CDR-H2 (Table 1 in Lee, C. V, et al., (2004), JMB, supra): library 3 (Lib-3) with Fab.zip template. See Lib-3 described in Lee, C. V, et al., (2004), supra. Two to four oligonucleotides for CDR-H1 and CDR-H2 were combined to increase the coverage of natural diversity. Lib-3 used oligonucleotides H1a and H1b (ratio 2:1) and H2a-c (ratio 1:2:0.1) for CDR-H1 and CDR-H2, respectively (see Table 1 of Lee, C. V. et al. (2004), JMB, supra, for a description of the oligonucleotides).

For positions 95-100 in CDR-H3, Lib-3 consists of a set of libraries with expanded CDR-H3 lengths containing either NNS codons (or NNK codons) or a modified version of the NNS codon (the XYZ codon) that contained unequal nucleotide ratios at each position of the codon triplet. The NNS codon encompassed 32 codons and encoded for all 20 amino acids. X contained 38% G, 19% A, 26% T and 17% C; Y contained 31% G, 34% A, 17% T and 18% C; and Z contained 24% G and 76% C. The CDR-H3 design for Lib-3 is described in Table 5 of Lee, C. V. et al., (2004), supra. Separate mutagenesis reactions were performed and electroporated for each CDR-H3 length, except for lengths 7 and 8 residues which were electroporated together.

Phage display level of complete Fabs in each library was examined by measuring the binding of 48 randomly picked clones to anti-gD antibody. For Lib-3, similar levels of display were observed for the different CDR-H3 lengths, except that libraries incorporating the longest CDR-H3s (from 15-19 residues) had a reduced percentage of Fab displaying clones (15-30%). This may reflect the reduced mutagenesis efficiency when using very long synthetic oligonucleotides.

Phage Sorting

Lib-3 described above was sorted against various Tie2 extracellular domain (ECD) proteins. The Tie2 ECD is composed, from membrane distal to membrane proximal, of 3 IgG domains (Ig1 and Ig2), 3 EGF domains (EGF1-3), a third IgG domain (Ig3) and 3 fibronectin type III domains (FN3) (see, e.g., FIG. 1). Constructs were generated to encode the full extracellular domain (ECD), the membrane-proximal FN3 domains, or the ECD without the FN3 domains (termed ECD5). The ligand binding domain, Ig2, is therefore encoded for by both ECD and ECD5 constructs but absent from the FN3 construct. Encoded proteins were fused at the C-terminal to either the Fc region of hIgG1 for human and cyno proteins or mIgG2a for murine and rat proteins, or a C-terminal Flag tag for all species. FIG. 1 illustrates proteins used for panning. Full ECD constructs for human, murine and rat Tie1 receptor were also generated with both C-terminal Fc fusions or Flag tag.

Expression and Purification of Tie2 ECD Proteins

The flag tagged Tie2 ECDs were expressed and purified from Chinese hamster ovary (CHO) cell conditioned media. After 11-14 days, the conditioned media was harvested and concentrated approximately tenfold. The concentrate was loaded onto an anti-flag-tag column and washed with 25 mM TRIS, 150 mM NaCl, 1 mM EDTA, pH 7.5, binding buffer, containing 0.1% Triton X-114 and 0.1% Triton X-110. The flag-tagged protein was then eluted with 50 mM N citrate, 150 mM NaCl, pH 3.0 and then neutralized to pH 5.0 using 1 M arginine, 400 mM succinic acid, pH 9.0. The eluted protein was loaded onto a size exclusion column (either Superdex 200 or Superdex 75) in phosphate buffered saline and fractions were collected; the monomer peak fraction was pooled, concentrated and 0.2 um filtered.

For panning, 96-well Nunc Maxisorp plates were coated with 100 ul/well of target Tie2 antigen (5 ug/ml) in PBS at 4° C. overnight. The plates were blocked with 65 ul 1% blocking protein for 30 minutes (min) and 40 ul 1% Tween20 for another 30 min (blocking protein: 1st round: bovine serum albumin (BSA), 2nd round: casein, 3rd round: bovine serum albumin (BSA), 4th round: casein). Next, the phage library was diluted to ~3-5 OD/ml with 1% BSA with 0.1% Tween 20 (1 OD=$1.13\times10^{13}$ phage/ml). In general, the phage input was: 1st round 3-5 OD/ml, 2nd round 3 OD/ml, 3rd round ~0.5-1 OD/ml and 4th round ~0.1-0.5 OD/ml. The diluted phage was incubated for 30 min at room temperature. The wells were washed at least 5 times continuously with PBS and 0.05% Tween 20. The blocked phage library was added 100 ul/well to 8 target antigen-coated wells and 2 uncoated wells at room temperature for 2 hours (hr). The plates were washed continuously at least 10 times with PBS and 0.05% Tween 20. Starting with the 3rd round of panning, 1 uM omalizumab as an irrelevant Fc containing protein, Tie2.ECD5, or antibody anti-Tie2.20 (ligand blocking) were added to the phage library for an hour before applying the mixture on Tie2 coated wells binding for 2 hr. The phage were eluted with 100 ul/well of 100 mM HCl at room temperature for 20 min. The eluted phage (from coated wells) and background phage (from uncoated wells) were collected in separate tubes. The eluted collections were neutralized by adding 1/10 volume 1 M Tris pH 11.0 to both tubes. BSA was added to a final 0.1% into the tube of eluted phage. To titer the phage, 90 ul of log phase XL-1 (OD 600 nm-0.1-0.3) was infected with 10 ul eluted phage or background phage at 37° C. for 30 min. Next, the infected cells were serially diluted in 10 fold increments with 90 ul 2YT. 10 ul aliquots of the infected cells were plated on carbenicillin plate.

To propagate the phage in between panning rounds, approximately 400 ul of eluted phage was used to infect ~4 ml log phase XL-1 (OD 600 nm-0.1-0.3) at 37° C. for 30-45 min. Helper phage KO7 and carbenicillin were added to the infection at a final concentration of $1\times10^{10}$ pfu/ml KO7 and 50 ug/ml cabenicillin at 37° C. for another hr. The culture was grown 2YT media with carbenicillin 50 ug/ml and 50 ug/ml kanamycin to final volumes of 20~25 ml at 37° C., 4 hr and 30° C. overnight (or at least 18 hr). The next day, library phage were purified by spinning down the cells at 8000 rpm for 10 min. The supernatant was collected. 20% PEG/2.5M NaCl was added at 1/5 of the supernatant volume, mixed and allowed to sit on ice for 5 min. The phage were pelleted at 12000 rpm for 15 min. The pellet was spun again for 5 min at 5000 rpm. The pellets were resuspended in 1 ml PBS and spun down at 12000 rpm for 15 min to clear debris and precipitated with the PEG/NaCl addition. The phage pellet was resuspended in PBS. The OD of the resupended phage pellet was read at 268 nm.

Screening ELISA Assays

Clones from the fourth round were screened for Tie2 binding and specificity by ELISA. Screening ELISAs were carried out by coating the wells of a 96-well microtiter plate with Tie2 protein or irrelevant protein at 65 ul per well (1 ug/ml in coating buffer) at 4° C. overnight. In a 96-tube plate, colonies from the fourth round were grown overnight at 37° C. in 400 ul 2YT media with 50 ug/ml carbenicillin and helper phage K07. The plate was spun down at 3000 rpm for 10 min. 30 ul of the culture supernatant was added with 60 ul of ELISA buffer (PBS with 0.5% BSA and 0.05% Tween20) to the Tie2-coated plate and incubated at room temperature for 1 hr. Plates were washed with PBS—0.05% Tween20 and 100 ul/well of horseradish peroxidase (HRP)-conjugated anti-M13 antibody (1/5000 dilution in PBS plus 0.5% BSA and 0.05% Tween20) at room temperature for 30 min (Sidhu et al., supra). The wells were washed with PBS—0.05% Tween20 prior to 100 ul/well of a 1:1 ratio of 3,3',5,5'-tetramethylbenzidine (TMB) peroxidase substrate and Peroxidase Solution B ($H_2O_2$) ((Kirkegaard-Perry Laboratories (Gaithersburg, MD)) being added per well and incubated for 5 min at room temperature. The reaction was stopped by adding 100 ul 1M phosphoric Acid ($H_3PO_4$) per well and the OD of wells was determined using a standard ELISA plate reader at 450 nm.

Clones that had Tie2 binding above background and possessed Tie2-binding species specificity and low binding to an irrelevant Fc-containing protein (omalizumab) were analyzed further. Tables 2-5 below summarizes the binding data. None in Tables 2-5 showed binding to omalizumab.

TABLE 2

| Ab | Panned Protein | ELISA Screening-Binding to | | | |
|---|---|---|---|---|---|
| | | huECD5 | mECD5 | huFN3 | mFN3 |
| Tie2.1 | huECD5.Fc | +++ | +++ | | |
| Tie2.2 | huECD5.Fc | +++ | − | | |
| Tie2.3 | huECD5.Fc | +++ | +++ | | |
| Tie2.4 | huECD5.Fc | +++ | +++ | | |
| Tie2.5 | huECD5.Fc | +++ | +++ | | |
| Tie2.6 | huECD5.Fc | +++ | +++ | | |
| Tie2.7 | huECD5.Fc | +++ | − | | |
| Tie2.8 | huECD5.Fc | +++ | +/− | | |
| Tie2.9 | huECD5.Fc | +++ | ++ | | |
| Tie2.10 | huECD5.Flag | +++ | +++ | | |
| Tie2.11 | huECD5.Flag | +++ | − | | |
| Tie2.12 | huECD5.Flag | +++ | +++ | | |
| Tie2.13 | huECD5.Flag | +++ | +++ | | |
| Tie2.14 | hFN3.fc | | | +++ | − |
| Tie2.15 | hECD5.Flag | +++ | +++ | | |
| Tie2.16 | hECD5.Flag | +++ | − | | |
| Tie2.17 | hFN3.Fc | | | +++ | − |
| Tie2.18 | mECD5.Fc | +++ | +++ | | |
| Tie2.19 | mECD5.Fc | +++ | +++ | | |
| Tie2.20 | mECD5.Fc | +++ | +++ | | |

TABLE 3

| Ab | Panned Protein | ELISA Screening-Binding to | |
|---|---|---|---|
| | | hFullECD | mFullECD |
| Tie2.21 | hfull.Flag | +++ | +++ |
| Tie2.22 | hECD5.Flag | +++ | +++ |
| Tie2.23 | hECD5.Flag | +++ | +++ |
| Tie2.24 | hECD5.Flag | +++ | +++ |
| Tie2.25 | hECD5.Flag | +++ | +++ |
| Tie2.26 | hECD5.Flag | +++ | ++ |
| Tie2.27 | mFN3.Fc | − | +++ |

TABLE 4

| Ab | Panned Protein | ELISA Screening-Binding to | | |
|---|---|---|---|---|
| | | hFull.Fc | mFull.Fc | rFull.Fc |
| Tie2.28 | hfull.Fc | +++ | ++ | +++ |
| Tie2.29 | hfull.Fc | +++ | +++ | +++ |
| Tie2.30 | hfull.Fc | +++ | +++ | +++ |
| Tie2.31 | hfull.Fc | +++ | +++ | +++ |
| Tie2.32 | hfull.Fc | +++ | +++ | +++ |
| Tie2.33 | hfull.Fc | +++ | +++ | +++ |
| Tie2.34 | rfull.Fc-ECD5 | +++ | +++ | +++ |
| Tie2.35 | mfull.Fc | +++ | +++ | +++ |
| Tie2.36 | mfull.Fc | +++ | +++ | +++ |
| Tie2.37 | mfull.Fc-ECD5 | +++ | +++ | +++ |
| Tie2.38 | mfull.Fc-aTie2.20 | +++ | +++ | +++ |

TABLE 5

| Ab | Panned Protein | ELISA Screening-Binding to | | | |
|---|---|---|---|---|---|
| | | hFullECD | rFull.ECD | hFN3 | rECD5 |
| Tie2.39 | mful.Fc-aTie2.20 | +++ | +++ | | |
| Tie2.40 | mful.Fc-aTie2.20 | +++ | +++ | | |
| Tie2.41 | mful.Fc-aTie2.20 | +++ | +++ | | |
| Tie2.42 | mful.Fc-aTie2.20 | ++ | +++ | +++ | |
| Tie2.43 | rfull.Fc-ECD5 | +++ | +++ | +++ | |
| Tie2.44 | rfull.Fc-ECD5 | − | +++ | − | +++ |
| Tie2.45 | rfull.Fc-ECD5 | +++ | +++ | ++ | |
| Tie2.46 | rfull.Fc-ECD5 | − | +++ | − | +++ |
| Tie2.47 | rfull.Fc-ECD5 | − | +++ | − | +++ |
| Tie2.48 | rfull.Fc-aTie2.20 | +++ | +++ | +++ | |
| Tie2.49 | rfull.Fc-aTie2.20 | +++ | +++ | +++ | |
| Tie2.50 | rfull.Fc-aTie2.20 | +++ | +++ | +++ | |
| Tie2.51 | rfull.Fc-aTie2.20 | − | +++ | − | +++ |
| Tie2.52 | rfull.Fc-aTie2.20 | +++ | +++ | +++ | |

Anti-Tie2 IgG Expression and Purification

Positive binders as identified above with desired species specificity and low irrelevant-protein binding were sequenced and the variable domain of the anti-Tie2 heavy chains were cloned into a vector previously designed for transient human IgG1 expression in mammalian cells. (Lee et al., 2004a).

The resultant anti-Tie2 human IgG was expressed using 293 transient transfection using the heavy chains encoded by the constructs generated above and the 4D5 light chain (SEQ ID NO:25). IgG was purified from transfection supernatants with protein A affinity chromatography and screened by ELISA for Tie2 binding confirmation, Tie1 binding, and epitope mapping. Eight antibodies were not further analyzed because the hIgG protein either did not express or expressed poorly.

Figure 2A:
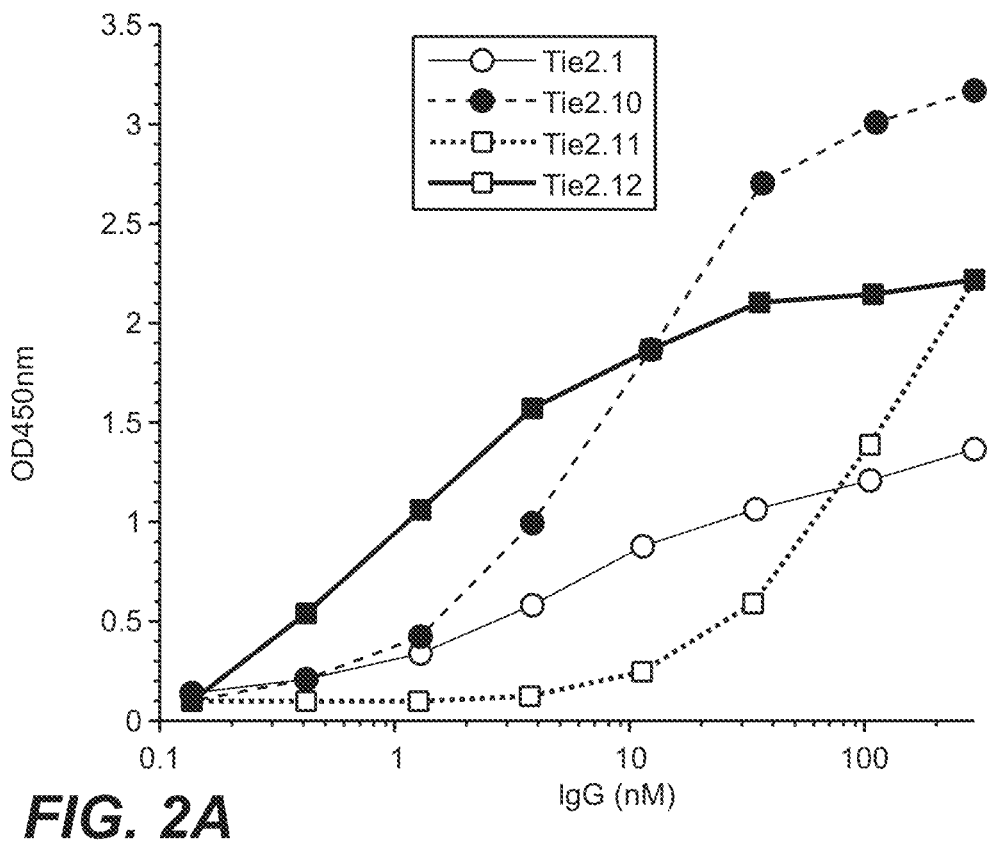
FIGS. 2A-2B show results of an assay to assess binding by anti-Tie2 antibodies Tie2.1, Tie2.10, Tie2.11 and Tie2.12 to mouse Tie2 ECD5 domain (FIG. 2A) and to human Tie2 ECD5 domain (FIG. 2B). The ECD5 domain comprises the Ig1, Ig2, EGF and Ig3 domains of Tie2.
Figure 2B:
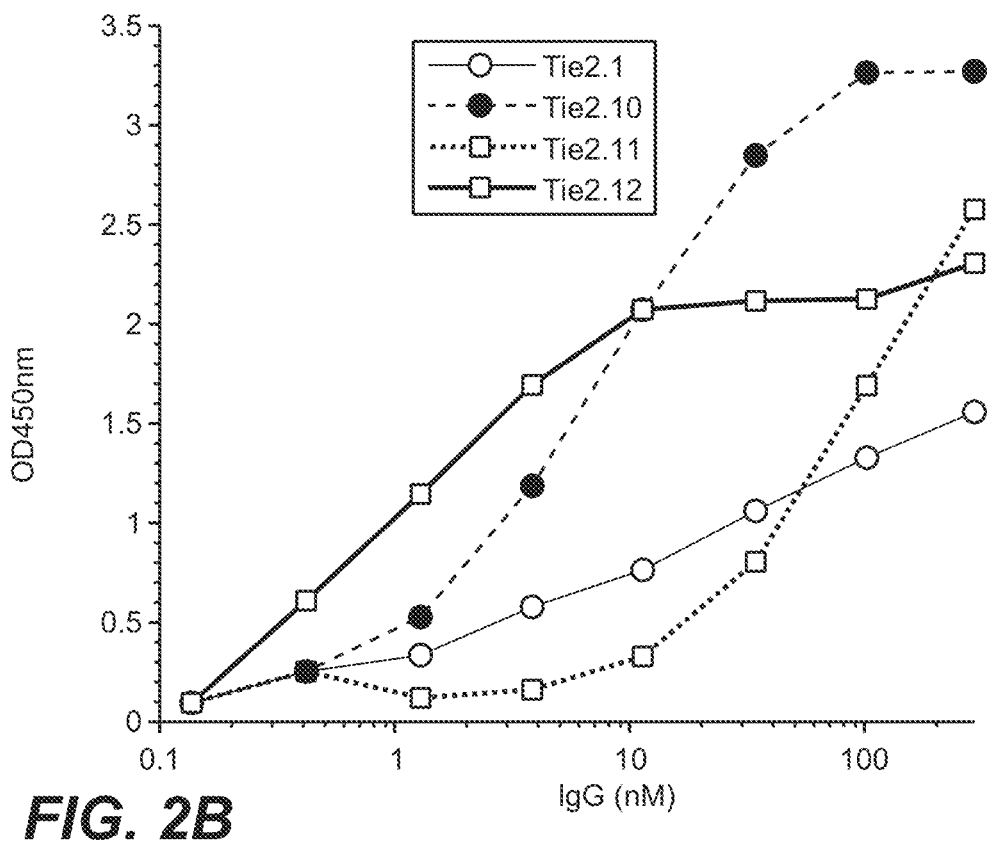

Example 2—Characterization of Anti-Tie 2 Antibodies Derived from Phage Libraries Tie2 Binding To confirm Tie2 binding by anti-Tie2 antibodies, an ELISA format was used in which Tie2 extracellular constructs prepared as an IgG1 format as described above was immobilized on Maxisorp immunoplates at 2 ug/ml in 65 ul PBS overnight at 4° C. overnight. Serial dilutions of anti-Tie2 IgGs were applied to plates with immobilized Tie2 that had been previously blocked with 1% BSA in PBS and incubated for 20 min at room temperature. Plates were washed and detected with anti-huFC-conjugated HRP secondary antibody using the methods above. FIG. 2A and FIG. 2B show the binding of various clones to human Tie2 ECDs.

Figure 3A:
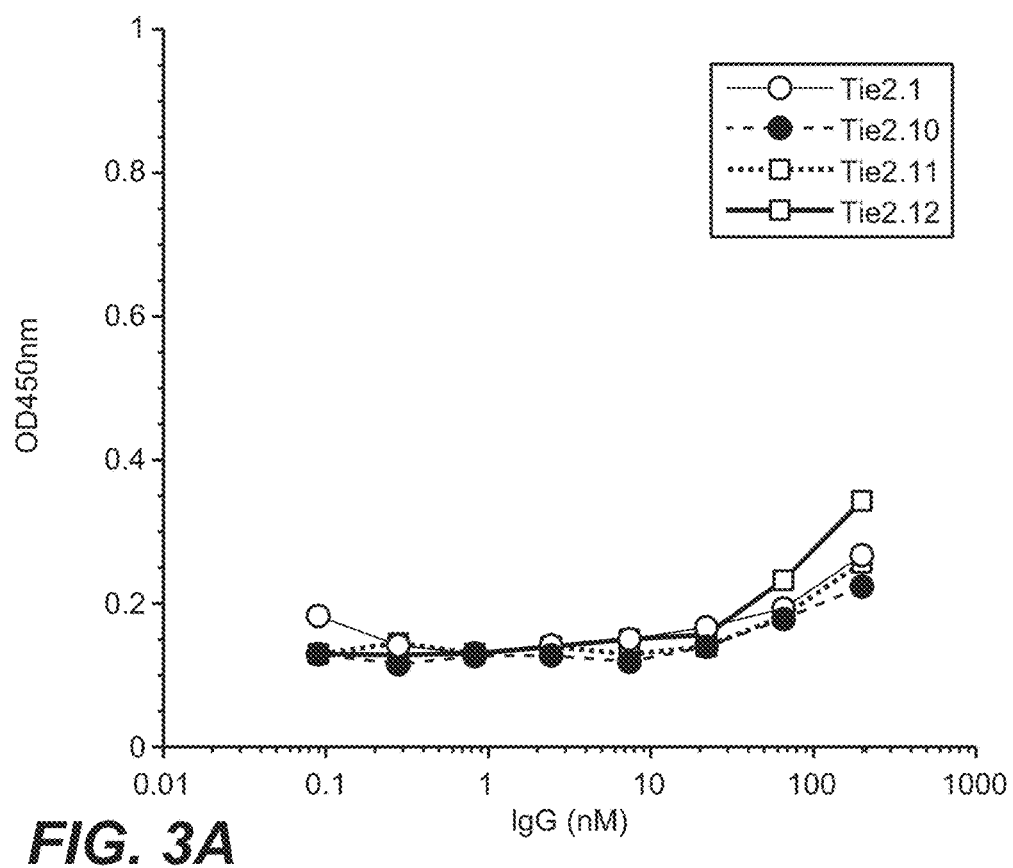
FIGS. 3A-3B show results of an assay to assess binding by anti-Tie2 antibodies Tie2.1, Tie2.10, Tie2.11, and Tie2.12 (FIG. 3A) and Tie2.2, Tie2.3, Tie2.4, Tie2.5, Tie2.7, Tie2.9, Tie2.15, Tie2.16, Tie2.17, and Tie2.20 (FIG. 3B) to human Tie1.
Figure 3B:
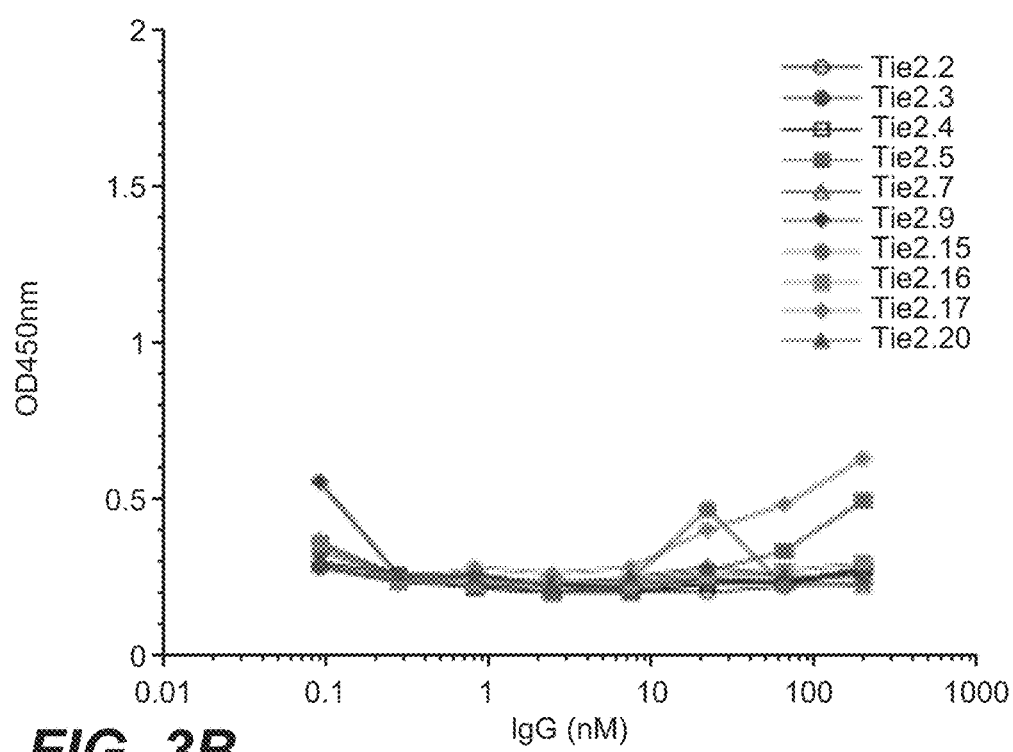

The binding ELISA was also used with immobilized Tie1 protein to assess Tie1 binding. The results, provided in FIG. 3A and FIG. 3B, show lack of Tie1 binding by several of the anti-Tie2 antibodies, demonstrating that these anti-Tie2 antibodies specifically bind Tie2.

Ligand Blocking

Figure 4A:
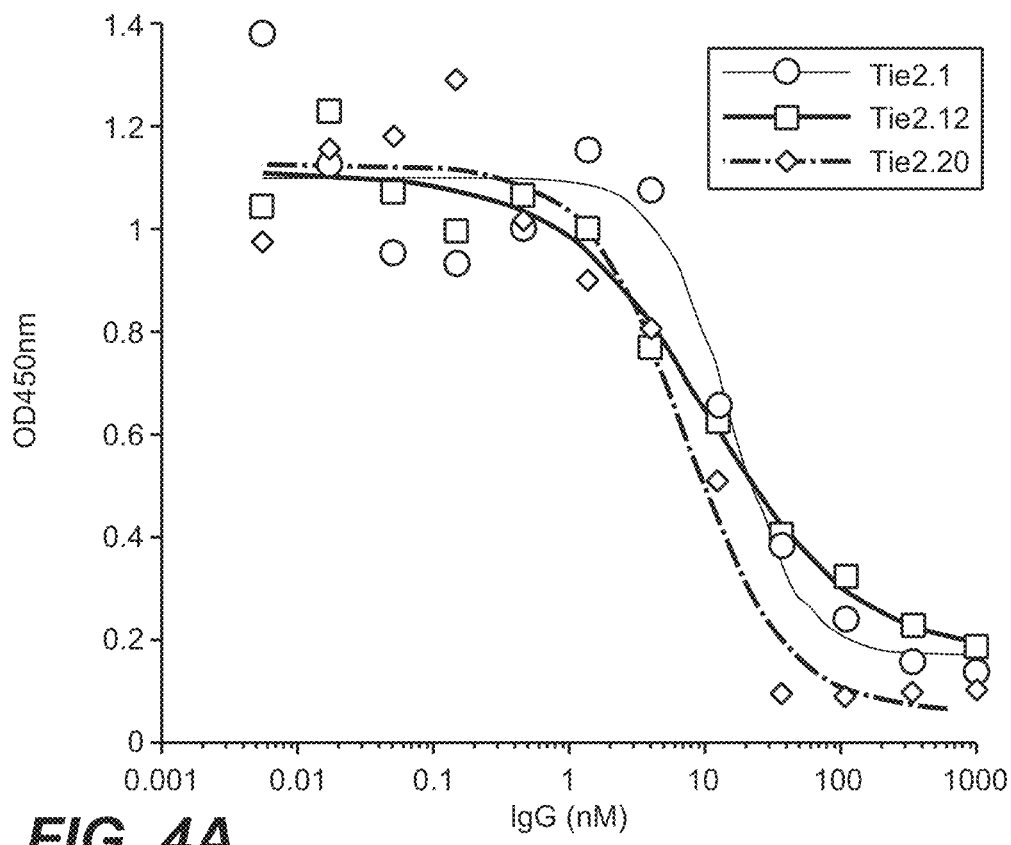
FIGS. 4A-4B show results of assays to assess blocking of interaction between Tie2 and Ang1 (FIG. 4A) and interaction between Tie2 and Ang2 (FIG. 4B) by anti-Tie2 antibodies Tie2.1, Tie2.12, and Tie2.20.
Figure 4B:
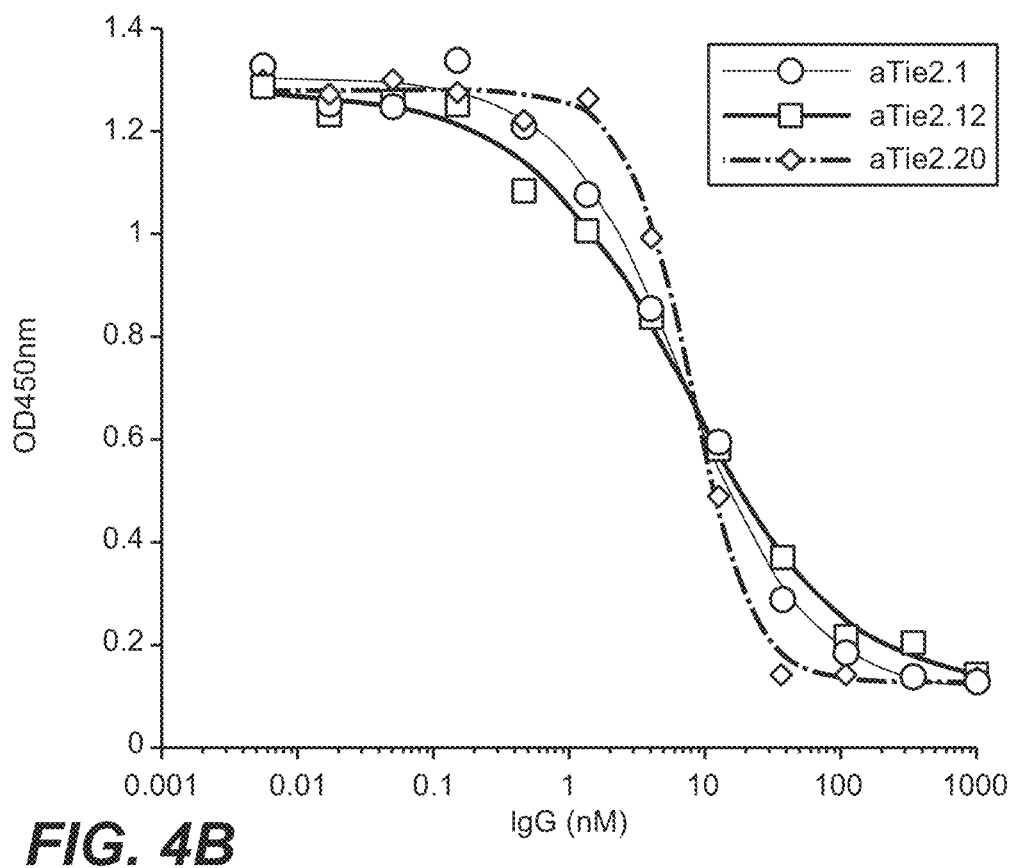

To assess Ang1 and Ang2 ligand blocking activity of the anti-Tie2 antibodies, a competitive ELISA format was used. In this assay, hAng2 (GenBank Acc. No. NP_001137) or hAng1 (GenBank Acc. No. NP_000450) was immobilized on Maxisorp immunoplates (2 ug/ml) and biotinylated huTie2ECD.Fc was equilibrated in solution with serial dilutions of anti-Tie2 antibodies prior to unbound biotin-Tie2.ECD.Fc being captured with the immobilized hAng1 or hAng2 and detected with streptavidin-conjugated HRP. These results show blocking of both Ang1 and Ang2 by at least the anti-Tie2 antibodies, Tie2.1, Tie2.12 and Tie2.20 (see FIG. 4A and FIG. 4B).

Example 3—Functional Analysis of Anti-Tie2 Antibodies

Figure 5A:
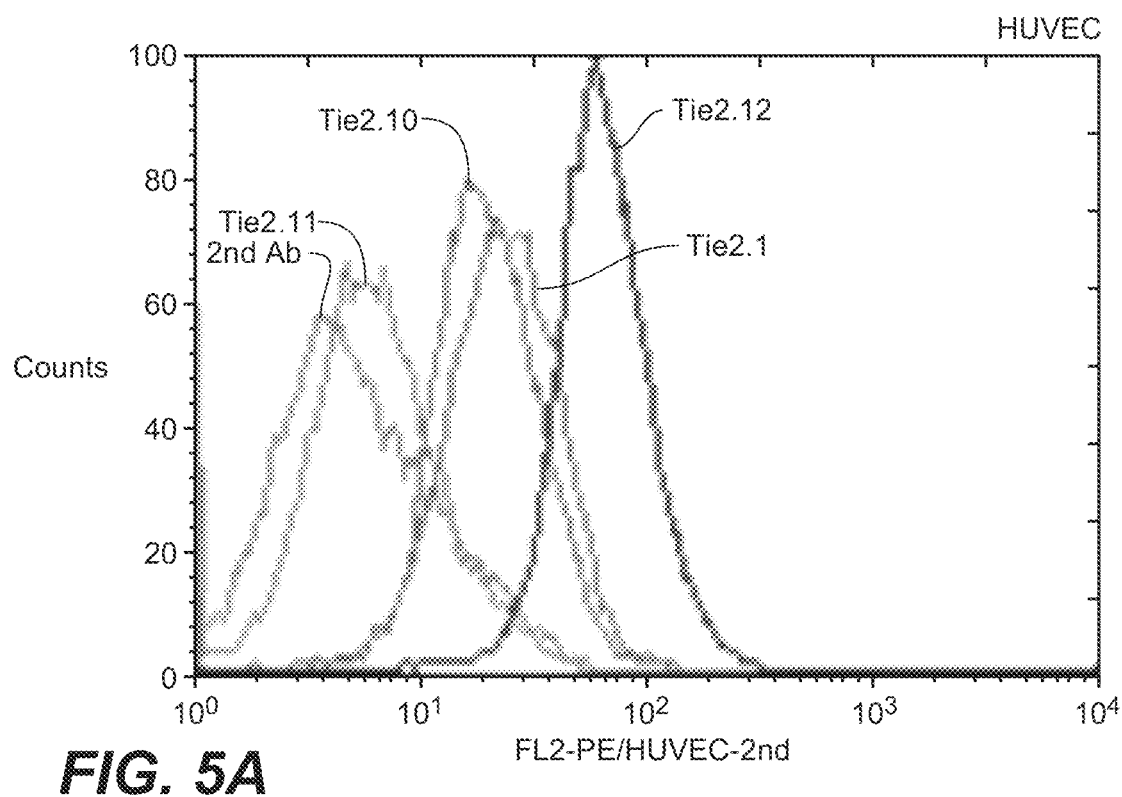
FIGS. 5A-5B show results of assays to assess binding by anti-Tie2 antibodies Tie2.1, Tie2.10, Tie2.11 and Tie2.12 on HUVEC (FIG. 5A) and RAEC (FIG. 5B).
Figure 5B:
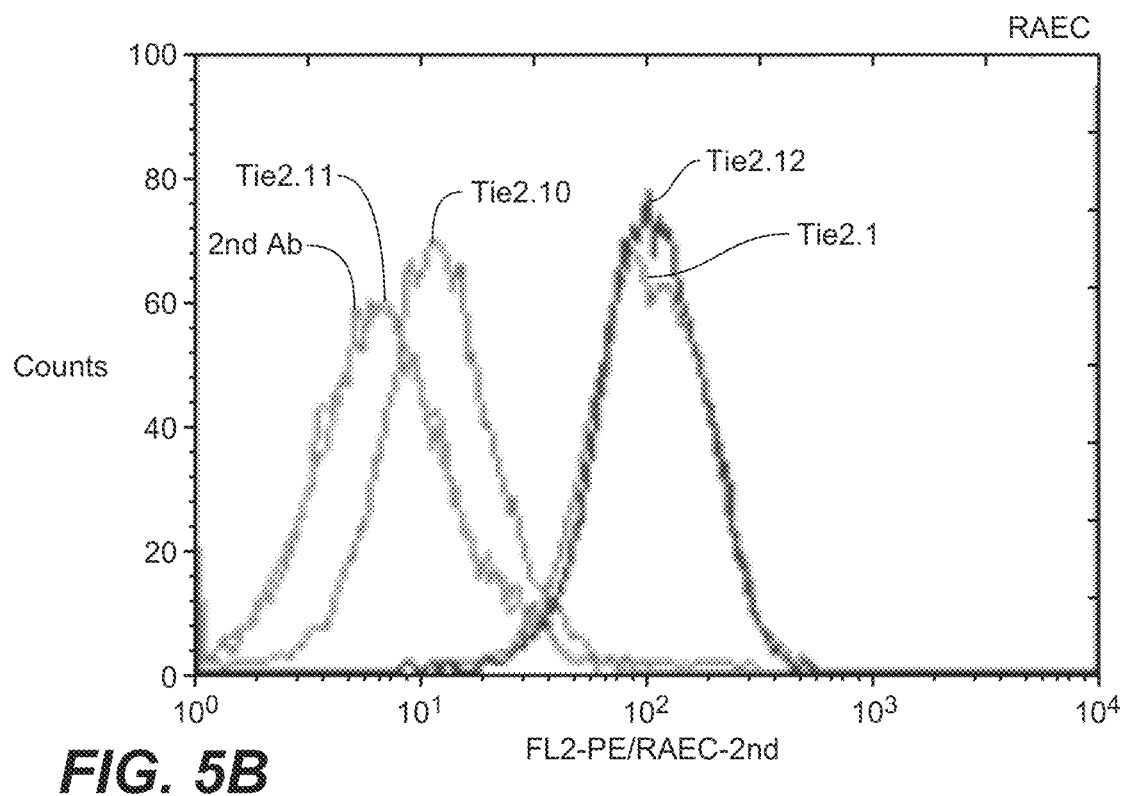

The anti-Tie2 antibodies identified above as able to specifically bind to Tie2 were further analyzed to identify those capable of functioning as a Tie2 agonist. The functional activity of anti-Tie2 IgGs with confirmed Tie2 binding was assessed using Human Umbilical Vein Endothelial Cells (HUVECs) and Rat Aortal Endothelial cells (RAECs), both known to express Tie2 (see FIG. 5A and FIG. 5B).

Stimulation of Phospho-AKT (pAKT)

Experiments were performed to assess function of the anti-Tie2 antibodies with respect to Tie2 activation. A Tie2 conjugate according to the present disclosure which is a Tie2 agonist is expected to bind to and activate Tie2, resulting in downstream activation of the AKT enzyme. Activation of AKT can be demonstrated by phosphorylation of the AKT protein to produce pAKT as described below. Phosphorylation of AKT was determined by western blot analysis using an antibody specific for phosphorylated AKT or by a FRET assay as described below.

Cells and antibodies: HUVECs were purchased from Lonza (Catalog #CC-2517; Lonza, Ltd., Basel, Switzerland). RAECs were purchased from VEC Technologies and cultured in growth medium (Catalog #MCDB-131 10; VEC Technologies, Inc., Rensselaer, NY). Anti-Tie2 antibodies were prepared at Genentech, Inc. (South San Francisco, CA). Polyclonal goat anti-hIgG was used as the cross linker (Jackson ImmunoResearch Laboratories, Inc., West Grove, PA).

Preparation of HUVECs: HUVECs (human vascular endothelial cells) were trypsinized and seeded into sterile 96-well plates (Corning® Costar®, Catalog #3997) at 0.4× $10^5$ cells/well in 100 µl culture medium and the plates were incubated in 37° C., 5% $CO_2$ incubator overnight. The culture medium was removed and 100 µL pre-warmed serum starvation media (Basal Medium EndoGRO™; Catalog #SCME-BM, MilliporeSigma) was added into each well of the plates. The plates were incubated in a 37° C., 5% $CO_2$ incubator for 3 hr prior to incubation with the anti-Tie2 antibodies.

Preparation of RAECs: RAECs (rat aortic endothelial cells) were seeded at a density of 12,000 cells/well in 96-well cell culture plate and cultured in 100 µl EGM2 MV medium (Lonza, Ltd.) overnight at 37° C. with 5% $CO_2$. After overnight culture, cells were starved in EBM2 basal medium (Lonza, Ltd.) with 0.1% BSA for 3 hours prior to incubation with the anti-Tie2 antibodies.

For testing the effects of cross-linking anti-Tie2 antibodies, 20 µg/ml cross-linker (Polyclonal goat ant-hIgG1) in assay buffer (Basal Medium+0.2% BSA) was mixed with an equal volume of anti-Tie2 bivalent antibody at 60 µg/ml and incubated at RT for 1 hr. After incubation, mixtures of the hIgG1 with an anti-Tie2-IgG antibody were subjected to a 3-fold serial dilution.

For testing other Tie2 antibodies the molecules were diluted to an initially high stock concentration (typically 30-1000 µg/ml) in assay buffer followed by (typically 2 to 10-fold) serial dilution. These dilutions (50 µl) were added to each well after removal of serum starvation media, and the plates were incubated at 37° C., 5% $CO_2$, for 15 minutes. The solution was removed and 50 µl of lysis buffer containing blocking buffer from a Phospho-AKT1/2/3 Ser473 Cellular Kit (Catalog #64AKSPEH; Cisbio, Codolet, France) was added to cells. The plates were incubated at room temperature for about 30-45 min with gentle shaking and kept at −80° C. until used, or directly used in FRET assay.

Western blot assay: HUVEC cells were plated at $1×10^6$ cells per well in Endogro Medium and cultured at 37° C. for 16-18 hours. Culture medium was changed to 0.1% BSA Endogro Basal medium for 4-5 hours prior to stimulation. Cells were incubated with the relevant Tie-2 agonists for 30 min at 37° C. and washed three times with cold phosphate buffered saline pH 7.4. Cells were placed on ice and incubated with 100 ul/well of RIPA buffer (Sigma, #20-188) containing Roche complete protease and phosphatase inhibitors (Thermo Scientific, #1861281) for 5 min. Lysates were harvested from wells using a cell scraper and centrifuged at 17,800×g for 10 min. Supernatant was assessed by SDS-PAGE (8% NuPAGE Bis-Tris (Invitrogen, NW800085)), followed by transfer to a nitrocellulose membrane. Membranes were blocked with 5% BSA in TBS-T for 1 hr at room temperature, and probed with Rabbit anti-pAKT (Cell Signaling Technologies, #9271S) in blocking buffer. Following 4 washes with TBS-T, membranes were probed with HRP anti-rabbit Ig (1:10,000) (GE Healthcare, NA934V) at RT for 1 hr. Membranes were washed 3 times with TBS-T, and incubated with ECL reagents (Thermo Scientific, 32132) at room temperature for 5 min prior to exposing blots to film.

FRET assay: Cell lysate (15 µl) was thawed on ice then mixed with 5 µl of 1:40 dilution of each Phospho-AKT d2 antibody and Phospho-AKT Cryptate antibody from the Phospho-AKT Ser473 Kit in a 384 well microplate (Catalog #784080; Greiner Bio-One North America, Inc., Monroe, NC) and the plates were incubated at room temperature for 4 hr or at 4° C. overnight and read at 620 nm and 665 nm on CLARIOstar (BMG LABTECH, software version: 5.01 R2). The data were calculated as the ratio of the acceptor and donor emission signals times 104 for each individual well.

Figure 6A:
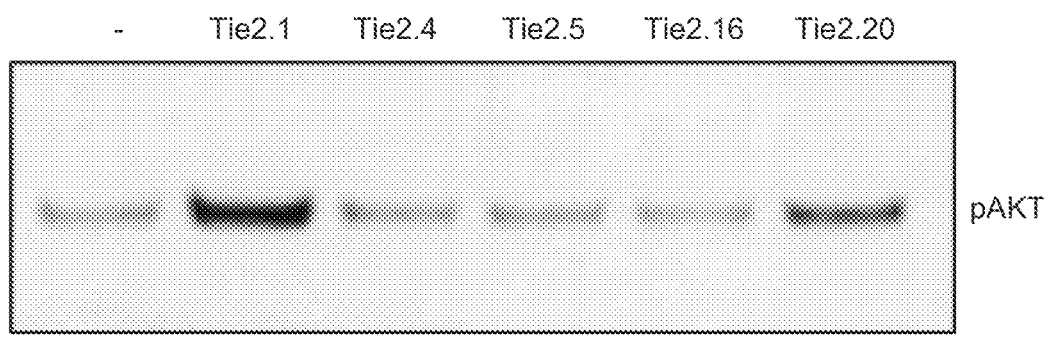
FIGS. 6A-6B show results of assays to assess activation of AKT phosphorylation by anti-Tie2 antibodies Tie2.1, Tie2.4, Tie2.5 and Tie2.20 in RAEC (FIG. 6A) and to assess the effect of anti-IgG cross-linking of an anti-Tie2 antibody on AKT phosphorylation (FIG. 6B). Levels of phosphorylated AKT were determined by western blot analysis.

In an effort to identify anti-Tie2 antibodies capable of activating Tie2 activity, the antibodies that bind Tie-2 identified as detailed above were formatted as human IgG1 (hIgG1) antibodies and tested for their ability to stimulate phosphorylation of AKT (to generate pAKT), which is downstream of Tie2 activation. RAECs were treated with the recombinant anti-Tie2 antibodies (hIgG1): Tie2.1, Tie2.4, Tie2.5, Tie2.16 and Tie.2.20 for 10 minutes. Cell lysates were subjected to western blot (WB) analysis of pAKT. FIG. 6A shows that incubation of the anti-Tie2 antibodies Tie2.1 and Tie2.20 increased phosphorylation of AKT in this in vitro cellular-based assay, with Tie2.1 having a stronger Tie2 agonist effect than Tie2.20.

Figure 6B:
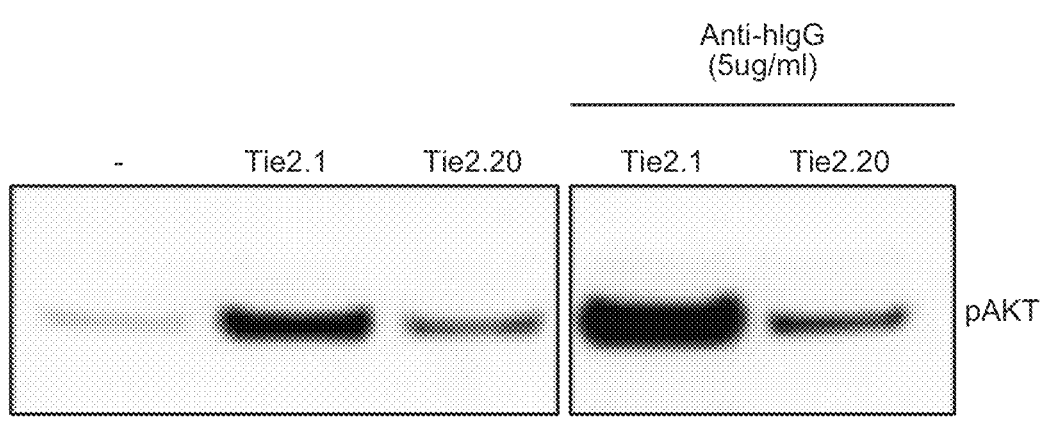

Next, an experiment was performed to assess the effects of cross-linking on the agonist activity of the anti-Tie2 antibodies. An anti-hIgG1 cross-linking antibody was incubated with Tie2.1 or Tie2.20 in the pAKT assay. As shown in FIG. 6B, cross-linking of Tie2.1 further increased its ability to activate Tie2, as determined by increased AKT phosphorylation.

In an effort to identify additional agonistic anti-Tie2 antibodies, an HTRF-based assay (Cisbio) was also used. RAECs were treated with recombinant anti-Tie2 antibodies (hIgG1) for 10 minutes. Cell lysates were subjected to HTRF analysis of pAKT (cisbio). As shown in FIG. 7A, antibodies found to significantly increase pAKT levels (act as Tie2 agonists) include at least Tie2.24, Tie2.31, Tie2.32, T2.33, Tie2.38, and Tie2.1, with Tie2.1 having the strong activity.

It was considered that the level of Tie2 activation upon binding by anti-Tie2 IgG (full length) antibodies may in part be due to non-specific aggregation of the IgG molecules within the reaction mixtures. As shown in FIG. 7B, a Tie2.1 antibody preparation with a higher percentage of aggregate (e.g., 3.5%) compared to a Tie2.1 antibody preparation with a lower percentage of aggregate (e.g., 0.15%), exhibited stronger agonistic activity. FIG. 7B further shows that cross-linking anti-hIgG1 enhanced the agonistic activity of Tie2.1. Without being bound by theory, it is believed that activation of Tie2 by an anti-Tie2 agonist antibody may be facilitated by cross-linking of the Tie2-bound antibody.

Example 4—Binning of Anti-Tie2 Antibodies Derived from Naive Phage Libraries

Binning of anti-Tie2 antibodies was carried out using both phage ELISAs and Octet measurements to further characterize binding of the anti-Tie2 antibodies to the Tie2 receptor protein and identify those antibodies with shared epitopes.

For phage ELISAs, huTie2ECD.Fc protein was immobilized on Maxisorp immunoplates at 2 ug/ml in 65 ul PBS overnight at 4° C. overnight. Serial dilutions of anti-Tie2 Antibodies Tie2.1, Tie2.20, Tie2.34 formatted as IgGs, or anti-Tie2 antibody 13H10 (anti-Tie2 receptor agonist antibody described in U.S. Pat. No. 6,365,154) were applied to the plates with immobilized huTie2ECD.Fc that had been previously blocked with 1% BSA in PBS and incubated for 1 hour at room temperature. The anti-Tie2 phage were added at OD268 nm/mL of 0.1 for 15 min at room temperature. Plates were then washed and detected with anti-M13-conjugated HRP secondary antibody using the methods above. An increase in signal with a decrease in the serially diluted antibody indicates that the test phage antibody competes with the serially diluted antibody, suggesting they bind the same site or epitope.

Figure 8A:
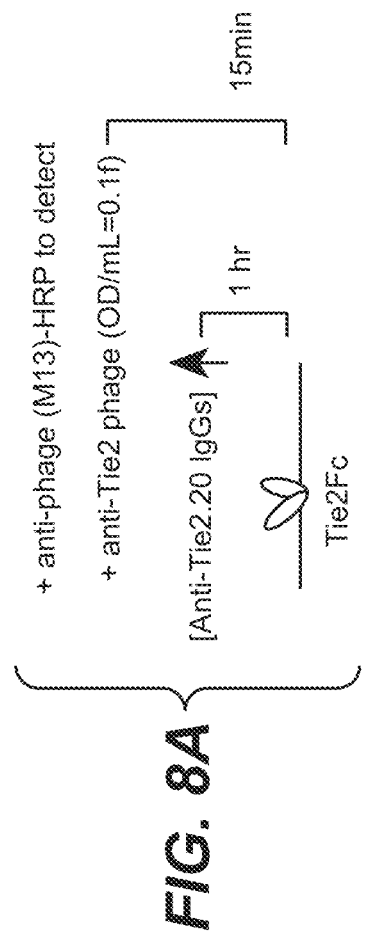
FIGS. 8A-8B illustrate a method (FIG. 8A) and results from a binning study of anti-Tie2 antibodies using ELISA (FIG. 8B).
Figure 8B:
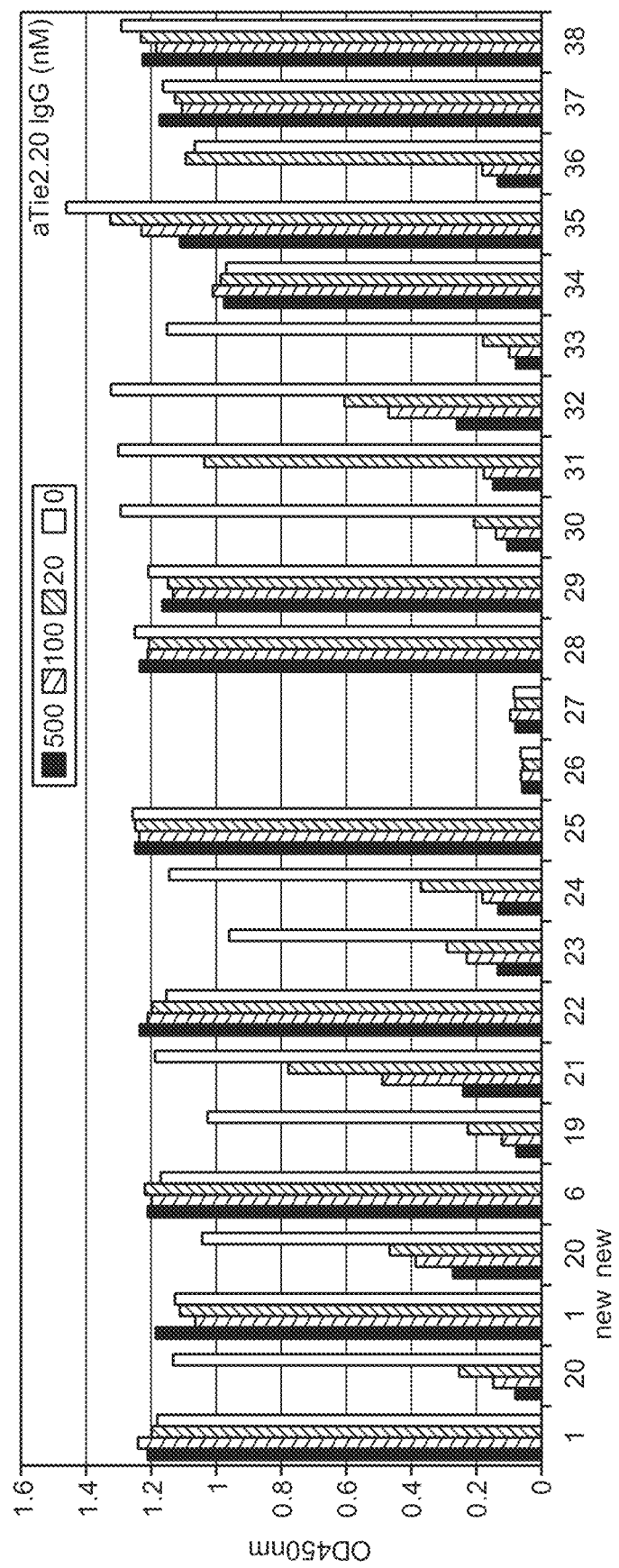

Epitope binning as determined by ELISA above was confirmed by an Octet epitope binning assay using an Octet RED384 (Pall Forte Bio Corporation, Menlo Park, CA) and a standard sandwich format binning assay. Specifically, Streptavidin Biosensors (Pall Forte Bio Corporation) were coated with biotinylated hTie2.ECD.Fc protein (10 ug/mL) then exposed to benchmark anti-Tie2 hIgG1 (50 ug/mL Ab1, Ab20, 13H10), followed by exposure to a second (test) anti-Tie2 hIgG1. Data were processed using Forte Bio's Data Analysis Software. Additional binding by the second (test) antibody indicates an unoccupied epitope (non-competitor), while no binding indicates epitope blocking (competitor). An illustration of the experiment with data obtained for Ab20 (Tie2.20) are provided in FIGS. 8A and 8B. Data are not shown for other anti-Tie2 antibodies.

Figure 9:
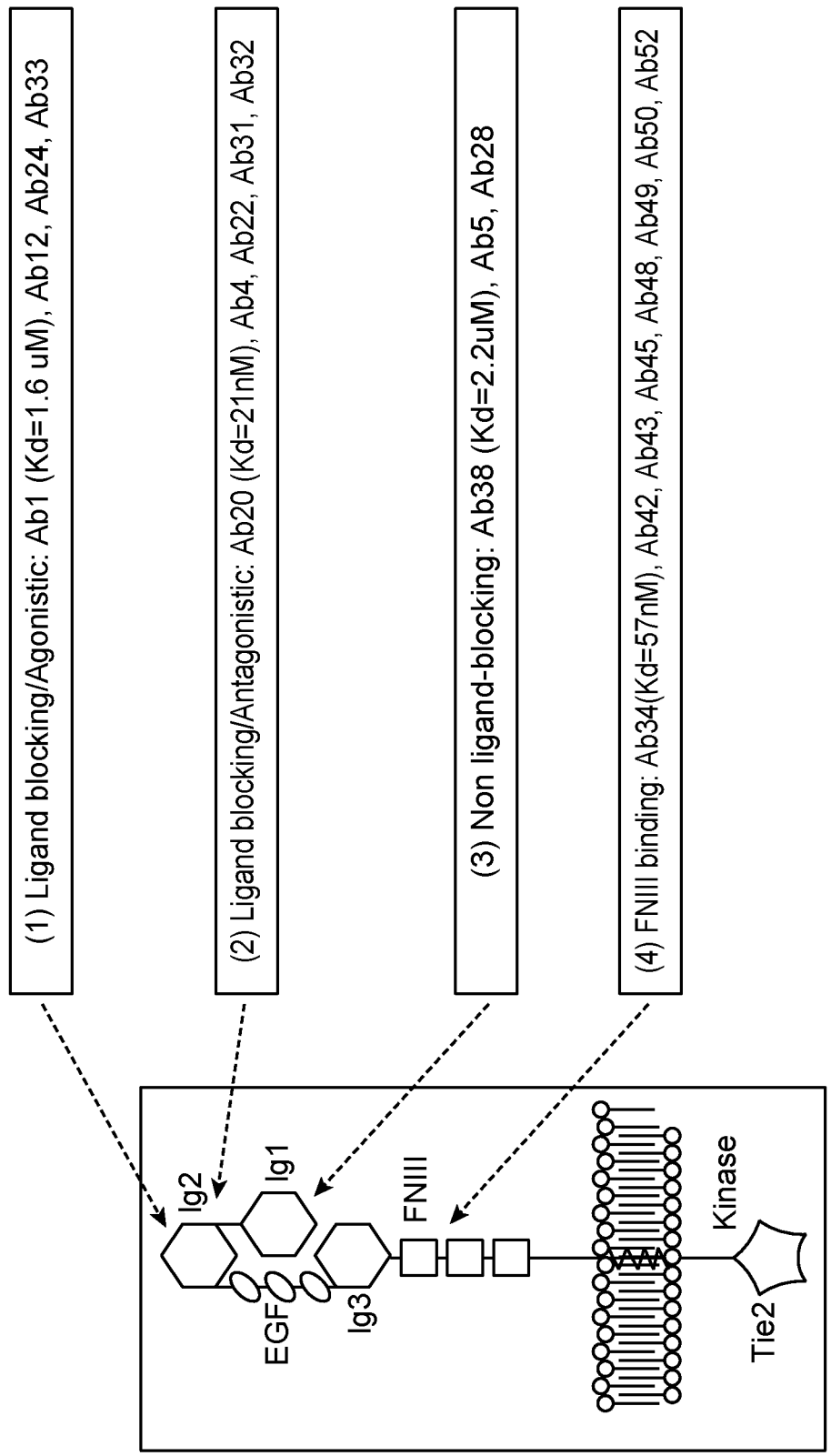
FIG. 9 is a schematic which illustrates epitope groups on Tie2 to which anti-Tie2 antibodies of the present disclosure bind.

The results of the ELISA and Octet binning assay analyses are summarized and illustrated in FIG. 9 showing which anti-Tie2 antibodies compete with one-another and likely bind the same or similar epitopes. Specifically, binding assays described above demonstrated that phage-derived antibodies Tie2.1 (Ab1), Tie2.12 (Ab12), Tie2.24 (Ab24) and Tie2.33 (Ab33) all bind to the Tie2 IgG2 domain, block binding of Ang1 and Ang2 to Tie2 and are Tie2 agonists (e.g., enhance phosphorylation of AKT and/or Tie2 and/or increase vascular endothelial membrane integrity).

Cumulatively, the results indicate that there are at least 3 epitope classes bound by the anti-Tie2 antibodies described herein. These at least 3 epitope classes are illustrated in FIG. 9.

Affinity Determination of Anti-Tie2 IgG Antibodies

Monovalent affinities of selected anti-Tie2 hIgGs were determined using a Biacore T200 instrument (GE Life Sciences). Anti-humanFc was covalently immobilized on a Series S CM5 Biacore sensor chip to enable non-covalent capture of anti-Tie2 antibodies and binding of human or rat Tie2ECD.flag was monitored in real time at 25° C. using a multi-cycle kinetics experiment format. Between cycles, the surface was regenerated with 3 M $MgCl_2$. Monovalent affinities were determined by kinetic analysis, using Biacore Evaluation Software (GE Life Sciences) to fit a 1:1 binding model to the data. Results are summarized in Table 6.

TABLE 6

| Antibody | Biacore Affinity (kD) | |
|---|---|---|
| | hTie2.flag | rTie2.flag |
| Ab1 | 1.2 uM | 1.6 uM |
| Ab4 | 59 nM | 250 nM |
| Ab12 | 52 nM | 116 nM |
| Ab20 | 7.6 nM | 21 nM |
| Ab24 | 822 nM | 2.8 uM |
| Ab31 | 31 nM | 221 nM |
| Ab32 | 408 nM | 901 nM |
| Ab34 | 155 nM | 57 nM |
| Ab38 | 376 nM | 2.2 uM |

Example 5—In Vivo Generation of Anti-Tie2 Antibodies

In addition to phage display, generation of anti-Tie2 antibodies which may be useful for therapeutic applications was done by animal immunizations.

Rabbit immunization. New Zealand White rabbits were immunized with the ECD of human and cyno Tie2 (SEQ ID NO:1, residues 23-442) and single B cells were isolated using a modified protocol related to published literature, e.g. see Seeber et al., PLoS ONE 9(2), 2014. The B cell culture supernatants were assayed by ELISA for binding to human, rat, and cynoTie2 and an irrelevant control protein, and assayed by FACS for binding to HUVEC cells. Tie2 specific B cells were lysed an immediately frozen at −80° C. for storage until molecular cloning. Variable regions (VH and VL) of each monoclonal antibody from rabbit B cells were cloned into expression vectors from extracted mRNA as previous described, e.g. see Seeber et al., PLoS ONE 9(2), 2014. Individual recombinant rabbit antibodies were expressed in Expi293 cells and subsequently purified with protein A. Purified anti-Tie2 antibodies were then subjected to functional activity assays and kinetic screening.

Rat immunization. Rats were immunized in a similar manner and hybridomas were generated using a modified fusion partner (e.g. see Price et al., J Immunol Methods 31; 343(1):28-41 (2009). Various conditions were optimized to enable sorting of individual IgG+ huTie2+ hybridomas into single wells followed by additional culture after sorting. The resulting hybridoma supernatants were assayed by ELISA for binding to human, murine, and cynoTie2 and an irrelevant control protein, and assayed by FACS for binding to HUVEC cells and positive samples were purified using protein A for subsequent functional and kinetic characterization.

Functional Screening of Rat and Rabbit Clones Using an Anti-IgG Crosslinker.

Antibodies generated from immunization of rat and rabbits as described above were characterized with respect to pAKT induction downstream of Tie2 agonism.

Cells and antibodies: Human Umbilical Vein Endothelial (HUVEC) cells were purchased from Lonza (Catalog #CC-2517; Lot #0000321046) while Rat Aorta Endothelial Cells (RAEC) were purchased from VEC Technologies and cultured in growth medium (VEC Technologies, INC, CAT #MCDB-131 10). Anti-Tie2 antibodies were prepared at Genentech. Species-specific antibodies used as cross linker were purchased from Jackson ImmunoResearch Laboratories Inc.

Preparation of HUVECs: HUVECs were trypsinized and seeded into Sterile 96-well plates (Costar Cat #3997) at $0.4 \times 10^5$ cells/well in 100 μl culture medium and the plates were incubated in 37° C., 5% $CO_2$ incubator overnight. The culture medium was removed and 100 µL pre-warmed serum starvation media (Basal Medium EndoGRO™, Cat #SCME-BM) was added into each well of the plates. The plates were incubated in 37° C., 5% $CO_2$ incubator for 3 hours prior to incubation with the Tie-2 agonists.

Preparation of RAECs: RAECs were seeded at a density of 12,000 cells/well in 96-well cell culture plate and cultured in 100 µl EGM2 MV medium overnight at 37° C. with 5% $CO_2$. After overnight culture, cells were starved in EBM2 basal medium with 0.1% BSA for 3 hrs prior to incubation with the Tie-2 agonists.

For testing cross-linked anti-Tie2 antibodies, 20 µg/ml cross-linker in assay buffer (Basal Medium+0.2% BSA from GNE media prep facility) was mixed with equal volume of anti-Tie2 bivalent antibody at 60 µg/ml and incubated at RT for 1 hr. After incubation, antibodies were subjected to a 3-fold serial dilution.

For testing other Tie2 agonists, the molecules were diluted to an initially high stock concentration (typically 30-1000 µg/ml) in assay buffer followed by (typically 2-10-fold) serial dilution. These dilutions (50 µl) were added to each well after removal of serum starvation media, and the plates were incubated at 37° C., 5% $CO_2$, for 15 min. The solution was removed and 50 ul of lysis buffer containing blocking buffer from pAKT Ser473 Kit (Cisbio, Ref #64AKSPEH) was added to cells. The plates were incubated at RT for 30-45 min with gentle shaking and kept in −80° C. freezer until used, or directly used in FRET assay.

FRET assay: Cell lysate (15 ul) was thaw on ice then mixed with 5 ul of 1:40 dilution of each Phospho-AKT d2 antibody and Phospho-AKT Cryptate antibody from pAKT Ser473 Kit in 384 well microplate (Greiner Bio-One North America, Inc., Cat #784080) and the plates were incubated at RT for 4 hrs or in 4° C. refrigerator overnight and read at 620 nm and 665 nm on CLARIOstar (BMG LABTECH, software version: 5.01 R2). The data were calculated as the ratio of the acceptor and donor emission signals times $10^4$ for each individual well.

Recombinant Antibody Generation.

DNA encoding antibody heavy and light chain variable domains was generated by gene synthesis and inserted into mammalian vectors for IgG1 antibody heavy chain and light chain expression respectively. Some variable domain sequences were edited to remove apparent unpaired cysteine residues and NX[S/T] N-glycosylation motifs. Recombinant antibodies were produced by transient transfection of Expi293 cells with mammalian expression vectors encoding the antibody heavy chain and light chain. Heavy chain and light chain were encoded on separate vectors, and were transfected using a 1:2 ratio of heavy chain expression vector to light chain expression vector. Antibodies were purified from the cell culture supernatant by affinity chromatography. In some cases, antibodies underwent an additional purification step based on SEC.

Antibodies were screened for binding to recombinant human and cyno Tie2 using a Biacore T200 instrument (GE Life Sciences). Briefly, a human antibody capture chip was generated using a Series S CM5 chip, a human antibody capture kit, and an amine coupling kit (GE Life Sciences). Antibodies diluted to 5 µg/ml were captured using a flow rate of 10 µl/minute and a contact time of 20 seconds. Binding of 300 nM and 1500 nM recombinant human and cyno Tie2 extracellular domain to the captured antibodies was analyzed at 37° C. using a single cycle kinetics method with a flow rate of 50 µl/minute, a contact time of 60 seconds and a dissociation time of 120 seconds. Between cycles, the chip was regenerated using 3M $MgCl_2$ injected for 30 seconds at 30 µl/minute. Data were evaluated using Biacore T200 Evaluation software (GE Life Sciences). Kinetic constants were obtained using a 1:1 binding model with the parameter RI set to zero. Selected antibodies (Table 7A-7B; ch denotes rabbit Abs; TEK denotes rat Abs) were taken forward for secondary activity screening in Fab-NDK format (see Example 8 below).

TABLE 7A

| | Recombinant human Tie2 ECD | | | | | |
|---|---|---|---|---|---|---|
| Antibody | Ligand Level (RU) | Binding response, 1500 nM hu Tie2 (RU) | Rmax (RU) | ka (1/Ms) | kd (1/s) | KD (M) |
| Anti-gD | 589.3 | 17.0 | 3.3 | — | — | — |
| Tie2.1 | 488.6 | 169.9 | 471.3 | 1E+05 | 3E−01 | 3E−06 |
| | 490.5 | 165.6 | 448.1 | 1E+05 | 3E−01 | 3E−06 |
| ch15E4.2 | 351.3 | 337.6 | 342.2 | 2E+05 | 1E−02 | 7E−08 |
| | 354.1 | 339.7 | 338.7 | 2E+05 | 1E−02 | 6E−08 |
| | 381.5 | 361.3 | 363.8 | 2E+05 | 1E−02 | 7E−08 |
| ch10D10.2 | 903.8 | 934.3 | 948.7 | 2E+05 | 1E−02 | 6E−08 |
| ch12B5.2 | 619.3 | 230.5 | 216.5 | 2E+05 | 4E−03 | 2E−08 |
| ch13H11.2 | 711.7 | 693.8 | 685.3 | 6E+04 | 1E−03 | 2E−08 |
| ch14A8.2 | 953.3 | 569.5 | 649.0 | 2E+04 | 1E−03 | 5E−08 |
| ch14D8.2 | 578.8 | 573.8 | 585.1 | 7E+04 | 5E−03 | 8E−08 |
| ch14E10.2 | 755.2 | 315.9 | 398.0 | 2E+05 | 8E−02 | 5E−07 |
| ch18E7.2 | 949.6 | 946.7 | 928.3 | 2E+05 | 1E−03 | 7E−09 |
| ch1B7.2 | 581.7 | 370.5 | 446.5 | 1E+05 | 4E−02 | 4E−07 |
| ch1B7.3 | 531.5 | 210.6 | 333.6 | 4E+07 | 4E+01 | 1E−06 |
| ch25C8.2 | 1117.6 | 998.5 | 990.4 | 5E+04 | 4E−04 | 7E−09 |
| ch28C9.2 | 470.2 | 313.5 | 433.5 | 1E+04 | 6E−04 | 4E−08 |
| ch28E12.2 | 849.7 | 750.8 | 754.6 | 4E+04 | 2E−04 | 5E−09 |
| ch6H6.2 | 625.1 | 605.8 | 630.7 | 8E+04 | 8E−03 | 9E−08 |
| ch6H6.3 | 522.9 | 490.6 | 519.2 | 9E+04 | 1E−02 | 1E−07 |
| TEK-1006 | 601.8 | 629.5 | 621.5 | 7E+04 | 6E−04 | 8E−09 |
| TEK-1053 | 354.2 | 369.6 | 364.0 | 7E+04 | 7E−04 | 1E−08 |
| TEK-1060 | 656.1 | 635.8 | 654.0 | 1E+05 | 8E−03 | 7E−08 |
| TEK-1194 | 649.1 | 604.9 | 591.0 | 1E+05 | 3E−03 | 2E−08 |
| TEK-1248 | 610.9 | 601.6 | 612.5 | 9E+05 | 2E−03 | 2E−09 |
| TEK-166 | 650.6 | 671.1 | 659.3 | 2E+05 | 5E−04 | 2E−09 |
| TEK-198 | 651.2 | 609.5 | 604.9 | 6E+04 | 7E−04 | 1E−08 |
| TEK-233 | 583.7 | 598.5 | 593.3 | 1E+05 | 3E−03 | 3E−08 |
| TEK-323 | 540.5 | 473.4 | 470.2 | 9E+04 | 3E−03 | 4E−08 |
| TEK-327 | 498.1 | 490.2 | 488.1 | 6E+04 | 8E−04 | 1E−08 |
| TEK-522 | 564.1 | 535.9 | 527.6 | 7E+04 | 6E−04 | 8E−09 |
| TEK-535 | 567.6 | 604.5 | 591.1 | 1E+05 | 1E−03 | 7E−09 |
| TEK-628 | 516.4 | 468.3 | 468.5 | 5E+04 | 2E−03 | 4E−08 |
| TEK-685 | 659.9 | 588.3 | 629.7 | 9E+04 | 1E−02 | 1E−07 |
| TEK-69 | 694.5 | 628.9 | 617.0 | 1E+05 | 3E−03 | 3E−08 |
| TEK-768 | 573.8 | 132.2 | 361.3 | 6E+04 | 2E−01 | 3E−06 |

TABLE 7B

| | Recombinant cyno Tie2 ECD | | | | | |
|---|---|---|---|---|---|---|
| Antibody | Ligand Level (RU) | Binding response, 1500 nM cy Tie2 (RU) | Rmax (RU) | ka (1/Ms) | kd (1/s) | KD (M) |
| Anti-gD | 591.1 | 16.1 | 2.3 | — | — | — |
| Tie2.1 | 488.9 | 158.4 | 516.9 | 9E+04 | 3E−01 | 4E−06 |
| | 488.2 | 151.9 | 498.0 | 9E+04 | 3E−01 | 4E−06 |
| ch15E4.2 | 350.5 | 320.5 | 325.7 | 1E+05 | 9E−03 | 8E−08 |
| | 348.6 | 318.4 | 317.9 | 1E+05 | 9E−03 | 6E−08 |
| | 382.3 | 344.5 | 347.6 | 1E+05 | 9E−03 | 8E−08 |
| ch10D10.2 | 913.5 | 853.7 | 928.1 | 2E+05 | 3E−02 | 2E−07 |
| ch12B5.2 | 618.3 | 214.0 | 201.0 | 3E+05 | 4E−03 | 1E−08 |
| ch13H11.2 | 713.6 | 667.8 | 662.4 | 5E+04 | 1E−03 | 3E−08 |
| ch14A8.2 | 952.1 | 676.1 | 695.8 | 3E+04 | 8E−04 | 3E−08 |
| ch14D8.2 | 579.4 | 557.7 | 568.6 | 7E+04 | 5E−03 | 8E−08 |
| ch14E10.2 | 761.9 | 292.9 | 378.5 | 2E+05 | 8E−02 | 5E−07 |

TABLE 7B-continued

| | Recombinant cyno Tie2 ECD | | | | | |
|---|---|---|---|---|---|---|
| Antibody | Ligand Level (RU) | Binding response, 1500 nM cy Tie2 (RU) | Rmax (RU) | ka (1/Ms) | kd (1/s) | KD (M) |
| ch18E7.2 | 932.2 | 899.5 | 883.1 | 2E+05 | 1E−03 | 8E−09 |
| ch1B7.2 | 583.7 | 396.5 | 445.4 | 6E+04 | 2E−02 | 2E−07 |
| ch1B7.3 | 535.1 | 263.4 | 407.2 | 8E+04 | 7E−02 | 9E−07 |
| ch25C8.2 | 1125.2 | 974.3 | 962.8 | 6E+04 | 5E−04 | 7E−09 |
| ch28C9.2 | 470.6 | 360.0 | 433.2 | 2E+04 | 5E−04 | 3E−08 |
| ch28E12.2 | 852.5 | 762.0 | 760.3 | 4E+04 | 2E−04 | 4E−09 |
| ch6H6.2 | 632.8 | 588.9 | 613.4 | 8E+04 | 7E−03 | 9E−08 |
| ch6H6.3 | 518.9 | 467.3 | 495.3 | 9E+04 | 1E−02 | 1E−07 |
| TEK-1006 | 602.5 | 597.2 | 590.1 | 6E+04 | 6E−04 | 9E−09 |
| TEK-1053 | 353.3 | 360.3 | 354.2 | 9E+04 | 8E−04 | 9E−09 |
| TEK-1060 | 650.1 | 617.3 | 628.6 | 1E+05 | 6E−03 | 5E−08 |
| TEK-1194 | 645.7 | 565.5 | 549.5 | 2E+05 | 2E−03 | 1E−08 |
| TEK-1248 | 603.8 | 572.2 | 580.6 | 9E+05 | 2E−03 | 2E−09 |
| TEK-166 | 647.5 | 646.3 | 635.1 | 2E+05 | 5E−04 | 2E−09 |
| TEK-198 | 640.6 | 574.5 | 571.2 | 5E+04 | 6E−04 | 1E−08 |
| TEK-233 | 582.0 | 559.4 | 552.9 | 8E+04 | 2E−03 | 3E−08 |
| TEK-323 | 536.8 | 449.3 | 442.9 | 1E+05 | 3E−03 | 3E−08 |
| TEK-327 | 496.4 | 475.0 | 472.6 | 7E+04 | 1E−03 | 2E−08 |
| TEK-522 | 566.7 | 511.7 | 505.3 | 6E+04 | 7E−04 | 1E−08 |
| TEK-535 | 565.4 | 583.3 | 569.9 | 2E+05 | 1E−03 | 8E−09 |
| TEK-628 | 516.5 | 453.5 | 454.3 | 4E+04 | 2E−03 | 4E−08 |
| TEK-685 | 658.8 | 543.7 | 598.6 | 7E+04 | 1E−02 | 2E−07 |
| TEK-69 | 692.7 | 588.1 | 573.4 | 1E+05 | 2E−03 | 2E−08 |
| TEK-768 | 572.0 | 122.2 | 368.2 | 5E+04 | 2E−01 | 4E−06 |

HTP Epitope Binning.

Figures 11, 11A:
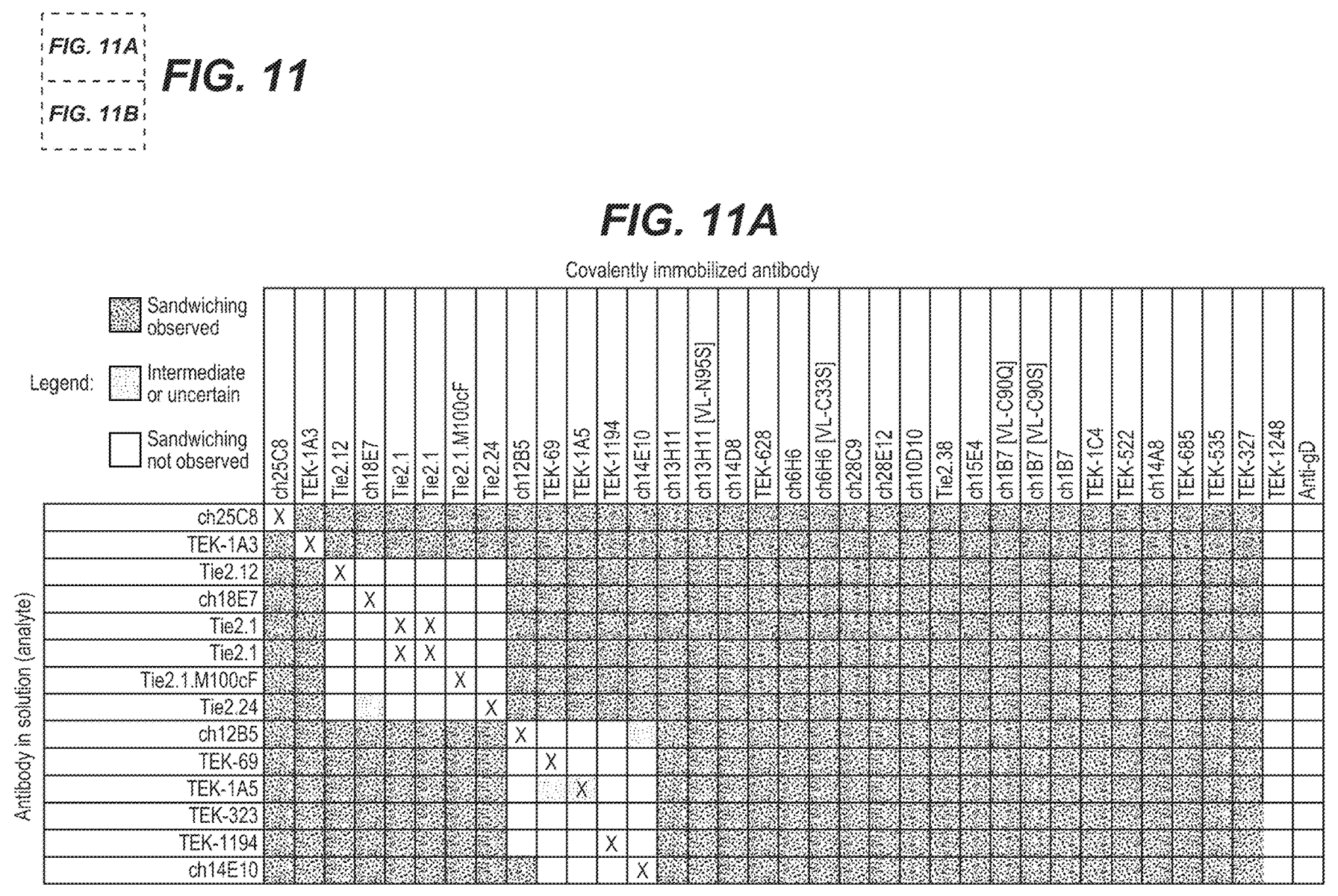
Figure 11B:
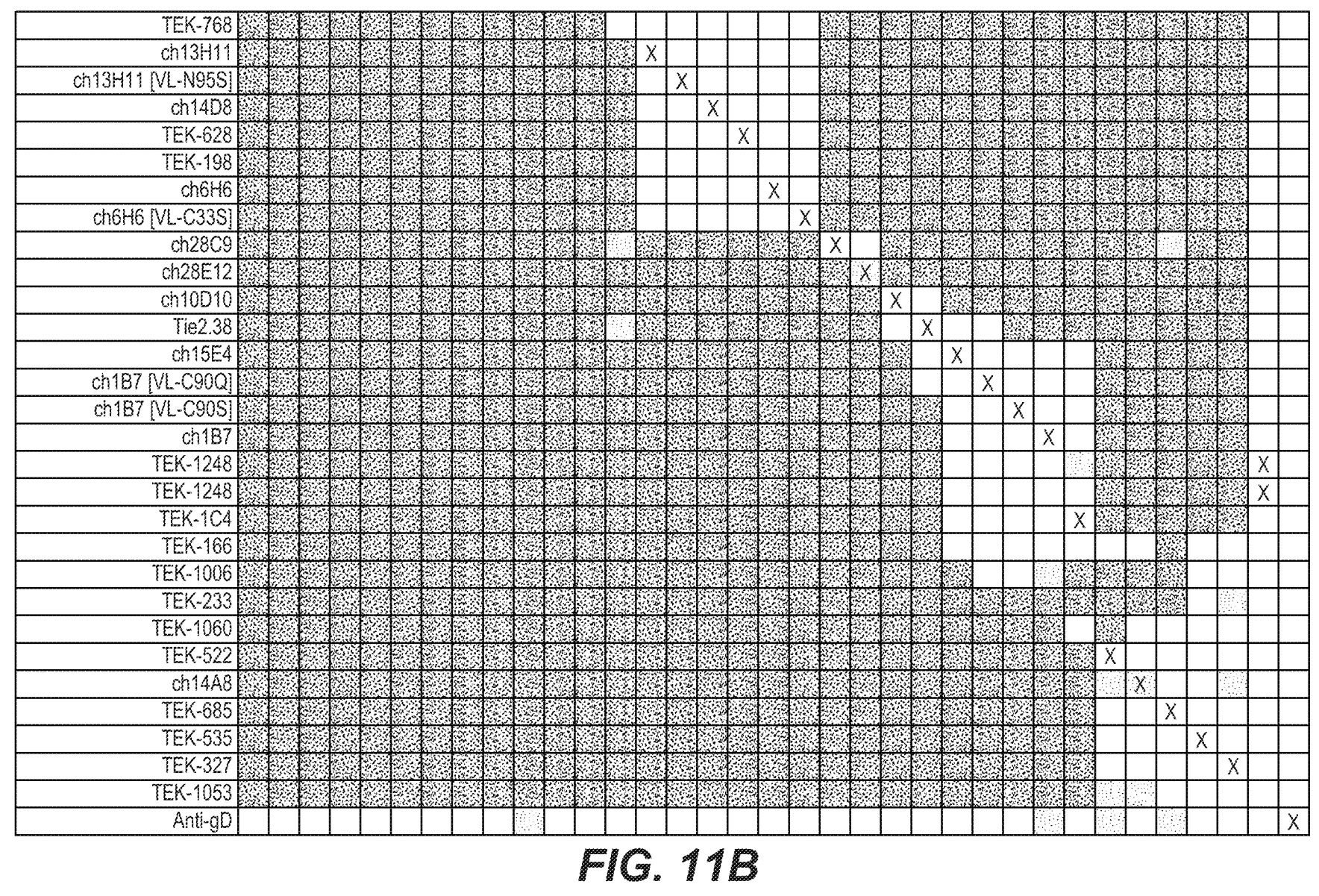

Antibodies generated by animal immunization, and select phage-derived antibodies described in Example 1, were reformatted into hIgG1 backbones and binning was performed using the CFM2/MX96 SPR system (Wasatch Microfluidics, now Carterra), equipped with DA v6.19.3, IBIS SUIT, SprintX & Carterra Epitope Tool software. Antibodies were immobilized on an SPR sensor prism CMD 200 M (Xantec Bioanalytics) by amine coupling using a 10 mM sodium acetate pH 4.5 immobilization buffer. Immobilization was performed with the CFM2 instrument and the sensor prism was then transferred to the *IBIS* MX96 instrument for SPR-based competition analysis. Immobilized antibodies were exposed first to 1 µM recombinant human Tie2 extracellular domain and then to 20 ug/ml antibody in solution, using an HBS-EP running buffer (10 mM HEPES, 150 mM NaCl, 0.05% Tween 20, pH 7.4, 1 mM EDTA). Results are shown in FIG. 11A-11B and indicate several different Tie2 sandwiching profiles. The results in FIG. 11A-11B would typically be interpreted as demonstrating the presence of multiple (e.g., at least 8) different Tie2 epitopes within the antibody panel analyzed. Interestingly, the data show that Tie2.1, Tie2.1M100cF (described later in Example 11), Tie2.12 and Tie2.24, all capable of functioning as Tie2 agonists, bin together.

Example 6—Generating PEG-Conjugated Anti-Tie2 Fab Multimers

As shown above in Example 3, activation of Tie2 by anti-Tie2 antibodies is facilitated by cross-linking of the bound anti-Tie2 antibodies. Accordingly, multimeric Tie2-binding compositions were designed and generated to determine a multimer configuration that will have optimal therapeutic efficacy.

One method of multimerization employed was the use of multi-armed polyethylene glycol (PEG) molecules as cores in which each arm is linked or conjugated to a single anti-Tie2 Fab molecule. The Tie2.1 Fab, shown to bind specifically to Tie2 with high affinity and to function as a Tie2 agonist (activates phosphorylation of AKT upon interaction with Tie2) was used to test varying multimer configurations. Specifically, the Tie2.1 Fab was modified such that the C-terminus of the heavy chain was modified to include the amino acid residues SPPC (SEQ ID NO:89), providing a linker and cysteine to which a PEG moiety can be conjugated. This "Tie2.1-SPPC" Fab was conjugated to PEG-maleimide backbones having varying numbers of arms and arm lengths (multi-arm PEG-maleimides were obtained from JenKem Technology USA, Plano, TX).

Fab Purification and Deblocking

All chromatography resins were sourced from GE Healthcare.

Fabs were expressed in *E. coli*. The *E. coli* pellet was resuspended 1.5 L/Kg in 25 mM TrisHCl, 150 mM NaCl, 5 mM EDTA, pH 7.5 (EQ) and microfluidized two times at 1000 bar. PEI was slowly added to a final concentration of 0.4% then stirred at 4° C. overnight. The suspension was then centrifuged at 15,000 g for 60 min and the supernatant 0.22 um filtered. The *E. coli* filtrate was then loaded over a 1.2 L Gammabind Plus (GBP) column equilibrated in EQ at 30 ml/min, then washed at 30 ml/min with 2 CV of EQ, 5 ml/min with 4 CV of EQ containing 0.1% TX114 and 0.1% TX100. This was followed with a 30 ml/min with 2 CV of EQ then 30 ml/min with 2CV of 25 mM succinate pH 6.0 and elution at 30 ml/min with 0.15M acetic acid. The elution was neutralized as it came off the column to pH 5.0 with 1 M Tris pH 9.0.

Alternatively, the *E. coli* filtrate was loaded over a 1.7 L Capto L column equilibrated in EQ at 35 ml/min, then washed at 50 ml/min with 2 CV of EQ, 4 ml/min with 5 CV of EQ containing 0.1% (v/v) Triton X114 and 0.1% (v/v) Triton X100, then 50 ml/min 2CV EQ, then 50 ml/min with 25 mM succinate pH 6.0, and eluted at 50 ml/min with 0.15 M acetic acid. The elution was neutralized as it came off the column to pH 5.0 with 1 M Tris pH 9.0.

The neutralized GBP or Capto L elution was diluted one to three fold with 20 mM sodium acetate, pH 5.0 (A) and loaded onto a cation exchange resin (SPHP). The column was washed with 2 CV (A) 5 CV (A) containing 0.1% Triton X114 and 0.1% Triton X100, followed by 2CV (A), then gradient eluted with a 10 CV 0-20% gradient of (A) containing 1M NaCl (B) with fraction collection. The fractions containing the Fab peak were pooled.

The purified Fab pool was adjusted to pH 8.0 using 1M Tris pH 8.5 and EDTA was added to a final concentration of 2 mM. To reduce the Fab a 50 fold molar excess of DTT was added to the solution and then incubated at 22° C. overnight and checked for adduct removal by mass spec.

After adjusting the pH to 5.2 with 10% acetic acid, the reduced Fab was bound to SPHP, washed with 10 CV of 25 mM sodium acetate, pH 5.0 and eluted with 50 mM Tris, 150 mM NaCl, pH 8.0. The eluted Fab pool was brought to pH 8.0 with 1 M Tris, pH 8.5, 2 mM EDTA was added and reoxidation proceeded using a 15 fold molar excess DHAA. After 1.5 hours the Fab was checked for reoxidation by mass spec; if necessary an additional 10 fold molar excess of DHAA was added and the sample was incubated for 1 hour and re-checked. The re-oxidized Fab was then pH'd to 5 with 10% acetic acid and purified on an SPHP column as above but eluted with a 20 CV 10-60% gradient (B=25 mM sodium acetate, 300 mM sodium chloride, pH 5.0; the main peak was 10 kD concentrated and 0.2 um filtered. Other Fabs can be purified and deblocked in essentially the same manner.

Hexamer Conjugation and Purification

Tie2.1-SPPC was conjugated to 6 KDa PEG hexamer from JenKem in 25 mM NaOAC, pH 5.0, 150 mM NaCl, 2 mM EDTA at a concentration around 10 mg/mL. After equilibrating to room temperature, 6 KDa PEG hexamer from JenKem was suspended in 25 mM NaAcetate pH 5.0 to a concentration of 3 mM. The pH was kept below pH 6 to avoid maleimide ring opening. Once PEG was solubilized, it was added to the Tie2.1-SPPC deblocked Fab at a molar ratio of 9:1 (Fab:PEG). The mixture was then left at room temperature with gentle shaking overnight. Following conjugation, Tie2.1 Fab PEG Hexamer was purified using size exclusion chromatography (SEC) on a Superdex-200 column in 20 mM His-acetate, pH 5.5, 150 mM NaCl, this purification step removes excess Fab and aggregation from the conjugation mixture. A NuPage 4-12% Bis tris Gel reduced and non-reduced was run to determine which conjugate fractions to further purify to enrich for hexamer. The conjugate fractions were pooled and further purified by cation exchange (CEX) using SP Sepharose High Performance strong cation exchange resin from GE to enrich for 6 Fabs/PEG. The CEX step was run in 25 mM sodium acetate pH 5.0 and eluted using a gradient from 20% to 33.4% in buffer B (Buffer B is 25 mM NaOAC, pH 5.0, 300 mM NaCl) in 44.5 CV, gradient from 33.4%-50% B at 10 min and finally eluted with 100% B. Few different minipools of different fractions are run on gel as above and the data is used to decide which fractions to pool. Minipool 3 was pooled and then formulated in PBS, pH 7.2 at 40 mg/mL.

The final sample was then run on analytical SEC using TSKgel G3000SW xl column in a 0.2 M KPO$_4$, 0.25 M KCl, pH 6.2, 15% isopropyl alcohol as a buffer to determine the percentage of aggregation present. It was also run on a gel as described earlier.

FabIgG Purification

CHO conditioned media was purified over a Mab Select Sure affinity column (GE Healthcare), followed by size exclusion chromatography (SEC) 5200 column. Alternatively the affinity elution was diluted and loaded onto a cation exchange (SPHP) then washed and eluted with a salt gradient. The purified monomer peak was then concentrated and dialyzed into formulation buffer and 0.2 um sterile filtered.

Comparison of FabIgG and Hexamer pAKT Activity

Figure 12A:
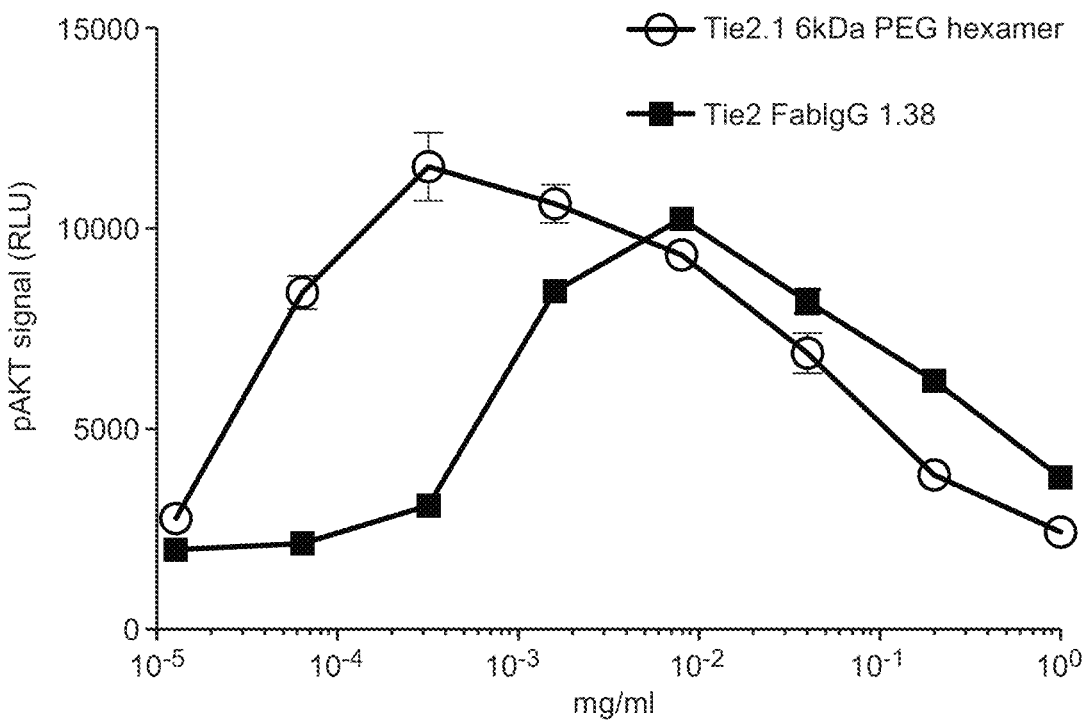
FIGS. 12A-12B show results assays assessing agonist activity of multimeric anti-Tie2 antibodies.

Tie2.1.38 is a biepitopic Fab-IgG which activates Tie2 (HC is provided herein as SEQ ID NO:54, LC is provided herein as SEQ ID NO:53. An experiment was performed to evaluate the ability of Tie2.1 in a PEG-hexamer format (6 kDa PEG linked at the C-terminus of the HC via SPPC) and Tie2.1.38 (cross-linking provided by the IgG format). Higher potency activation was seen with the Tie2.1-PEG-hexamer (FIG. 12A).

Figure 12B:
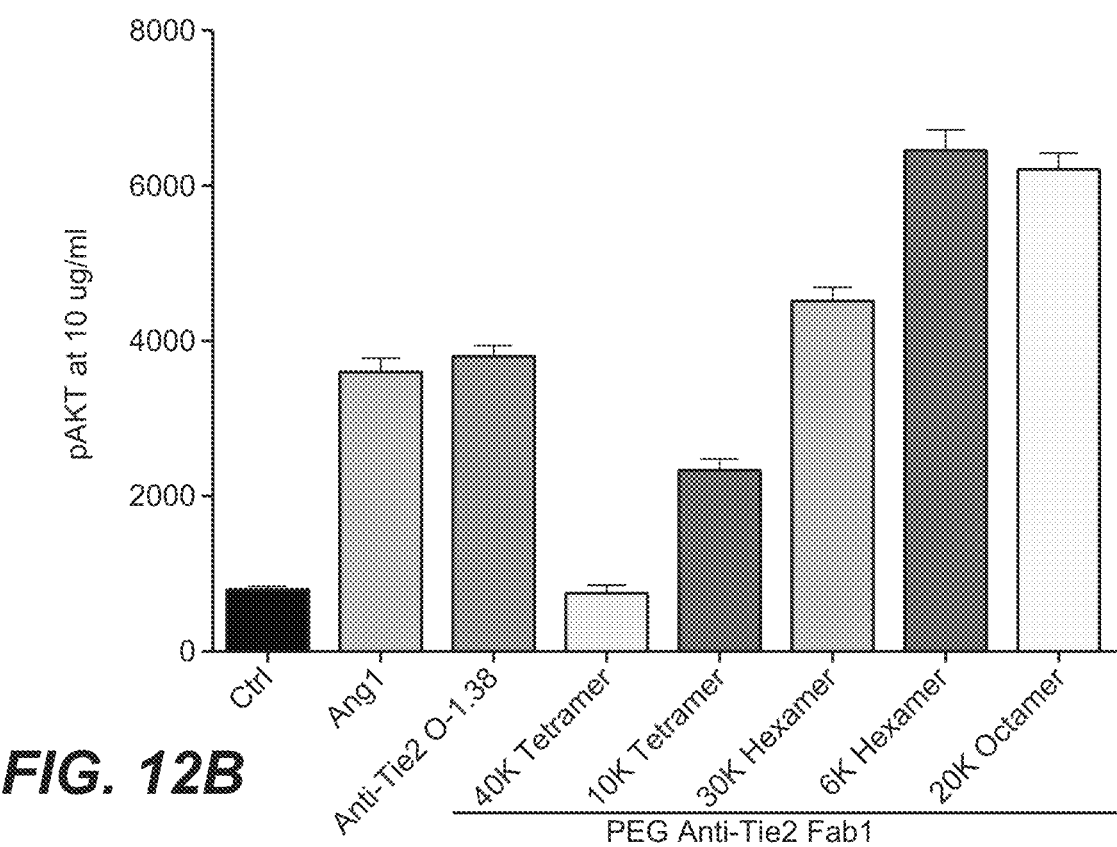

Agonist activity of anti-Tie2 Fabs multimerized via multi-armed PEGs Ten µg/ml of the PEG-multimers were incubated with RAECs and changes in pAKT levels were assessed as described (Example 3). Trends towards higher activity with more arms and/or with shorter arms with the 6-arm, 6 kDa core and 8-arm, 20 kDa core showing near maximal activity (FIG. 12B).

Example 7—Multimerization of Anti-Tie2 Fabs Using an IgM Format

Another method to multimerize an anti-Tie2 Fab was developed using an IgM format. DNA encoding VH from Tie2.1 was fused onto the IgM CH1. Without being bound by theory, It is believed that avid binding of multiple variable fragments (Fvs) enables IgMs to bind targets without substantial affinity maturation (Boes, 2000, Mol Immunol, 37:1141-1149).

Optimization of IgM Expression and Purification.

Figure 13A:
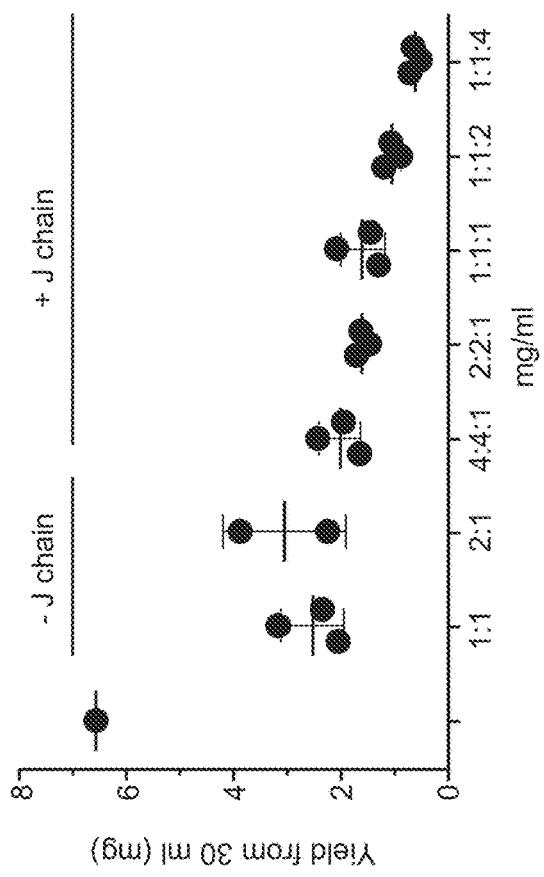
FIGS. 13A-13B shows effects of various ratios of huIgM heavy chain to light chain, without or with the J-chain, on the total yield of protein isolated off of an affinity column as measured by A280 of total protein (FIG. 13A) and SEC profile (FIG. 13B).

Human IgM (huIgM) was expressed in 30 ml cultures of Expi293 cells as recommended by the manufacturer (e.g. see "Expi293 Expression System, User Guide," publication number MAN0007814, from ThermoFisher Scientific). Various ratios of IgM heavy chain to light chain (hexamer) or heavy chain to light chain to J-chain (pentamer) were transfected into the cells. Harvested supernatant was affinity purified using Capto L resin (GE healthcare) according the manufacturer's recommendation (e.g. see Lombana et al., 2019, mAbs, 11:1122-1138). Total yields of protein were assessed by A280 and purity was assessed by analytical SEC using a Waters Xbridge BEH SEC 450 angstrom column. FIG. 13A shows the impact of various ratios of huIgM heavy chain to light chain to J-chain (when included) on the total yield of protein isolated off of the affinity column.

Figure 13B:
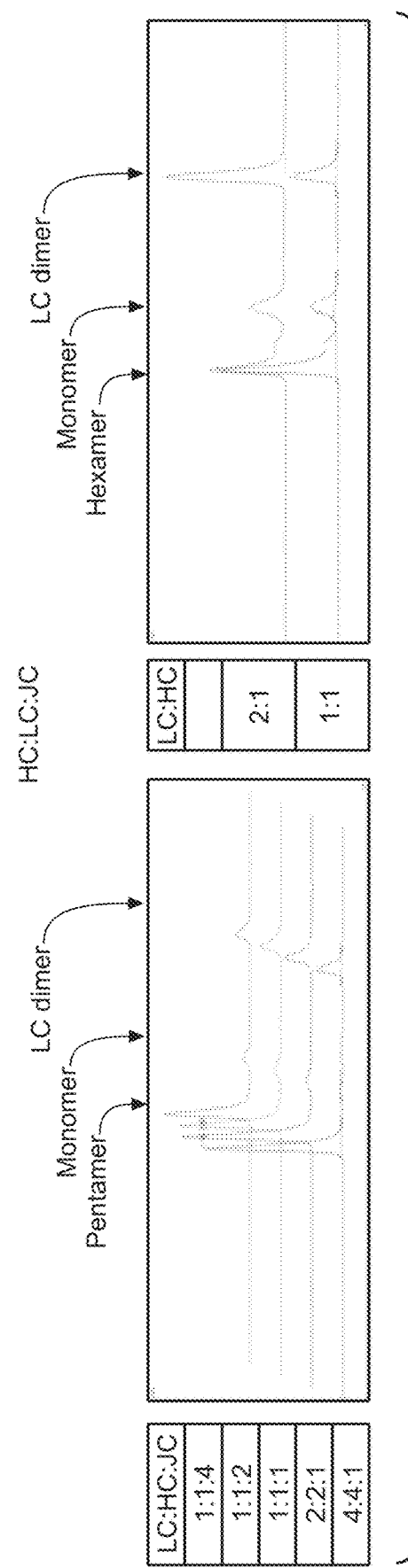

Hexamer optimization proceeded by transfecting cells with plasmids containing LC and HC at a 1:1 or 2:1 ratio of plasmid DNA. Each ratio resulted in similar total protein yields (2.5-3 mg from a 30 ml expression), however product quality appeared improved at a 1:1 ratio with reduced amounts of LC-dimer present. Expression of putative pentamers was conducted by including J-chain in the transfection. The optimal ratio of 4:4:1 LC:HC:JC, maximized both expression and product quality (FIG. 13A-13B). Notably, the high level of LC and HC DNA relative to JC in the optimized conditions approximates the 10:10:1 chain ratio in the final IgM pentamer.

Having optimized chain ratios for expression of pentameric and hexameric IgMs, expression and purification of human and murine hexameric and pentameric IgMs was scaled up. Approximately 20 mg/L of purified hexameric or pentameric IgM was isolated via two-step purification from CHO cells. Though the transient yields are 3-4 fold lower than typical for IgGs expressed under this process, the relatively facile purification combined with the low material requirements for ocular drugs should facilitate manufacturing feasibility. Chain composition of the human IgMs was confirmed by SDS-PAGE and LC-MS of the reduced and deglycosylated species showing the presence of LC, HC, and JC if present. Size exclusion chromatography showed monodisperse peaks for pentameric and hexameric murine IgM and for hexameric human IgM. Pentameric human IgM eluted from the SEC in two closely related peaks, both containing J-chains and with high apparent MW by SEC. Assessment by light scattering found hydrodynamic radii ($R_h$) of approximately 12 nM with predicted molecular weights for the hexamers (~1050 kDa) slightly exceeding those for the pentamers (~950 kDa) (Table 9 below).

TABLE 9

| | Mw (kDa) | Rg(avg) (nm) | Rh(avg) (nm) | Rg/Rh |
|---|---|---|---|---|
| BSA | 66.6 (±0.3%) | N.D. | 3.5 (±0.7%) | N.D. |
| Lucentis | 50.5 (±0.5%) | N.D. | 3.0 (±0.9%) | N.D. |
| Herceptin | 149.9 (±0.4%) | N.D. | 5.3 (±0.5%) | N.D. |
| Murine IgM pentamer | 958.3 (±0.3%) | 10.8 (±1.1%) | 12.3 (±0.4%) | 0.878 |
| Murine IgM hexamer | 1047.7 (±0.3%) | 10.8 (±0.9%) | 12.6 (±0.3%) | 0.857 |

TABLE 9-continued

|  | Mw (kDa) | Rg(avg) (nm) | Rh(avg) (nm) | Rg/Rh |
|---|---|---|---|---|
| Human IgM hexamer | 1023.1 (±0.3%) | 11.5 (±0.8%) | 12.6 (±0.3%) | 0.913 |
| Human IgM pentamer Pk 1 (major peak) | 948.2 (±0.3%) | 11.3 (±1.2%) | 12.6 (±0.4%) | 0.897 |
| Human IgM pentamer Pk 2 (major peak) | 938.2 (±0.3%) | 9.2 (±1.6%) | 11.6 (±0.4%) | 0.793 |

The ratio of radius of gyration to hydrodynamic radius (Rg/Rh) provides some insight into molecular shape with spherical molecules averaging 0.775, and more elongated species trending higher. Monodisperse IgMs ranged from 0.85-0.91 consistent with the anticipated structures. To further assess the polymeric identity of the IgMs negative stain TEM and reference free 2D classification was used to describe the architecture of IgM particles, which appear to match their anticipated geometries. No obvious difference was observed between the two peaks corresponding to putative human pentamers. The human IgM hexamer peak was selected for further investigation. 110 TEM micrographs were manually collected, resulting in a total of 1500 particles. Following three rounds of reference free 2D classification using the Relion suite (Scheres, 2015, J Struct Biol, 189:114-122) it was found that the majority of the particles organized into a hexameric structure. A small number of particles (<2%) refined into pentamers. Consistent with previous structural investigations into IgM pentamers (Czajkowsky and Shao, 2009, Proc Natl, Acad Sci USA, 106:14960-14965) the CH3 and CH4 domains appear to form a stem-like domain that is orthogonal to the plane of the image. Furthermore, while pairs of Fabs attached to the same Fc appear coplanar, there is some indication that Fabs on adjacent Fcs are offset. A partial offset may allow the hexamer to accommodate all chains in a sterically crowded environment. Based on these data, human hexameric IgMs were selected as the preferred therapeutic scaffold due to the improved purity of production and the absence of JC which both simplifies manufacturing and obviates the need to consider polymeric-Ig receptor mediated binding in vivo.

Characterization of IgMs for Ocular Administration

Figure 13C:
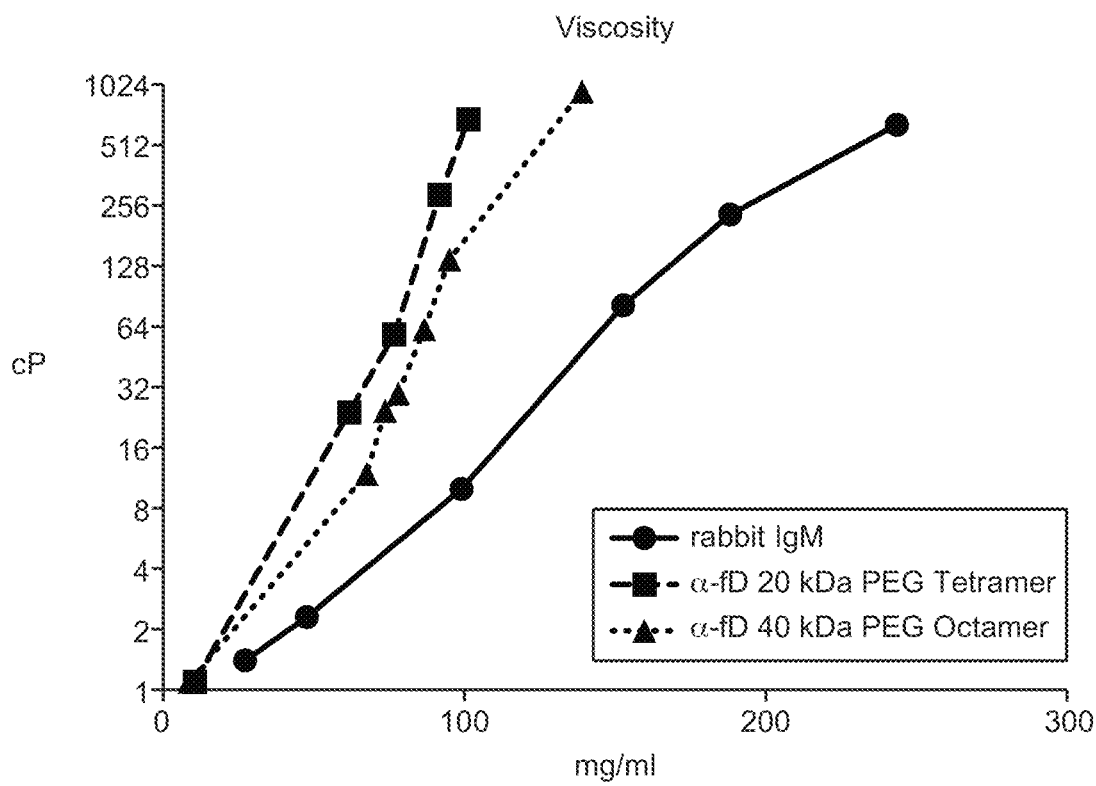
FIG. 13C shows rheology measurements of IgMs compared to ocular multivalent PEG formats targeting factor D (fD).

Next, the suitability of IgMs for ocular applications was investigated using New Zealand White Rabbits as a model system. PK parameters in rabbits have previously been correlated to the results in cynomologous monkeys and humans. To minimize the risk of anti-drug antibodies interfering with the pharmacokinetic evaluation of IgMs a fully rabbit IgM hexamer (rabbit IgM Fc with rabbit Fvs targeting an intracellular epitope) was generated. To avoid frequent repeated injections, the amount and therefore the concentration of protein injected is maximized. Accordingly, protein viscosity is of considerable interest. The viscosity of the IgM hexamer was evaluated versus other multivalent compounds that have previously been explored (Shatz et al., 2019, PLoS ONE, 14:e0218613-e0218613), specifically, both an 8-armed 40 kDa branched PEG and a four armed 20 kDa branched PEG terminating in 8 and 4 Fabs respectively (FIG. 13C). Viscometer readings for all three species show the anticipated log-linear response. Under viscosities conducive to intravitreal administration without patient pain or undue backpressure on the syringe (~10-50 cP) approximately twice the mass of IgM can be administered in comparison to the other formats.

Figure 13D:
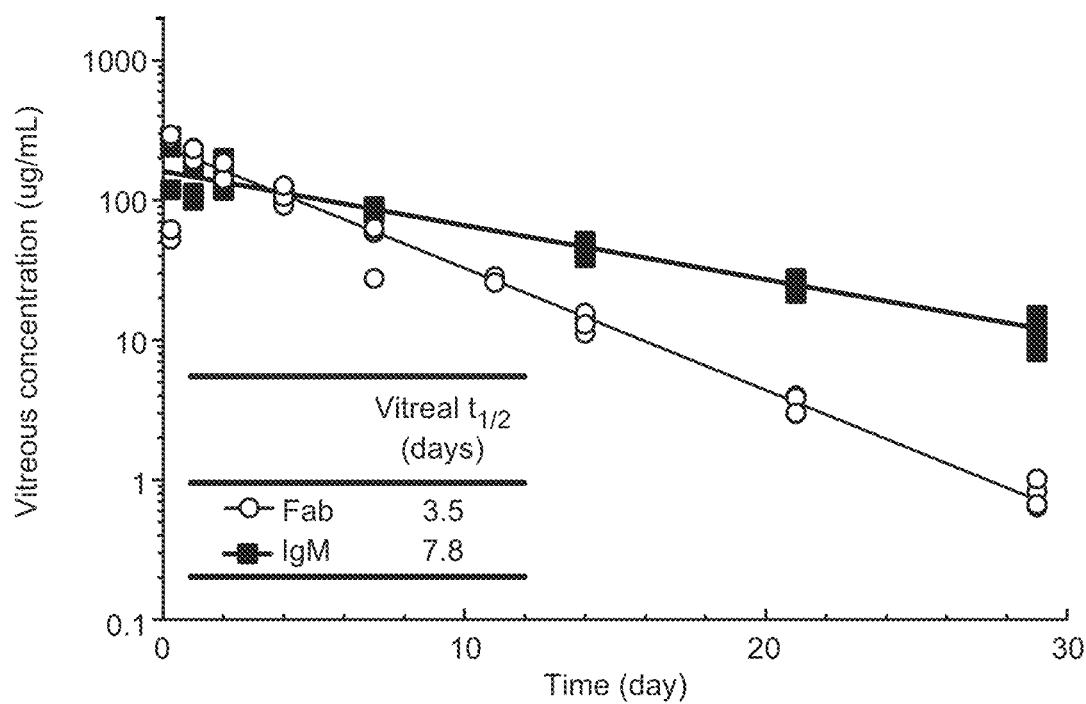
FIG. 13D shows vitreal pharmacokinetic analysis of non-binding IgM and a non-binding Fab.

SEC-MALS analysis of the rabIgM found a hydrodynamic radius of 12.9+/−1.1 nM, considerably larger than the 2.5 nM radius previously observed for Fabs. To assess the functional consequence of this increase in molecular size, a rabbit Fab and IgM were labeled with Alexafluor 488, and 0.5 mg or 1.2 mg, respectively, were intravitreally administered to New Zealand White rabbits. In-life quantitative fluorescent measurements were taken over 28 days revealing the durability of each of the two therapeutics (FIG. 13D). In this experiment, the Fab showed a half-life of 3.5 days, comparable to the typical half-life of ~3.4 days observed for the other Fabs in rabbit vitreous (Crowell et al., 2019, Trans Vis Sci Tech, 8:1-9). The IgM showed substantially extended exposure of 7.8 days, consistent with its larger size.

Figure 13E:
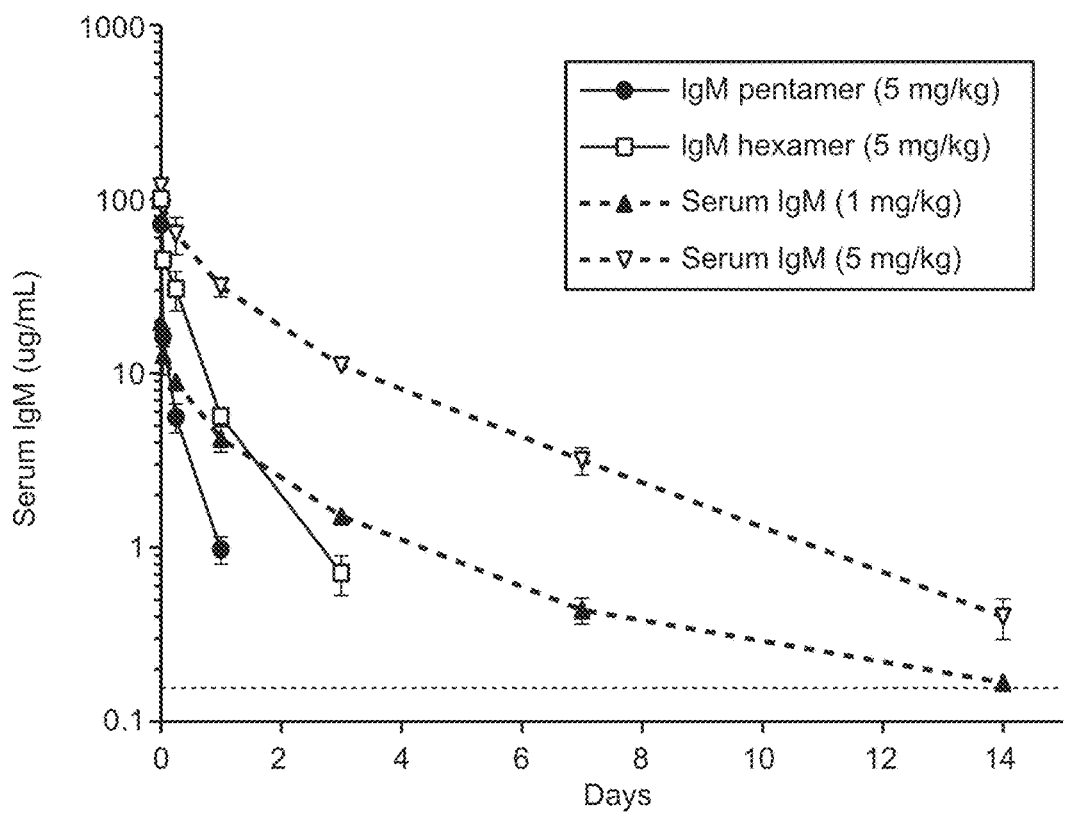
FIG. 13E shows systemic pharmacokinetic analysis of IgMs, comparing non-binding recombinant hIgM pentamers and recombinant hIgM hexamers with IgMs isolated from human serum injected i.v. into female SCID mice.
Figure 13F:
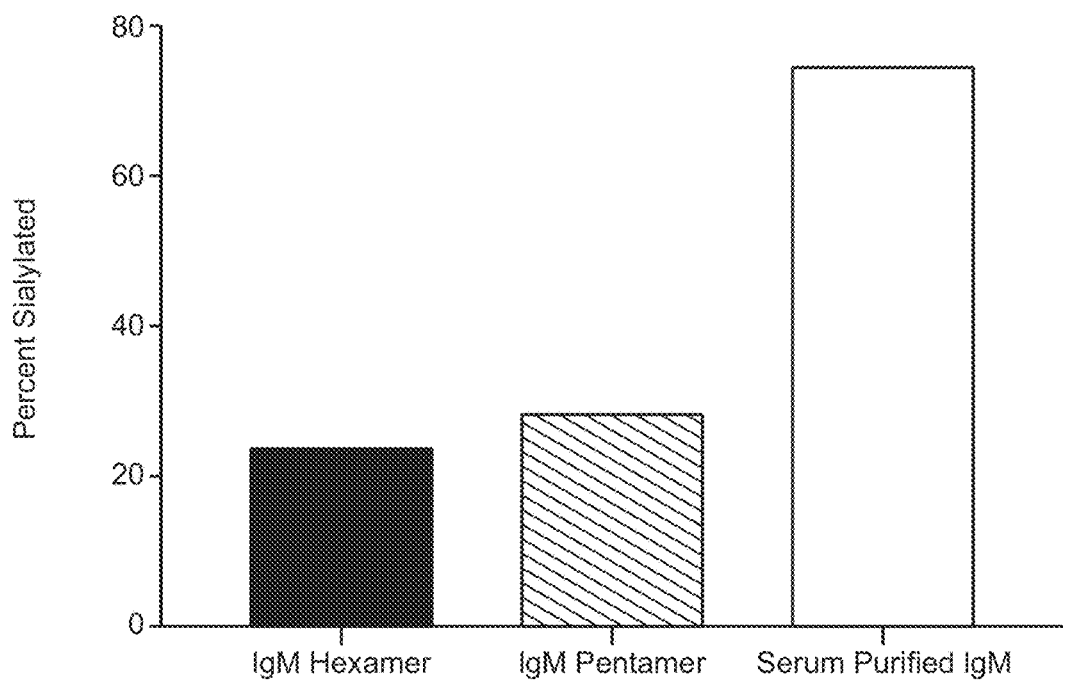
FIG. 13F shows LC-MS analysis of global N-linked glycan profiles from the serum samples.

Systemic exposure of IgMs is also of interest, as rapid systemic clearance helps restrict activity of ocular therapeutics to the eye. While previous investigations of IgMs isolated from serum or ascites fluid have reported half-lives of a few days (e.g., Maiorella et al., Biotechnology (NY), 1993, 11:387-392) recombinantly produced material clears much more quickly (e.g., Rasche et al., 2015, Haematologica, 100:377-384). To confirm these findings the PK of non-binding recombinant human IgM pentamer and hexamer was compared to IgM isolated from human serum (FIG. 13E). Following intravenous injection into SCID mice, recombinant IgM pentamers and hexamers were rapidly cleared (t½ of 0.25 and 0.50 days respectively), while isolated IgM showed more prolonged exposure (t½=2.1-2.9 d). Is is hypothesized that rapid clearance may be due to differential glycan occupancy or composition of the IgMs. There are up to 51 N-linked glycans per human pentamer and 60 per human hexamer. In support of this theory, glycan analysis showed 75% of glycans on IgMs purified from human serum contained at least one sialic acid, versus 24% and 29% of recombinant hexamers and pentamers, respectively (FIG. 13F).

Protein Engineering to Minimize Complement Activity of huIgM Mutants.

Figure 13G:
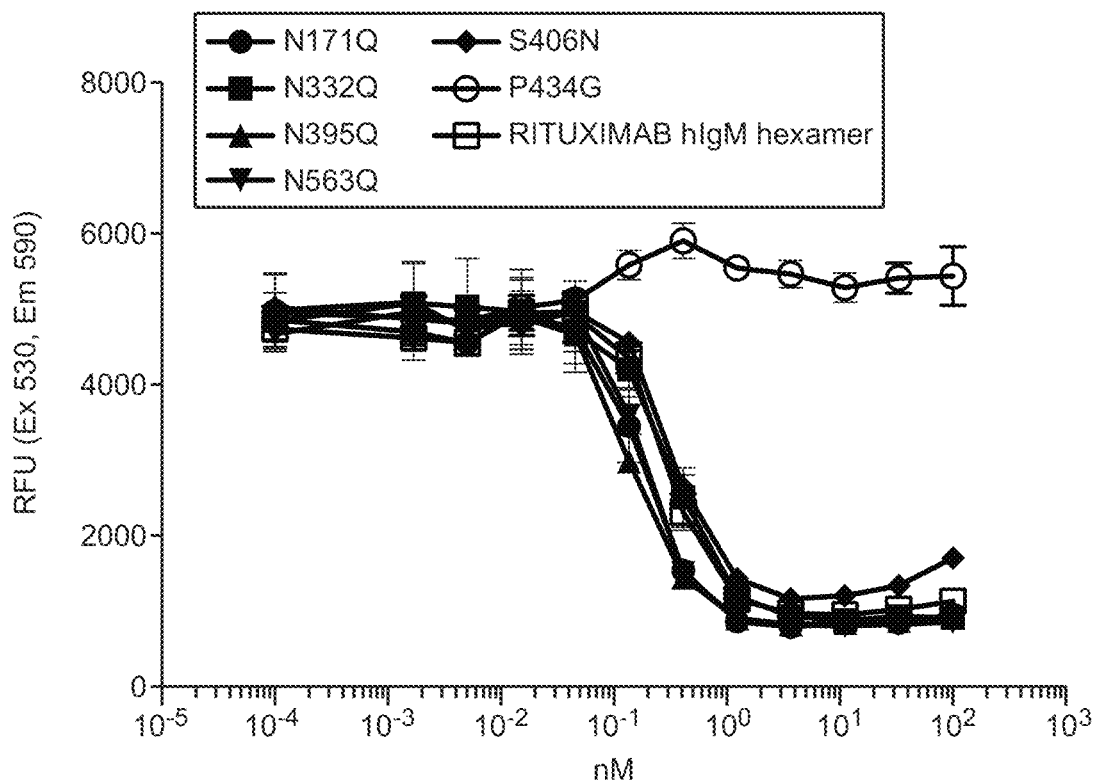
FIGS. 13G-13H show results of assays to characterize an anti-Tie2 antibody in an IgM multimeric format.

IgMs have well established complement-dependent cytotoxicity (CDC) that could be undesirable for a Tie-2 agonist. To identify hIgM Fc-mutants that would reduce potential CDC, the variable regions from rituximab (anti-CD20 antibody) were fused onto the constant regions of hIgM. Rituximab IgGs are well known to induce CDC. This rituximab-IgM along with selected Fc mutations were expressed as hIgM hexamers and purified. To study the impact of the IgMs, complement activity was assessed essentially as described (e.g. see Gazzano-Santoro et al. J Immunol Meth, 22, 163-171 (1997)). Briefly, 3-fold serial dilutions of IgMs were added to 50,000 Wil-2S cells in the presence of a 1/5 human complement dilution (final volume of 100 uL) and the mixture was incubated for 2 h at 37° C. Alamar Blue (Aldrich) 50 uL was added to the plates, and they were incubated for an additional 5 h at 37° C. The plates were cooled to RT for 10 min, and fluorescence was read using a 96-well fluorometer with excitation at 530 nM and emission at 590 nM with a decrease in fluorescence indicating CDC-mediated cell lysis. Four sites (N171Q, N332Q, N395Q, N563Q) were evaluated with mutations in consensus N-linked glycosylation motifs (FIG. 13G).

While these mutations may improve manufacturability or systemic PK, they did not impact CDC. Additionally, a S406N mutation shown to reduce CDC for murine IgM (e.g. see Wright et al. J Biol Chem, 265(18), 10506-10513, (1990)) did not impact human IgM. Importantly, the P434G mutant completely abrogated CDC activity, rendering the IgM hexamers useful as ocular therapeutics Comparison of IgM and PEG-Hexamer Activity.

Figure 13H:
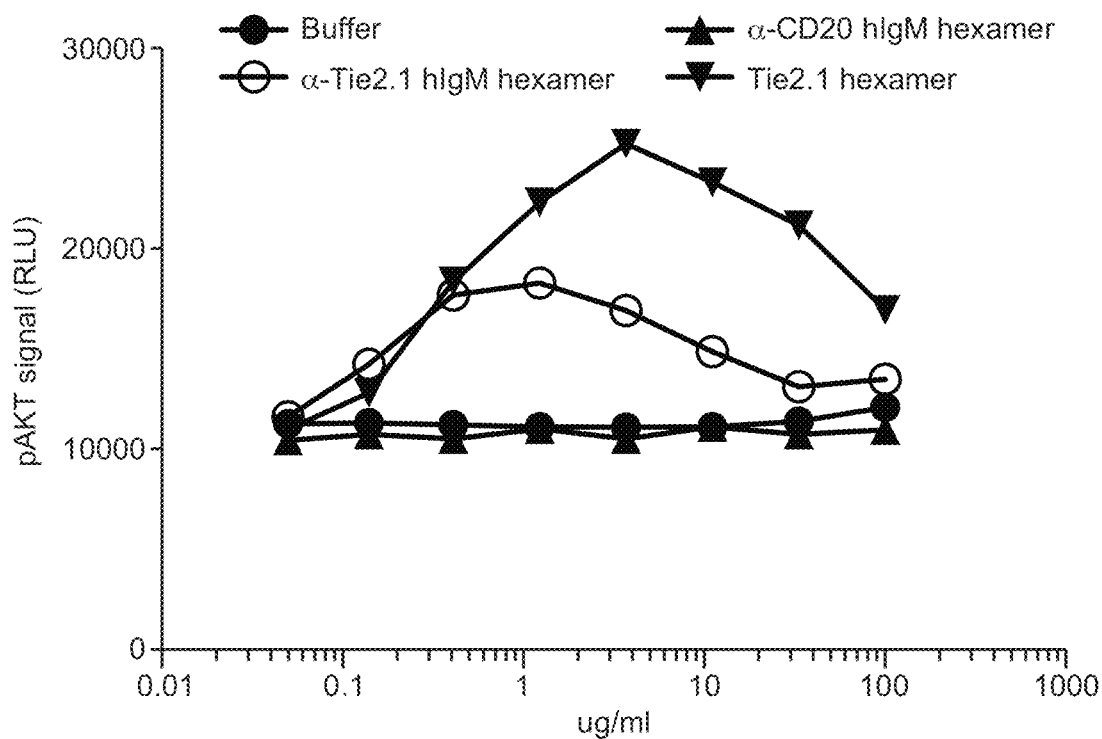

Having characterized the suitability of IgMs to ocular administration, we next turned to probing their ability to activate relevant signaling pathways. Tie2 targeted IgM hexamers were expressed and analyzed for their ability to drive phospho-AKT signaling downstream of Tie2. Rat aortic endothelial cells were treated with increasing doses of either endothelial-targeted Tie2.1-hIgM hexamers, Tie2.1 PEG hexamer (Tie2.1 Fab terminated with SPPC conjugated to a PEG-hexamer) or untargeted anti-CD20 hIgM hexamers for 15 minutes, lysed, and intracellular phospho-AKT levels were evaluated using homogeneous time-resolved fluorescence. Increases in cellular phospho-AKT levels were seen only for the Tie2.1-hIgM and Tie2.1 PEG hexamers (FIG. 13H). No activity was seen for the corresponding IgG in the absence of cross-linking (data not shown). Interestingly, while the Tie2.1hIgM hexamer and Tie2.1 PEG hexamers were active at picomolar concentrations, pAKT production is partially suppressed at high concentrations. It is speculated that super-saturation of the hexamers on the cell-surface reduces the extent of clustering of Tie2, and as a consequence reduces the downstream signaling. Still, at 100 nM IgM (approximately 100 ug/ml) approximately 30% of the maximum activity was attained. These data suggest that Tie2.1 hexamers are likely to drive Tie2 signaling over at least 3 orders of magnitude in protein concentration.

Figure 14A:
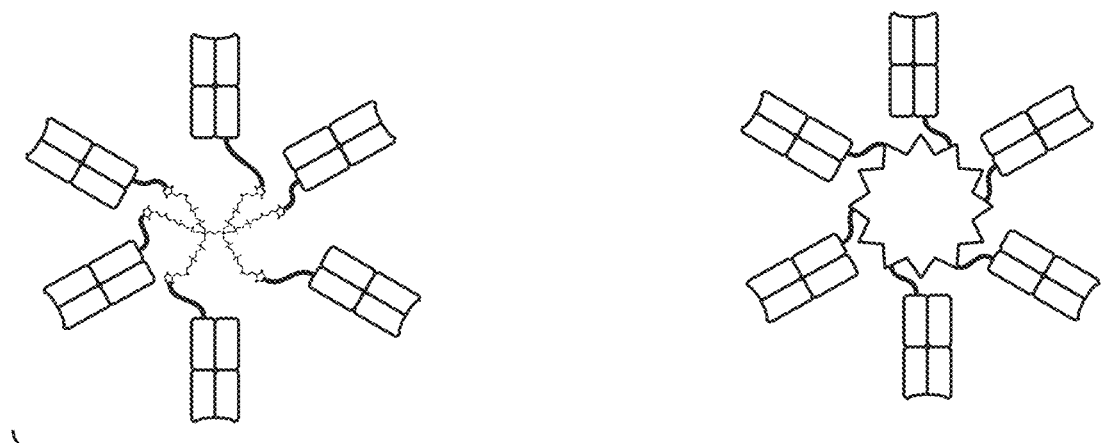
FIGS. 14A-14B show design and analysis of anti-Tie2 antibodies in a hexamer format via a peptide moiety.

Example 8—Development of a Surrogate Hexamer Format for Identification and Comparison of Tie2 Agonist Antibodies In an effort to increase the throughput and relevancy of candidate antibody screening methods, a homo-hexameric protein was searched for and identified which could be used as a surrogate for conjugation of an anti-Tie2 Fab to hexamer multi-arm PEG by genetically fusing the C-terminus of the Fab heavy chain to the N-terminus of the constituent subunit of the hexamer (see FIG. 14A). It was reasoned that such a fusion protein would facilitate production of Fab hexamer for in vitro analysis without requiring chemical conjugation of the purified Fab. Furthermore, such a fusion protein could be used as an in vitro surrogate for PEG-Fab hexamer for in vitro activity evaluation of potential new anti-Tie2 agonist antibody candidates.

The eukaryotic nucleoside diphosphate kinase (NDK) enzymes have a homo-hexameric quaternary structure (Lascu et al., 2000, J Bioenerg Biomembr, 32:227-236) with exposed N-termini (Moréra et al., 1994, J Mol Biol, 243: 873-890). In addition, cysteine-free, highly thermostable NDK sequences have been reported (Akanuma et al., 2013, Proc Natl Acad Sci USA, 110:11067-11072). It was reasoned that genetic fusion of amino acid sequences derived from this enzyme family to the C-terminal of test Fab may enable expression and purification of Fab hexamers with similar geometry to the PEG-Fab hexamers but which are more amenable to routine expression and purification methods, facilitating cell-based activity analysis of multiple candidate antibodies, for example in the HUVEC pAKT assay.

Design and Generation of Fab-NDK Fusion Proteins.

A panel of Fab-NDK fusion proteins were therefore generated in which the heavy chain C-terminus of a Fab encoding either Tie2.1 or a negative control antibody (gD.5B6) was genetically fused to one of 5 different candidate NDK sequences. NDK sequences were selected from the literature (Table 10), modified as described below, and expression vectors encoding Fab heavy chain fused to the NDK sequences were constructed via gene synthesis. Ratios of heavy chain expression vector to light chain expression vector were 2:1, 1:1 and 1:2 and are indicated by the column headers H2L1, H1L1 and H1L2 respectively. Table 10 provides fusion protein yields.

TABLE 10

| Fusion Protein* | NDK sequence source | Purified protein yield (mg) | | | | | |
|---|---|---|---|---|---|---|---|
| | | Tie2.1 Fab | | | gD.5B6 Fab | | |
| | | H2L1 | H1L1 | H1L2 | H2L1 | H1L1 | H1L2 |
| Fab-NDK1 (SEQ ID NO: 69) | Akanuma et al, 2013 (supra) | 0.05 | 0.26 | 0.78 | 0.00 | 0.00 | 0.21 |
| Fab-NDK2 (SEQ ID NO: 70) | Akanuma et al, 2013 (supra) | 0.16 | 0.60 | 1.22 | 0.00 | 0.03 | 0.25 |
| Fab-NDK3 (SEQ ID NO: 71) | Uniprot P22887 | 0.23 | 0.65 | 1.53 | 0.10 | 0.34 | 0.86 |
| Fab-NDK4 (SEQ ID NO: 72) | Uniprot P15532 | 0.18 | 0.57 | 1.59 | 0.00 | 0.20 | 0.47 |
| Fab-NDK5 (SEQ ID NO: 73) | Uniprot Q01768 | 0.24 | 0.98 | 1.91 | 0.09 | 0.33 | 0.80 |

*SEQ ID NOs are for NDK peptide sequences only

In each case, the Fab HC included and terminated at amino acids KTHT (amino acids 222-225 per EU numbering), and a short linker sequence consisting of 4 glycine residues was inserted in between the Fab heavy chain and the NDK sequences to provide additional flexibility. NDK sequences were also edited by removal of the N-terminal methionine residue and by mutation of Histidine 118 to Phenylalanine, a mutation reported in the literature to inactivate catalytic activity (Postel and Ferrone, 1994, J Biol Chem, 269:8627-8630). Fab light chains were encoded on separate expression vectors without additional modifications.

Expi293 cells were co-transfected with the Fab-NDK heavy chain and light chain expression vectors and the products were purified using affinity chromatography resin Capto L resin (GE Healthcare), which is designed for purification of antibody fragments containing kappa light chains. Fab-NDK3 and Fab-NDK5 fusion proteins were selected for additional purification by size exclusion chromatography, and the purity of the resulting samples was confirmed by analytical size exclusion chromatography (SEC) using a phosphate-based running buffer (200 mM $KH_2PO_4$, 250 mM KCl, pH 7.0) and a TSK3000 column (Tosoh Biosciences).

The hydrodynamic radius of Tie2.1 formatted as Fab-NDK3 or Fab-NDK5 was determined by multi-angle light scattering (MALS) and the results are summarized in Table 11 below. It is clear that the hydrodynamic radius of Tie2.1 formatted as Fab-NDK3 or Fab-NDK5 compares favorably with that determined separately for Tie2.1 PEG-Fab hexamer.

TABLE 11

| Fusion protein | Predicted from protein sequence Molecular Weight | From SEC-MALS analysis Molecular Weight | Hydrodynamic Radius |
|---|---|---|---|
| Tie2.1 Fab-NDK3 | 386 kDa | 403 kDa | 7.5 nm |
| Anti-gD Fab-NDK3 | 389 kDa | 408 kDa | 6.2 nm |
| Tie2.1 Fab-NDK5 | 389 kDa | 409 kDa | 7.3 nm |
| Anti-gD Fab-NDK5 | 392 kDa | Not determined (insufficient signal) | |

Functional Evaluation of Tie2.1 Fab-NDK Constructs

Figure 14B:
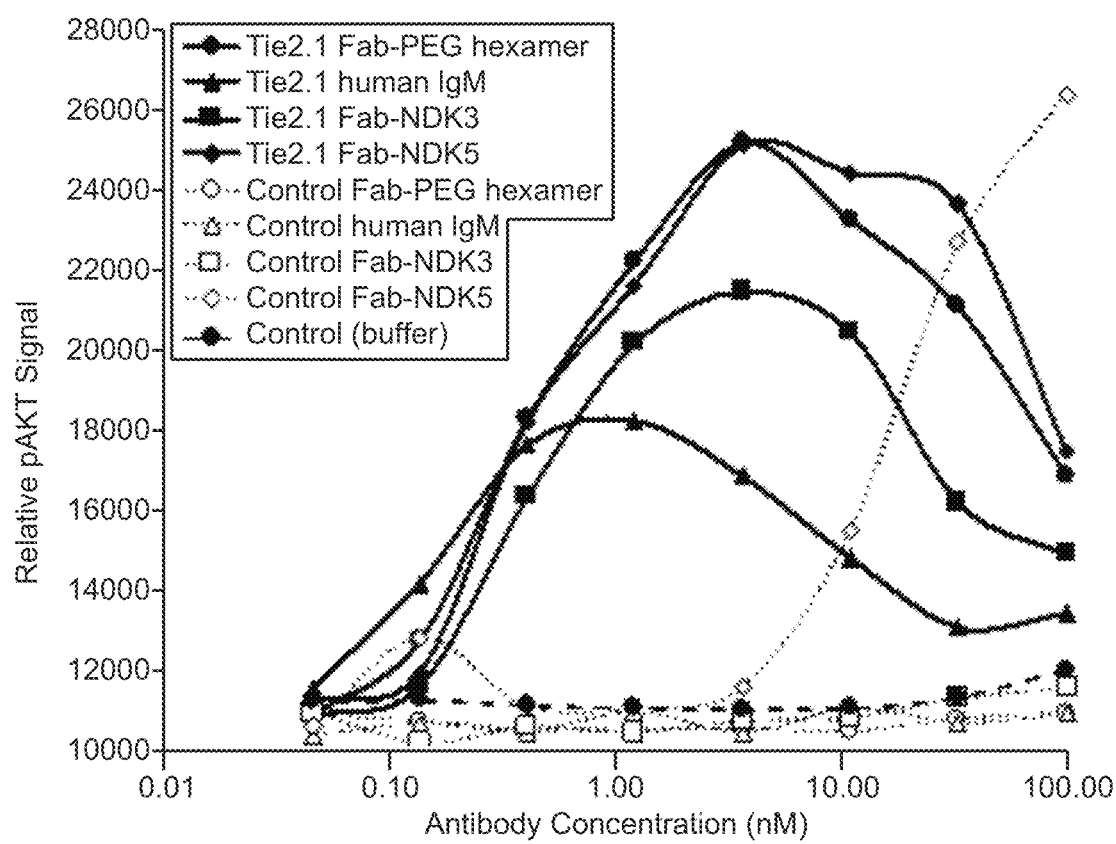
Figure 15A:
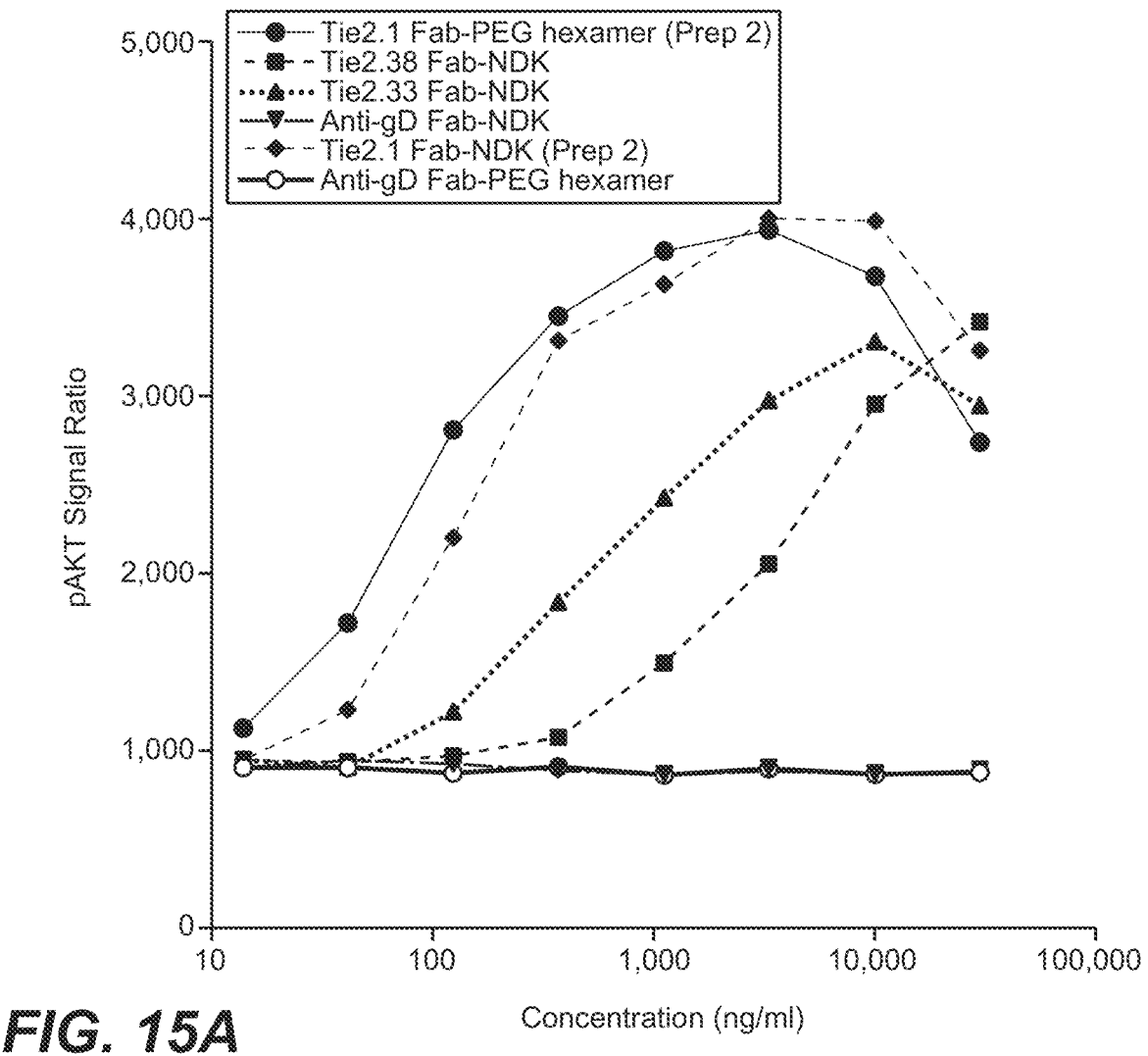
FIGS. 15A-15B show results of an AKT phosphorylation assay to assess agonist activity of various anti-Tie2 antibodies in a hexameric format. Results are shown for Tie2.1, Tie2.38, Tie2.33 (FIG. 15A) and Tie2.1, Tie2.1.M100cF, Tie2.12, Tie2.24 (FIG. 15B).
Figure 15B:
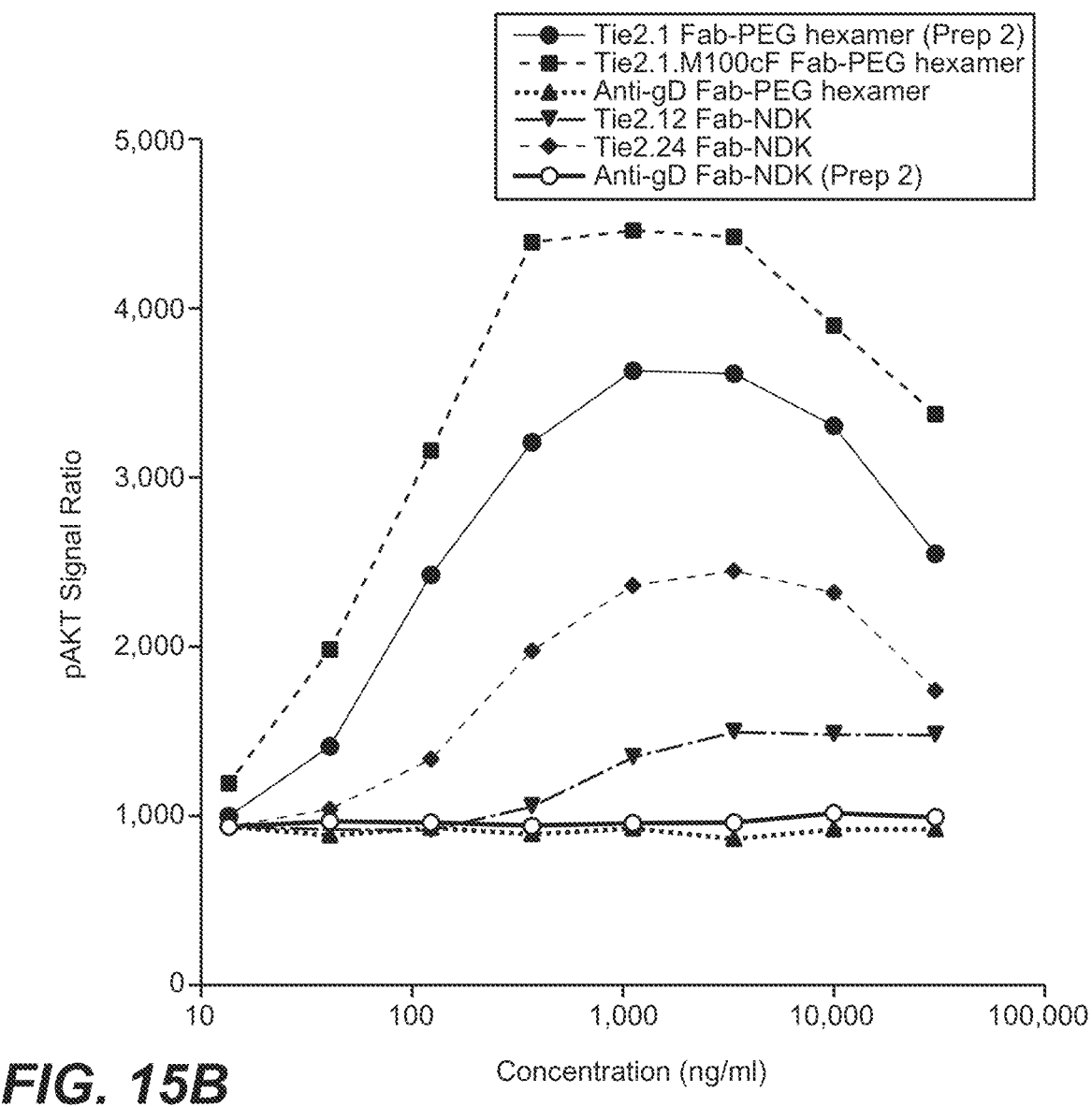

The Fab-NDK3 and Fab-NDK5 formats were then evaluated for Tie2 activation in the HUVEC pAKT assay using methods described in Example 3. Tie2.1 and negative control antibody were evaluated for Tie2 activation in the HUVEC pAKT assay in Fab-NDK3 and Fab-NDK5 formats. The results are provided in FIG. 14B.

Tie2.1 in Fab-NDK3 and Fab-NDK5 format showed a similar response profile to Tie2.1 in PEG-Fab hexamer format. The negative control antibody showed a similar response profile to the other negative controls, such as buffer and negative control PEG-Fab hexamer, when evaluated in Fab-NDK3 format, but when evaluated in Fab-NDK5 format the negative control antibody caused pAKT signaling at some concentrations. Therefore, we decided to use the Fab-NDK3 format for secondary screening of new anti-Tie2 antibodies, and also more generally as an in vitro surrogate for the PEG-Fab hexamer.

Screening Protein Hexamers for Tie2 Agonism in the HUVEC pAKT Assay.

Anti-Tie2 antibodies in the surrogate hexamer Fab-NDK3 format were screened for activation of pAKT signaling in HUVEC cells. With 2 exceptions, antibodies were evaluated at 8 concentrations, which consisted of three-fold dilutions from a top concentration of 30 μg/ml and covered more than three orders of magnitude. The 2 exceptions were due to sample availability and consisted of TEK-1053, which was evaluated at lower concentrations only, and ch18E7, which we were unable to generate in the Fab-NDK3 format. As demonstrated by FIG. 14A, the activity of the Tie2.1 Fab-PEG hexamer is very similar to that of the Tie2.1 Fab-NDK molecule confirming that the NDK hexamer conjugate is effective as a surrogate for the hexameric PEG conjugate. Accordingly, the NDK hexamer format is useful for assessing the agonist activity of anti-Tie2 various antibody Fabs as multimers (e.g., see FIG. 14A and FIG. 14B).

Example 9—Effects of Anti-Tie2 Antibodies on Cellular Levels of Tie2

As described in detail herein, therapeutic use of anti-Tie2 agonist antibodies relies in part on binding of the antibodies to the Tie2 receptor protein. Accordingly, experiments were done to determine if administration of the anti-Tie2 to cell samples or to animals had any effect on Tie2 protein levels. Compositions comprising anti-Tie2 antibodies generated as described above were evaluated and compared for their ability to induce reduction of cellular Tie2 levels in vitro using HUVECs.

In Vitro Analysis of the Effects of Anti-Tie2 Antibodies on Tie2 Levels.

HUVECs (Millipore, Cat #SCCE001) were seeded at $1\times10^6$ per well of 6 well-plate in Endogro Medium. Anti-Tie2 antibodies were added to a final concentration of 10 ug/ml and incubated 16-18 hours at 37° C. Cells were then washed with ice-cold PBS three times, and lysed on ice in 100 ul RIPA buffer (Sigma, Cat #20-188) supplemented with a cocktail of protease inhibitor and phosphatase inhibitors (Thermo Scientific, Cat #1861281). Cell lysates were centrifuged at 14,000 rpm at 4° C. for 10 min before being subjected to anti-Tie2 western blot (WB) analysis. A standard WB analysis was performed using a mouse anti-Tie2 primary antibody (BD, Cat #557039) and a secondary detecting antibody (HRP anti-mouse Ig, GE Healthcare, Cat #NA931V). The results are shown in FIGS. 16A-16C. As seen in FIG. 16A, anti-Tie2 antibodies generated by animal immunization (rat antibodies TEK-1A5, TEK-166, TEK-535, TEK-1248, TEK-69, TEK233-V2, and rabbit antibodies ch1B7.C90Q, CH6H6.3, significantly reduced Tie2 levels as detected by WB when assessed in the hexameric format. In contrast, the anti-Tie2 binding agents Tie2.12, Tie2.24, Tie2.1.M100cF, and Tie2.1-PEG-hexamer caused a much smaller decrease in Tie2 protein levels (FIGS. 16A-16C).

In Vivo Analysis of the Effects of Anti-Tie2 Antibodies on Tie2 Levels.

Figure 17:
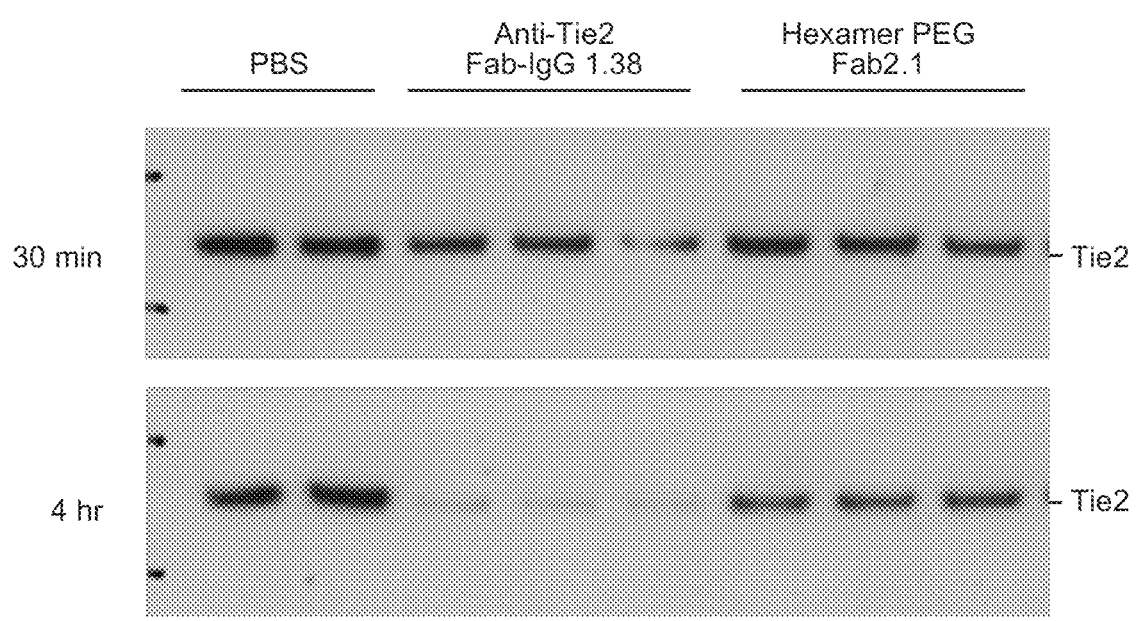
FIG. 17 shows results of an in vivo assay to assess the effect of anti-Tie2 antibodies on cellular levels of the Tie2 protein levels.

To assess the effects of anti-Tie2 antibodies on Tie2 levels in an in vivo assay, 8-9 week-old C57BL/6 mice (Charles River) were dosed with Tie2 agonist at 20 mg/kg, via IP injection. Mice were euthanized under $CO_2$ at different time points after anti-Tie2 antibody administration. Mouse lung tissues were dissected out and stored at −80° C. after snap freezing. About 20 mg of mouse lung tissue was homogenized in 1 ml of ice-cold RIPA buffer (Sigma, Cat #20-188) containing cocktail of proteinase and phosphatase inhibitors (Thermo Scientific, Cat #1861281). After clarification by centrifugation, tissue lysates were subjected to WB analysis using mouse anti-Tie2 (BD, Cat #557039) together with HRP anti-moue IgG Ab (GE Healthcare, Cat #NA931V) as secondary detecting antibody. WB membrane was developed using chemiluminescence (EC) reagents (Thermo Scientific, Cat #32132). As shown in FIG. 17, the effects of Fab2.1 PEG hexamer antibody on a decrease in Tie2 protein levels were much less than the effects elicited by the anti-Tie2 Fab-IgG 1.38.

Example 10—Protective Effects of Anti-Tie2 Antibodies

Effect of Anti-Tie2 Agonists on Endothelial Integrity

Figure 18A:
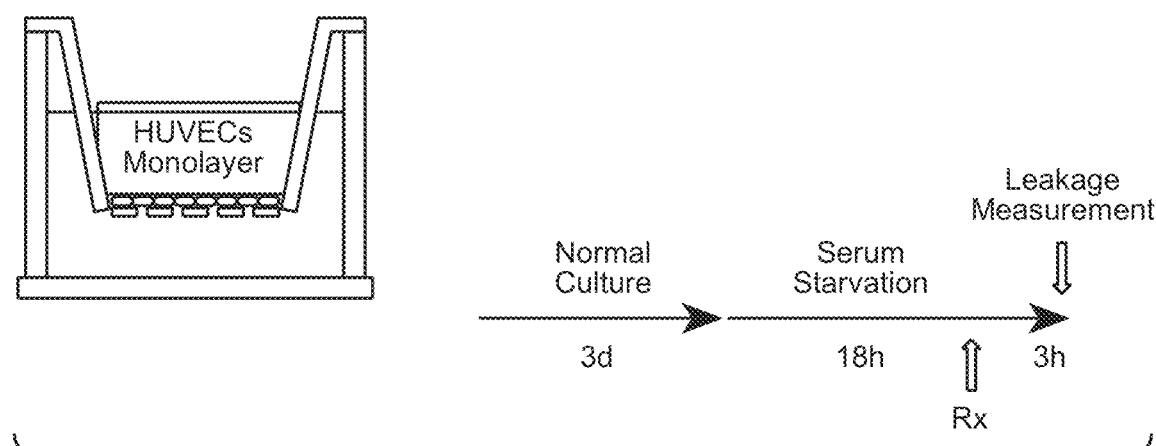
FIGS. 18A-18B illustrate an assay method (FIG. 18A) and results (FIG. 18B) of an in vitro endothelial cell assay to study the effects of anti-Tie2.1 antibodies on endothelial cell barrier permeability.

It is hypothesized that a protective effect of activating Tie2 is to reduce disruption of the endothelial barrier. A HUVEC permeability assay was used to measure the endothelial cell (EC) leakage of a presently disclosed anti-Tie2 agonistic antibody, Tie2.1. The assay method is illustrated in FIG. 18A.

HUVEC cells (Millipore, Cat #SCCE001) were seeded at $0.1\times10^6$ per well of 24 trans-well plate (Millipore, cat #: ECM644) in complete Endogro Medium (Millipore, Cat #SCME002). Three days later, culture medium was changed to basal Endogro Medium, followed by 16 hours of incubation. Then agonistic Tie2 antibodies, 10 ug/ml, was added. After an incubation of 30 mins or 16-18 hours, FITC-dextran (Sigma, Cat #FD40), 50 ul of 5 mg/ml, was added into each insert. 50 ul of medium was taken from the receiver tray of each well at different time points and measured by a microplate reader (excitation filter: 485 nm, emission filter 535 nm).

Figure 18B:
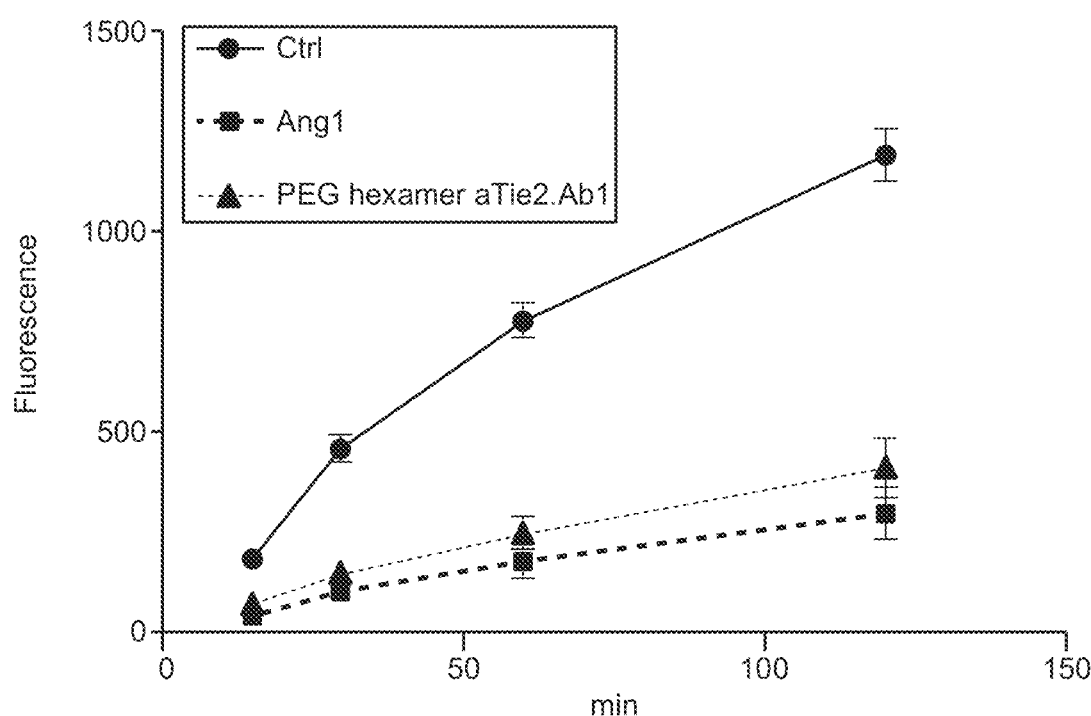

The results, presented in FIG. 18B, show that the Tie2.1 PEG hexamer was effective in protecting the HUVEC cells from starvation-induced leakage. The recombinant Ang1, an agonistic Tie2 ligand, was used as a positive control.

In Vivo Vascular Permeability Assay with Systemic Administration of Tie2 Agonist.

Figure 19A:
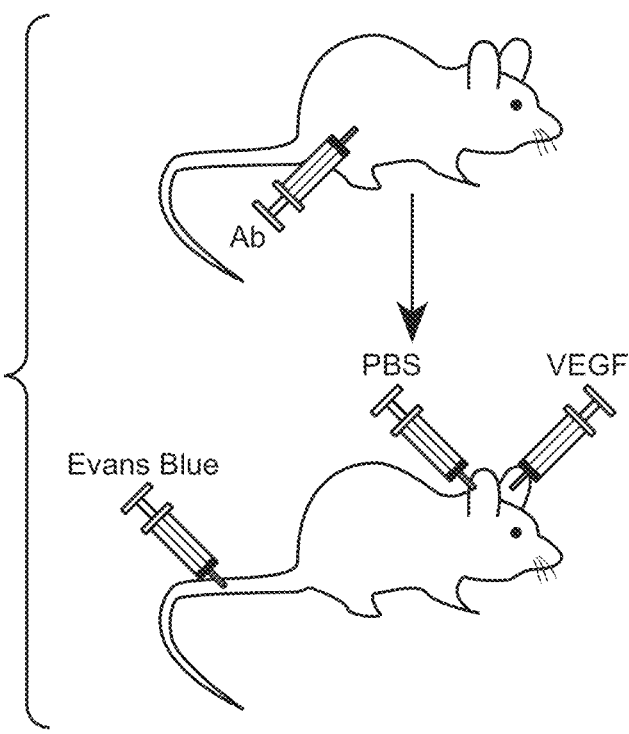
FIGS. 19A-19B illustrate an assay method (FIG. 19A) and results (FIG. 19B) of an in vivo vascular permeability assay to study the effects of anti-Tie2.1 antibodies on VEGF-induced vascular leak.
Figure 19B:
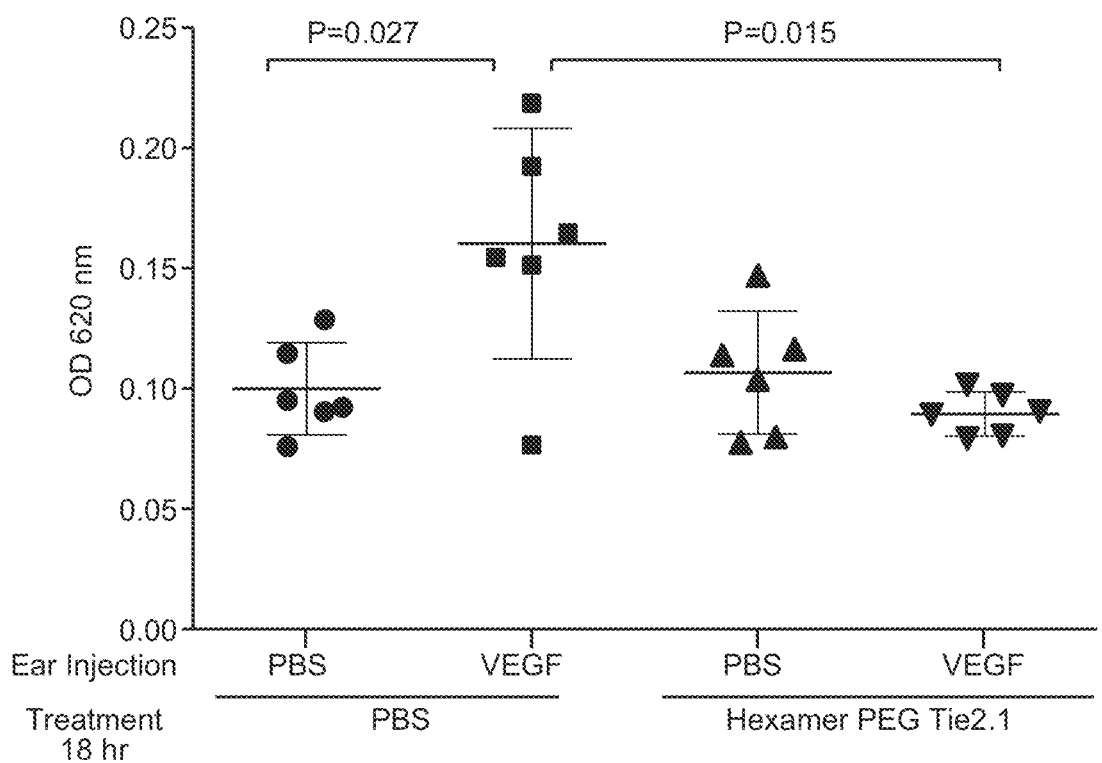

Five to eight-week-old Balb/c mice (Charles River) were dosed with Tie2 agonists, via intraperitoneal (IP) or intravenous (IV) injection. After 18 hours, 1% of Evans Blue (Sigma, Cat #206334) was given via IV injection. Ten minutes later, the mice were anaesthetized under isoflurane, VEGF (produced in house) was injected into the mouse ears. Thirty minutes after VEGF injection, animals were euthanized by $CO_2$ and mouse ears were excised. Evans Blue that had extravasated into the ear tissues was extracted with formamide (Sigma, Cat #47670-1L-F) and quantified spectrophotometrically at 620 nm. The assay method is illustrated in FIG. 19A. As shown in FIG. 19B, the Tie2.1-PEG-hexamer reduces leakage of Evans Blue into the ear tissues.

In Vivo Vascular Permeability Assay with Local Administration of Tie2 Agonist.

Five to eight-week-old Balb/c mice (Charles River) were dosed with 1% of Evans Blue (Sigma, Cat #206334) was given via IV injection. Ten minutes later, the mice were anaesthetized under isoflurane, anti-VEGF G6.31 or Tie2 agonist Hexamer PEG Fab2.1 together with VEGF (produced in house) were injected intradermally into the mouse ears. Thirty minutes later, mice were euthanized by $CO_2$ and mouse ears were excised. Evans Blue that had extravasated into the ear tissues was extracted with formamide (Sigma, Cat #47670-1L-F) and quantified spectrophotometrically at 620 nm. The assay protocol is illustrated in FIG. 20A. FIG. 20B shows that the Tie2.1-PEG-hexamer is able to reduce VEGF-induced vascular permeability.

In Vivo Vascular Permeability Assay with Systemic Administration of Tie2 Agonist.

Figure 21A:
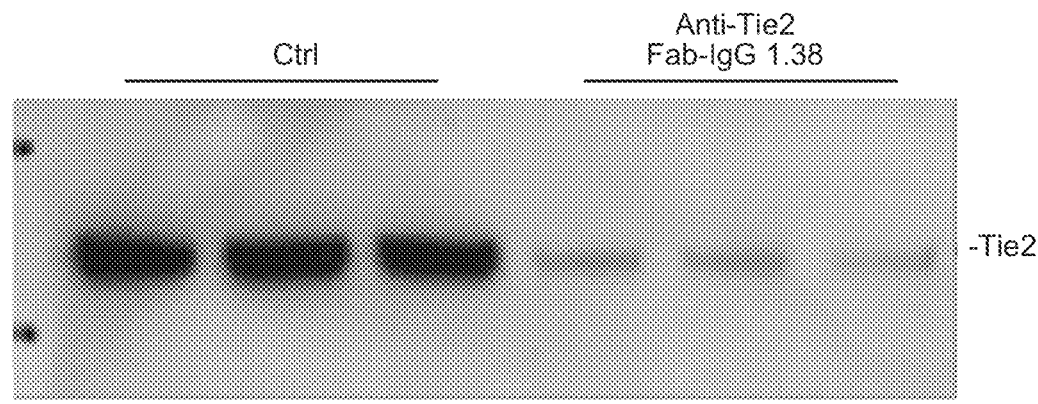
FIGS. 21A-21B illustrates the in vivo effect of a bi-epitopic anti-Tie2 agonist (anti-Tie2 Fab-IgF 1.38) on the protein level of Tie2 determined by western blot analysis (FIG. 21A) and results of an in vivo vascular permeability assay to study the effect of anti-Tie2 Fab-IgG 1.38 on VEGF-induced vascular leak (FIG. 21B).

Five to eight-week-old Balb/c mice (Charles River) were dosed with anti-Tie2 Fab-IgG 1.38, via intraperitoneal. 7 days later, lung tissues were harvested and analyzed for Tie2 protein level by western blot (FIG. 21A).

Figure 21B:
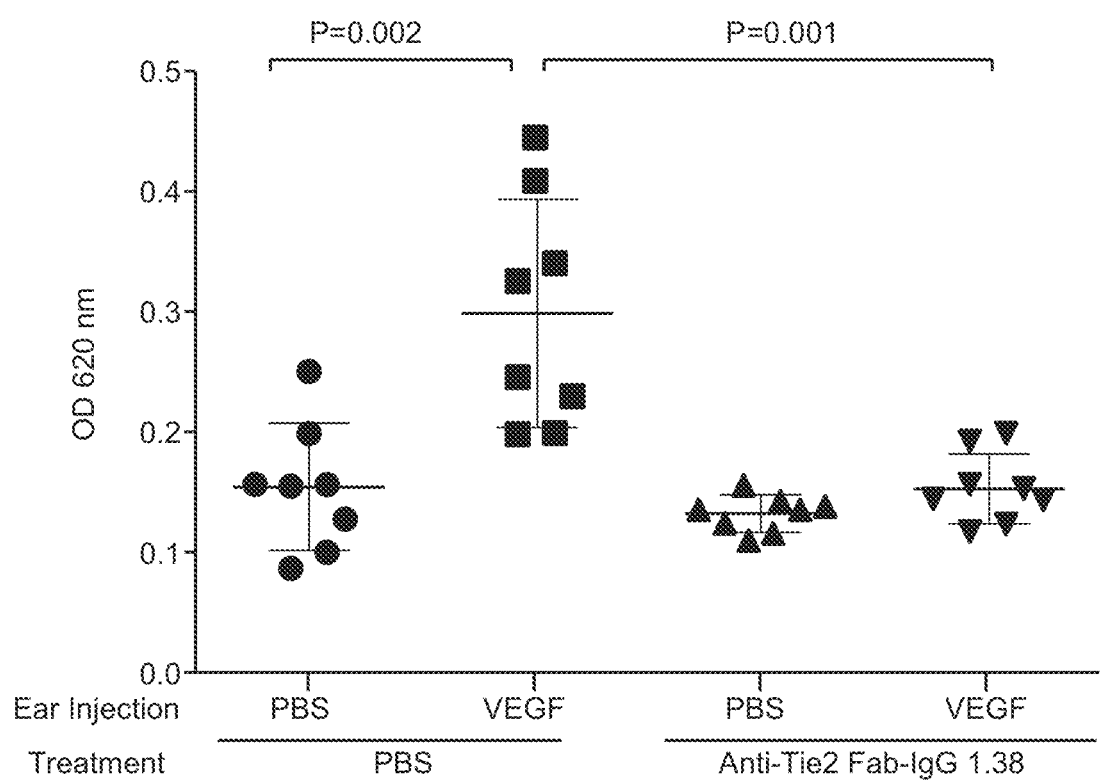

Five to eight-week-old Balb/c mice (Charles River) were dosed with anti-Tie2 Fab-IgG 1.38, via intraperitoneal. After 4 hours to 24 hours, 1% of Evans Blue (Sigma, Cat #206334) was given via IV injection. Ten minutes later, the mice were anaesthetized under isoflurane, VEGF (produced in house) or LPS (Sigma, Cat #L3012) was injected into the mouse ears. Thirty minutes after VEGF or LPS injection, mice were euthanized by $CO_2$ and mouse ears were excised. Evans Blue that had extravasated into the ear tissues was extracted with formamide (Sigma, Cat #47670-1L-F) and quantified spectrophotometrically at 620 nm. FIG. 21B shows that the anti-Tie2.1.38 IgG antibody decreased VEGF-induced vascular permeability.

Effect of Anti-Tie2 Agonists on VE-Cadherin and F-Actin.

Figure 22:
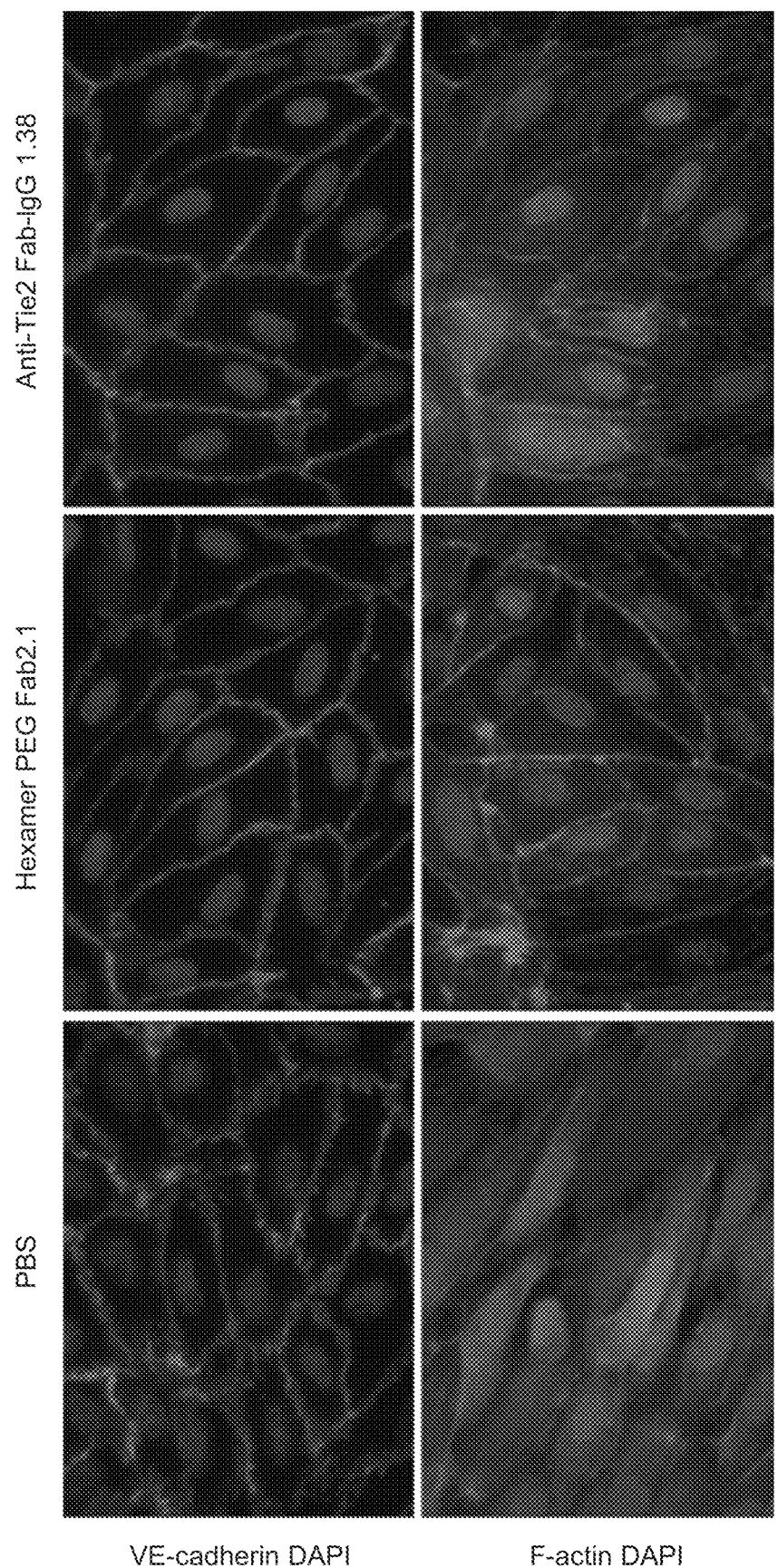
FIG. 22 shows the effects of anti-Tie2 agonists on cellular organization of VE-cadherin (top panel) and F-actin (bottom panel) in cultured HUVECs.

HUVEC cells (Millipore, Cat #SCCE001) were seeded at $0.2 \times 10^6$ per well on 4-well chamber slides in complete Endogro Medium. Three days later, culture medium was changed to basal Endogro Medium. After an incubation of 3 hours, 10 ug/ml Tie2 agonistic antibodies were added. After antibody treatment, cells were washed 3× with ice-cold PBS and fixed with 3% Paraformaldehyde (PFA) (Electron Microscopy Sciences, Cat #15710-S) at room temperature (RT) for 20 minutes. Fixed cells were washed 3× with ice-cold PBS and permeabilized with 0.1% Triton-PBS at RT for 10 min. After blocking with blocking buffer (10% normal donkey serum+PBS+0.1% Triton-X100) for 1 hour at RT, cells were incubated with mouse anti-human VE-cadherin (BD, Cat #555661) at a dilution of 1:250 overnight at 4° C. Alexa Fluor™ 633 Phalloidin (Invitrogen, Cat #A22284) was used for F-actin staining. Slides were washed with PBS-T, 5× at RT and then incubated with Alexa Fluor 549 donkey anti-mouse IgG (H+L) (Jackson ImmunoResearch, Cat #715-505-150), 1:500 dilution, for 2 hours at RT in the dark. Slides were washed with PBS-T, 4×, followed PBS, 2×, at RT. Slides were then stained with DAPI (Sigma, Cat #D9542-1MG), 1:10000 dilution of 5 mg/ml, for 10 min at RT, mounted with Prolong Gold antifade reagent (Invitrogen, Cat #P36930). Fluorescence images were obtained using Leica confocal microscopy. FIG. 22 shows that exposure to anti-Tie2 Tie2.1-PEG-hexamer or Tie1.1.38 results in a change from dynamic cell-cell junctions to linear cell-cell junctions (top panel), and reduced F-actin stress fiber and increased cortical actin (bottom panel).

Example 11—Design of a Therapeutic Tie2 Binding Molecule

Stability, e.g., chemical stability and oxidative stability, is important for a viable therapeutic agent. Stability characteristics of a unique biologic should be understood when designing a therapeutic which may have optimal manufacture, storage, and in vivo half-life.

Chemical Stability.

To assess chemical stability for both protein developability and in vivo stability, the Tie2.1 Fab (HC having SEQ ID NO:90, LC having SEQ ID NO:25) was buffer exchanged into low ionic strength histidine buffer and concentrated to 1 mg/ml, into phosphate buffered saline (PBS) pH 7.4 and concentrated to 1 mg/ml, or into high ionic strength arginine buffer with polysorbate and concentrated to 150 mg/ml (e.g. see Xu et al. Mol Pharm, 2018, 15:4529-4537). Samples were incubated at 40° C. (histidine buffer) or 37° C. (PBS) for 2 weeks, and analyzed by size-exclusion chromatography (SEC) and imaged capillary isoelectric focusing (iCIEF) for disappearance of the main peak and appearance of additional peaks. The heat-stressed materials were also digested by trypsin, chyomotrypsin, and/or LysC and peptides containing CDR residues analyzed by LC-MS/MS for evidence of asparagine deamidation and or aspartic acid isomerization.

Under these conditions, Tie2.1 Fab at 1 mg/ml in histidine buffer showed no loss in main peak by SEC and a 1.3% loss in the main peak by iCIEF. At 150 mg/ml, it showed 0.3% and 3.0% losses respectively. Under PBS stress, 0.1% and 9.6% of the main peaks were lost. All detectable asparagines and aspartic acids in the CDRs showed less than 0.2% change in levels of modifications under the tested conditions.

Oxidative Stability of Tie2.1

To assess oxidative stability for both protein developability and in vivo stability, Tie2.1 Fab (same as above) was buffer-exchanged into low ionic strength histidine buffer and stressed with 2,2'-azo-bis-(2-amidinopropane) dihydrochloride (AAPH) (e.g., see Xu et al., 2018, Mol Pharm, 15:4529-4537). The stressed material was also digested by trypsin, chyomotrypsin, and/or LysC and peptides containing CDR residues analyzed by LC-MS/MS for evidence of methionine and/or tryptophan oxidation.

Under these conditions, Tie2.1 Fab showed a 39.3% increase in oxidation of W98 and W100a and a 3.1% increase in oxidation of M100c.

Design of Variants with Improved Oxidative Stability

Figure 23:
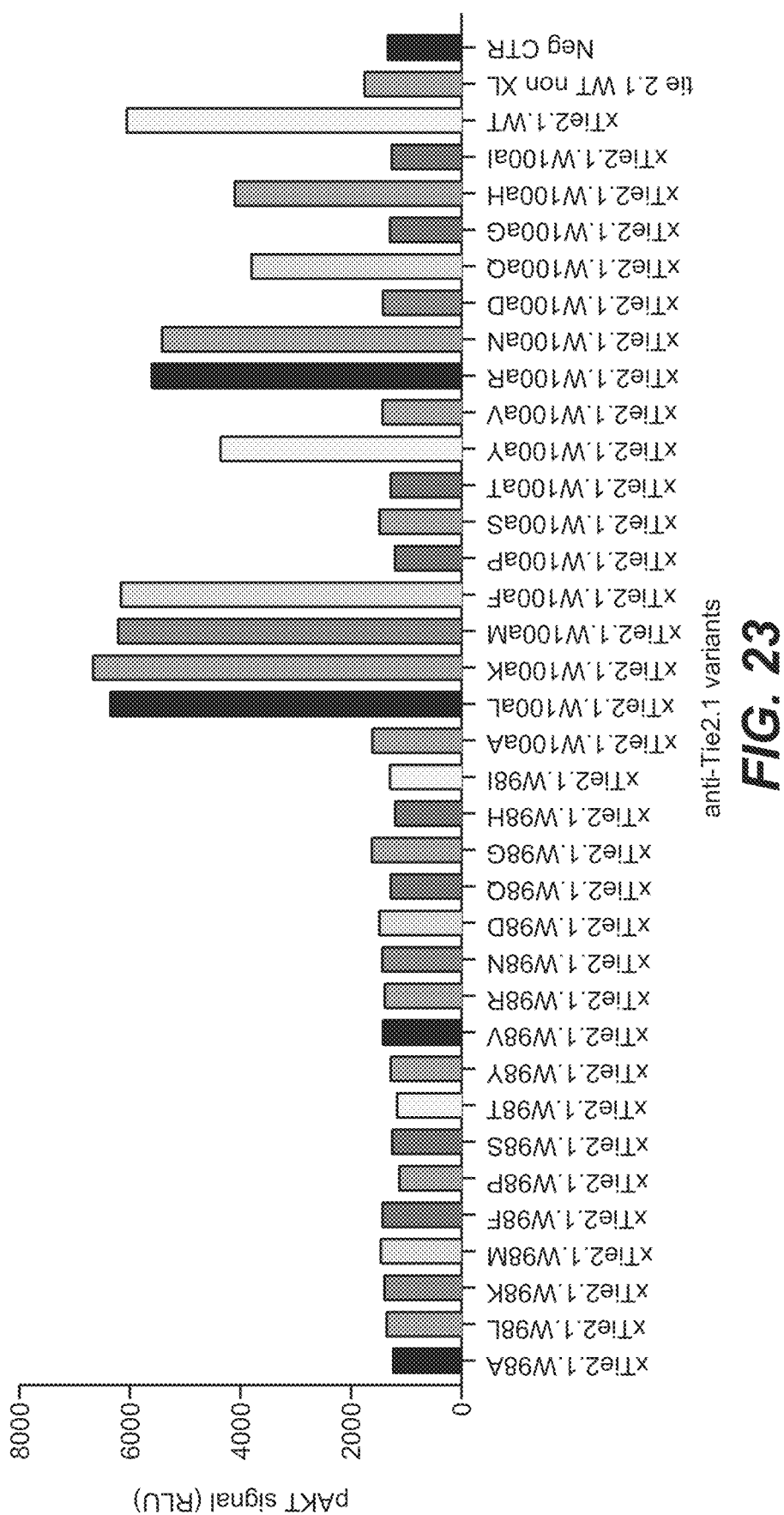
FIG. 23 shows results of an AKT phosphorylation assay to assess the agonist activity of variants of the Tie2.1 anti-Tie2 antibody in an IG1 format.
Figure 24:
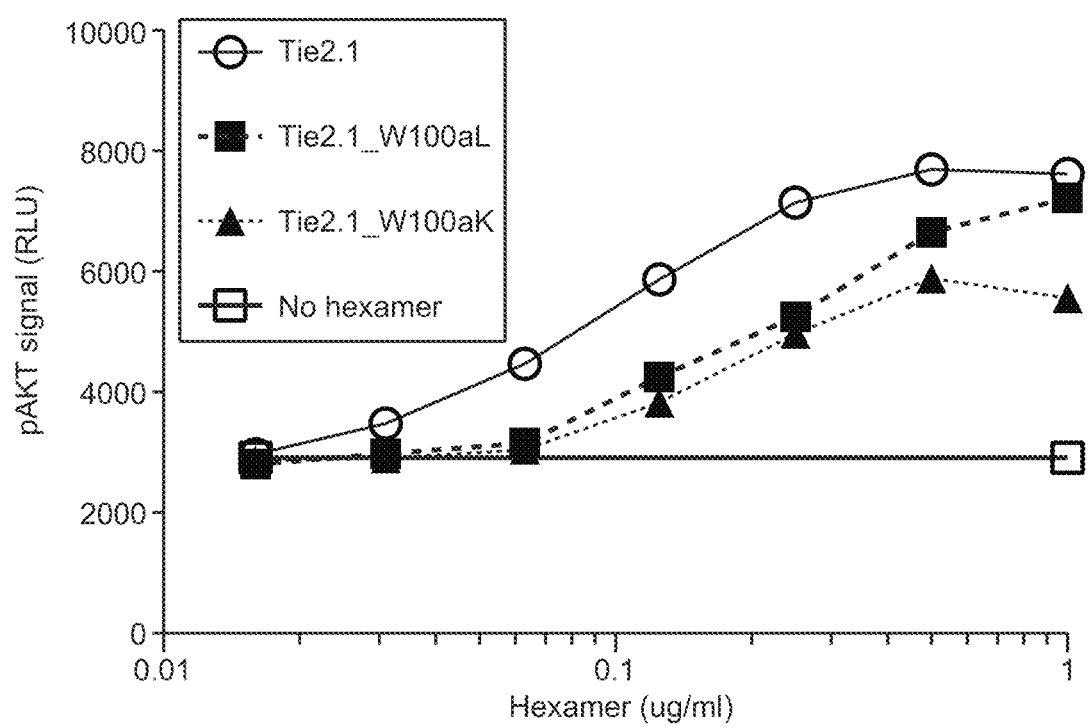
FIG. 24 shows results of an AKT phosphorylation assay to assess the agonist activity of variants of the Tie2.1 anti-Tie2 conjugates in a hexameric format compared to a non PEG-conjugated Tie2.1 Fab (No hexamer).

Multiple variants of Tie2.1 W98 and W100a were expressed and purified in hIgG1 format. Anti-Tie-2 variants were cross-linked with goat anti-human IgG Fc, and the mixture was added in duplicate to rat aortic endothelial cells at 20 ug/ml and 7 ug/ml final concentration. Changes in phospho-AKT levels were assessed as described above (Example 3) and plotted as the average change in phospho-AKT signal FIG. 23 shows the impact of tryptophan 98 and 100a variants of Tie2.1 hIgG1 to drive phospho-AKT signaling downstream of Tie-2. No tested mutations at W98 maintained activity under this set of 25. At a single point, several mutations at W100a appeared to maintain activity. Specifically, at least variants Tie2.1.W100aL, Tie2.1.W100aK, Tie2.1.W100aM, Tie2.1.W1001F, Tie2.1.W100aY, Tie2.1.W100aR, Tie2.1.W100aN, Tie2.1.W100aN, Tie2.1.W100aQ, Tie2.1.W100aH maintain the ability to activate phospho-AKT signaling (act as Tie2 agonists).

Two W100a variants (W100aL and W100aK) were expressed as Fabs with a C-terminal SPPC sequence and conjugated to a six armed, 6 kDa PEG-core as described (Example 6). Various concentrations of the PEG-hexamers were incubated with primary human retinal microvascular endothelial cells (ACBRI 181, Cell Systems Inc., Kirkland, WA), and changes in phospho-AKT levels were assessed as described (Example 3). Both W100aL and W100aK show slightly reduced activity at lower concentrations (FIG. 24)

Example 12—In Vivo Study of Anti-Tie2 Antibody Conjugates

A nonclinical study with cynomolgus monkeys was done to assess a subject's ability to tolerate administration of an anti-Tie2 antibody conjugates and to determine if any adverse effects occurred. The Tie 2.1 Fab-SPPC (HC having SEQ ID NO:89 and LC having SEQ ID NO:25) with 6 kDa PEG-maleimide hexamer core was administered via 50 ul intravitreal (ITV) injection (2 mg dose) every 2 weeks (total of 3 doses) in both eyes of 2 male cynomolgus monkeys. Doses were administered by a board-certified veterinary ophthalmologist. In order to mimic clinical dosing, eyes were dosed in the infero-temporal quadrant. The animals were observed for 5 weeks and tolerability assessment was based on a comprehensive clinical ophthalmic evaluation (slit lamp biomicroscopy, indirect ophthalmoscopy and intraocular pressure measurements), clinical and anatomic pathology of the eyes.

This 5-wk ITV repeat dosing study showed that administration with Tie 2.1 Fab-SPPC with 6 kDa PEG-maleimide hexamer core in the monkeys is well tolerated. Transient ocular inflammation peaked on Day 3 that decreased by Day 8 and diminished with repeated dosing. Minimal to slight mononuclear inflammatory cell infiltrates noted on ocular histopathology evaluation were consistent with an immunogenic response to a humanized protein.

Example 13—In Vivo Study of Anti-Tie2 Antibody Conjugates

In another preclinical study, ocular PK of anti-Tie2.1 PEG-hexamer was studied in male cynomolgus monkey following a single intravitreal (ITV) bilateral injection at 2 mg/eye. This study was performed to measure levels of Tie2.1 PEG-hexamer in vitreous humor, aqueous humor and serum. Additionally, vitreal samples were assessed for oxidation of the Tie2.1 Fab molecule in vivo and effects of the oxidation on ex vivo activity of the molecule. Animal care was in accordance with the Animal Welfare Act, the Guide for the Care and Use of Laboratory Animals, and the Office of Laboratory Animal Welfare of Covance.

Anti-gD Fab hexamer-SPPC served as control group and was also tested at same dose level (2 mg/eye). To a separate group of animals, Tie2.1 PEG-hexamer was dosed at 4 mg/animal by IV route. Naïve male cynomolgus monkeys of 2 to 4 kg body weight and approximately 2 to 4 years of age were assigned to dose groups. For ITV dose groups, test and control articles were administered to anesthetized animals via a single ITV injection to each eye and were observed for up to 21 days. Ocular dose administration was performed by veterinary ophthalmologist at approximately the 7 o'clock position to the right eye and approximately the 5 o'clock position to the left eye. Injection volume was limited to 50 μL/eye. Post ITV dosing, animals were euthanized (2 animals/group/time point) on 1 d (4-hours post dose), 2 d (test article group only), 7 d, 14 d and on 21 d for collection of ocular samples (vitreous and aqueous humor) for PK estimation. Blood samples were also collected from all surviving animals in serum separator tubes at 0.25 hrs, 2 hrs, 4 hrs, 8 hrs, 12 hrs, 24 hrs, 3 d, 5 d, 7 d, 10 d, 14 d and 21 d for PK estimation. In the case of the IV group, the dose was administered via saphenous vein and non-terminal blood samples were collected (but no ocular samples) at 0.083 hrs, 0.25 hrs, 0.5 hrs, 2 hrs, 4 hrs, 8 hrs, 12 hrs, 24 hrs, 2 d, 3 d, 4 d, 5 d, 7 d, 10 d, 14 d and 21 d for PK estimation. Blood samples were allowed to sit for 60 min post collection and were spun down to decant serum into 2D barcoded tubes.

All serum samples were stored at −70° C. until assayed for drug concentrations using a human IgG ELISA. Nunc® MaxiSorp™ 384-well plates (Nalge Nunc International, Rochester, NY) were coated with 0.5 μg/mL sheep anti-human IgG antibody (Binding Site, San Diego, CA, USA) diluted in coat buffer (0.05 M carbonate/bicarbonate buffer pH 9.6) and incubated overnight at 4° C. The plates were washed 3 times with wash buffer (0.5% Tween-20 in PBS buffer, pH 7.4) and treated with block buffer (PBS/0.5% BSA/15 ppm Proclin, pH 7.4) for 1 to 2 hours at RT. The plates were washed 3 times with wash buffer, then samples diluted in sample diluent (PBS/0.5% BSA/0.05% Tween 20/5 mM EDTA/0.25% CHAPS/0.35 M NaCl/15 ppm Proclin, pH 7.4) were added to the wells and incubated for 2 hrs at RT. After washing the plates 6 times with wash buffer, the detection antibody, goat anti-human IgG (H+L)-horseradish peroxidase (HRP) (Bethyl Laboratories, Inc., Montgomery, TX, USA), was diluted to 100 ng/mL in assay buffer (PBS/0.5% BSA/15 ppm Proclin/0.05% Tween 20, pH7.4) and added to the wells. The plates were incubated on a shaker for 1 hour at RT then washed 6 times with wash buffer and developed using TMB peroxidase substrate (Moss Inc., Pasadena, Maryland) for 20 minutes followed by 1 M Phosphoric acid to stop the reaction. Absorbance was measured at 450 nm against a reference wavelength of 620 nm. The concentration of the samples were extrapolated from a 4-parameter fit of the standard curve. The reportable assay range was 0.16-5 ng/mL (LLOQ isat 2 ng/mL for cyno serum and 16 ng/mL for aqueous and vitreous humor).

Serum samples for anti-drug antibody (ADA) estimation were also collected from all groups at −7 d, 7 d, 14 d and 21 d. ADA was determined by directly coating the anti-Tie2 hexamer or the anti-gD hexamer at 1 ug/mL in coat buffer (0.05 M carbonate/bicarbonate buffer pH 9.6) on to Nunc® MaxiSorp™ 384-well plates (Nalge Nunc International, Rochester, NY) and incubated overnight at 4° C. The plates were washed 3 times with wash buffer (0.5% Tween-20 in PBS buffer, pH 7.4) and treated with block buffer (PBS/0.5% BSA/15 ppm Proclin, pH 7.4) for 1 to 2 hours at RT. The plates were again washed 3 times with wash buffer and then samples diluted in sample diluent (PBS/0.5% BSA/0.05% Tween 20/5 mM EDTA/0.25% CHAPS/0.35 M NaCl/15 ppm Proclin, pH 7.4) were added to the wells and incubated for 2 hrs at RT. After washing the plates 6 times with wash buffer, the detection antibody, goat anti-human IgG (Fcγ)-horseradish peroxidase (HRP) (Jackson ImmunoResearch, West Grove, PA), was diluted to 80 ng/mL in assay buffer (PBS/0.5% BSA/15 ppm Proclin/0.05% Tween 20, pH7.4) and added to the wells. The plates were incubated on a shaker for 1 hour at RT then washed 6 times with wash buffer and developed using TMB peroxidase substrate (Moss Inc., Pasadena, Maryland) for 20 minutes followed by 1 M Phosphoric acid to stop the reaction. Absorbance was measured at 450 nm against a reference wavelength of 620 nm. The cutpoint is statistically derived based on the distribution of the naive individual animals. The results report the titer for each sample, which is the log of the dilution at which the sample OD crosses the cutpoint OD. The minimum dilution for this assay is 1:100. A log titer of <2.0 means it is below the cutpoint at the minimum dilution and therefore, the animal is negative.

In addition to above mentioned groups, an ocular combo group was also tested in this study where anti-gD Fab hexamer and Tie2.1 PEG-hexamer were dosed together (10 min apart; Tie2.1 PEG-hexamer followed by anti-gD Fab hexamer) by ITV injection. Objective of this group was to assess potential impact on ocular PK of control group, with predosing of test article. Both compounds were dosed at same dose level as in single agent groups (i.e., 2 mg/eye) and dose volume in these groups was limited to 100 µL/eye (including both compounds).

Levels of anti-Tie2 Fab hexamer concentration was determined with an anti-Tie2 ELISA. Nunc® MaxiSorp™ 384-well plates (Nalge Nunc International, Rochester, NY) were coated with 1.0 µg/mL recombinant human Tie2 (Abcam, Cambridge, MA) diluted in coat buffer (0.05 M carbonate/bicarbonate buffer pH 9.6) and incubated overnight at 4° C. The plates were washed 3 times with wash buffer (0.5% Tween-20 in PBS buffer, pH 7.4) and treated with block buffer (PBS/0.5% BSA/15 ppm Proclin, pH 7.4) for 1 to 2 hours at RT. The plates were again washed 3 times with wash buffer and then samples diluted in sample diluent (PBS/0.5% BSA/0.05% Tween 20/5 mM EDTA/0.25% CHAPS/0.35 M NaCl/15 ppm Proclin, pH 7.4) were added to the wells and incubated for 2 hrs at RT. The plates were washed 6 times with wash buffer, then the detection antibody, goat anti-human IgG (H+L)-horseradish peroxidase (HRP) (Bethyl Laboratories, Inc., Montgomery, TX, USA), was diluted to 100 ng/mL in assay buffer (PBS/0.5% BSA/15 ppm Proclin/0.05% Tween 20, pH7.4) and added to the wells and incubated on a shaker for 1 hour at RT. The plates were washed 6 times with wash buffer and developed using TMB peroxidase substrate (Moss Inc., Pasadena, Maryland) for 20 minutes followed by 1 M Phosphoric acid to stop the reaction. Absorbance was measured at 450 nm against a reference wavelength of 620 nm. The concentration of the samples were extrapolated from a 4-parameter fit of the standard curve. The reportable assay range was 0.31-10 ng/mL (LLOQ is at 6 ng/mL for cyno serum and 31 ng/mL for aqueous and vitreous humor).

Levels of anti-gD Fab hexamer concentration was determined with an anti-gD ELISA. Nunc® MaxiSorp™ 384-well plates (Nalge Nunc International, Rochester, NY) were coated with 1.0 µg/mL gD (produced in house, Req 361937) diluted in coat buffer (0.05 M carbonate/bicarbonate buffer pH 9.6) and incubated overnight at 4° C. The plates were washed 3 times with wash buffer (0.5% Tween-20 in PBS buffer, pH 7.4) and treated with block buffer (PBS/0.5% BSA/15 ppm Proclin, pH 7.4) for 1 to 2 hours at RT. The plates were again washed 3 times with wash buffer and then samples diluted in sample diluent (PBS/0.5% BSA/0.05% Tween 20/5 mM EDTA/0.25% CHAPS/0.35 M NaCl/15 ppm Proclin, pH 7.4) were added to the wells and incubated for 2 hr at RT. After washing the plates 6 times with wash buffer, the detection antibody, goat anti-human IgG (H+L)-horseradish peroxidase (HRP) (Bethyl Laboratories, Inc., Montgomery, TX, USA), was diluted to 100 ng/mL in assay buffer (PBS/0.5% BSA/15 ppm Proclin/0.05% Tween 20, pH7.4) and added to the wells. The plates were incubated on a shaker for 1 hour at RT then washed 6 times with wash buffer and developed using TMB peroxidase substrate (Moss Inc., Pasadena, Maryland) for 20 min followed by 1 M Phosphoric acid to stop the reaction. Absorbance was measured at 450 nm against a reference wavelength of 620 nm. The concentration of the samples were extrapolated from a 4-parameter fit of the standard curve. The reportable assay range was 0.31-10 ng/mL (LLOQ is at 6 ng/mL for cyno serum and 31 ng/mL for aqueous and vitreous humor).

PK analyses of concentration-time data across matrices were performed using a non-compartmental analysis method (on Phoenix WinNonlin version 6.4, Pharsight Corp, Mountain View, CA) with nominal time and dose. Both Tie2.1 PEG-hexamer and anti-gD Fab hexamer showed comparable PK profiles in ocular compartments. Half-life in vitreous humor was approximately 5 days for both compounds and it was approximately 4 days in aqueous humor (Table 12). This is in agreement with size based ocular kinetics proposed by Shatz et al. (2016, Mol Pharm, 13:2996-3003) and Crowell et al. (2019, Transl Vis Sci Technol 8(6):1) where authors have shown in rabbits that ocular PK of biologics post ITV injection is predominantly influenced by molecular size i.e., Rh (Shatz et al., 2016, supra).

Figure 25:
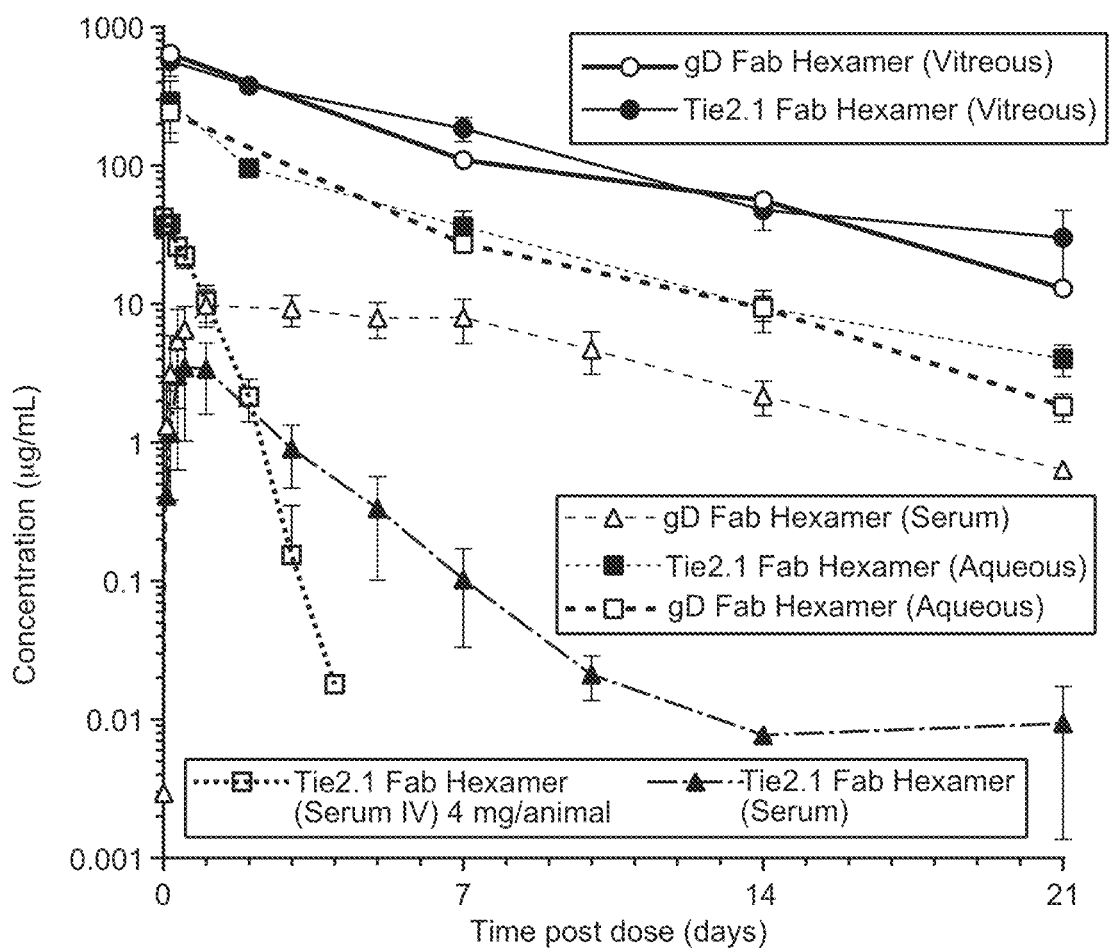
FIG. 25 shows pharmacokinetics of anti-Tie2 Fab hexamer conjugates after ocular injection in cynomolgus monkeys.

FIG. 25 provides the pharmacokinetic profiles of anti-Tie2.1 Fab hexamer and anti-gD Fab hexamer following a single intravitreal or intravenous dosing in male cynomolgus monkeys.

Table 12 below details pharmacokinetic parameters of anti-Tie2.1 Fab hexamer and anti-gD Fab hexamer following a single intravitreal or intravenous dosing in male cynomolgus monkeys.

TABLE 12

| Matrix | Group | $C_{max}$ (µg/mL) | $T_{max}$ (days) | $AUC_{0-t}$ (µg · day/mL) | $t_{1/2}$ (day) | CL (mL/day) | % F |
|---|---|---|---|---|---|---|---|
| Serum | 1 (ITV, 2 mg/eye) | 9.80 ± 1.22 | 1.00 | 101 ± 10.1 | 3.83 | NA | NA |
|  | 2 (ITV, 2 mg/eye) | 3.48 ± 0.868 | 0.500 | 9.00 ± 1.44 | 2.26 | NA | 28.8 |
|  | 3 (IV, 4 mg/animal) | 42.5 ± 5.12 | 0.0579 | 31.3 ± 5.19 | 0.261 | 130 ± 23 | NA |
| Aqueous Humor | 1 (ITV, 2 mg/eye) | 245 ± 48.7 | 0.167 | 1120 ± 171 | 3.59 | NA | NA |
|  | 2 (ITV, 2 mg/eye) | 290 ± 59.1 | 0.167 | 918 ± 68.4 | 4.11 | NA | NA |
| Vitreous Humor | 1 (ITV, 2 mg/eye) | 641 ± 25.4 | 0.167 | 3500 ± 102 | 4.55 | 0.559 | NA |
|  | 2 (ITV, 2 mg/eye) | 570 ± 63.3 | 0.167 | 3460 ± 152 | 4.99 | 0.543 | NA |

IV—Intravenous; ITV—Intravitreous; NA—Not applicable.

$C_{max}$, AUC and CL are described as value ± SE (where possible)

Group 1 was administered Anti-gD Fab hexamer (40 mg/mL).

Group 2 was administered Anti-Tie 2.1 Fab hexamer (40 mg/mL)

Group 3 was administered Anti-Tie2.1 Fab hexamer (4 mg/mL)

Interestingly, the PK of anti-gD hexamer Fab was comparable across all matrices including serum with half-lives ranged from 4 to 5 days. In contrast to this, anti-Tie2.1 Fab hexamer had distinct PK profiles in ocular vs. serum compartments i.e., relatively fast systemic PK (serum half-life approximately 2.3 days) compared to ocular PK (half-life 4 to 5 days). Without being bound by theory, the observation (fast systemic PK of anti-Tie2.1 Fab hexamer post ITV dosing) in this study may be is attributable to drug-target interaction leading to an impact on PK, commonly referred to as target mediated drug disposition (TMDD). In addition to ocular compartments, the target (Tie2) is known to be expressed in vascular tissues. Due to the abundant nature of vascular tissue, in comparison to ocular tissue, the impact of TMDD may be is likely more apparent in the serum compartment as opposed to the ocular compartments. ADA analysis of serum samples showed that minimal ADAs were observed for both test and control articles and that there was no apparent impact of ADAs on serum PK. No ADA samples were collected to assess impact on ocular kinetics. Impact of ADAs on PK in ocular matrices was not investigated in this study. The PK of the Tie2.1 PEG-hexamer in serum post IV bolus dosing was also relatively further fast as indicated by a half-life of approximately 0.3 days. This difference in serum half-lives post IV and IVT administrations has clearly demonstrated occurrence of flip-flop kinetics in serum for the Tie2.1 PEG-hexamer post ITV dosing. Absolute bioavailability of the Tie2.1 PEG-hexamer was 29% post ITV dosing. The results of the ITV dose group in this study suggest that serum PK post ITV may not always adequately represent ocular PK for novel formats. Hence, in addition to serum PK, investigation of ocular PK, especially for novel formats and mechanisms of action, are critical in molecule selection for ocular therapeutics.

PK of both compounds from combo group (anti-gD Fab hexamer+Tie2.1 PEG-hexamer co-dosing) were comparable to their respective single agent treatment groups, across matrices (data not shown). Co-dosing had no notable impact on PK of either compounds, in any matrix.

Quantifying In Vivo Tie2.1 PEG-Hexamer Deconjugation Products in Samples from an In Vivo Study Lower Limit Quantitation of Deconjugation Products.

Tie2.1 PEG-hexamer deconjugation products generated after intravitreal administration of the Tie2.1 PEG-hexamer to cynomolgus monkeys were quantified using capillary electrophoresis laser induced fluorescence (CE-LIF). To evaluate the lower limit of quantitation of Tie2.1 PEG-hexamer and its degradants, Tie2.1 PEG-hexamer, Tie2.1 PEG-pentamer and unconjugated Tie2.1 Fab monomer standards were made, mixed at a 1:1:1 mass ratio, and spiked into either PBS buffer or VH matrix at different concentrations, ranging from 500 µg/mL to 10 µg/mL. Samples were prepared using a protocol reported previously with minor modifications (Salas-Solano et al., 2006, Anal Chem, 78:6583-6594). Briefly, samples were mixed with $Na_3PO_4$ at pH 6.7 first at a volume ratio of 1:1. Then 4% sodium dodecyl sulfate (SDS) with 150 mM N-ethylamleimide (NEM) was added to the sample mixture and incubated at 70° C. for 5 minutes. After cooling to room temperature, 3-(2-furoyl) quinolone-2-carboxaldehyde (FQ) dye (ThermoFisher Scientific) was added followed by the addition of potassium cyanide. The sample mixture was then incubated at 50° C. for 10 min. After cooling to room temperature, the samples were loaded onto a PA 800 plus capillary electrophoresis instrument (Sciex). The CE-LIF method was described previously (Michels et al., 2007, Anal Chem, 79:5963-5971) with minor modification on the sample injection time to maximize sensitivity for in vivo samples. For LIF detection, the excitation wavelength was 488 nm and the detection wavelength was 600 nm.

Figure 26:
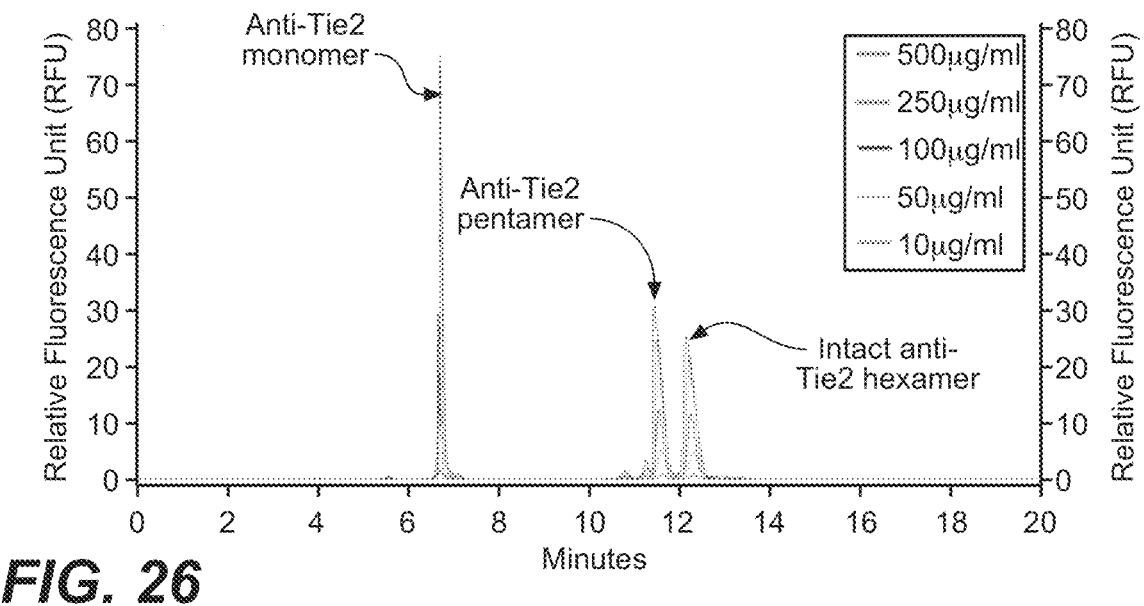
FIGS. 26-27 show electropherogram analysis of anti-Tie2.1 PEG conjugates in which the monomer peak was (FIG. 26) and was not (FIG. 27) factored into relative quantitations.

As shown in FIG. 26, in the buffer spike-in experiment, the hexamer, the pentamer and the monomer were well separated on the overlaid electropherograms from all the spike-in concentrations.

The percentage abundance of each species was calculated using the integrated peak area. The relative percentages of the intact Tie2.1 PEG-hexamer, the Tie2.1 PEG-pentamer and the Tie2.1 Fab monomer with different spike-in concentrations into buffer at 1:1:1 mass ratio is presented below in Table 13 (other minor species not shown).

TABLE 13

| Spike-in concentrations of each species (ug/ml) | Monomer %:Pentamer %:Hexamer % |
|---|---|
| 500 | 30:33:34 |
| 250 | 31:32:34 |
| 100 | 31:32:34 |
| 50 | 31:32:34 |
| 10 | 31:32:34 |

Figure 27:
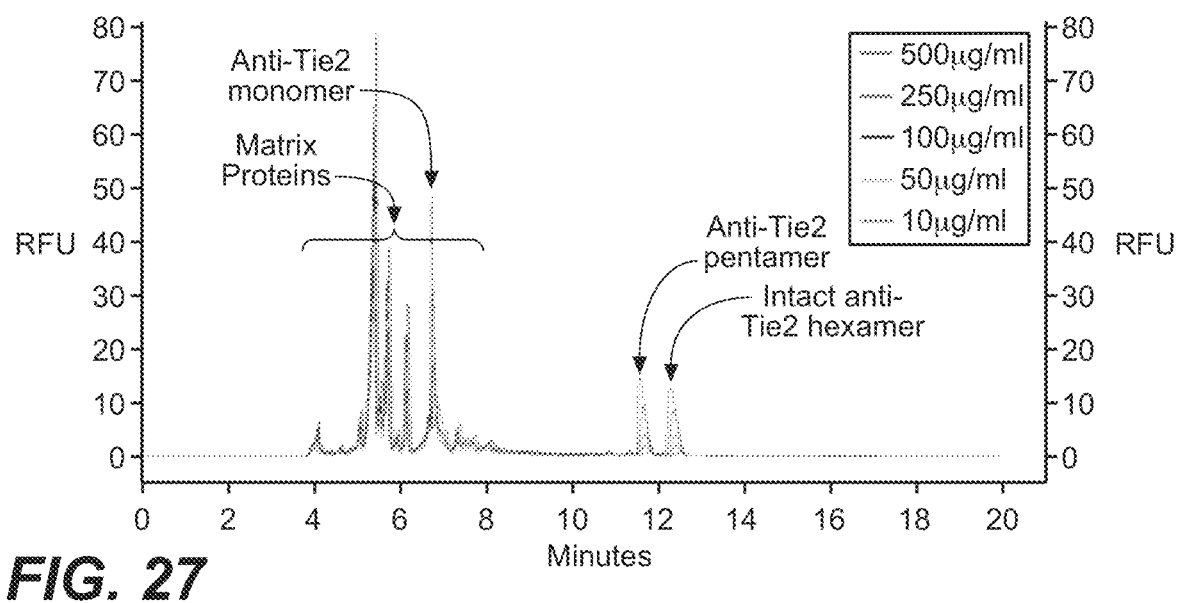

These data suggest that the hexamer, the pentamer and the monomer Fab can be consistently quantified (in this case at a ratio close to 1:1:1) down to 10 µg/mL. Because of matrix protein interference, the monomer peak was not factored into the relative quantitation of the VH spike-in experiment as shown in FIG. 27. However, the hexamer and the pentamer peaks were well separated and showed unnoticeable matrix interference on the overlaid electropherograms thanks to their large sizes and later migration times.

When the relative abundance of the two species was calculated using integrated peak area, the ratio of the intact hexamer over the pentamer was consistently close to 1:1 as shown below in Table 14.

TABLE 14

| Spike-in concentrations of each species (ug/ml) | Pentamer %:Hexamer % |
|---|---|
| 500 | 46:50 |
| 250 | 46:49 |
| 100 | 46:49 |
| 50 | 47:49 |
| 10 | 48:50 |

Relative Quantitation of Anti-Tie2 Hexamer and its Degradants in Cyno Pharmacokinetic Samples.

Figure 28:
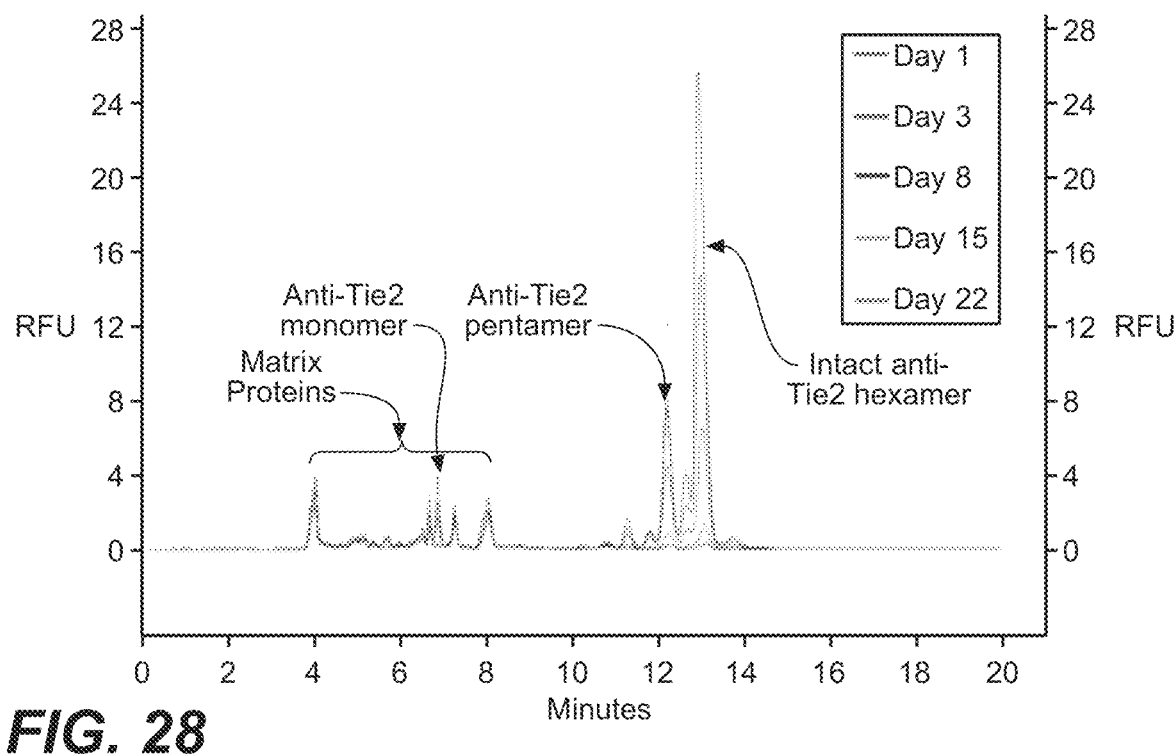
FIG. 28. shows electropherogram analysis of anti-Tie2.1 PEG conjugates in samples taken from cynomolgus vitreous humor.

Tie2.1 PEG-hexamer and its degradants was measured in samples from the cynomolgus monkey study described above. PK samples were collected from the vitreous humor (VH) tissue in cyno monkeys at several time points including Day 1, 3, 8, 15, and 22. The collected samples were processed in the same way described above. The overlaid CE-LIF electropherograms from the PK samples collected at different time points is shown in FIG. 28, which overlays Tie2.1-PEG-hexamer PK samples from different time points.

The intact hexamer peak and the degradant pentamer peak were quantified using the integrated peak areas and shown in Table 15 below (other minor species quantified but data not shown).

TABLE 15

| PK sample time points | Pentamer % | Hexamer % |
|---|---|---|
| Starting material | 10% | 80% |
| Day 1 | 17% | 71% |
| Day 5 | 27% | 57% |
| Day 8 | 31% | 50% |
| Day 15 | 33% | 50% |
| Day 22 | 32% | 49% |

Figure 29:
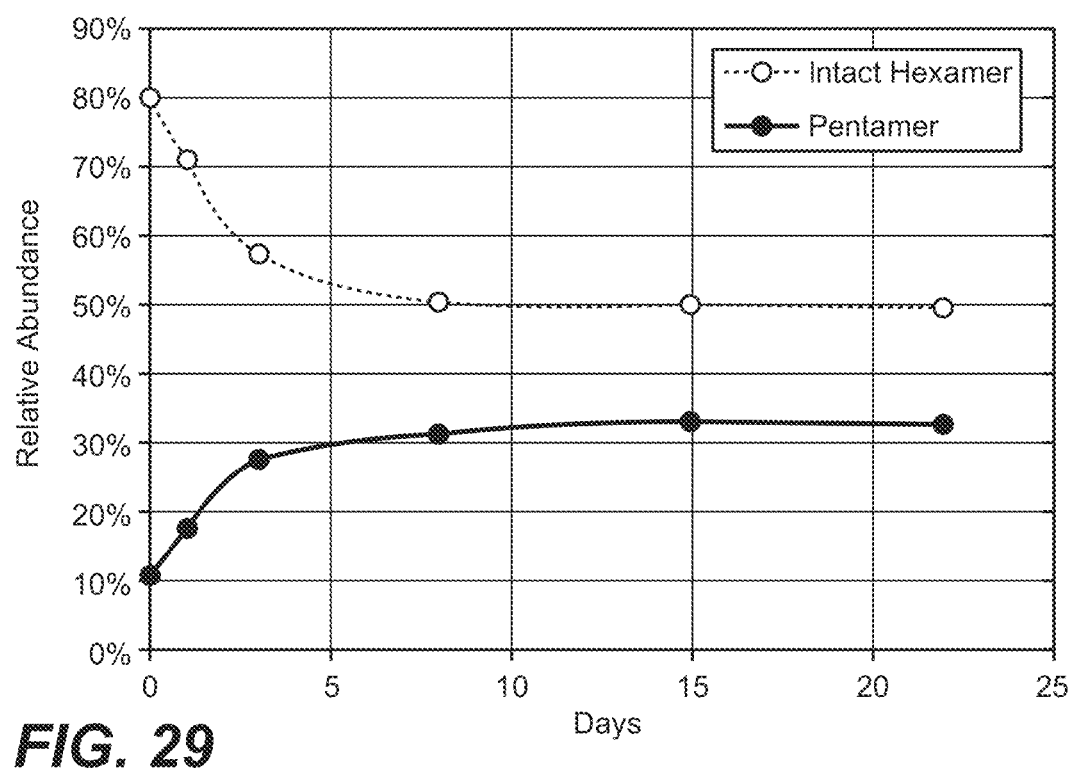
FIG. 29 shows relative amounts of anti-Tie2 PEG conjugate hexamers and pentamers.

The anti-Tie2 hexamer and the pentamer relative abundance were plotted against the different time points shown in FIG. 29. These results suggested that there was some pentamer in the starting materials and deconjugation occurred in vivo which further increased the relative abundance of the pentamer but stabilized around Day 8.

Analytical Characterization of Tie2.1-PEG Hexamer Obtained from Cynomolgus Samples.

Figure 30A:
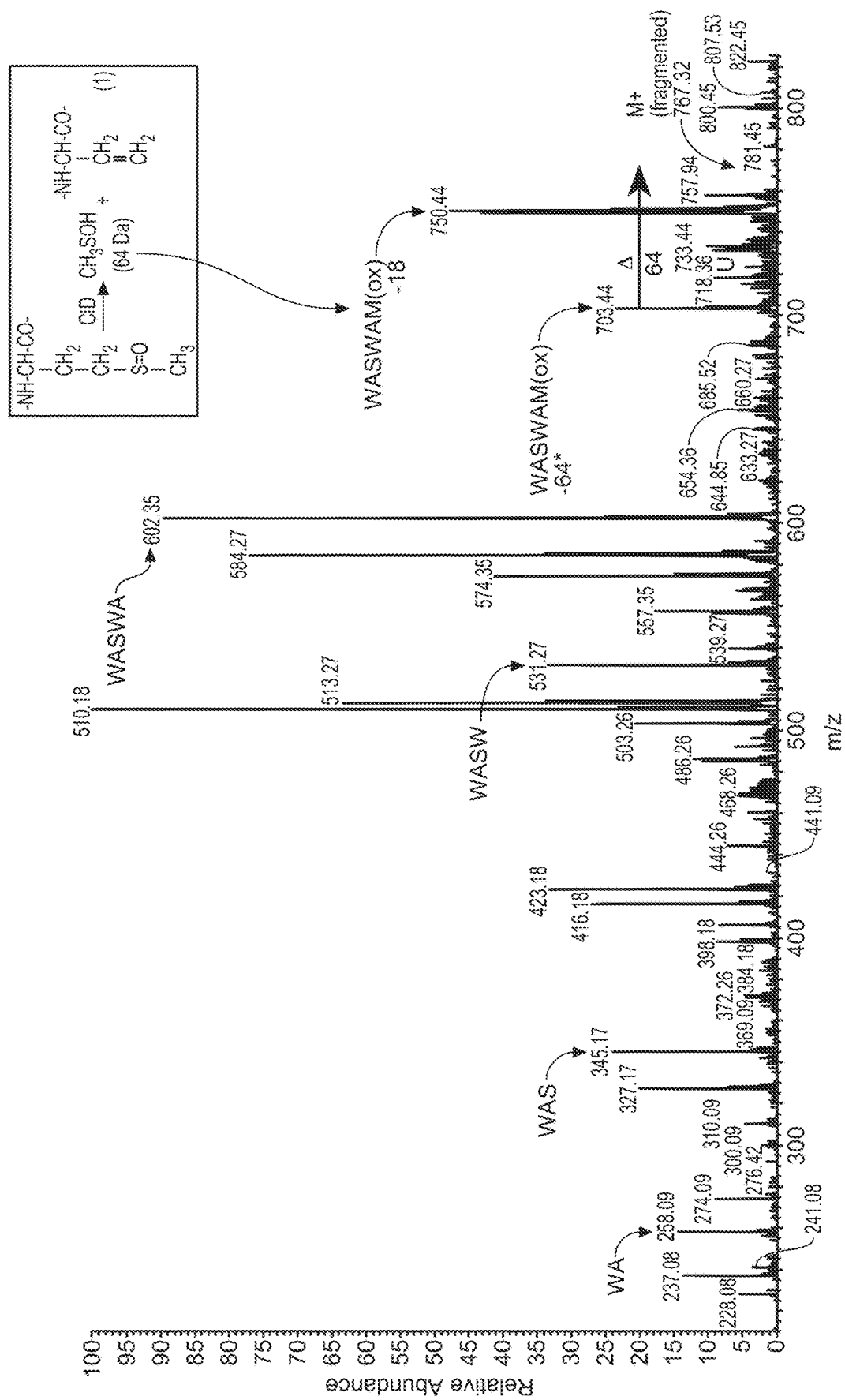
FIGS. 30A-30B provide data illustrating oxidation of M100c (FIG. 30A) in samples taken from eyes of cynomolgus monkeys over 21 days (FIG. 30B).

Samples from the cynomolgus monkeys were analyzed to assess oxidation of the Tie2.1 conjugates. Detection and quantitation of oxidation present at the amino acid residue level of Tie2.1 conjugates were determined as follows. 40 uL biological matrix (e.g. vitreous humor) containing the Tie2.1 conjugates was mixed with 80 uL of denaturing solution (8 M urea, 25 mM 1,4-dithiothreitol, 100 mM ammonium bicarbonate, all solubilized in water). The mixture was incubated at 25° C. for 30 minutes. 10 uL of 500 mM iodoactamide was then added to the mixture and the mixture was incubated for 30 minutes at 25° C. in the dark. 10 uL Asp-N (Promega) at a concentration of 0.1 mg/mL (in water) was then added to the mixture. Additionally, 180 uL of water was added to the mixture. The mixture was then incubated at 37° C. for 1 hour. 10 uL Trypsin/Lys-C (Promega) at a concentration of 0.2 mg/mL (in water) was added to the mixture. The mixture was incubated at 37° C. for 3 hours. 35 uL of the mixture was injected onto a Waters Nanoacquity LC coupled to a Thermo Orbitrap Elite MS. The raw data collected were then analyzed using Thermo Fisher Scientific BioPharma Finder software. Using the software, modifications (e.g., oxidation) at the amino acid level were identified through a combination of high resolution mass data and CID fragmentation data. Specifically, oxidation was identified by observing mass shifts of +16 Da (or an integer multiple). The specific location was determined through peptide sequencing using tandem MS (CID fragmentation mode). The data showed that the specific location of in vivo oxidation was at M100c of FIG. 30A (also disclosed herein as M at position 107 of SEQ ID NO:22) No oxidation of tryptophan residues was observed in this analysis of samples from cynomolgous monkeys.

Figure 30B:
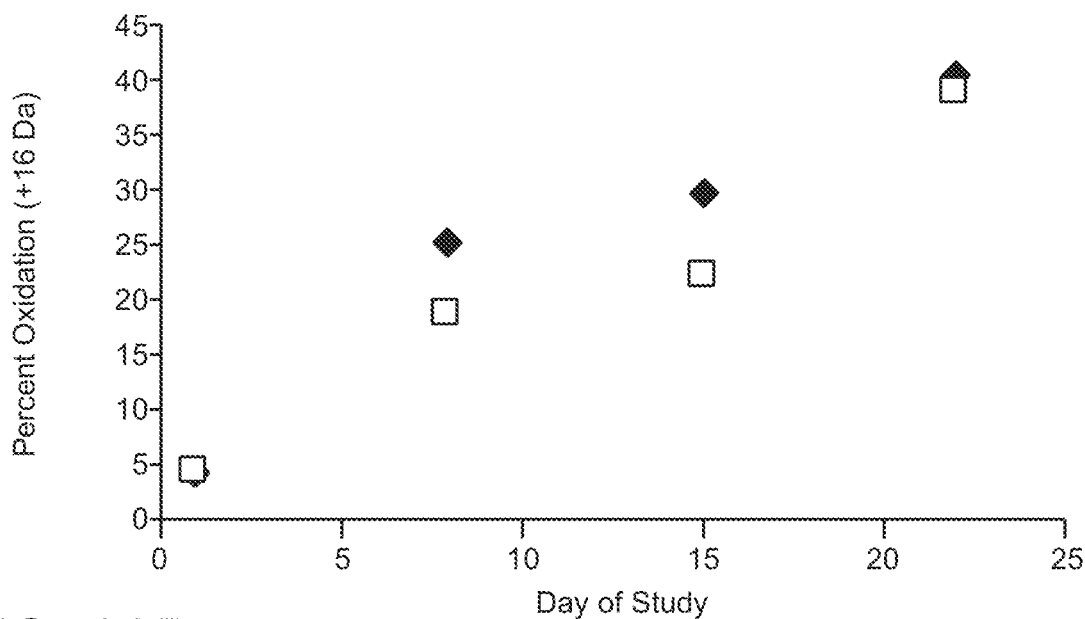

Furthermore, methionine oxidation was confirmed by observing characteristic −64 Da mass shifts after CID fragmentation. Quantitation was determined via MS by dividing ion intensities associated with oxidized species by the ion intensity of naïve (unoxidized species). The quantitation data are illustrated in FIG. 30B showing the surprisingly high extent of oxidation of M100c in the eyes of 2 different cynomolgous monkeys. These data were unexpected as this extent of oxidation of M100c was not observed in vitro (see Example 11).

Effects of M100c Oxidation on Activity of Tie2.1 In Vitro.

Figure 31:
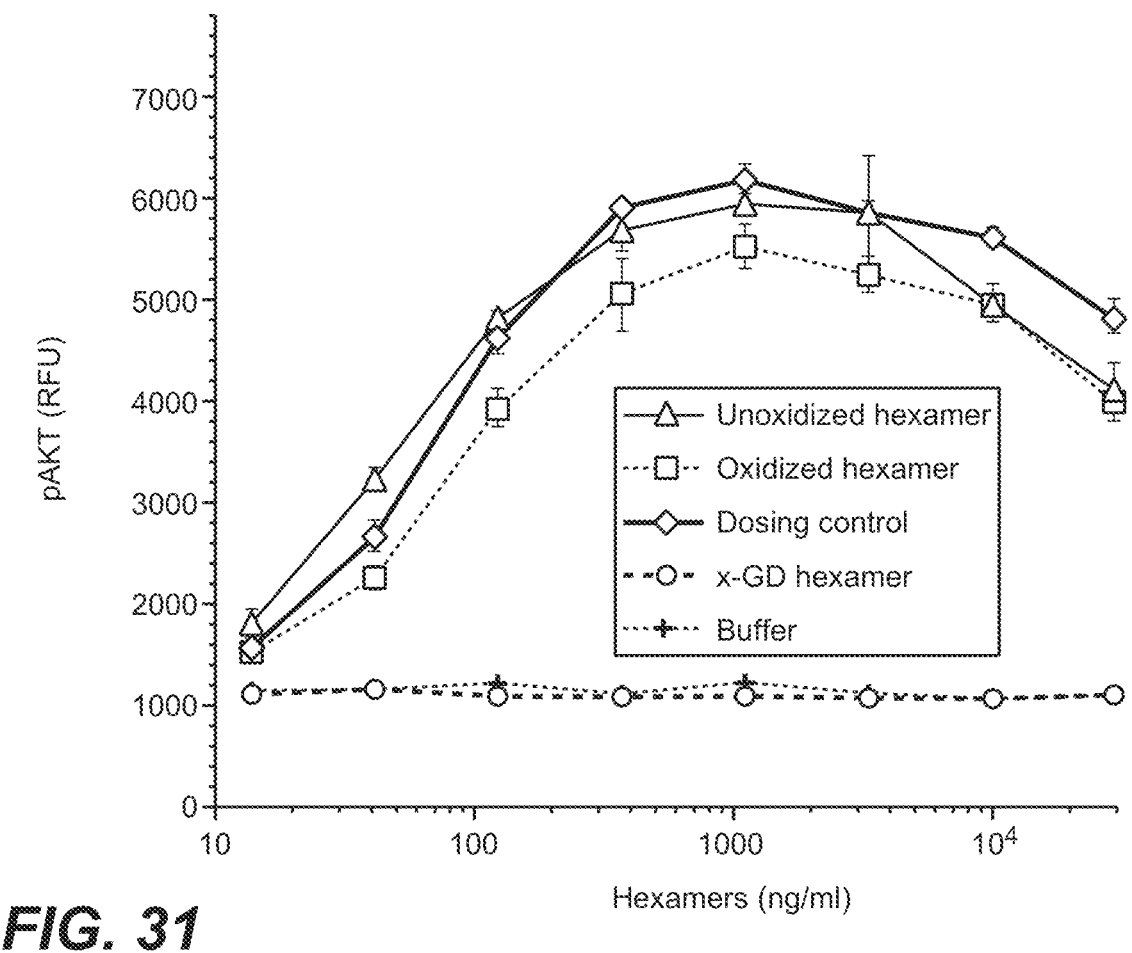
FIG. 31 shows effects of oxidation on pAKT activity.

To confirm that oxidation of Tie2.1 M100c can cause reduced function of this anti-Tie2 molecule, Tie2.1 was subjected to oxidation conditions to generate these molecules oxidized at M100c. Preparations of the anti-Tie2 Fab and hexamer were buffer exchanged into 20 mM histidine acetate, pH 5.5. Both samples were diluted to 1 mg of protein/ml. 30% (w/v) hydrogen peroxide was diluted in water to provide a 5% (w/v) stock solution. Hydrogen peroxide stock solution was added to each sample to give a final $H_2O_2$ concentration of 0.06% (w/v). Separate aliquots of each sample were spiked with an equivalent volume of buffer to serve as a control. All samples were protected from light and incubated for 15 hours at 5° C. The oxidation reactions were quenched via the addition of a 20-fold molar excess of L-methionine, followed by desalting using a PD-10 column. Extent of oxidation of the hexamer was determined using the LC-MS method described above to be about 65%. Various concentrations of the oxidized hexamer, buffer-treated (unoxidized) hexamer, and various controls were assessed by the previously described pAKT assay. Oxidation was found to reduce the activity of the oxidized material by approximately 50% as shown in FIG. 31.

Specific Activity of Hexamer Isolated from Cyno Vitreous Humor.

Figure 32:
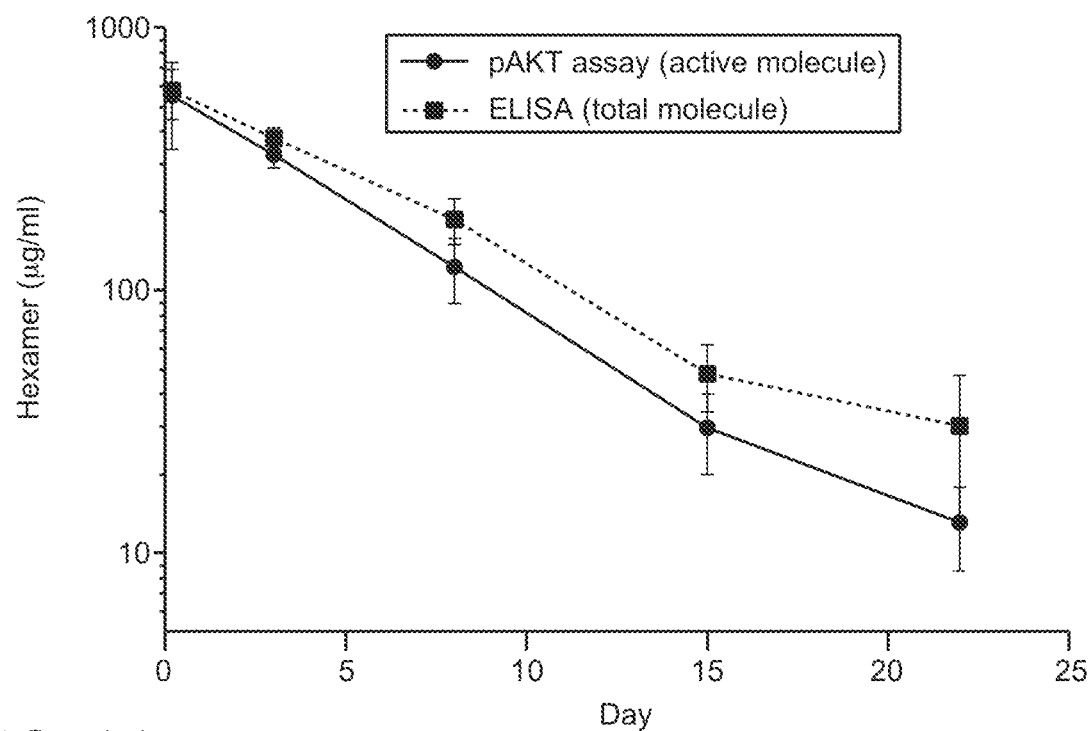
FIGS. 32-33 show effects of deconjugation on pAKT activity (FIG. 32) with normalized values graphed in FIG. 33.
Figure 33:
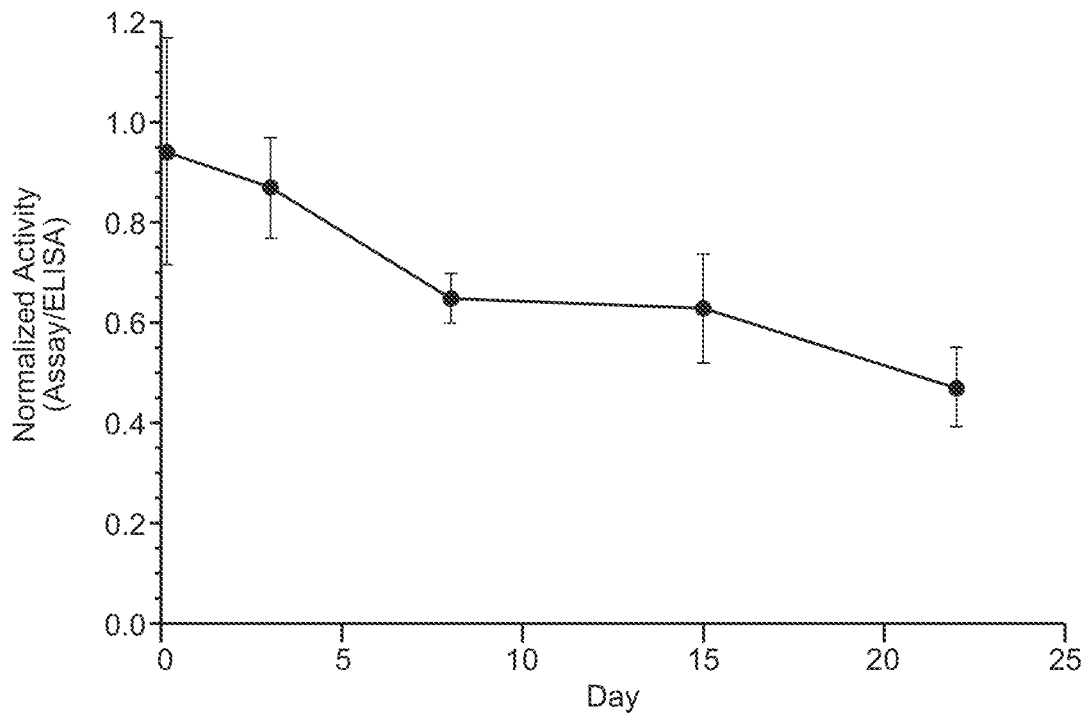

To understand the impact of in vivo oxidation on hexamer function, the amounts of active Tie2.1 PEG-hexamers were determined by comparing the activity of the cyno vitreal samples versus a standard curve of dosing solution dosed into cyno vitreal isolate. These numbers were compared to the concentrations found by ELISA (described above). FIG. 32 shows the amount of Tie2.1 PEG-hexamer as determined by ELISA and the total activity of that molecule as determined by the pAKT assay. FIG. 33 shows the specific activity of Tie2.1 PEG-hexamer isolated from the cynomolgus vitreal samples. The normalized activity (Active concentration/Total concentration) shows a progressive loss of specific activity over 21 days in the cyno vitreous, resulting in 47% remaining activity at the final time point.

Example 14—Selection of a Stable Tie2.1 M100c Variant

Human IgG1 heavy chain expression vectors encoding 19 variants of Tie2.1, in which VH residue M100c was replaced by each of the 19 alternative natural amino acids, were generated using gene synthesis. The Tie2.1 variants were expressed in IgG format by transient co-transfection of Expi293 cells with expression vectors encoding the desired heavy chain and light chain sequences, and the antibody proteins were purified by affinity chromatography.

Binding of recombinant human and cyno Tie2 to the Tie2.1 hIgG1 variants was evaluated using surface plasmon resonance (SPR) on a Biacore T200 instrument (GE Life Sciences). A human antibody capture chip was prepared using a Series S CM5 chip (GE Life Sciences), a human antibody capture kit (GE Life Sciences) and an amine coupling kit (GE Life Sciences). Antibodies diluted to 5 µg/ml in running buffer (10 mM HEPES, 150 mM NaCl, 0.05% Tween 20, 1 mM EDTA, pH 7.4) were non-covalently captured using a contact time of 20 seconds and a flow rate of 10 µl/minute. Binding to 300 nM and 1500 nM recombinant Tie2 was analyzed at 37° C. using a Single Cycle Kinetics method with a contact time of 60 seconds, a dissociation time of 120 seconds and a flow rate of 50 µl/min. Between cycles, the surface was regenerated by a 30 second injection of 3M $MgCl_2$ at a flow rate of 30 µl/min. Values for antibody capture levels and analyte binding levels were obtained from the Report Point Table (Biacore Evaluation Software v3.0, GE Life Sciences). The results were analyzed by normalizing the sensorgrams for the antibody capture level, then comparing the magnitude of the observed Tie2 binding signals. Results are shown as Normalized Binding Signals, calculated by dividing the Analyte Binding Response (measured in arbitrary Response Units) by the Antibody Capture Level (measured in arbitrary Response Units). Results from 2 experiments are shown providing results of SPR analysis of binding by Tie2.1 and Tie2.1 variants to recombinant Tie2 ECD. Table 16: Experiment A; Table 17: Experiment B.

cyno Tie2, the SPR experiment described above was repeated with a number of modifications intended to improve the resolution of the results. Tie2.1 and Tie2.1 variant hIgG1 antibodies were diluted to 0.5 μg/ml and noncovalently captured using contact times of 15, 30 and 45 seconds each, generating three different surface densities for

TABLE 16

| | | Normalized Binding Signal | | | | | |
|---|---|---|---|---|---|---|---|
| | | | Injection 1 | | | Injection 2 | |
| | Experiment A | Buffer | Hu Tie2 (300 nM) | Cyno Tie2 (300 nM) | Buffer | Hu Tie2 (1500 nM) | Cyno Tie2 (1500 nM) |
| Ctrl. | Anti-gD | 0.00 | 0.01 | 0.01 | 0.02 | 0.03 | 0.03 |
| Tie2.1 | Tie2.1.M100c | 0.00 | 0.10 | 0.08 | 0.01 | 0.35 | 0.33 |
| (replicates) | Tie2.1.M100c | 0.00 | 0.09 | 0.08 | 0.01 | 0.34 | 0.32 |
| | Tie2.1.M100c | 0.00 | 0.10 | 0.08 | 0.02 | 0.35 | 0.32 |
| Selected | Tie2.1.M100cF | 0.00 | 0.14 | 0.12 | 0.01 | 0.44 | 0.42 |
| Tie2.1 | Tie2.1.M100cY | 0.01 | 0.15 | 0.13 | 0.02 | 0.46 | 0.44 |
| variants | Tie2.1.M100cL | 0.01 | 0.13 | 0.11 | 0.02 | 0.42 | 0.40 |
| | Tie2.1.M100cQ | 0.00 | 0.10 | 0.09 | 0.02 | 0.33 | 0.31 |
| | Tie2.1.M100cI | 0.00 | 0.04 | 0.03 | 0.01 | 0.14 | 0.12 |

TABLE 17

| | | Normalized Binding Signal | | | | | |
|---|---|---|---|---|---|---|---|
| | | | Injection 1 | | | Injection 2 | |
| | Experiment B | Buffer | Hu Tie2 (300 nM) | Cyno Tie2 (300 nM) | Buffer | Hu Tie2 (1500 nM) | Cyno Tie2 (1500 nM) |
| Additional | Tie2.1 | 0.00 | 0.09 | 0.08 | 0.02 | 0.30 | 0.29 |
| controls | Tie2.1 | 0.00 | 0.08 | 0.07 | 0.02 | 0.29 | 0.28 |
| | Tie2.1 | 0.00 | 0.09 | 0.08 | 0.02 | 0.31 | 0.29 |
| VH.M100c | Tie2.1.M100c | 0.00 | 0.10 | 0.09 | 0.02 | 0.36 | 0.34 |
| panel | Tie2.1.M100cF | 0.01 | 0.16 | 0.14 | 0.02 | 0.48 | 0.46 |
| | Tie2.1.M100cY | 0.00 | 0.15 | 0.13 | 0.03 | 0.47 | 0.45 |
| | Tie2.1.M100cL | 0.00 | 0.12 | 0.10 | 0.01 | 0.41 | 0.39 |
| | Tie2.1.M100cK | 0.00 | 0.13 | 0.11 | 0.02 | 0.41 | 0.39 |
| | Tie2.1.M100cH | 0.00 | 0.11 | 0.10 | 0.02 | 0.39 | 0.36 |
| | Tie2.1.M100cN | 0.00 | 0.11 | 0.10 | 0.02 | 0.38 | 0.36 |
| | Tie2.1.M100cC | 0.00 | 0.11 | 0.10 | 0.01 | 0.37 | 0.35 |
| | Tie2.1.M100cQ | 0.01 | 0.09 | 0.08 | 0.03 | 0.32 | 0.31 |
| | Tie2.1.M100cW | 0.00 | 0.08 | 0.07 | 0.01 | 0.31 | 0.29 |
| | Tie2.1.M100cS | 0.01 | 0.06 | 0.05 | 0.03 | 0.23 | 0.21 |
| | Tie2.1.M100cR | 0.00 | 0.06 | 0.05 | 0.01 | 0.22 | 0.20 |
| | Tie2.1.M100cG | 0.00 | 0.06 | 0.05 | 0.02 | 0.21 | 0.20 |
| | Tie2.1.M100cD | 0.00 | 0.04 | 0.03 | 0.01 | 0.16 | 0.15 |
| | Tie2.1.M100cV | 0.00 | 0.04 | 0.04 | 0.02 | 0.16 | 0.15 |
| | Tie2.1.M100cI | 0.01 | 0.03 | 0.03 | 0.03 | 0.14 | 0.13 |
| | Tie2.1.M100cA | 0.00 | 0.03 | 0.03 | 0.01 | 0.14 | 0.13 |
| | Tie2.1.M100cE | 0.00 | 0.03 | 0.03 | 0.02 | 0.12 | 0.11 |
| | Tie2.1.M100cP | 0.00 | 0.02 | 0.02 | 0.03 | 0.11 | 0.10 |
| | Tie2.1.M100cT | 0.00 | 0.02 | 0.02 | 0.01 | 0.10 | 0.09 |

Design of Tie2.1.M100cF.

Initial screening of VH.M100c variants by SPR indicates that several different amino acids could replace residue VH.M100c while retaining binding to Tie2 (see above). Human germline antibody sequences frequently contain either Methionine (M) or Phenylalanine (F) at the position corresponding to VH.M100c in phage-derived antibody Tie2.1 (www.IMGT.org, Giudicelli et al., 2005, Nucleic Acids Res, 33:D256-D261). We therefore reasoned that the variant Tie2.1.M100cF may be less likely than other variants to elicit anti-drug immune responses, and proceeded to analyze this variant more closely.

High Resolution Affinity Evaluation of Tie2.1.M100cF.

To confirm that the M100cF mutation resulted in an antibody with similar or improved affinity for human and each of the antibodies tested. Binding to recombinant human and cyno Tie2 was analyzed using a high performance multi-cycle kinetics format with a contact time of 60 seconds, a dissociation time of 60 seconds, a flow rate of 100 μl/minute and Tie2 concentrations of 5 μM, 2.5 μM, 1.25 μM, 625 nM, 313 nM and 156 nM. Tie2 concentrations of 5 μM, 2.5 μM and 1.25 μM were injected twice. Results were analyzed using Biacore T200 Evaluation Software v3.0 (GE Life Sciences). Results from all three surface densities were analyzed together using the 1:1 Binding model with multiple Rmax and the RI parameter set to zero. Kinetic constants were obtained with high confidence (T values >100 for Rmax1, Rmax2, Rmax3, ka and kd) for human Tie2 binding to both Tie2.1 and Tie2.1.M100cF (Table 18).

TABLE 18

|  | Tie2.1 | | Tie2.1.M100cF | |
| --- | --- | --- | --- | --- |
|  | Kinetic Analysis | Steady State Analysis | Kinetic Analysis | Steady State Analysis |
| Association rate constant (ka) | $1.8 \times 10^5 \text{ M}^{-1}\text{s}^{-1}$ | Not applicable | $2.2 \times 10^5 \text{ M}^{-1}\text{s}^{-1}$ | Not applicable |
| Dissociation rate constant (kd) | $4.5 \times 10^{-1} \text{ s}^{-1}$ | Not applicable | $3.9 \times 10^{-1} \text{ s}^{-1}$ | Not applicable |
| Equilibrium Dissociation Constant (Kd) | 3 µM | 3 µM | 2 µM | 2 µM |

Steady-state analysis of the same datasets resulted in similar KD values to those obtained via the kinetic analysis (Table 18). Similar values for ka, kd and KD were observed for binding to recombinant cyno Tie2 (Table 19).

TABLE 19

|  | Tie2.1 | | Tie2.1.M100cF | |
| --- | --- | --- | --- | --- |
|  | Kinetic Analysis | Steady State Analysis | Kinetic Analysis | Steady State Analysis |
| Association rate constant (ka) | $1.5 \times 10^5 \text{ M}^{-1}\text{s}^{-1}$ | Not applicable | $1.9 \times 10^5 \text{ M}^{-1}\text{s}^{-1}$ | Not applicable |
| Dissociation rate constant (kd) | $4.4 \times 10^{-1} \text{ s}^{-1}$ | Not applicable | $3.7 \times 10^{-1} \text{ s}^{-1}$ | Not applicable |
| Equilibrium Dissociation Constant (Kd) | 3 µM | 3 µM | 2 µM | 2 µM |

Example 15—Analysis of Variant Anti-Tie2 PEG Conjugates

While the disclosure provided herein demonstrates that a composition comprising anti-Tie2.1 antibodies conjugated to a multi-armed moiety and which can activate Tie2 activity have beneficial activities and therapeutic value such as in treating eye disorders, it is desirable to identify a conjugate with optimal properties including stability. For this reason, different Tie2.1 PEG hexamer conjugates were designed and tested to assess effects of different conjugations sites. In this example, a 6 kDa PEG-hexamer maleimide was conjugated to Tie2.1 Fabs engineered (ThioFabs) to contain cysteines at strategic locations within the Fab protein.

Cysteines were introduced by replacing the amino acid residue of the heavy or light chain at the indicated position (e.g., HC T120C means that the HC of Tie2.1M100cF was engineered such that the Thr at position 120 was changed to a Cys. "SPPC" indicates a ThioFab molecule in which the C terminus of the heavy chain C1 domain was engineered to change the residues CPPC at positions 226-229 (EU numbering) of Tie2.1M100cF to SPPC.

The variant Tie2.1M100cF ThioFab molecules were conjugated with commercially available maleimide-functionalized six-armed PEG (JenKem Technology, No. 6ARM(DP)-MAL-6000) having the core structure shown in FIG. 39.

Figure 34:
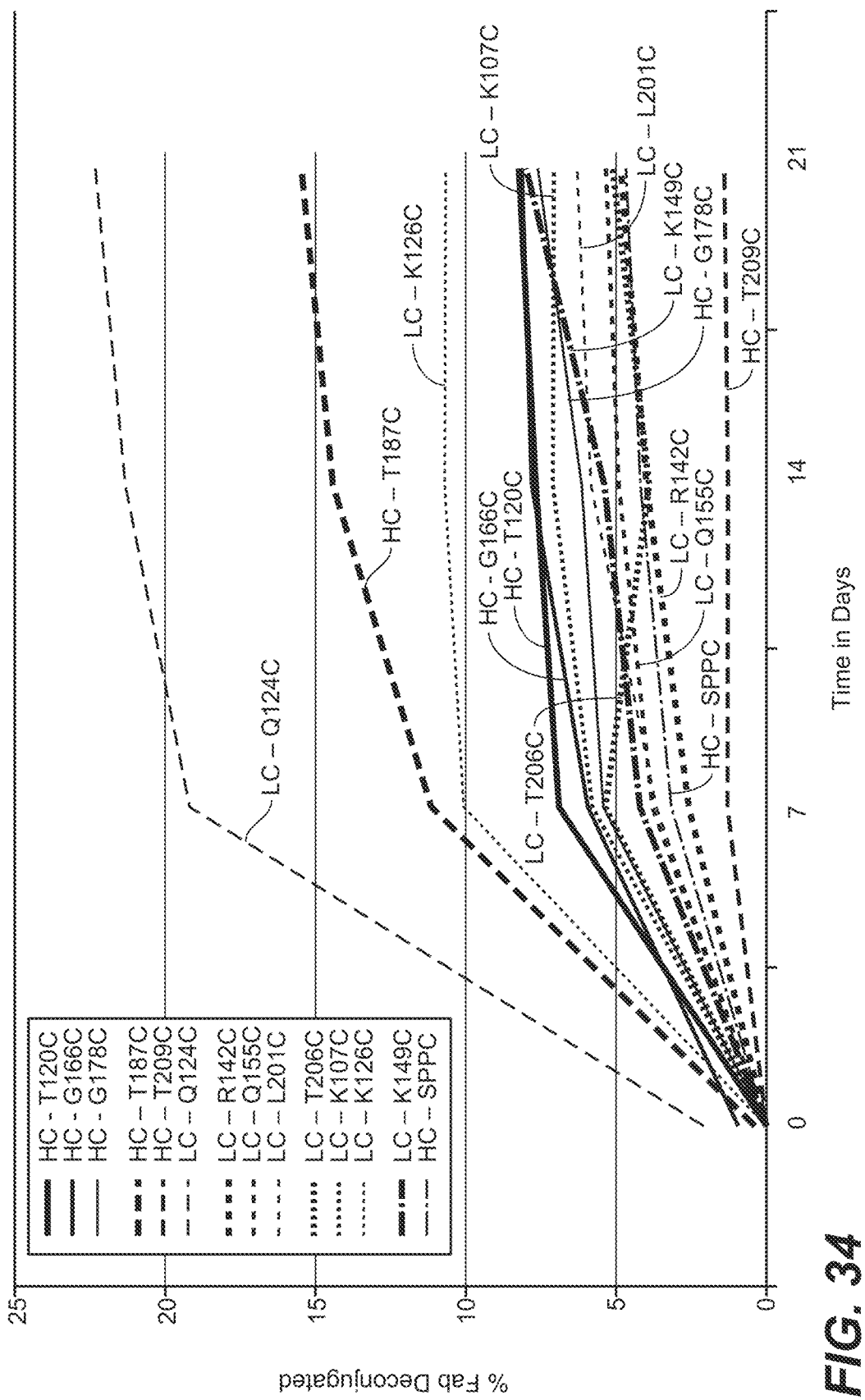
FIG. 34 illustrates effects of the PEG conjugation site location on deconjugation.

The variant Tie2.1M100cF conjugates were prepared and stored at a concentration of 1 mg/ml at 37° C. for 4 weeks. Deconjugation was measured as described in Example 13. The percent deconjugation of each conjugate over 21 days. The results are provided in FIG. 34.

Figure 35A:
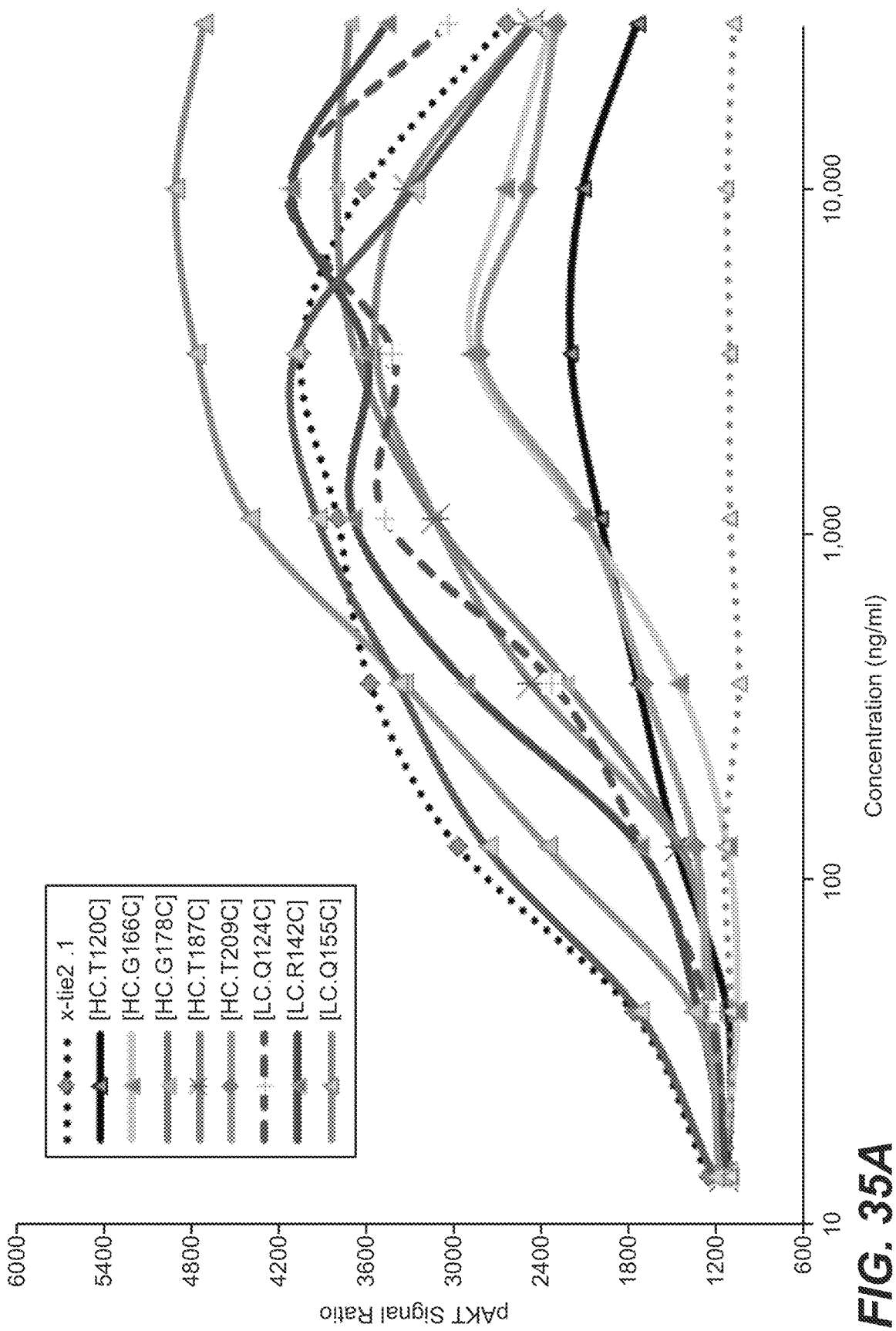
FIG. 35A shows effects of the PEG conjugation site location on activity.
Figure 35B:
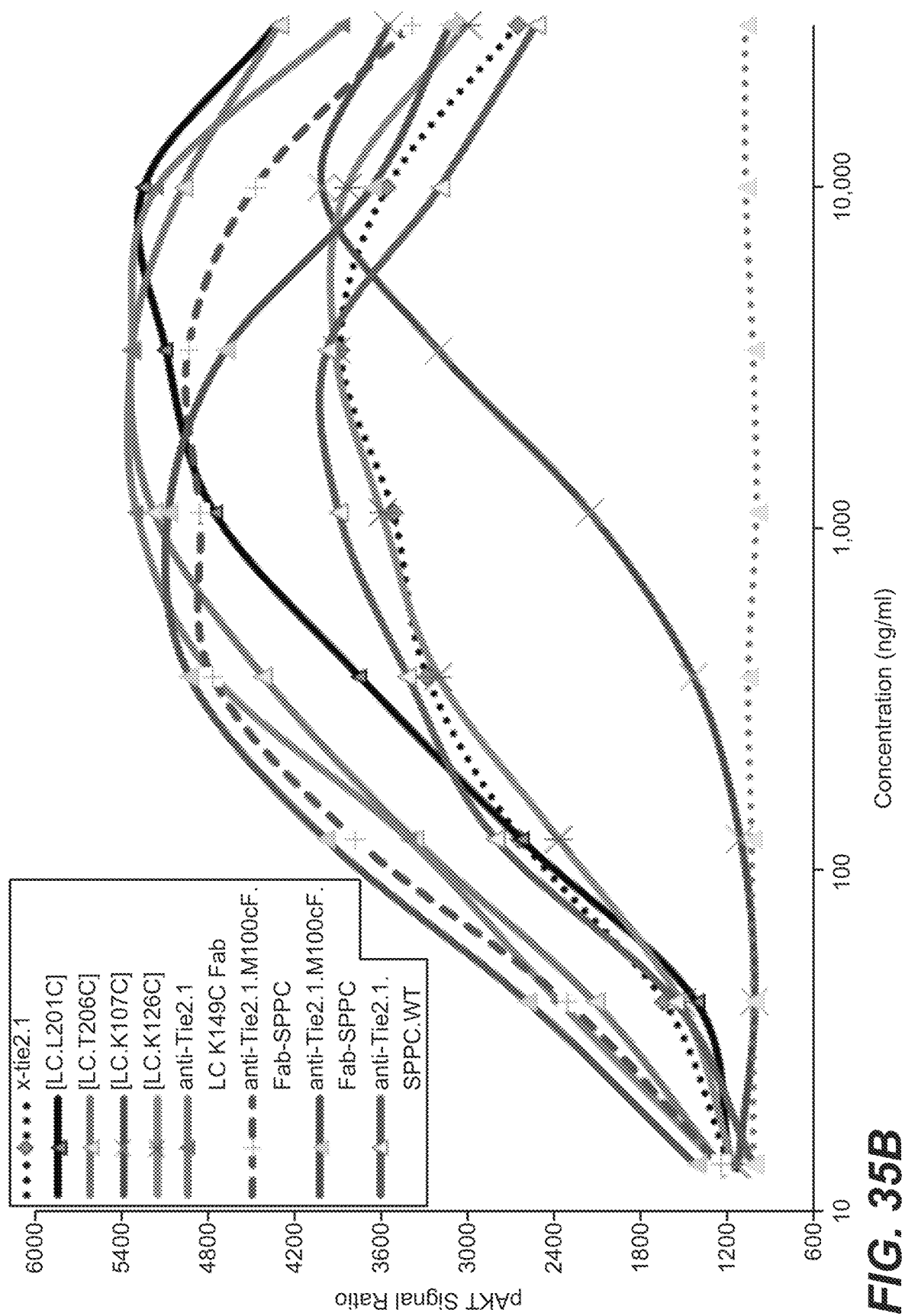
FIG. 35B shows effects of the PEG conjugation site location on activity.

The activity of each of these conjugates was measured using HUVEC pAKT assays as described in Example 3 and results are shown in FIG. 35A and FIG. 35B.

Example 16—In Vivo Stability of Variant Anti-Tie2 PEG Conjugate

To study the in vivo stability of variant anti-Tie2 PEG conjugates described above, 3 were chosen for administration to cynomolgus monkeys in a single dose study. The 3 conjugates were Tie2.1M100cF Fab-SPPC, Tie2.1M100cF, LC T206C, and Tie2.1M100cF, HC T209C. Specifically, a bilateral injection was administered, at 2 mg/eye. A total of 18 animals were included in 3 groups: Group 1: 6 animals administered Tie2.1M100cF Fab-SPPC; Group 2: 6 animals administered Tie2.1M100cF, LC T206C; Group 3: 6 animals administered Tie2.1M100cF, HC T209C. Assessments included ocular and serum PK, serum ADA, and blood pressure (in 2 animals in Group 1) in addition to conjugate stability analyses.

Figure 36:
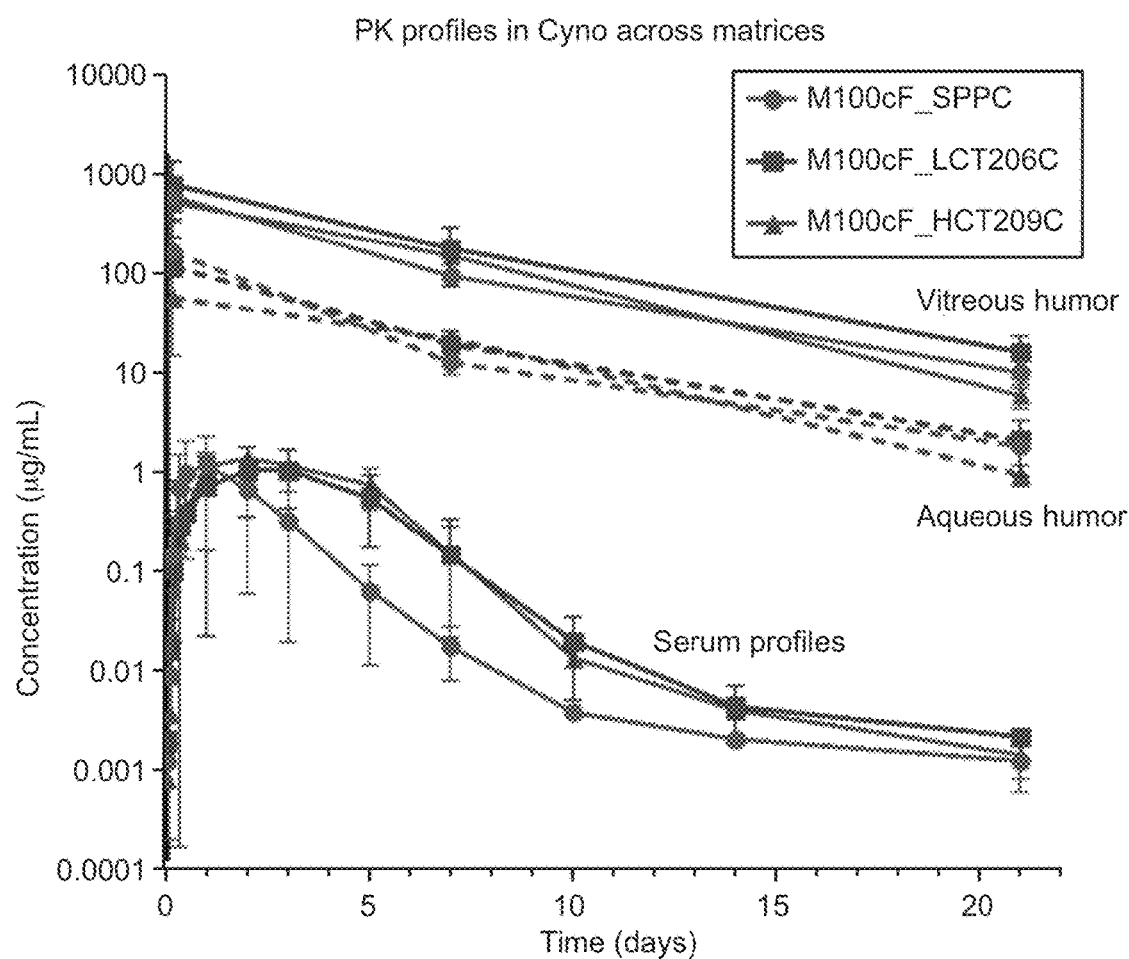
FIG. 36 shows pharmacokinetics of different Tie2.1M100cF PEG conjugates.

The PK profiles in serum, vitreous humor and aqueous humor samples are provided in FIG. 36 and PK parameters are reported in Table 20.

Although there are minor difference such as slightly lower Cmax observed in aqueous humor for Tie2.1M100cF HC-T209C Fab-PEG hexamer, overall ocular PK (in vitreous and aqueous humor) is largely comparable between all 3 tested conjugates. All 3 conjugates showed relatively longer residence time in ocular compartments (tv2 ranged from 3.20 to 3.76 days) and had relatively higher $t_{1/2}$ compared to typical Fab $t_{1/2}$ reported in monkey vitreous humor (~2-3 days, based on historical data with Fabs in cynomolgus monkeys from ITV studies by Genentech (Crowell et al. (2019, Transl Vis Sci Technol 8(6):1)) indicating size based PK of hexamer conjugates in ocular compartments.

Serum PK of ThioFab conjugates (Tie2.1M100cF LC-T206C Fab-PEG hexamer and Tie2.1M100cF HC-T209C Fab-PEG hexamer) is superior to SPPC conjugate (Tie2.1M100cF SPPC Fab-PEG hexamer). Differences in vivo stability due to conjugation method differences could possibly be a driving factor for this systemic PK differences between conjugates. It appears that flip-flop kinetics might be occurring in serum (based on serum PK) for all 3 test conjugates post ITV dosing and illustrates that drug release from vitreous humor may be a rate limiting step that might be driving PK in serum compartment.

TABLE 20

| Matrix | Group (Dose) | $C_{max}$ (µg/mL) | $AUC_{0-t}$ (µg · day/mL) | $t_{1/2}$ (day) | CL or CL/F* (mL/day) |
|---|---|---|---|---|---|
| Vitreous humor | 1 (ITV, 2 mg/eye) | 591 ± 85.9 | 3180 ± 309 | 3.65 | 0.697 |
| | 2 (ITV, 2 mg/eye) | 788 ± 278 | 4810 ± 1120 | 3.76 | 0.502 |
| | 3 (ITV, 2 mg/eye) | 520 ± 94.8 | 3460 ± 340 | 3.20 | 0.585 |
| Aqueous humor | 1 (ITV, 2 mg/eye) | 122 ± 53.4 | 575 ± 188 | 3.63[a] | 3.83 |
| | 2 (ITV, 2 mg/eye) | 118 ± 13.0 | 634 ± 55.3 | 3.70[a] | 3.81 |
| | 3 (ITV, 2 mg/eye) | 57.4 ± 21.2 | 440 ± 77.2 | 3.46[a] | 4.59 |
| Serum | 1 (ITV, 2 mg/eye) | 1.23 ± 0.533 | 2.76 ± 0.59 | 6.95 | 1620 |
| | 2 (ITV, 2 mg/eye) | 1.06 ± 0.356 | 4.99 ± 0.799 | 3.66 | 984 |
| | 3 (ITV, 2 mg/eye) | 1.39 ± 0.200 | 6.18 ± 0.505 | 3.49 | 659 |

$C_{max}$ and AUC are described as value ± SE.

Group 1: Anti-Tie2.1_M100cF_SPPC_Fab-PEG Hexamer

Group 2: Anti-Tie2.1_M100cF_LCT206C_Fab-PEG Hexamer

Group 3: Anti-Tie2.1_M100cF_HCT209C_Fab-PEG Hexamer

*CL for vitreous humor, CL/F for aqueous humor and serum

[a]$C_{max}$ was used for calculation of $t_{1/2}$.

Figure 37:
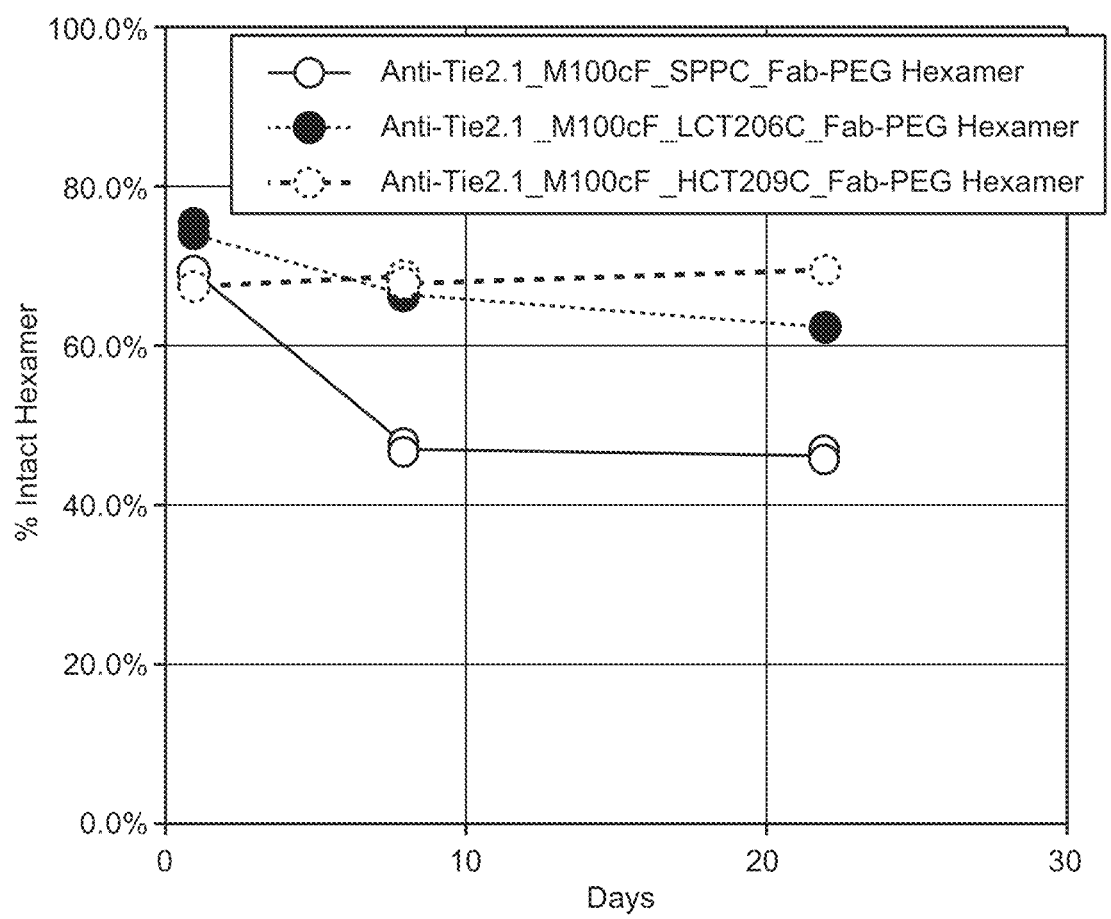
FIG. 37 compares in vivo stability of different Tie2.1M100cF PEG conjugates.

Stability of the ThioFab conjugates were assessed using vitreous humor samples taken from the animals in which the percentage of intact conjugate at Days 0, 7 and 21 was measured. The results are presented in FIG. 37.

Figure 38A:
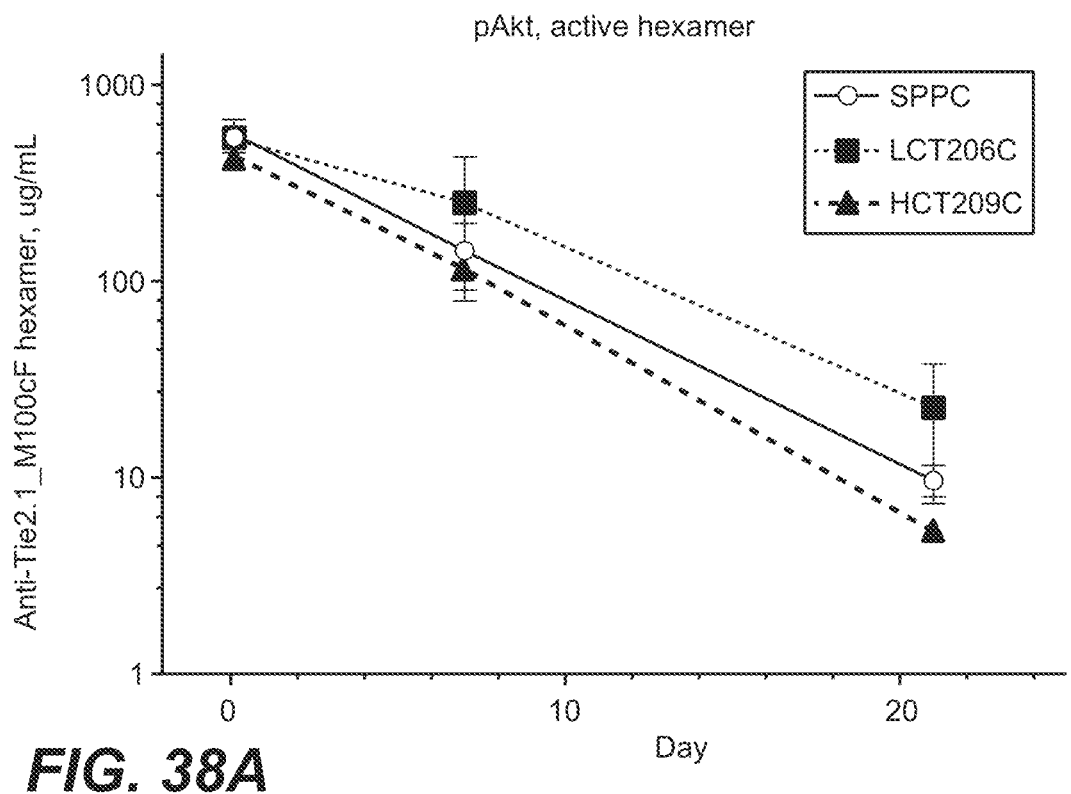
FIGS. 38A-38B compare activity of different Tie2.1M100cF PEG conjugates.
Figure 38B:
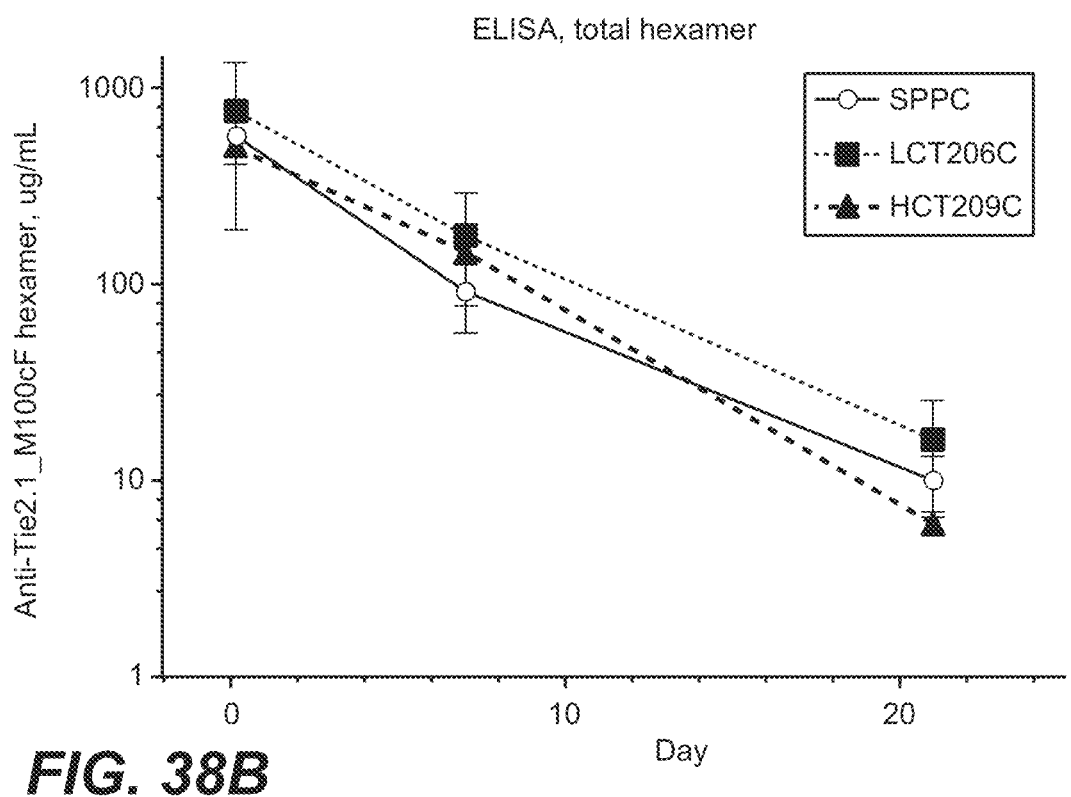

Activity of the conjugates in the samples was also measured at Days 0, 7 and 21. pAkt activity was measured by testing the vitreous humor in a pAkt FRET assay as described in Example 3. Active hexamer was quantified by use of a standard curve in the pAkt FRET assay. As shown in FIGS. 38A and 39A, all conjugates retained ex vivo activity in vitreous humor through Day 21.

Table of Sequences

| SEQ ID NO | Description | Sequence |
|---|---|---|
| 3 | Tie 2.1 HC CDR1 | NTDIS |
| 4 | Tie 2.1 HC CDR2 | RISPSDGNTYYADSVKG |
| 5 | Tie 2.1 HC CDR3 | RTRWASX1AX2DY,(where X1 is M, L, K, F, Y, R, N, Q, H or W; and/or X2 is F, Y, L, Q, I, K or H) |
| 6 | Tie 2.1 HC CDR3 | RTRWASWAMDY |
| 7 | Tie 2.1 HC CDR3M100cF | RTRWASWAFDY |
| 8 | Tie 2.1 LC CDR1 | RASQDVSTAVA |
| 9 | Tie 2.1 LC CDR2 | SASFLYS |
| 10 | Tie 2.1 LC CDR3 | QQSYTTPPT |
| 11 | Tie 2.1 HC FR1 | EVQLVESGGGLVQPGGSLRLSCAASGFTFS |
| 12 | Tie 2.1 HC FR2 | WVRQAPGKGLEWVG |
| 13 | Tie 2.1 HC FR3 | RFTISADTSKNTAYLQMNSLRAEDTAVYYCAR |
| 14 | Tie 2.1 HC FR4 | QGTLVTVSS |
| 15 | Tie 2.1 LC FR1 | DIQMTQSPSSLSASVGDRVTITC |
| 16 | Tie 2.1 LC FR2 | WYQQKPGKAPKLLIY |
| 17 | Tie 2.1 LC FR3 | GVPSRFSGSGSGTDFTLTISSLQPEDFATYYC |
| 18 | Tie 2.1 LC FR4 | FGQGTKVEI |
| 19 | Tie 2.1 HC variable domain (CDR3 with X1 and X2) | EVQLVESGGGLVQPGGSLRLSCAASGFTFSNTDISWVRQAPGKG LEWVGRISPSDGNTYYADSVKGRFTISADTSKNTAYLQMNSLRA EDTAVYYCARRTRWASX1AX2DYWGQGTLVTVSS |
| 20 | Tie 2.1 HC M100cF variable domain | EVQLVESGGGLVQPGGSLRLSCAASGFTFSNTDISWVRQAPGKG LEWVGRISPSDGNTYYADSVKGRFTISADTSKNTAYLQMNSLRA EDTAVYYCARRTRWASWAFDYWGQGTLVTVSS |
| 21 | Tie 2.1 LC variable domain | DIQMTQSPSSLSASVGDRVTITCRASQDVSTAVAWYQQKPGKAP KLLIYSASFLYSGVPSRFSGSGSGTDFTLTISSLQPEDFATYYC QQSYTTPPTFGQGTKVEIK |
| 22 | Tie 2.1 HC variable domain (no mutations) | EVQLVESGGGLVQPGGSLRLSCAASGFTFSNTDISWVRQAPGKG LEWVGRISPSDGNTYYADSVKGRFTISADTSKNTAYLQMNSLRA EDTAVYYCARRTRWASWAMDYWGQGTLVTVSS |
| 23 | Tie 2.1 full HC.M100cF | EVQLVESGGGLVQPGGSLRLSCAASGFTFSNTDISWVRQAPGKG LEWVGRISPSDGNTYYADSVKGRFTISADTSKNTAYLQMNSLRA EDTAVYYCARRTRWASWAFDYWGQGTLVTVSSASTKGPSVFPLA PSSKSTSGGTAALGCLVKDYFPEPVTVSWNSGALTSGVHTFPAV LQSSGLYSLSSVVTVPSSSLGTQTYICNVNHKPSNTKVDKKVEP KSCD |

-continued

| SEQ ID NO | Description | Sequence |
|---|---|---|
| 24 | Tie 2.1 HC (HV & C1 T209C) | EVQLVESGGGLVQPGGSLRLSCAASGFTFSNTDISWVRQAPGKG<br>LEWVGRISPSDGNTYYADSVKGRFTISADTSKNTAYLQMNSLRA<br>EDTAVYYCARRTRWASWAMDYWGQGTLVTVSSASTKGPSVFPLA<br>PSSKSTSGGTAALGCLVKDYFPEPVTVSWNSGALTSGVHTFPAV<br>LQSSGLYSLSSVVTVPSSSLGTQTYICNVNHKPSNCKVDKKVEP<br>KSCD |
| 25 | Tie 2.1 full LC | DIQMTQSPSSLSASVGDRVTITCRASQDVSTAVAWYQQKPGKAP<br>KLLIYSASFLYSGVPSRFSGSGSGTDFTLTISSLQPEDFATYYC<br>QQSYTTPPTFGQGTKVEIKRTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGLSSPVTKSFNRGEC |
| 26 | Tie2.1 HC constant domain (C1 only) | ASTKGPSVFPLAPSSKSTSGGTAALGCLVKDYFPEPVTVSWNSG<br>ALTSGVHTFPAVLQSSGLYSLSSVVTVPSSSLGTQTYICNVNHK<br>PSNCKVDKKVEPKSCD |
| 27 | Tie2.1 LC constant domain (C1 only) | RTVAAPSVFIFPPSDEQLKSGTASVVCLLNNFYPREAKVQWKVD<br>NALQSGNSQESVTEQDSKDSTYSLSSTLTLSKADYEKHKVYACE<br>VTHQGLSSPVTKSFNRGEC |
| 28 | Tie 2.12 HC CDR1 | SYWIH |
| 29 | Tie 2.12 HC CDR2 | AISPNDGSTYYADSVKG |
| 30 | Tie 2.12 HC CDR3 | SRYYGQRLVYYVMDY |
| 31 | Tie 2.12 HC variable domain | EVQLVESGGGLVQPGGSLRLSCAASGFTFSSYWIHWVRQAPGKG<br>LEWVAAISPNDGSTYYADSVKGRFTISADTSKNTAYLQMNSLRA<br>EDTAVYYCARSRYYGQRLVYYVMDYWGQGTLVTVSS |
| 32 | Tie 2.12 HC | EVQLVESGGGLVQPGGSLRLSCAASGFTFSSYWIHWVRQAPGKG<br>LEWVAAISPNDGSTYYADSVKGRFTISADTSKNTAYLQMNSLRA<br>EDTAVYYCARSRYYGQRLVYYVMDYWGQGTLVTVSSASTKGPSV<br>FPLAPSSKSTSGGTAALGCLVKDYFPEPVTVSWNSGALTSGVHT<br>FPAVLQSSGLYSLSSVVTVPSSSLGTQTYICNVNHKPSNTKVDK<br>KVEPKSCD |
| 33 | Tie 2.24 HC CDR1 | SSGIS |
| 34 | Tie 2.24 HC CDR2 | TINPYGGDTYYADSVKG |
| 35 | Tie 2.24 HC CDR3 | FYRFLSSGMDY |
| 36 | Tie 2.24 HC variable domain | EVQLVESGGGLVQPGGSLRLSCAASGFTFTSSGISWVRQAPGKG<br>LEWVATINPYGGDTYYADSVKGRFTISADTSKNTAYLQMNSLRA<br>EDTAVYYCARFYRFLSSGMDYWGQGTLVTVSS |
| 37 | Tie 2.24 HC | EVQLVESGGGLVQPGGSLRLSCAASGFTFTSSGISWVRQAPGKG<br>LEWVATINPYGGDTYYADSVKGRFTISADTSKNTAYLQMNSLRA<br>EDTAVYYCARFYRFLSSGMDYWGQGTLVTVSSASTKGPSVFPLA<br>PSSKSTSGGTAALGCLVKDYFPEPVTVSWNSGALTSGVHTFPAV<br>LQSSGLYSLSSVVTVPSSSLGTQTYICNVNHKPSNTKVDKKVEP<br>KSCD |
| 38 | Tie 2.33 HC CDR1 | GSWIS |
| 39 | Tie 2.33 HC CDR2 | RINPYDGNTYYADSVKG |
| 40 | Tie 2.33 HC CDR3 | NNRFPTWFDY |

-continued

Table of Sequences

| SEQ ID NO | Description | Sequence |
|---|---|---|
| 41 | Tie 2.33 HC variable domain | EVQLVESGGGLVQPGGSLRLSCAASGFTFSGSWISWVRQAPGKG LEWVARINPYDGNTYYADSVKGRFTISADTSKNTAYLQMNSLRA EDTAVYYCARNNRFPTWFDYWGQGTLVTVSS |
| 42 | Tie 2.33 HC | EVQLVESGGGLVQPGGSLRLSCAASGFTFSGSWISWVRQAPGKG LEWVARINPYDGNTYYADSVKGRFTISADTSKNTAYLQMNSLRA EDTAVYYCARNNRFPTWFDYWGQGTLVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKKVEPK SCD |
| 43 | Tie 2.34 HC CDR1 | DTYIH |
| 44 | Tie 2.34 HC CDR2 | VIYPDNGATYYADSVKG |
| 45 | Tie 2.34 HC CDR3 | EFACARCVYG |
| 46 | Tie 2.34 HC | EVQLVESGGGLVQPGGSLRLSCAASGFTFSDTYIHWVRQAPGKG LEWVAVIYPDNGATYYADSVKGTYYADSVKGRFTISADTSKNTA YLQMNSLRAEDTAVYYCAREFACARCVYGMDYWGQGTLVTVSSA STKGPSVFPLAPSSKSTSGGTAALGCLVKDYFPEPVTVSWNSGA LTSGVHTFPAVLQSSGLYSLSSVVTVPSSSLGTQTYICNVNHKP SNTKVDKKVEPKSCD |
| 47 | Tie 2.34 HC variable domain | EVQLVESGGGLVQPGGSLRLSCAASGFTFSDTYIHWVRQAPGKG LEWVAVIYPDNGATYYADSVKGTYYADSVKGRFTISADTSKNTA YLQMNSLRAEDTAVYYCAREFACARCVYGMDYWGQGTLVTVSS |
| 48 | Tie 2.38 HC CDR1 | NSAIH |
| 49 | Tie 2.38 HC CDR2 | SITPYNGYTYYADSVKG |
| 50 | Tie 2.38 HC CDR3 | RQSYSYVMDY |
| 51 | Tie 2.38 VH | EVQLVESGGGLVQPGGSLRLSCAASGFTFSNSAIHWVRQAPGKG LEWVASITPYNGYTYYADSVKGRFTISADTSKNTAYLQMNSLRA EDTAVYYCARRQSYSYVMDYWGQGTLVTVSS |
| 52 | Tie 2.38 HC | EVQLVESGGGLVQPGGSLRLSCAASGFTFSNSAIHWVRQAPGKG LEWVASITPYNGYTYYADSVKGRFTISADTSKNTAYLQMNSLRA EDTAVYYCARRQSYSYVMDYWGQGTLVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKKVEPK SCD |
| 53 | anti-Tie2 Fab-IgG 1.38 LC | DIQMTQSPSSLSASVGDRVTITCRASQDVSTAVAWYQQKPGKAP KLLIYSASFLYSGVPSRFSGSGSGTDFTLTISSLQPEDFATYYC QQSYTTPPTFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 54 | anti-Tie2 Fab-IgG 1.38 HC | EVQLVESGGGLVQPGGSLRLSCAASGFTFSNTDISWVRQAPGKG LEWVGRISPSDGNTYYADSVKGRFTISADTSKNTAYLQMNSLRA EDTAVYYCARRTRWASWAMDYWGQGTLVTVSSASTKGPSVFPLA PSSKSTSGGTAALGCLVKDYFPEPVTVSWNSGALTSGVHTFPAV LQSSGLYSLSSVVTVPSSSLGTQTYICNVNHKPSNTKVDKKVEP KSCDKTHTGGGGSGGEVQLVESGGGLVQPGGSLRLSCAASGFTF SNSAIHWVRQAPGKGLEWVASITPYNGYTYYADSVKGRFTISAD TSKNTAYLQMNSLRAEDTAVYYCARRQSYSYVMDYWGQGTLVTV SSASTKGPSVFPLAPSSKSTSGGTAALGCLVKDYFPEPVTVSWN SGALTSGVHTFPAVLQSSGLYSLSSVVTVPSSSLGTQTYICNVN HKPSNTKVDKKVEPKSCDKTHTCPPCPAPEAAGGPSVFLFPPKP KDTLMASRTPEVTCVVVDVSHEDPEVKFNWYVDGVEVHNAKTKP REEQYNSTYRVVSVLTVLAQDWLNGKEYKCKVSNKALGAPIEKT ISKAKGQPREPQVYTLPPSREEMTKNQVSLTCLVKGFYPSDIAV EWESNGQPENNYKTTPPVLDSDGSFFLYSKLTVDKSRWQQGNVF SCSVMHEALHNAYTQKSLSLSPGK |

| SEQ ID NO | Description | Sequence |
|---|---|---|
| 55 | Tie2.1M100cF-HC-T209C | EVQLVESGGGLVQPGGSLRLSCAASGFTFSNTDISWVRQAPGKG<br>LEWVGRISPSDGNTYYADSVKGRFTISADTSKNTAYLQMNSLRA<br>EDTAVYYCARRTRWASWAFDYWGQGTLVTVSSASTKGPSVFPLA<br>PSSKSTSGGTAALGCLVKDYFPEPVTVSWNSGALTSGVHTFPAV<br>LQSSGLYSLSSVVTVPSSSLGTQTYICNVNHKPSNCKVDKKVEP<br>KSCD |
| 56 | Tie2.1M100cF-LC-T206C | DIQMTQSPSSLSASVGDRVTITCRASQDVSTAVAWYQQKPGKAP<br>KLLIYSASFLYSGVPSRFSGSGSGTDFTLTISSLQPEDFATYYC<br>QQSYTTPPTFGQGTKVEIKRTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGLSSPVCKSFNRGEC |
| 57 | Tie2.1M100cF-HC-SPPC | EVQLVESGGGLVQPGGSLRLSCAASGFTFSNTDISWVRQAPGKG<br>LEWVGRISPSDGNTYYADSVKGRFTISADTSKNTAYLQMNSLRA<br>EDTAVYYCARRTRWASWAFDYWGQGTLVTVSSASTKGPSVFPLA<br>PSSKSTSGGTAALGCLVKDYFPEPVTVSWNSGALTSGVHTFPAV<br>LQSSGLYSLSSVVTVPSSSLGTQTYICNVNHKPSNTKVDKKVEP<br>KSCDKTHTSPPC |
| 58 | Tie2.1M100cF-HC-T120C | EVQLVESGGGLVQPGGSLRLSCAASGFTFSNTDISWVRQAPGKG<br>LEWVGRISPSDGNTYYADSVKGRFTISADTSKNTAYLQMNSLRA<br>EDTAVYYCARRTRWASWAFDYWGQGTLVTVSSASTKGPSVFPLA<br>PSSKSTSGGTAALGCLVKDYFPEPVTVSWNSGALTSGVHTFPAV<br>LQSSGLYSLSSVVTVPSSSLGTQTYICNVNHKPSNTKVDKKVEP<br>KSCD |
| 59 | Tie2.1M100cF-HC-G166C | EVQLVESGGGLVQPGGSLRLSCAASGFTFSNTDISWVRQAPGKG<br>LEWVGRISPSDGNTYYADSVKGRFTISADTSKNTAYLQMNSLRA<br>EDTAVYYCARRTRWASWAFDYWGQGTLVTVSSASTKGPSVFPLA<br>PSSKSTSGGTAALGCLVKDYFPEPVTVSWNSGALTSCVHTFPAV<br>LQSSGLYSLSSVVTVPSSSLGTQTYICNVNHKPSNTKVDKKVEP<br>KSCD |
| 60 | Tie2.1M100cF-HC-G178C | EVQLVESGGGLVQPGGSLRLSCAASGFTFSNTDISWVRQAPGKG<br>LEWVGRISPSDGNTYYADSVKGRFTISADTSKNTAYLQMNSLRA<br>EDTAVYYCARRTRWASWAFDYWGQGTLVTVSSASTKGPSVFPLA<br>PSSKSTSGGTAALGCLVKDYFPEPVTVSWNSGALTSGVHTFPAV<br>LQSSCLYSLSSVVTVPSSSLGTQTYICNVNHKPSNTKVDKKVEP<br>KSCD |
| 61 | Tie2.1M100cF-HC-T187C | EVQLVESGGGLVQPGGSLRLSCAASGFTFSNTDISWVRQAPGKG<br>LEWVGRISPSDGNTYYADSVKGRFTISADTSKNTAYLQMNSLRA<br>EDTAVYYCARRTRWASWAFDYWGQGTLVTVSSASTKGPSVFPLA<br>PSSKSTSGGTAALGCLVKDYFPEPVTVSWNSGALTSGVHTFPAV<br>LQSSGLYSLSSVVCVPSSSLGTQTYICNVNHKPSNTKVDKKVEP<br>KSCD |
| 62 | Tie2.1M100cF-LC-Q124C | DIQMTQSPSSLSASVGDRVTITCRASQDVSTAVAWYQQKPGKAP<br>KLLIYSASFLYSGVPSRFSGSGSGTDFTLTISSLQPEDFATYYC<br>QQSYTTPPTFGQGTKVEIKRTVAAPSVFIFPPSDECLKSGTASV<br>VCLLNNFYPREAKVQWKVDNALQSGNSQESVTEQDSKDSTYSLS<br>STLTLSKADYEKHKVYACEVTHQGLSSPVTKSFNRGEC |
| 63 | Tie2.1M100cF-LC-R142C | DIQMTQSPSSLSASVGDRVTITCRASQDVSTAVAWYQQKPGKAP<br>KLLIYSASFLYSGVPSRFSGSGSGTDFTLTISSLQPEDFATYYC<br>QQSYTTPPTFGQGTKVEIKRTVAAPSVFIFPPSDEQLKSGTASV<br>VCLLNNFYPCEAKVQWKVDNALQSGNSQESVTEQDSKDSTYSLS<br>STLTLSKADYEKHKVYACEVTHQGLSSPVTKSFNRGEC |
| 64 | Tie2.1M100cF-LC-Q155C | DIQMTQSPSSLSASVGDRVTITCRASQDVSTAVAWYQQKPGKAP<br>KLLIYSASFLYSGVPSRFSGSGSGTDFTLTISSLQPEDFATYYC<br>QQSYTTPPTFGQGTKVEIKRTVAAPSVFIFPPSDEQLKSGTASV<br>VCLLNNFYPREAKVQWKVDNALCSGNSQESVTEQDSKDSTYSLS<br>STLTLSKADYEKHKVYACEVTHQGLSSPVTKSFNRGEC |
| 65 | Tie2.1M100cF-LC-L201C | DIQMTQSPSSLSASVGDRVTITCRASQDVSTAVAWYQQKPGKAP<br>KLLIYSASFLYSGVPSRFSGSGSGTDFTLTISSLQPEDFATYYC<br>QQSYTTPPTFGQGTKVEIKRTVAAPSVFIFPPSDEQLKSGTASV<br>VCLLNNFYPREAKVQWKVDNALQSGNSQESVTEQDSKDSTYSLS<br>STLTLSKADYEKHKVYACEVTHQGCSSPVTKSFNRGEC |

Table of Sequences

| SEQ ID NO | Description | Sequence |
|---|---|---|
| 66 | Tie2.1M100cF-LC-K107C | DIQMTQSPSSLSASVGDRVTITCRASQDVSTAVAWYQQKPGKAP KLLIYSASFLYSGVPSRFSGSGSGTDFTLTISSLQPEDFATYYC QQSYTTPPTFGQGTKVEICRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC |
| 67 | Tie2.1M100cF-LC-L126C | DIQMTQSPSSLSASVGDRVTITCRASQDVSTAVAWYQQKPGKAP KLLIYSASFLYSGVPSRFSGSGSGTDFTLTISSLQPEDFATYYC QQSYTTPPTFGQGTKVEIKRTVAAPSVFIFPPSDEQLCSGTASV VCLLNNFYPREAKVQWKVDNALQSGNSQESVTEQDSKDSTYSLS STLTLSKADYEKHKVYACEVTHQGLSSPVTKSFNRGEC |
| 68 | Tie2.1M100cF-LC-K149C | DIQMTQSPSSLSASVGDRVTITCRASQDVSTAVAWYQQKPGKAP KLLIYSASFLYSGVPSRFSGSGSGTDFTLTISSLQPEDFATYYC QQSYTTPPTFGQGTKVEIKRTVAAPSVFIFPPSDEQLKSGTASV VCLLNNFYPREAKVQWCVDNALQSGNSQESVTEQDSKDSTYSLS STLTLSKADYEKHKVYACEVTHQGLSSPVTKSFNRGEC |
| 69 | NDK1 peptide | ERTFVMIKPDGVQRGLIGEIISRFERKGLKIVAMKMMRISREMA EKHYAEHREKPFFSALVDYITSGPVVAMVLEGKNAVEVVRKMVG ATNPKEAAPGTIRGDFGLDVGKNVIFASDSPESAEREISLFFKD EELVEW |
| 70 | NDK2 peptide | ERTFVMIKPDGVQRGLIGEIISRFERKGFKIVAMKLMRISQELA EKHYAEHREKPFFSGLVDFITSGPVVAMVLEGKNVVEVVRKMIG ATNPKEAAPGTIRGDFGMSVGKNVIFGSDSLESAEREISLFFKD EELVEW |
| 71 | NDK3 peptide | STNKVNKERTFLAVKPDGVARGLVGETIARYEKKGFVLVGLKQL VPTKDLAESHYAEHKERPFFGGLVSFITSGPVVAMVFEGKGVVA SARLMIGVTNPLASAPGSIRGDFGVDVGRNIIFGSDSVESANRE IALWFKPEELLTEVKPNPNLYE |
| 72 | NDK4 peptide | ANSERTFIAIKPDGVQRGLVGEIIKRFEQKGFRLVGLKFLQASE DLLKEHYTDLKDRPFFTGLVKYMHSGPVVAMVWEGLNVVKTGRV MLGETNPADSKPGTIRGDFCIQVGRNIIFGSDSVKSAEKEISLW FQPEELVEYKSCAQNWIYE |
| 73 | NDK5 peptide | ANLERTFIAIKPDGVQRGLVGEIIKRFEQKGFRLVAMKFLRASE EHLKQHYIDLKDRPFFPGLVKYMNSGPVVAMVWEGLNVVKTGRV MLGETNPADSKPGTIRGDFCIQVGRNIIFGSDSVESAEKEIHLW FKPEELIDYKSCAHDWVYE |
| 74 | Tie2.1.M100cF.Fab.NDK3 | EVQLVESGGGLVQPGGSLRLSCAASGFTFSNTDISWVRQAPGKG LEWVGRISPSDGNTYYADSVKGRFTISADTSKNTAYLQMNSLRA EDTAVYYCARRTRWASWAFDYWGQGTLVTVSSASTKGPSVFPLA PSSKSTSGGTAALGCLVKDYFPEPVTVSWNSGALTSGVHTFPAV LQSSGLYSLSSVVTVPSSSLGTQTYICNVNHKPSNTKVDKKVEP KSCDKTHTGGGGSTNKVNKERTFLAVKPDGVARGLVGETIARYE KKGFVLVGLKQLVPTKDLAESHYAEHKERPFFGGLVSFITSGPV VAMVFEGKGVVASARLMIGVTNPLASAPGSIRGDFGVDVGRNII FGSDSVESANREIALWFKPEELLTEVKPNPNLYE |
| 75 | | CDKTHT |
| 76 | | CDKTHL |
| 77 | | CDKTH |
| 78 | | CDKT |
| 79 | | CDKTHX, wherein X is any amino acid other than T |
| 80 | | CDKTHTC |
| 81 | | CDKTHTCPPC |
| 82 | | CDKTHTCPPS |
| 83 | | CDKTHTSPPC |
| 84 | | CDKTHTAPPC |

-continued

| SEQ ID NO | Description | Sequence |
|---|---|---|
| 85 | | CDKTHTSGGC |
| 86 | | CYGPPC |
| 87 | | CPPC |
| 88 | | SPPC |
| 89 | Tie2.1M100cF-HC-SPPC | EVQLVESGGGLVQPGGSLRLSCAASGFTFSNTDISWVRQAPGKG LEWVGRISPSDGNTYYADSVKGRFTISADTSKNTAYLQMNSLRA EDTAVYYCARRTRWASWAMDYWGQGTLVTVSSASTKGPSVFPLA PSSKSTSGGTAALGCLVKDYFPEPVTVSWNSGALTSGVHTFPAV LQSSGLYSLSSVVTVPSSSLGTQTYICNVNHKPSNTKVDKKVEP KSCDKTHTSPPC |
| 90 | Tie2.1 HC (M100c, T1209) | EVQLVESGGGLVQPGGSLRLSCAASGFTFSNTDISWVRQAPGKG LEWVGRISPSDGNTYYADSVKGRFTISADTSKNTAYLQMNSLRA EDTAVYYCARRTRWASWAMDYWGQGTLVTVSSASTKGPSVFPLA PSSKSTSGGTAALGCLVKDYFPEPVTVSWNSGALTSGVHTFPAV LQSSGLYSLSSVVTVPSSSLGTQTYICNVNHKPSNTKVDKKVEP KSCD |
| 91 | Tie2.1 HC (CDR3X1X2, T209) | EVQLVESGGGLVQPGGSLRLSCAASGFTFSNTDISWVRQAPGKG LEWVGRISPSDGNTYYADSVKGRFTISADTSKNTAYLQMNSLRA EDTAVYYCARRTRWASX1AX2DYWGQGTLVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNTKVDKKV EPKSCD |
| 92 | Tie2.1 HC (CDR3X1X2 T209C) | EVQLVESGGGLVQPGGSLRLSCAASGFTFSNTDISWVRQAPGKG LEWVGRISPSDGNTYYADSVKGRFTISADTSKNTAYLQMNSLRA EDTAVYYCARRTRWASX1AX2DYWGQGTLVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNCKVDKKV EPKSCD |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A conjugate that binds to Tie2, wherein the conjugate comprises two, three, four, five, six, seven, or eight antibodies or antigen-binding fragments thereof, wherein each of the antibodies or fragments thereof bind Tie2 and comprises:
   a heavy chain variable domain (VH) comprising (a) CDR-H1 comprising the amino acid sequence NTDIS (SEQ ID NO:3), (b) CDR-H2 comprising the amino acid sequence RISPSDGNTYYADSVKG (SEQ ID NO:4), and (c) CDR-H3 comprising the amino acid sequence RTRWASWAFDY (SEQ ID NO:7), and a light chain variable domain (VL) comprising (d) CDR-L1 comprising the amino acid sequence RASQDVSTAVA (SEQ ID NO:8), (e) CDR-L2 comprising the amino acid sequence SASFLYS (SEQ ID NO:9), and (f) CDR-L3 comprising the amino acid sequence QQSYTTPPT (SEQ ID NO:10), and
   wherein each of the antibodies or antigen-binding fragment thereof is linked to a multimerizing moiety.

2. The conjugate of claim 1, wherein the multimerizing moiety comprises a polyol, wherein the polyol is a is a multi-armed polyol, selected from a dimer, a tetramer, a hexamer, and an octamer.

3. The conjugate of claim 2, wherein the multi-armed polyol is a hexamer.

4. The conjugate of claim 2, wherein the polyol is a polyethylene glycol (PEG).

5. The conjugate of claim 4, wherein the PEG has a weight average molecular weight of from about 500 Daltons (Da) to about 300,000 Da.

6. The conjugate of claim 4, wherein the PEG has the structure of general formula (Ib):

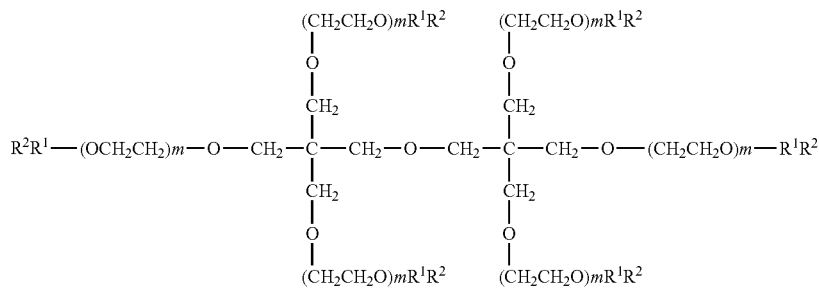

wherein each m is independently an integer from 3-250; each $R^1$ is independently either absent or is a linking group; and each $R^2$ is independently either hydrogen or a terminal reactive group;

wherein at least one $R^2$ is a terminal reactive group and is covalently linked to the antibody or antigen-binding fragment thereof.

7. The conjugate according to claim 6, wherein at least one $R^1$ is a linking group, wherein $R^1$ and $R^2$ when taken together are selected from:

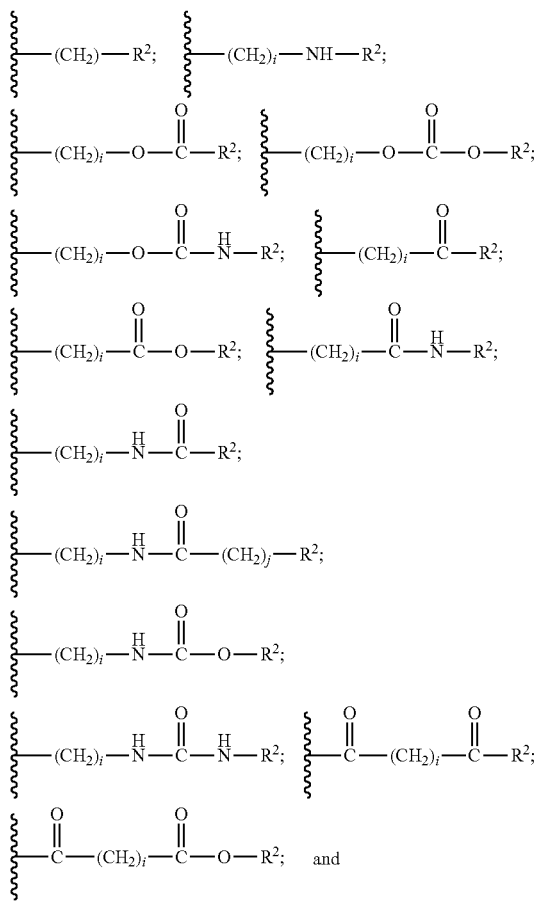

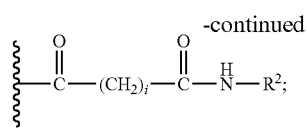

and combinations thereof; wherein each i is independently an integer of 0-10; j is an integer of 0-10; and $R^2$ is a terminal reactive group selected from the group consisting of a thiol reactive group, an amino reactive group, and combinations thereof.

8. The conjugate of claim 6, wherein each $R^2$ is a maleamide and is covalently linked to the antibody or antigen-binding fragment thereof.

9. The conjugate of claim 2, wherein each of the antibodies or antigen-binding fragment thereof is a Fab and the polyol is covalently linked to the Fab through a free sulfhydryl group of an engineered cysteine amino acid, wherein the engineered cysteine is selected from the group consisting of T120C, G166C, G178C, T187C, and T209C in the heavy chain (HC); or the engineered cysteine is selected from the group consisting of Q124C, R142C, Q155C, L201C, T206C, K107C, K126C, and K149C in the light chain (LC);

wherein the residue number is according to EU numbering.

10. The conjugate of claim 9, wherein the engineered cysteine is T209C in the HC, wherein the residue number is according to EU numbering.

11. A pharmaceutical composition comprising the conjugate of claim 1 and a pharmaceutically acceptable carrier.

12. The conjugate of claim 1, wherein the VH of each of the antibodies or antigen-binding fragments thereof comprises SEQ ID NO:20 and the VL of each of the antibodies or antigen-binding fragments thereof comprises SEQ ID NO:21.

13. The conjugate of claim 12, wherein each of the antibodies or antigen-binding fragments thereof is a Fab comprising the Fab HC sequence of SEQ ID NO: 55 and the Fab LC sequence of SEQ ID NO:25.

14. A conjugate which binds Tie2 comprising:
a Fab comprising a heavy chain (HC) having SEQ ID NO:55 and a light chain (LC) having SEQ ID NO:25; conjugated to a polyol which has the structure of Formula 1 (b)

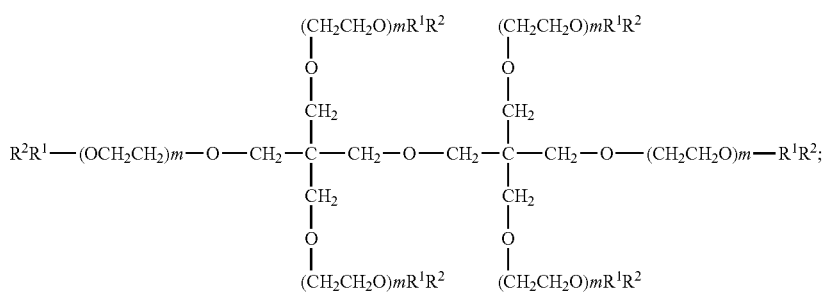

wherein each m is independently an integer from 10-30, wherein R¹ and R² taken together has the structure

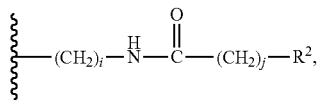

wherein R² is a maleamide; and
wherein the polyol is linked to the Fab HC at residue C209 (EU numbering).

15. A pharmaceutical composition comprising the conjugate of claim 14 and a pharmaceutically acceptable carrier.

16. A conjugate that binds to Tie2,
wherein the conjugate comprises six Fabs that bind Tie2, wherein each of the six Fabs comprises:
a heavy chain variable domain (VH) comprising (a) CDR-H1 comprising the amino acid sequence NTDIS (SEQ ID NO:3), (b) CDR-H2 comprising the amino acid sequence RISPSDGNTYYADSVKG (SEQ ID NO:4), and (c) CDR-H3 comprising the amino acid sequence RTRWASWAFDY (SEQ ID NO:7), and a light chain variable domain (VL) comprising (d) CDR-L1 comprising the amino acid sequence RASQDVSTAVA (SEQ ID NO:8), (e) CDR-L2 comprising the amino acid sequence SASFLYS (SEQ ID NO:9), and (f) CDR-L3 comprising the amino acid sequence QQSYTTPPT (SEQ ID NO:10), and
wherein each of the Fabs is linked to an arm of a hexameric polyethylene glycol (PEG) molecule.

17. The conjugate of claim 16, wherein each of the Fabs is linked to the arm of the PEG through a free sulfhydryl group of an engineered cysteine amino acid, wherein
the engineered cysteine is selected from the group consisting of T120C, G166C, G178C, T187C, and T209C in the Fab heavy chain (HC); or
the engineered cysteine is selected from the group consisting of Q124C, R142C, Q155C, L201C, T206C, K107C, K126C, and K149C in the Fab light chain (LC);
wherein the residue number is according to EU numbering.

18. The conjugate of claim 17, wherein the engineered cysteine is T209C in the HC, wherein the residue number is according to EU numbering.

19. The conjugate of claim 17, wherein the PEG has a weight average molecular weight of from about 500 Daltons (Da) to about 300,000 Da.

20. The conjugate of claim 19, wherein the PEG has the structure of general formula (Ib):

wherein each m is independently an integer from 3-250; each R¹ is independently either absent or is a linking group; and each R² is independently either hydrogen or a terminal reactive group; and
wherein at least one R² is a terminal reactive group and is covalently linked to the antibody or antigen-binding fragment thereof.

21. The conjugate of claim 20, wherein the VH of each of the six Fabs comprises SEQ ID NO:20 and the VL of each of the six Fabs comprises SEQ ID NO:21.

22. The conjugate of claim 21, wherein the Fab HC of each of the six Fabs comprises the sequence of SEQ ID NO:55 and the Fab LC of each of the six Fabs comprises the sequence of SEQ ID NO:25.

23. The conjugate of claim 22, wherein the PEG has a weight average molecular weight of from about 1000 Daltons (Da) to about 10,000 Da.

24. The conjugate of claim 23, wherein each of the six Fabs is linked to the arm of the PEG through a free sulfhydryl group of an engineered cysteine amino acid in each of the six Fabs, wherein the engineered cysteine is T209C in the Fab heavy chain (HC), wherein the residue number is according to EU numbering.

25. The conjugate of claim 24, wherein each R² is a terminal reactive group and is covalently linked to the Fab HC.

26. The conjugate of claim 25, wherein each R² is a maleimide and is covalently linked to the Fab HC.

27. A pharmaceutical composition comprising the conjugate of claim 26 and a pharmaceutically acceptable carrier.

28. A pharmaceutical composition comprising the conjugate of claim 16 and a pharmaceutically acceptable carrier.

29. A conjugate that binds to Tie2,
wherein the conjugate comprises six Fabs that bind Tie2,
wherein each of the six Fabs comprises a Fab heavy chain (HC) comprising the sequence of SEQ ID NO: 55 and a Fab light chain (LC) comprising the sequence of SEQ ID NO: 25,
wherein each of the six Fabs is linked to an arm of a hexameric polyethylene glycol (PEG) molecule, wherein the hexameric PEG molecule has the structure of general formula (Ib):

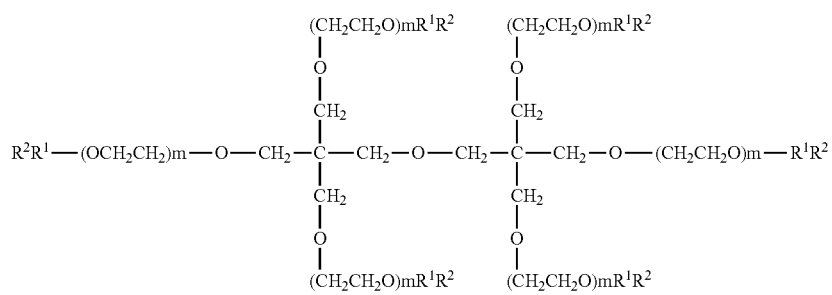

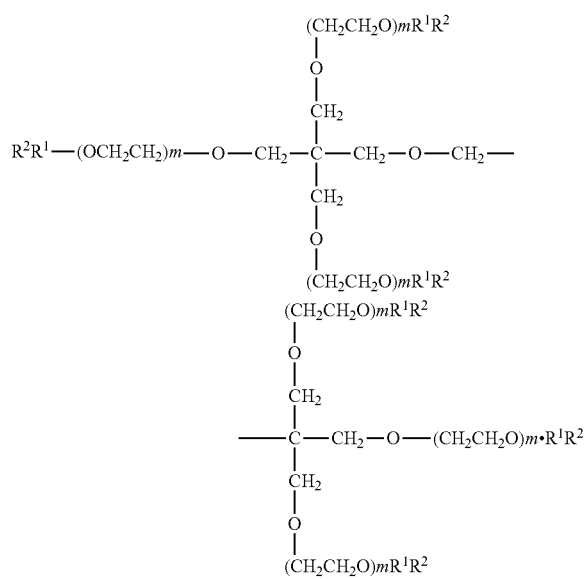

wherein each m is independently an integer from 10-30, wherein $R^1$ and $R^2$ when taken together has the structure

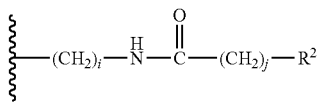

wherein i and j are 2, wherein $R^2$ is a maleamide and is covalently linked to one of the six Fabs through a free sulfhydryl group of engineered cysteine amino acid T209C of the Fab HC (EU numbering).

30. A pharmaceutical composition comprising the conjugate of claim 29 and a pharmaceutically acceptable carrier.

* * * * *

UNITED STATES PATENT AND TRADEMARK OFFICE
CERTIFICATE OF CORRECTION

PATENT NO. : 11,999,787 B2
APPLICATION NO. : 17/208292
DATED : June 4, 2024
INVENTOR(S) : Minhong Yan et al.

It is certified that error appears in the above-identified patent and that said Letters Patent is hereby corrected as shown below:

In the Claims

Correction for Claim 29 beginning on Column 218, Line 41, is shown below:
29. A conjugate that binds to Tie2,
    wherein the conjugate comprises six Fabs that bind Tie2,
    wherein each of the six Fabs comprises a Fab heavy chain (HC) comprising the sequence of SEQ ID NO: 55 and a Fab light chain (LC) comprising the sequence of SEQ ID NO: 25,
    wherein each of the six Fabs is linked to an arm of a hexameric polyethylene glycol (PEG) molecule, wherein the hexameric PEG molecule has the structure of general formula (Ib):

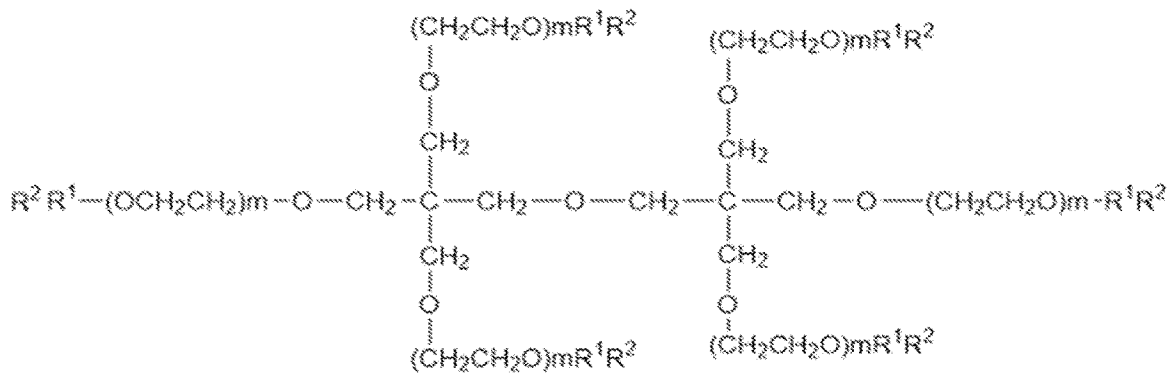

wherein each m is independently an integer from 10-30,
wherein $R^1$ and $R^2$ when taken together has the structure

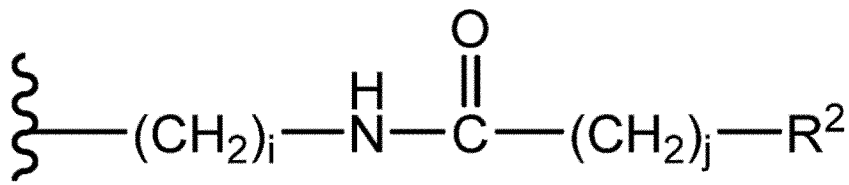

Signed and Sealed this
Twelfth Day of August, 2025

Coke Morgan Stewart
*Acting Director of the United States Patent and Trademark Office*